15 US009730976B2

(12) United States Patent
Seneci et al.

(10) Patent No.: US 9,730,976 B2
(45) Date of Patent: *Aug. 15, 2017

(54) HOMO- AND HETERODIMERIC SMAC MIMETIC COMPOUNDS AS APOPTOSIS INDUCERS

(71) Applicants: Pierfausto Seneci, Desenzano del Garda (IT); Laura Belvisi, Villasanta (IT); Federica Cossu, Milan (IT); Domenico Delia, Milan (IT); Carmelo Drago, Milan (IT); Daniele Lecis, Arese (IT); Stefano Maiorana, Milan (IT); Leonardo Pierpaolo Manzoni, Lissone (IT); Eloise Mastrangelo, Milan (IT); Mario Milani de Mayo de Mari, Milan (IT); Paola Maria Chiara Perego, Monza (IT); Francesca Vasile, Milan (IT)

(72) Inventors: Pierfausto Seneci, Desenzano del Garda (IT); Laura Belvisi, Villasanta (IT); Federica Cossu, Milan (IT); Domenico Delia, Milan (IT); Carmelo Drago, Milan (IT); Daniele Lecis, Arese (IT); Stefano Maiorana, Milan (IT); Leonardo Pierpaolo Manzoni, Lissone (IT); Eloise Mastrangelo, Milan (IT); Mario Milani de Mayo de Mari, Milan (IT); Paola Maria Chiara Perego, Monza (IT); Francesca Vasile, Milan (IT)

(73) Assignee: BioNTech AG, Mainz (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/071,677

(22) Filed: Mar. 16, 2016

(65) Prior Publication Data

US 2016/0317605 A1 Nov. 3, 2016

Related U.S. Application Data

(63) Continuation of application No. 14/379,675, filed as application No. PCT/IB2012/000297 on Nov. 25, 2014, now Pat. No. 9,321,808.

(51) Int. Cl.
| | |
|---|---|
| A61K 31/5517 | (2006.01) |
| A61K 38/07 | (2006.01) |
| C07K 5/083 | (2006.01) |
| C07D 519/00 | (2006.01) |
| A61K 38/06 | (2006.01) |
| A61K 45/06 | (2006.01) |
| C07K 5/103 | (2006.01) |
| A61K 38/00 | (2006.01) |

(52) U.S. Cl.
CPC .............. *A61K 38/07* (2013.01); *A61K 38/06* (2013.01); *A61K 45/06* (2013.01); *C07D 519/00* (2013.01); *C07K 5/0804* (2013.01); *C07K 5/0806* (2013.01); *C07K 5/0808* (2013.01); *C07K 5/101* (2013.01); *C07K 5/1005* (2013.01); *C07K 5/1008* (2013.01); *A61K 38/00* (2013.01)

(58) Field of Classification Search
CPC ................................... A61K 31/5517
See application file for complete search history.

(56) References Cited

FOREIGN PATENT DOCUMENTS

WO 2009/060292 A2 5/2009

*Primary Examiner* — Bruck Kifle
(74) *Attorney, Agent, or Firm* — McDonnell Boehnen Hulbert & Berghoff LLP

(57) ABSTRACT

The present invention relates to conformationally constrained homo- and heterodimeric mimetics of Smac with function as inhibitors of Inhibitor of Apoptosis Proteins (IAPs), the invention also relates to the use of these compounds in therapy, wherein the induction of apoptotic cell death is beneficial, especially in the treatment of cancer, alone or in combination with other active ingredients.

24 Claims, 2 Drawing Sheets

HOMO- AND HETERODIMERIC SMAC MIMETIC COMPOUNDS AS APOPTOSIS INDUCERS

This application is a continuation of U.S. patent application Ser. No. 14/379,675, filed on Nov. 25, 2014, which is a US national phase of International Application No. PCT/IB2012/000297 filed on Feb. 20, 2012, the entirety of which applications, including specification and claims, is hereby incorporated by reference into the specification.

FIELD OF THE INVENTION

The present invention relates to conformationally constrained homo- and heterodimeric mimetics of Smac (Second mitochondria-derived activator of caspases) with function as inhibitors of Inhibitor of Apoptosis Proteins (IAPs). The invention also relates to the use of these compounds, alone or in combination with other active ingredients, in the treatment of cancer, wherein the induction of apoptotic cell death is beneficial.

TECHNICAL BACKGROUND

Apoptosis is absolutely necessary for human development and survival, with millions of cells committing suicide daily as a way to prevent uncontrolled growth. Defects in apoptosis, together with amplified growth signals, often lead to cancer. Targeting apoptosis defects in cancer has a tremendous potential.

The first human apoptotic protein identified was BCL-2, as inhibitor of apoptosis, in 1984. The role of caspases-proteases that act as the cell's direct executioners by cleaving other cellular proteins was revealed in humans beginning in 1993. In cell ready to die, pro-apoptotic BCL-2 family members, like BAX, disrupt mitochondria, causing the release of other proteins that lead to caspase release and cell death.

Activation of this so-called "intrinsic" apoptotic pathway is the goal of many of the new cancer drugs.

A second, "extrinsic", cell death pathway is also an important target, and the first so-called death receptor, DR4, was discovered around 1996.

Most of the current cancer therapies, including chemotherapeutic agents, radiation, and immunotherapy, work by indirectly inducing apoptosis in cancer cells. The inability of cancer cells to execute an apoptotic program due to defects in the normal apoptotic machinery is thus often associated with an increase in resistance to chemotherapy, radiation or immunotherapy-induced apoptosis.

In this regard, targeting crucial negative regulators that play a central role in directly inhibiting apoptosis in cancer cells represents a highly promising therapeutic strategy for new anticancer drug design.

Two classes of central negative regulators of apoptosis have been identified. The first class is the BCL-2 family of proteins. Anti-Bcl-2 biologicals (antisense, antibodies, etc.) were tested in Phase III clinical trials for the treatment of solid and not solid tumors, while recently several small molecules (obatoclax, gossypol, ABT-763) have also entered Phase II clinical trials for the same indications.

The second class of central negative regulators of apoptosis is the inhibitor of apoptosis proteins (IAPs). IAPs potently suppress apoptosis induced by a large variety of apoptotic stimuli, including chemotherapeutic agents, radiation, and immunotherapy in cancer cells.

X-linked IAP (XIAP) is the most studied IAP family member, and one of the most potent inhibitors in suppressing apoptosis among all of the IAP members. XIAP plays a key role in the negative regulation of apoptosis in both the death receptor-mediated and the mitochondria-mediated pathways. XIAP functions as a potent endogenous apoptosis inhibitor by directly binding and potently inhibiting three members of the caspase family enzymes, caspase-3, -7, and -9. XIAP contains three baculovirus inhibitor of apoptosis repeat (BIR) domains. The third BIR domain (BIR3) selectively targets caspase-9, the initiator caspase in the mitochondrial pathway, whereas the linker region between BIR1 and BIR2 inhibits both caspase-3 and caspase-7. While binding to XIAP prevents the activation of all three caspases, it is apparent that the interaction with caspase-9 is the most critical for its inhibition of apoptosis. Because XIAP blocks apoptosis at the downstream effector phase, a point where multiple signalling pathways converge, strategies targeting XIAP may prove to be especially effective to overcome resistance of cancer cells to apoptosis.

More recently, cellular IAPs 1 and 2 (cIAP-1 and cIAP-2) were also identified and characterized as potent inhibitors in suppressing apoptosis via two distinct pathways. Direct caspase inhibition happens through binding to the same BIR domains as XIAP, but inhibition of TNF-α induced apoptosis and induction of non-canonical NF-κB activation is also observed.

A balance between endothelial cell survival and apoptosis contributes to the integrity of the blood vessel wall during vascular development and pathological angiogenesis.

It has been shown that both cIAP-1 and cIAP-2 are essential for maintaining this balance. Thus, both cIAPs may play an important role in the control of angiogenesis and blood vessel homeostasis in several pathologies involving regeneration and tumorigenesis.

There is evidence to indicate that XIAP and cIAPs are widely overexpressed in many types of cancer and may play an important role in the resistance of cancer cells to a variety of current therapeutic agents. There is thus a strong rationale for pan-IAP inhibitors as potent and effective pro-apoptotic agents in oncology.

Recently, Smac/DIABLO (second mitochondria-derived activator of caspases) was identified as a protein released from mitochondria into the cytosol in response to apoptotic stimuli. Smac is synthesized with an N-terminal mitochondrial targeting sequence that is proteolytically removed during maturation to the mature polypeptide. Smac was shown to directly interact with XIAP, cIAP-1, cIAP-2 and other IAPs, to disrupt their binding to caspases and facilitate caspases activation. Smac is a potent endogenous inhibitor of XIAP.

Smac/DIABLO interacts with both the BIR2 and BIR3 domains of XIAP. The crystal structure of Smac/DIABLO reveals that it forms a homodimer through a large, hydrophobic interface, and that homodimerization is essential for its binding to the BIR2, but not BIR3, domain of XIAP. The four amino-terminal residues of Smac/DIABLO (Ala-Val-Pro-Ile, AVPI) make specific contact with a surface groove of the BIR2 and BIR3 domains, but not with the BIR1 domain, of XIAP. Significantly, the conserved tetrapeptide motif has remarkable homology to the IAP-interacting motif found in the p12 amino-terminal sequence of caspase-9 (Ala-Thr-Pro-Phe) and the *Drosophila* proteins Hid (Ala-Val-Pro-Phe), Reaper (Ala-Val-Ala-Phe) and Grim (Ala-Ile-Ala-Tyr).

The $K_d$ value of Smac peptide AVPI binding to XIAP (Kd=0.4 μM) is essentially the same as the mature Smac protein (Kd=0.42 μM).

Full length Smac-BIR domain complexes of cIAP-1 or cIAP-2 are not reported. A complex between the BIR3 domain of cIAP-1 and N-terminal Smac sequences was reported, showing similar binding modes and strengths compared with XIAP.

OBJECTS OF THE INVENTION

Object of the present invention is to provide new non-peptidic compounds and a process for their preparation.

Still another object of the present invention is to provide new non-peptidic compounds showing activity as inhibitors of those substances that act as inhibitors of Apoptosis Proteins (IAPs), thus being able to re-establish the spontaneous human apoptosis process.

Additional object of the present invention is to overcome the intrinsic limitations of peptide-based IAP inhibitors by providing non-peptidic compounds.

Another object of the present invention is to provide non-peptide, homo- and heterodimeric small molecules able to mimic the binding of Smac to XIAP, to cIAP-1 and to cIAP-2.

DESCRIPTION OF THE INVENTION

Figure 1:
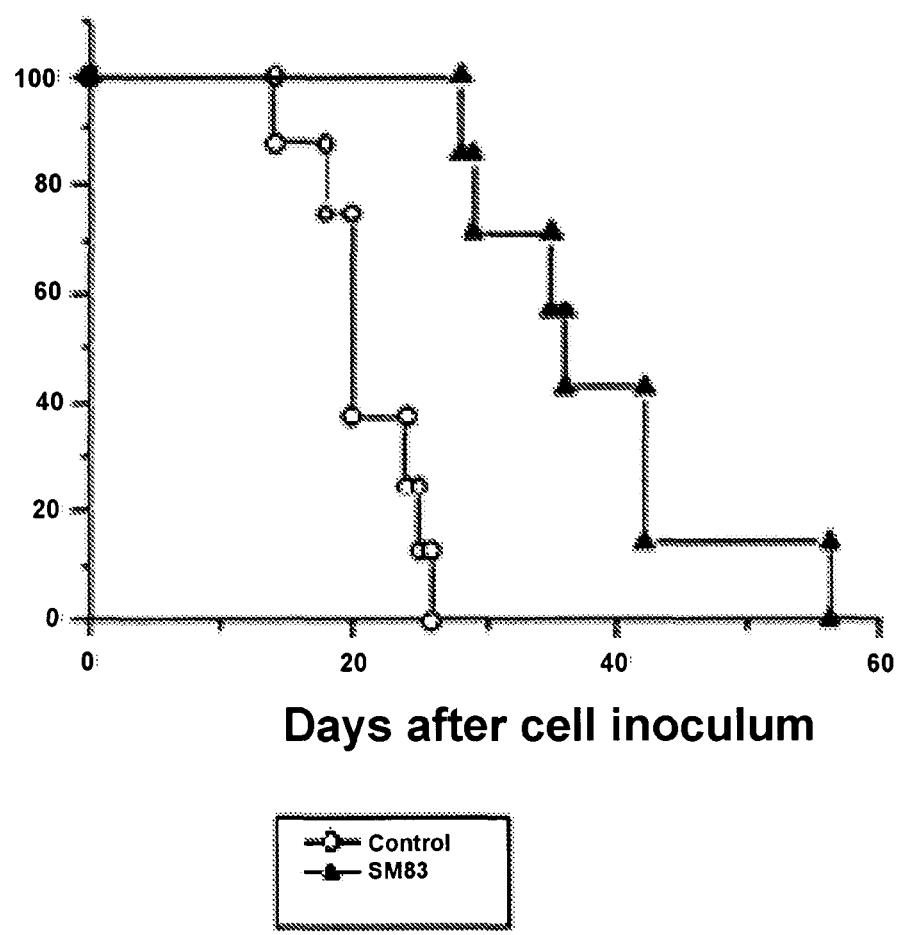
FIG. 1 shows the activity of 28a against i.p. ovarian tumors.
Figure 2:
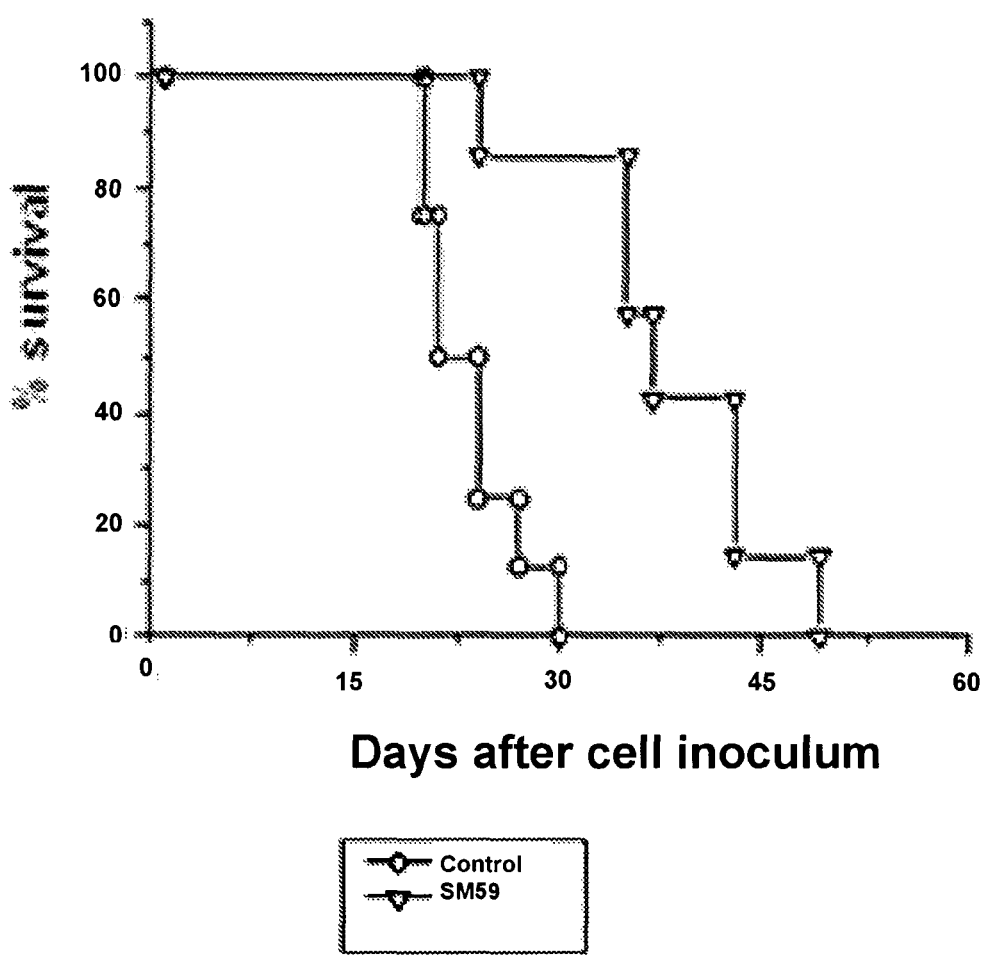
FIG. 2 shows the activity of SM164 against i.p. ovarian tumors

These and also other aspect of the invention are reached by a homodimeric compound of formula (I)

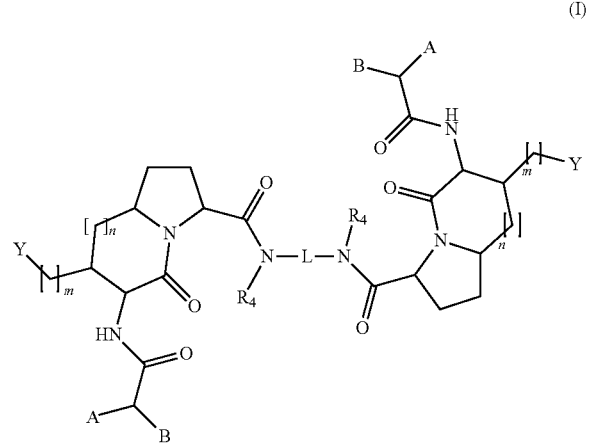

wherein:
n is 1 or 2
m is an integer from 0 to 3
A is
  $NR_1R_2$, or
  $N^+R_1R_2R_3$ where
    $R_1$, $R_2$ and $R_3$ are, each independently,
      hydrogen;
      $C_{1-8}$ alkyl or heteroalkyl; $C_{2-8}$ alkenyl or heteroalkenyl; $C_{2-8}$ alkynyl or heteroalkynyl;
      optionally substituted aryl, alkylaryl, heteroaryl, alkylheteroaryl; or
      any two of $R_1$, $R_2$, and $R_3$ taken together with the nitrogen to which they are attached form a heterocyclic group, optionally substituted by one or more oxo, thioxo, and optionally comprising a heteroatom selected from O, S, and N, provided that the heteroatom is separated from the nitrogen atom by a least two carbon atoms;
$R_4$ is
  hydrogen;
  optionally substituted $C_{1-18}$ alkyl or heteroalkyl; $C_{2-18}$ alkenyl or heteroalkenyl; $C_{2-18}$ alkynyl or heteroalkynyl;
  optionally substituted aryl, alkylaryl, heteroaryl, or alkylheteroaryl;
B is
  $C_{1-4}$ alkyl; $C_{2-4}$ alkenyl; $C_{2-4}$ alkynyl;
  aryl, alkylaryl, heteroaryl or alkylheteroaryl;
    all optionally substituted by one or more halogen;
Y is selected among:
  $OR_5$,
  $NHR_5$,
  $NR_5R_6$,
  $NH-S(O)_2-R_5$,
  $N^+(R_5)_3$,
  $SR_5$,
  $N_3$,
  $C(O)OR_5$,
  CN,
  $C(S)OR_5$,
  $C(S)NHR_5$,
  $C(NH)NHR_5$,
  $NH(CNH)NHR_5$,
  $NH(CS)NHR_5$,
  $NH(CO)NHR_5$

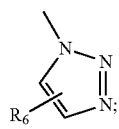

where
  $R_5$ is
  hydrogen;
  optionally substituted $C_{1-8}$ alkyl; $C_{2-8}$ alkenyl; $C_{2-8}$ alkynyl;
  optionally substituted aryl; alkylaryl; heteroaryl;
  $R_6$ is
  optionally substituted $C_{1-8}$ alkyl; $C_{2-8}$ alkenyl; or $C_{2-8}$ alkynyl;
  optionally substituted aryl; alkylaryl; or heteroaryl;
L is a "linker", preferably but not exclusively selected among those listed in the following Table I.

TABLE 1
| LINKER L | |
|---|---|
| L1 | 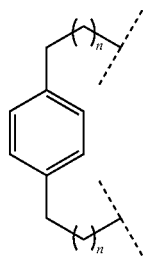 n = 1-6, each independently |
| L2 | 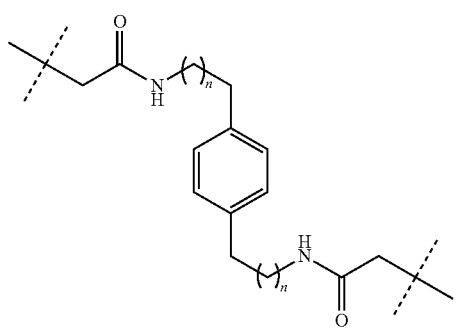 n = 1-6, each independently |
| L3 | 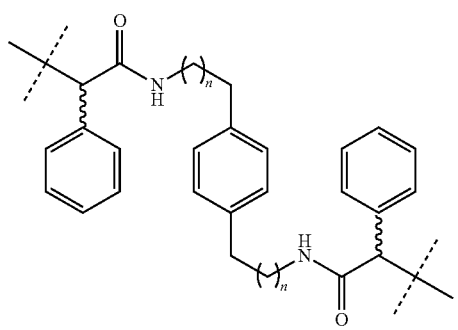 n = 1-6, each independently |
| L4 | 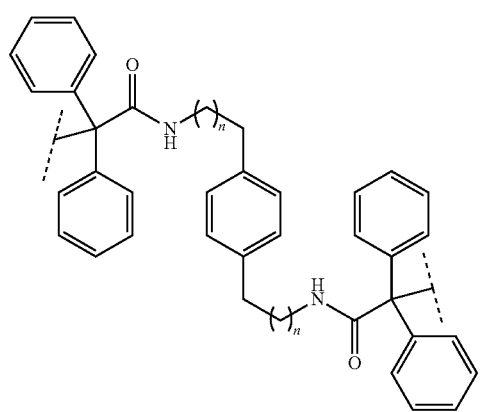 n = 1-6, each independently |

TABLE 1-continued
LINKER L
L5
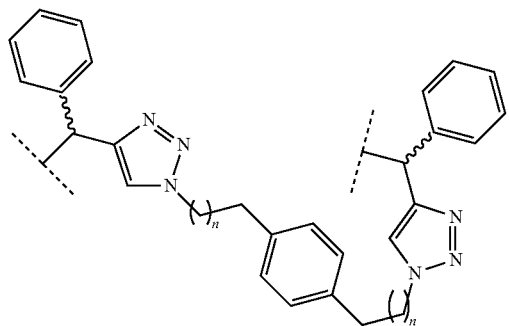
n = 1-6, each independently
L6
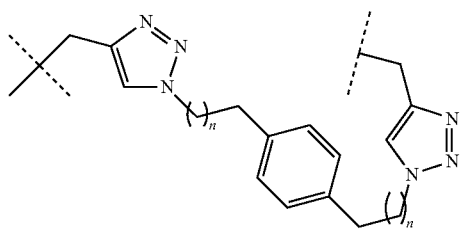
n = 1-6, each independently
L7
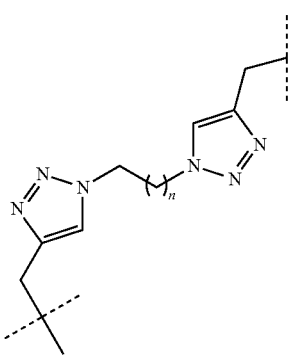
n = 1-10
L8
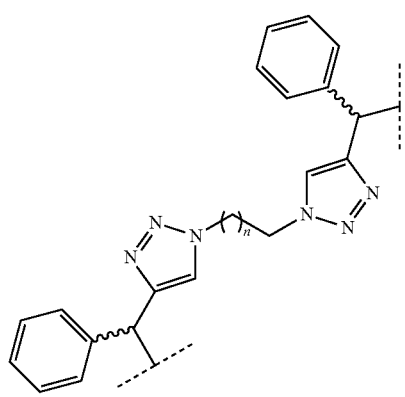
n = 1-10

TABLE 1-continued
| LINKER L | |
|---|---|
| L9 | 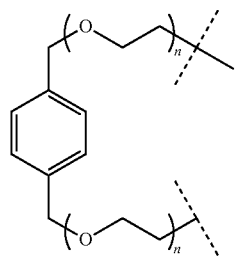<br>n = 1-3, each independently |
| L10 | 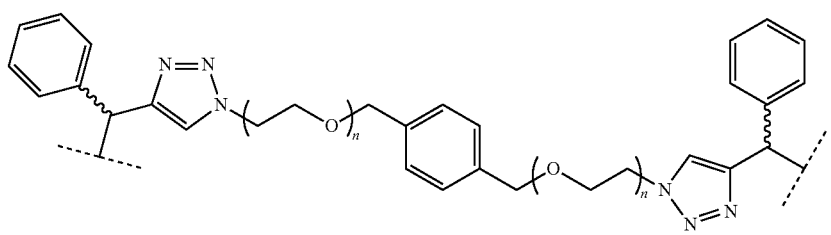<br>n = 1-3, each independently |
| L11 | 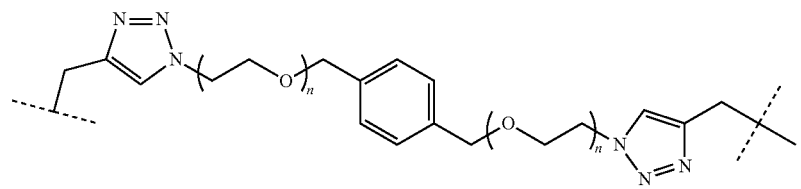<br>n = 1-3, each independently |
| L12 | 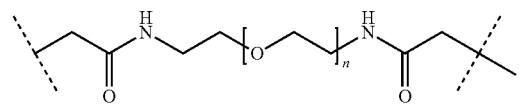<br>n = 1-4 |
| L13 | 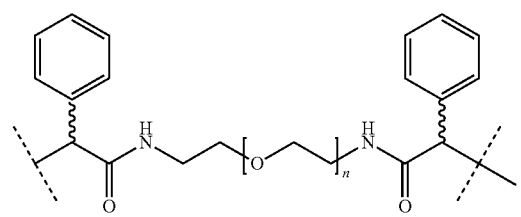<br>n = 1-4 |
| L14 | 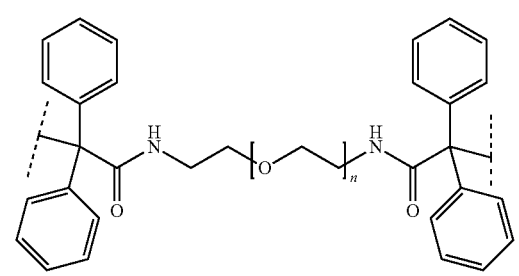<br>n = 1-4 |

TABLE 1-continued
| LINKER L | |
|---|---|
| L15 | 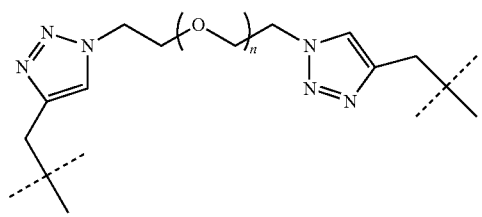<br>n = 1-4 |
| L16 | 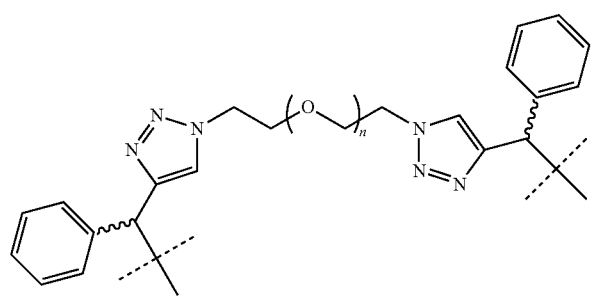<br>n = 1-4 |
| L17 | <br>n = 2-12 |
| L18 | 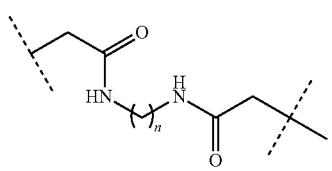<br>n = 2-12 |
| L19 | 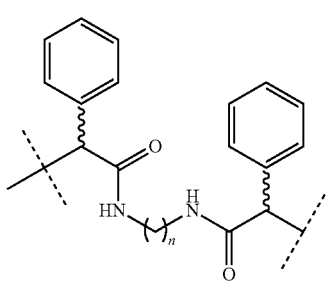<br>n = 2-12 |
| L20 | 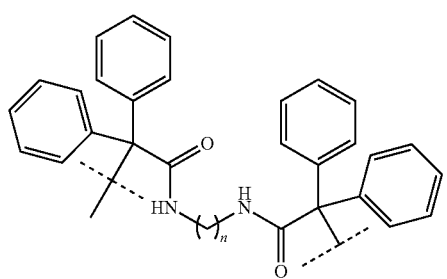<br>n = 2-12 |

TABLE 1-continued
| LINKER L | |
|---|---|
| L21 | 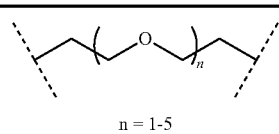
n = 1-5 |
| L22 | 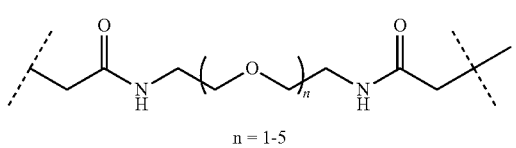
n = 1-5 |
| L23 | 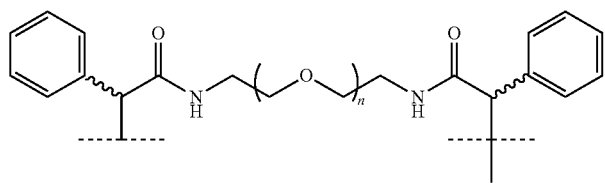
n = 1-5 |
| L24 | 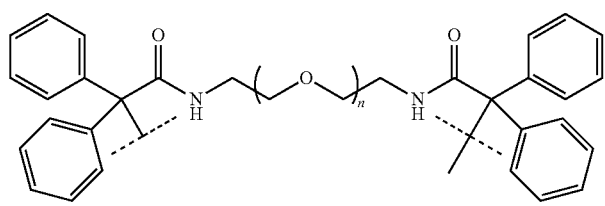
n = 1-5 |
| L25 | 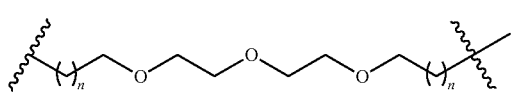
n = 1-3 |
| L26 | 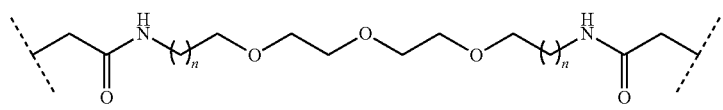
n = 1-3 |
| L27 | 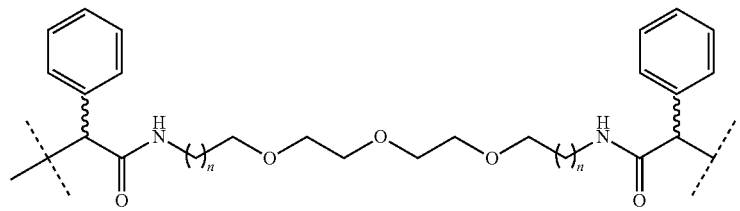
n = 1-3 |
| L28 | 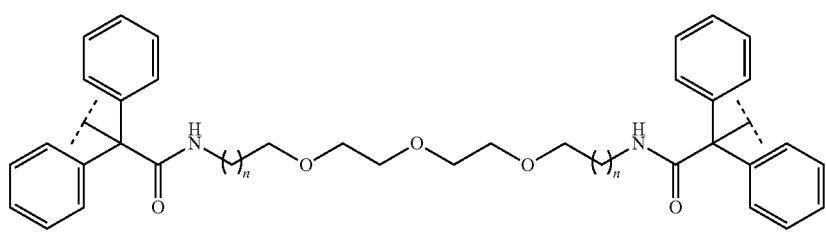
n = 1-3 |

TABLE 1-continued
| LINKER L | |
|---|---|
| L29 | 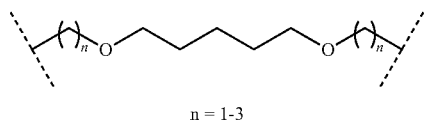<br>n = 1-3 |
| L30 | 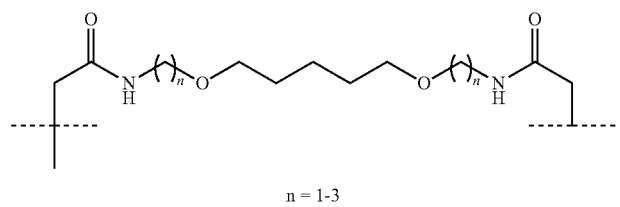<br>n = 1-3 |
| L31 | 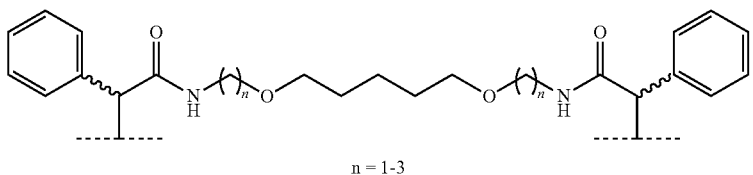<br>n = 1-3 |
| L32 | 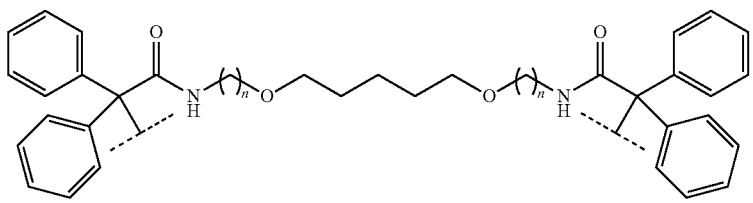<br>n = 1-3 |
| L33 | 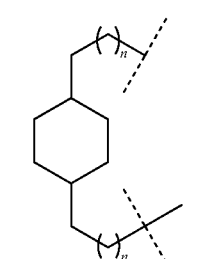<br>n = 1-6, each independently |
| L34 | 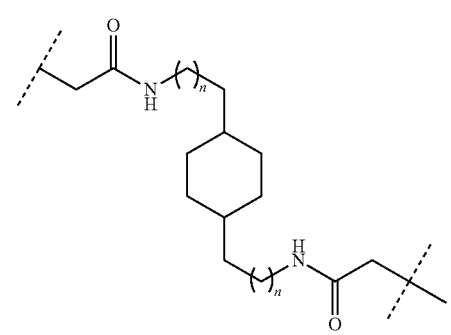<br>n = 1-6, each independently |

TABLE 1-continued
| LINKER L | |
|---|---|
| L35 | 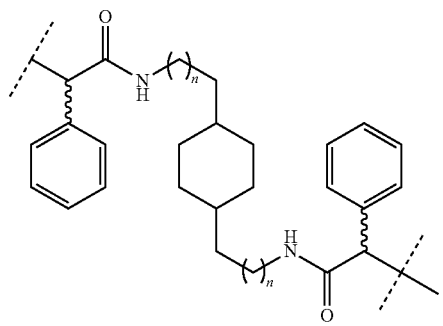<br>n = 1-6, each independently |
| L36 | 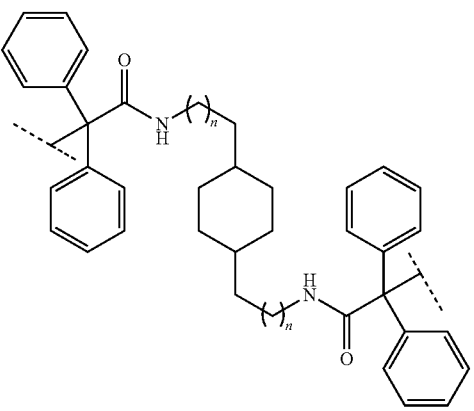<br>n = 1-6, each independently |
| L37 | 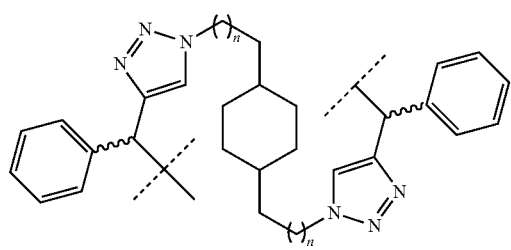<br>n = 1-6, each independently |
| L38 | 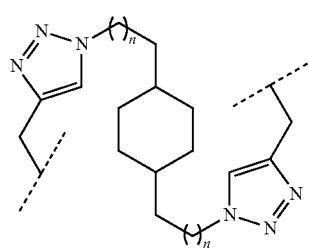<br>n = 1-6, each independently |

TABLE 1-continued
| LINKER L | |
|---|---|
| L39 | 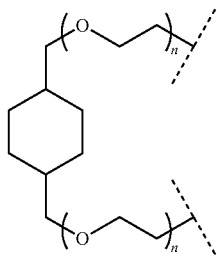<br>n = 1-3, each independently |
| L40 | 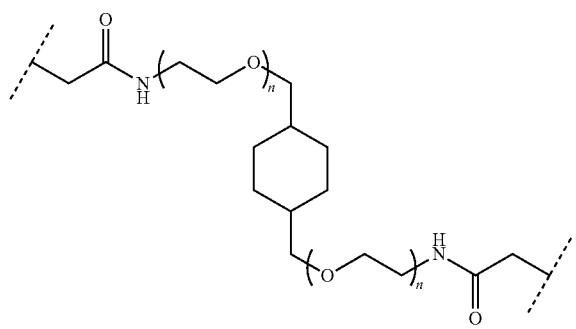<br>n = 1-3, each independently |
| L41 | 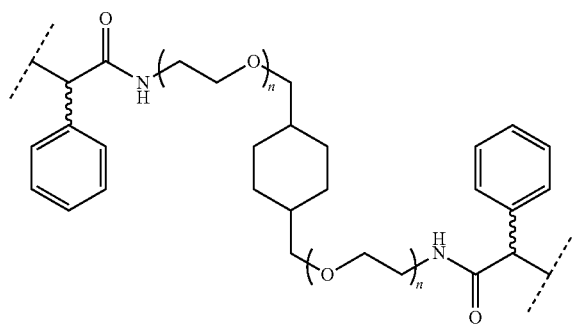<br>n = 1-3, each independently |
| L42 | 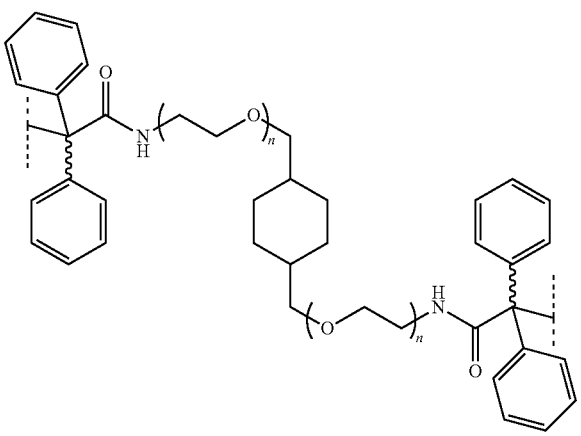<br>n = 1-3, each independently |

TABLE 1-continued
| LINKER L | |
|---|---|
| L43 | 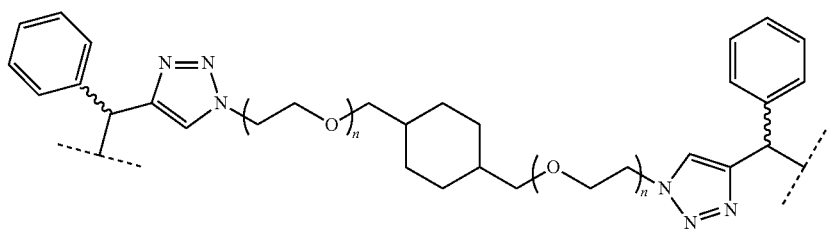<br>n = 1-3, each independently |
| L44 | 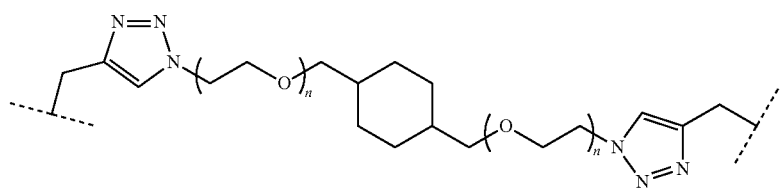<br>n = 1-3, each independently |
| L45 | 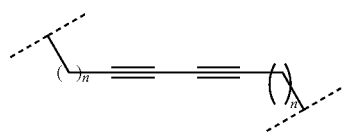<br>n = 1-6, each independently |
| L46 | 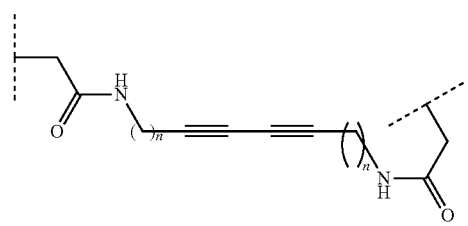<br>n = 1-6, each independently |
| L47 | 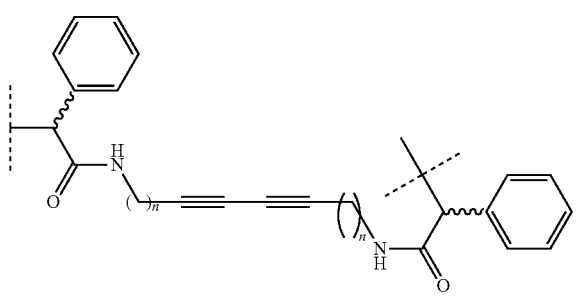<br>n = 1-6, each independently |
| L48 | 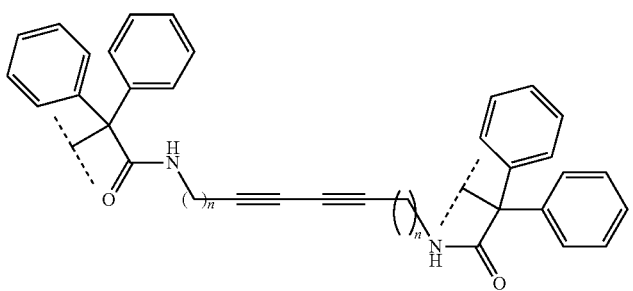<br>n = 1-6, each independently |

TABLE 1-continued
LINKER L
L49
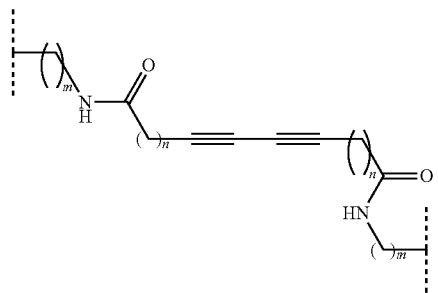
n, m = 1-6, each independently
L50
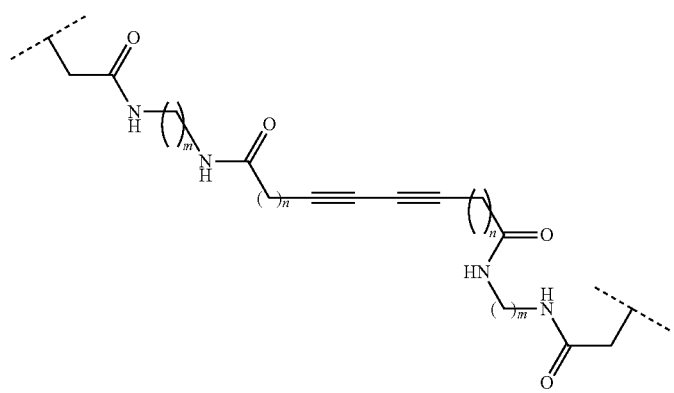
n, m = 1-6, each independently
L51
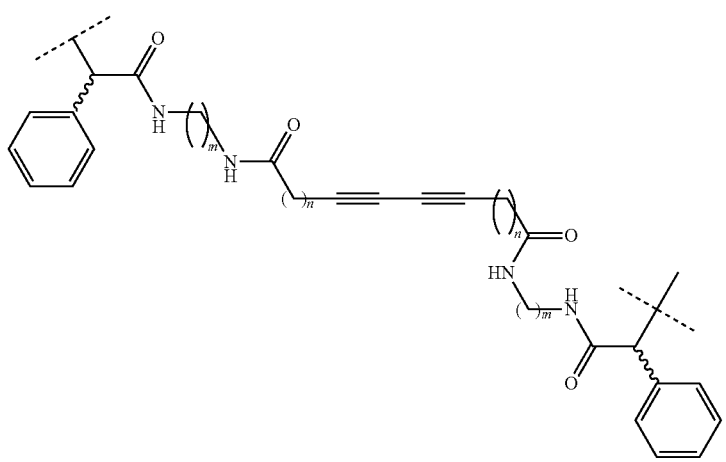
n, m = 1-6, each independently TABLE 1-continued
| LINKER L | |
|---|---|
| L52 | 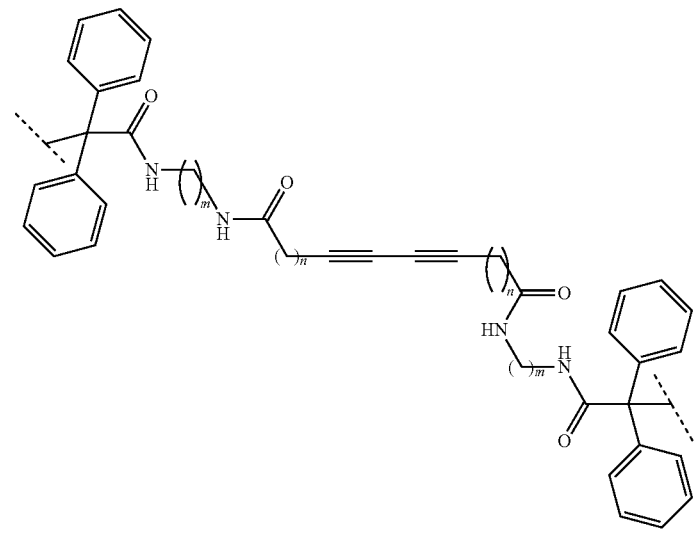<br>n, m = 1-6, each independently |
| L53 | 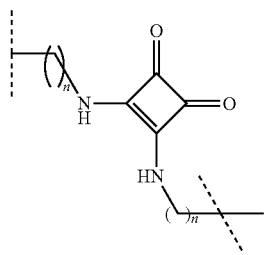<br>n = 1-6, each independently |
| L54 | 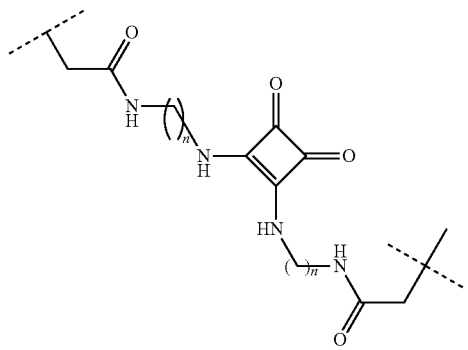<br>n = 1-6, each independently |
| L55 | 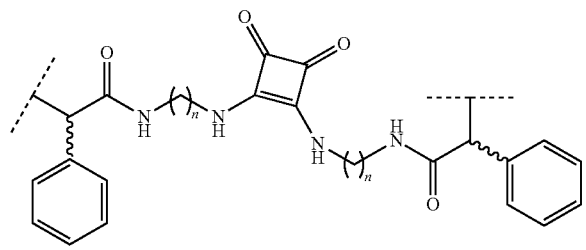<br>n = 1-6, each independently |

TABLE 1-continued

| LINKER L | |
|---|---|
| L56 | 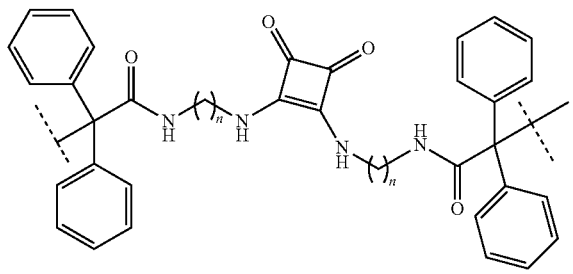 |
| | n = 1-6, each independently | said $R_4$, A, B and Y being independently selected as above indicated.

Most of the linkers of Table 1 are well known and commercially available from, for example, Aldrich Neosystem and Peptides International catalogues. Any other linker may be easily prepared according to known methods. For example, linker 21 can be prepared according to *Tetrahedron Lett.* 1998, 39, 6277; *Makromol. Chem.* 1979, 180, 2539. Details are given in the experimental section of this description.

Always according to the present invention are heterodimeric compounds of formula (II)

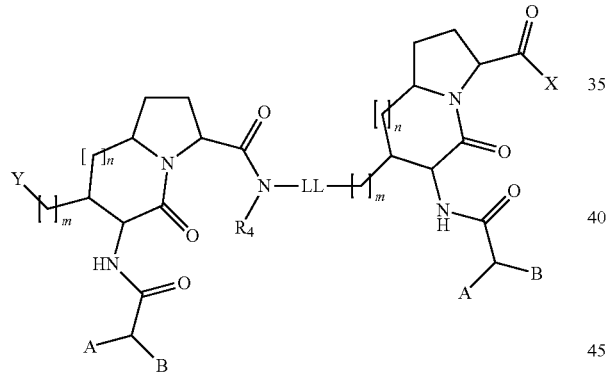

wherein:

n, m, A, $R_4$, B, Y are defined as above indicated (same definitions as in formula (I)) while:

X is optionally substituted $C_{1-18}$ alkyl, $C_{2-18}$ alkenyl, $C_{2-18}$ alkynyl, aryl, heteroaryl, and one or more hydrogens in CH, $CH_2$ or $CH_3$ groups can be replaced by a branched or unbranched alkyl or cycloalkyl, optionally substituted aryl, alkylaryl, heteroaryl, or alkylheteroaryl, $OR_7$, $SR_7$, $NR_7R_8$;

LL is a "linker", selected among those listed in the following Table II.

TABLE II

| LINKER LL | |
|---|---|
| L57 | 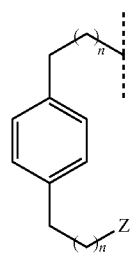 |
| | n = 1-6, each independently |

TABLE II-continued
| LINKER LL | |
|---|---|
| L58 | 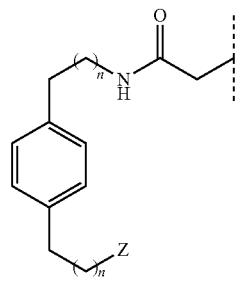<br>n = 1-6, each independently |
| L59 | 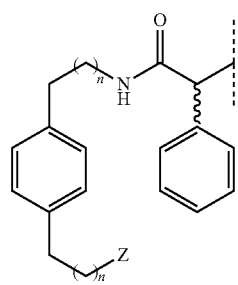<br>n = 1-6, each independently |
| L60 | 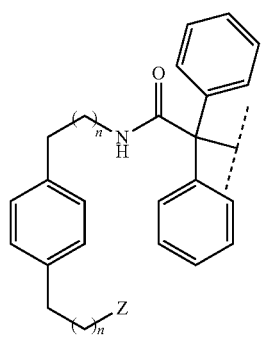<br>n = 1-6, each independently |
| L61 | 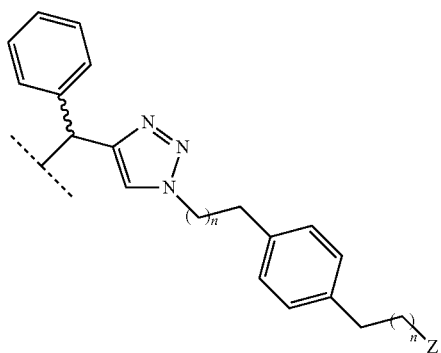<br>n = 1-6, each independently |

TABLE II-continued
| LINKER LL | |
|---|---|
| L62 | 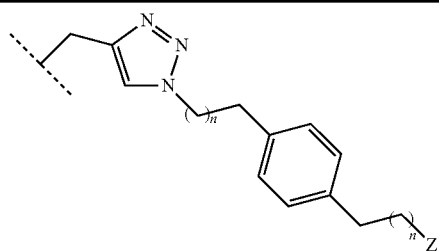 |
| | n = 1-6, each independently |
| L63 | 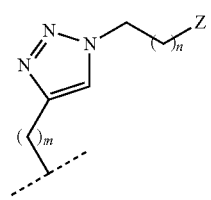 |
| | n, m = 1-10 each independently |
| L64 | 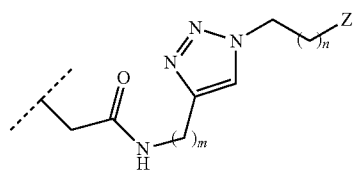 |
| | n, m = 1-10 each independently |
| L65 | 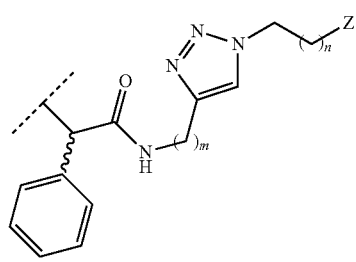 |
| | n, m = 1-10 each independently |
| L66 | 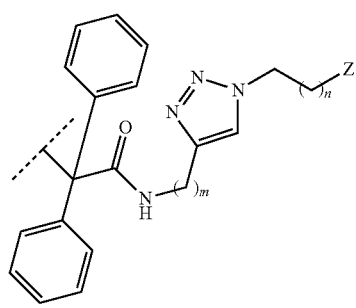 |
| | n, m = 1-10 each independently |

TABLE II-continued
| LINKER LL | |
|---|---|
| L67 | 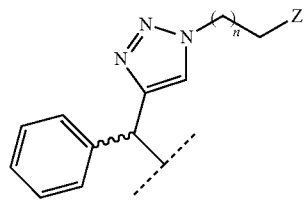<br>n = 1-10 |
| L68 | 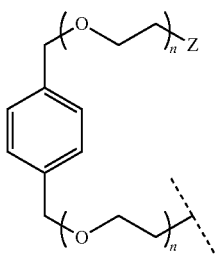<br>n = 1-3, each independently |
| L69 | 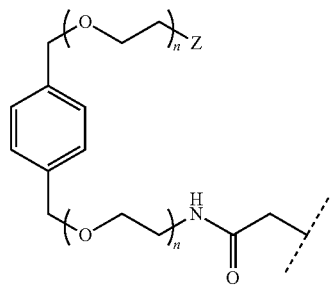<br>n = 1-3, each independently |
| L70 | 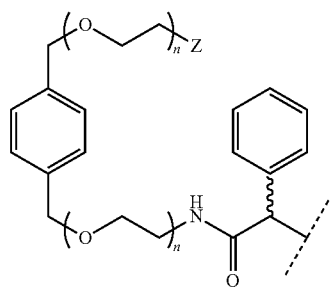<br>n = 1-3, each independently |

TABLE II-continued
| LINKER LL | |
|---|---|
| L71 | 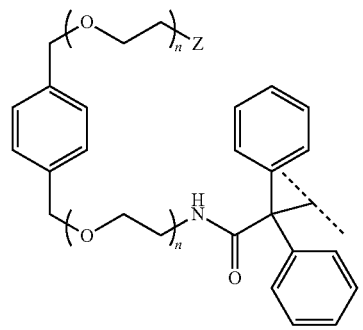<br>n = 1-3, each independently |
| L72 | 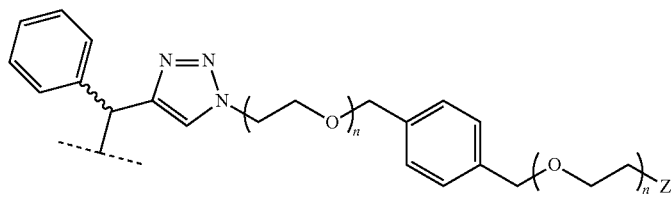<br>n = 1-3, each independently |
| L73 | 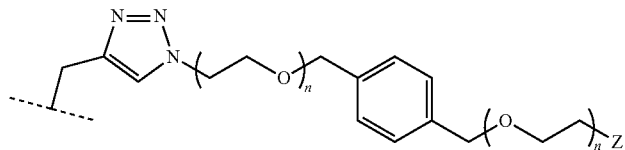<br>n = 1-3, each independently |
| L74 | 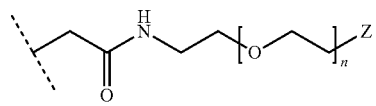<br>n = 1-4, each independently |
| L75 | 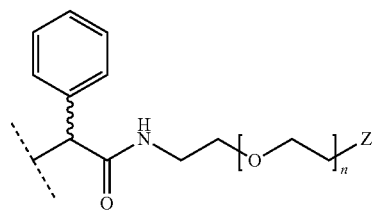<br>n = 1-4, each independently |

TABLE II-continued
| LINKER LL | |
|---|---|
| L76 | 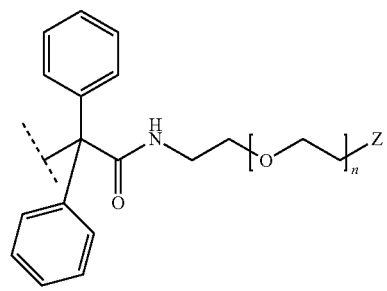<br>n = 1-4, each independently |
| L77 | 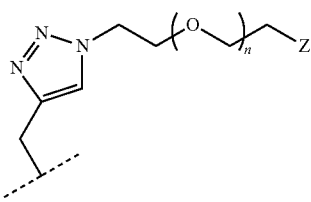<br>n = 1-4 |
| L78 | 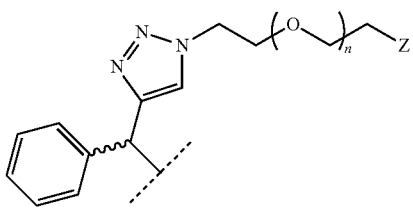<br>n = 1-4 |
| L79 | <br>n = 2-12 |
| L80 | 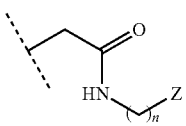<br>n = 2-12 |
| L81 | 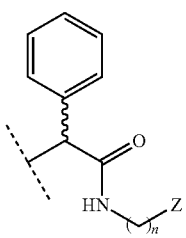<br>n = 2-12 |

TABLE II-continued
LINKER LL
L82
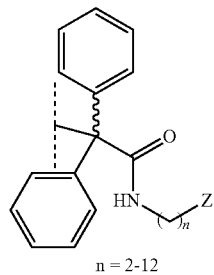
n = 2-12
L83
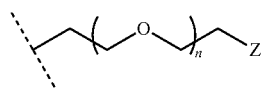
n = 1-5
L84
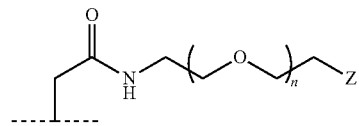
n = 1-5
L85
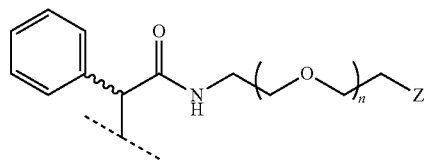
n = 1-5
L86
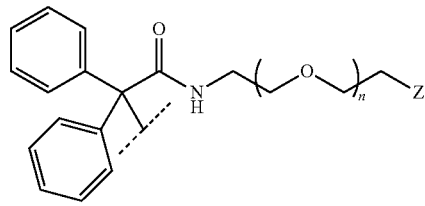
n = 1-5
L87
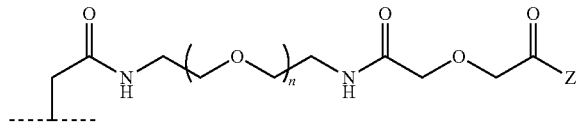
n = 1-5
L88
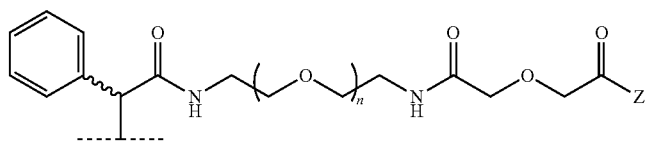
n = 1-5

TABLE II-continued
LINKER LL
L89 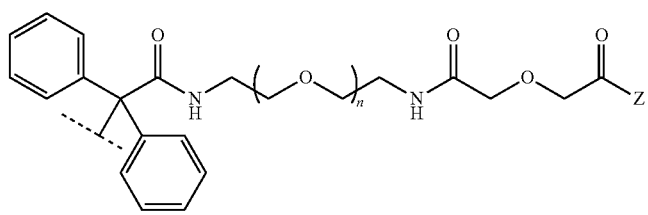
n = 1-5
L90 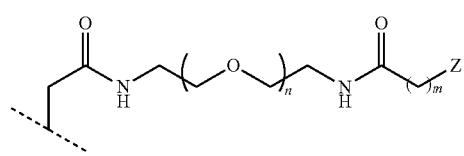
n = 1-5; m = 1-12 each independently
L91 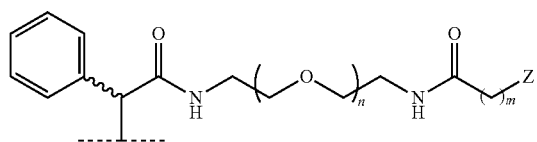
n = 1-5; m = 1-12 each independently
L92 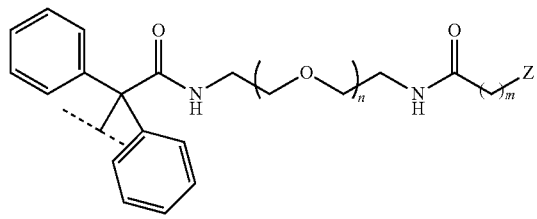
n = 1-5; m = 1-12 each independently
L93 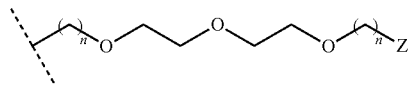
n = 1-5 each independently
L94 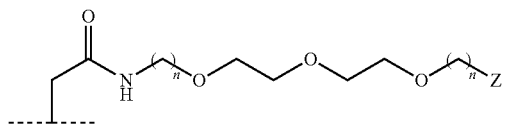
n = 1-5 each independently
L95 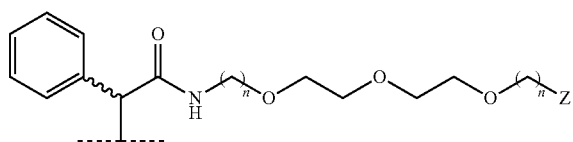
n = 1-5 each independently

TABLE II-continued
| LINKER LL |
| --- |
L96
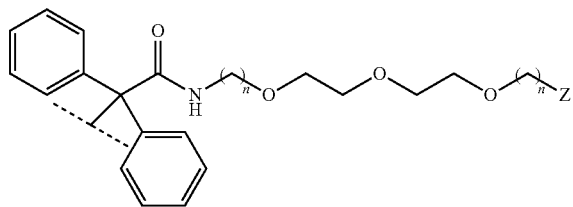
n = 1-5 each independently
L97
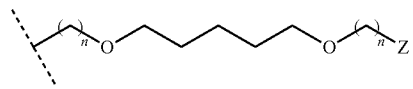
n = 1-5 each independently
L98
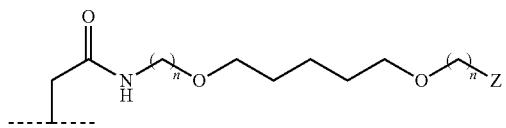
n = 1-5 each independently
L99
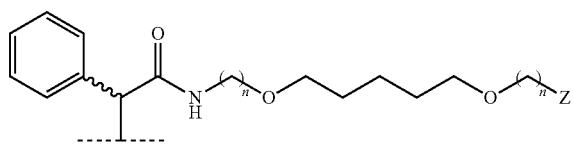
n = 1-5 each independently
L100
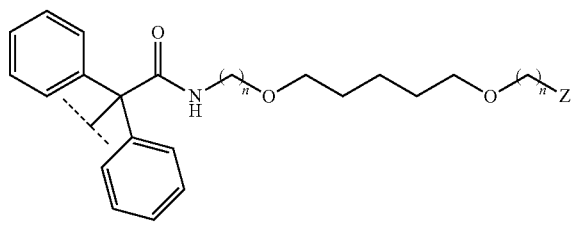
n = 1-5 each independently
L101
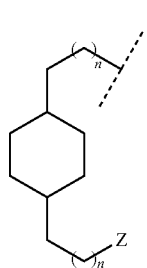
n = 1-6, each independently

TABLE II-continued
LINKER LL
L102
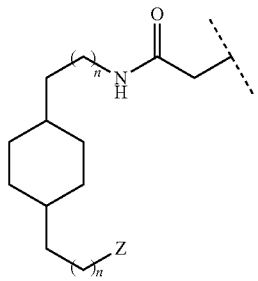
n = 1-6, each independently
L103
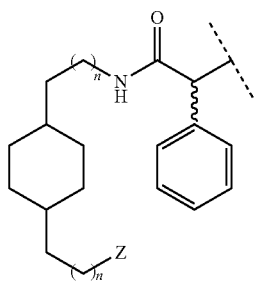
n = 1-6, each independently
L104
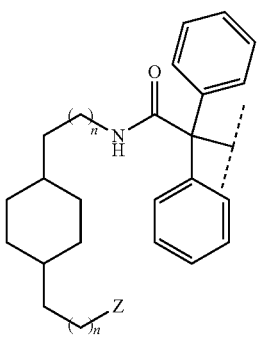
n = 1-6, each independently
L105
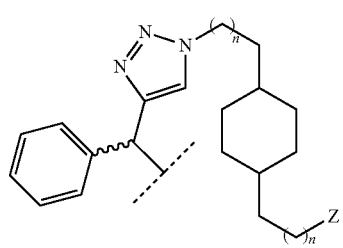
n = 1-6, each independently

TABLE II-continued
LINKER LL
L106
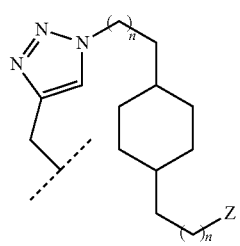
n = 1-6, each independently
L107
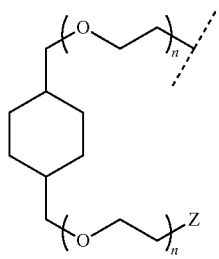
n = 1-3, each independently
L108
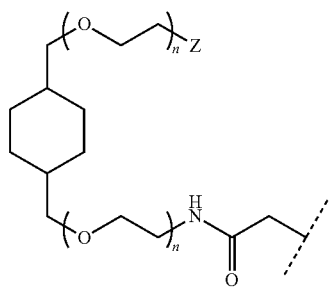
n = 1-3, each independently
L109
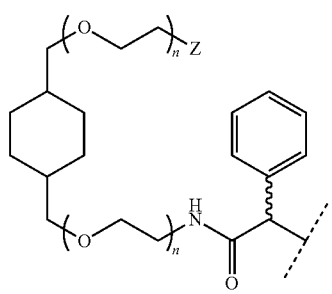
n = 1-3, each independently TABLE II-continued
| LINKER LL | |
|---|---|
| L110 | 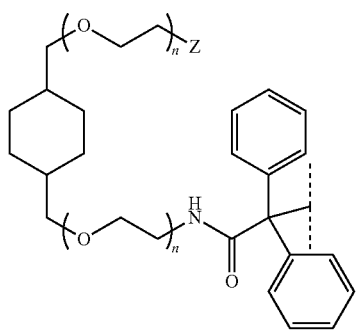<br>n = 1-3, each independently |
| L111 | 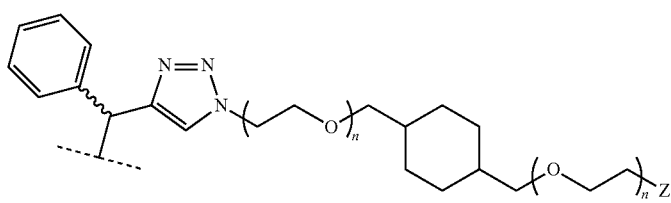<br>n = 1-3, each independently |
| L112 | 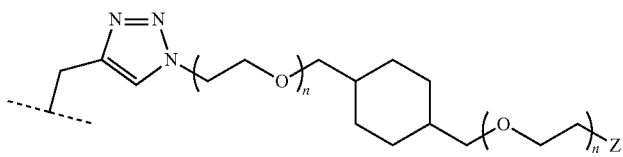<br>n = 1-3, each independently |
| L113 | 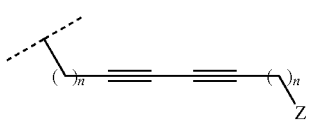<br>n = 1-6, each independently |
| L114 | 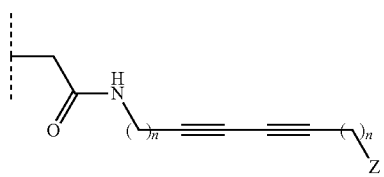<br>n = 1-6, each independently |
| L115 | 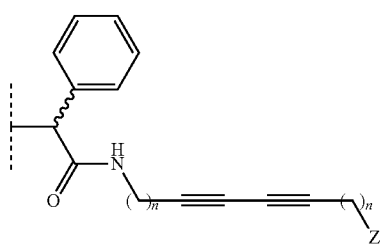<br>n = 1-6, each independently |

TABLE II-continued
LINKER LL
L116
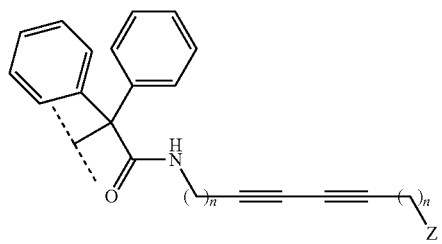
n = 1-6, each independently
L117
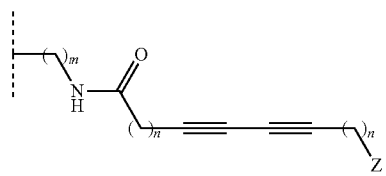
n, m = 1-6, each independently
L118
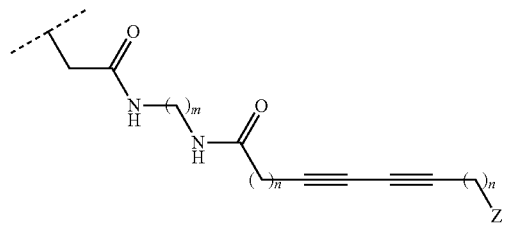
n, m = 1-6, each independently
L119
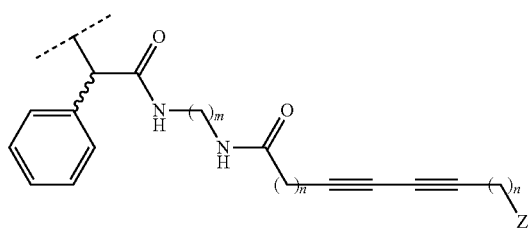
n, m = 1-6, each independently
L120
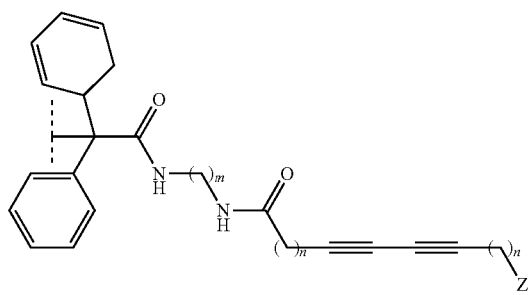
n, m = 1-6, each independently TABLE II-continued

LINKER LL

L121 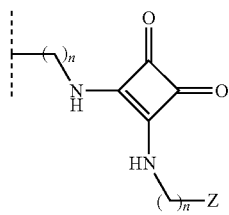

n = 1-6, each independently

L122 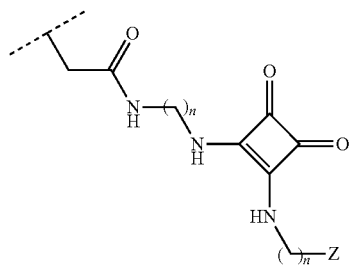

n = 1-6, each independently

L123 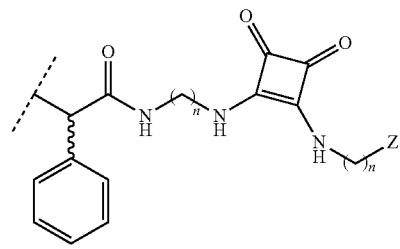

n = 1-6, each independently

L124 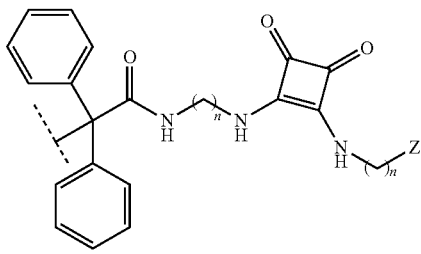

n = 1-6, each independently

Z is selected among
 $CR_7R_8$,
 O,
 $NR_7$,
 $NR_7C(O)$,
 $C(O)NR_7$,
 S,
 $C(O)O$,
 $C(S)O$,
 $C(S)NR_7$,
 $C(NR_8)NR_7$,
 $NR_7C(NR_8)NR_9$,
 $NR_7C(O)NR_8$,
 $NR_7C(S)NR_8$

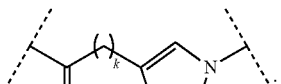

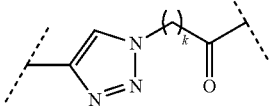

where
 k=1-10 each independently;
 $R_7$, $R_8$, $R_9$ are independently hydrogen or optionally substituted $C_{1-4}$ alkyl, $C_{2-5}$ alkenyl, or $C_{2-5}$ alkynyl, in which one or more carbons can be replaced by a heteroatom selected from O, S, and N, or optionally substituted aryl, alkylaryl, heteroaryl, or alkylheteroaryl; or any two of $R_7$, $R_8$, and $R_9$ taken together with the nitrogen to which they are attached form a heterocyclic group, in which one or more carbon atom can be replaced by C=O, C=S, or a heteroatom selected from O, S, and N, with the proviso that the heteroatom is separated from the nitrogen atom by a least two carbons;

Most of the linkers of Table 2 are well known and commercially available from, for example, Aldrich Neosystem and Peptides International catalogues. Any other linker may be easily prepared according to known methods. For example, linker 83 can be prepared according to *Tetrahedron Lett.* 1998, 39, 6277; *Makromol. Chem.* 1979, 180, 2539. Details are given in the experimental section of this description.

According to the present invention and with reference to those compounds belonging to formula (I) and (II), the terms "heteroalkyl", "heteroalkenyl", "heteroalkynyl" and "heteroaryl" define alkyl, alkenyl, alkynyl and aryl groups, respectively, wherein one or more carbon atoms are replaced by a heteroatom selected among O, S and N.

According to the present invention, the alkyl, alkenyl, alkynyl groups can be linear or branched; such groups may be for example selected as methyl, ethyl, propyl, isopropyl, butyl, tert-butyl, ethenyl, propenyl, isopropenyl, butenyl, isobutenyl, hexenyl, ethynyl, propynyl, butynyl.

Unless otherwise indicated, alkyl groups are lower alkyl groups, i.e. they have 1 to 6 carbon atoms and alkenyl and alkynyl groups are lower alkenyl and alkynyl groups, i.e. they have 2 to 6 carbon atoms.

According to the present invention, the term "optionally substituted", if not expressly defined, means that any substitution is possible, provided that the resulting molecule is chemically stable. Preferably, unless otherwise indicated, the expression "optionally substituted" means that the designated groups may be optionally substituted for instance by alkyl, cycloalkyl, optionally substituted aryl, alkylaryl, heteroaryl, alkylheteroaryl, $OR_4$, $SR_4$, $NR_4R_5$ or $COOR_4$.

Always according to the invention, a preferred embodiment is that where the optionally substituted alkyl, heteroalkyl, alkenyl, heteroalkenyl, alkynyl, heteroalkynyl, alkylaryl or alkylheteroaryl groups are substituted on the aliphatic chains by oxo or thioxo groups.

According to another preferred embodiment, A is $NH_2$ or —NH-Alkyl or —N(Alkyl)$_2$.

According to another preferred embodiment, B is an alkyl group, more preferably methyl, ethyl or an optionally substituted alkylaryl group, such as a benzyl group.

According to another preferred embodiment, n is 2.
According to another preferred embodiment, m is 1.
According to another preferred embodiment, m is 2.

The expression "each independently" means that each designated groups represents any of the given definitions and can therefore be equal or different to the others.

According to another preferred embodiment, $NR_4$ is a NH, thus $R_4$ being preferably selected as hydrogen.

The compounds of the invention present some chiral carbons and therefore may exist in the form of racemates or diastereoisomers, all being encompassed by the scope of the invention.

According to a preferred embodiment, the present invention relates to homodimeric compounds of formula (I) having the following stereochemical configuration

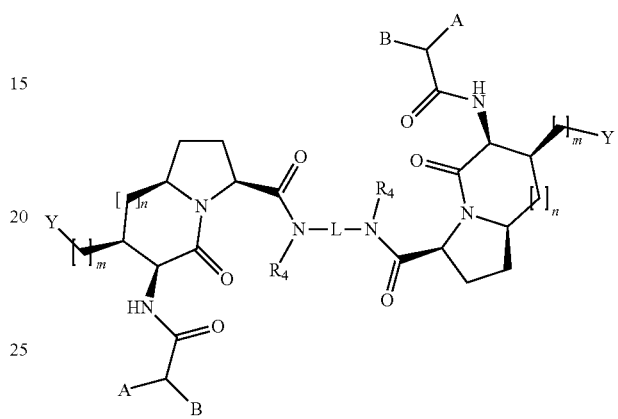

wherein the substituents are as defined above and the wedge-shaped bonds indicate that the substituents are positioned above the plane.

According to another preferred embodiment, the present invention relates to heterodimeric compounds of formula (II) having the following configuration

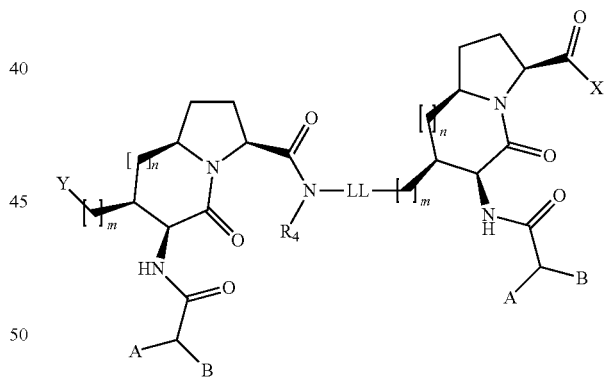

wherein the substituents are as defined above and the wedge-shaped bonds indicate that the substituents are positioned above the plane.

Each of the above described compound can be obtained as such, as its saline form or as a pharmaceutically acceptable salt or a prodrug.

According to the present invention the term "prodrug" means that compounds of the invention are in the form of a precursor of the active ingredient, said precursor being metabolized, after administration, to the active compound of formula (I).

Illustrative preferred embodiments of the invention are compounds of the following table:

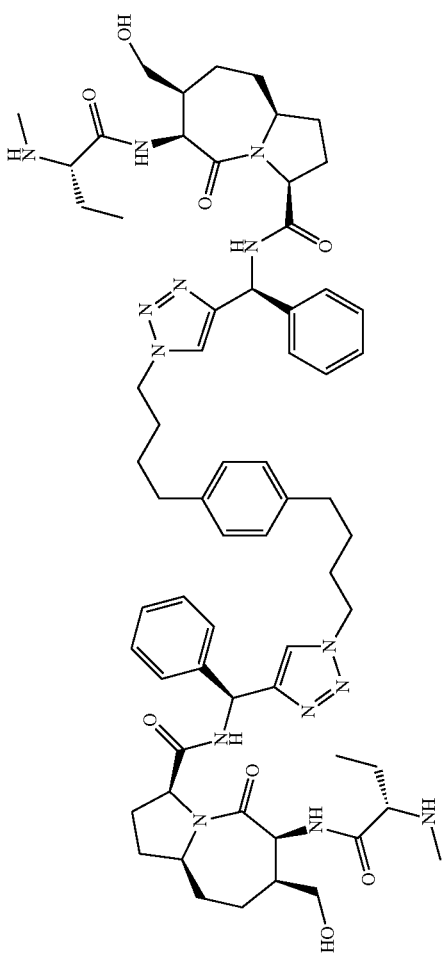
P1
Compound 28a
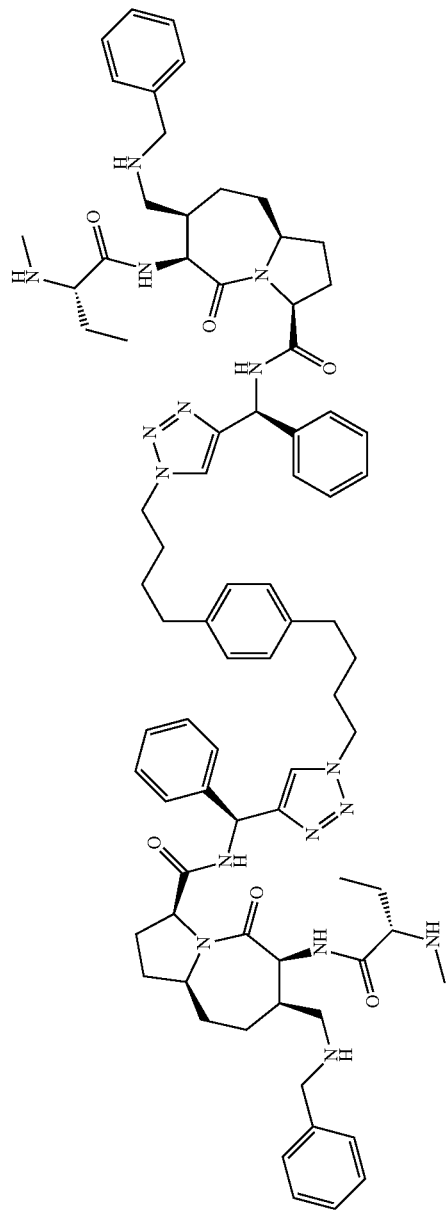
P2
Compound 29a

-continued
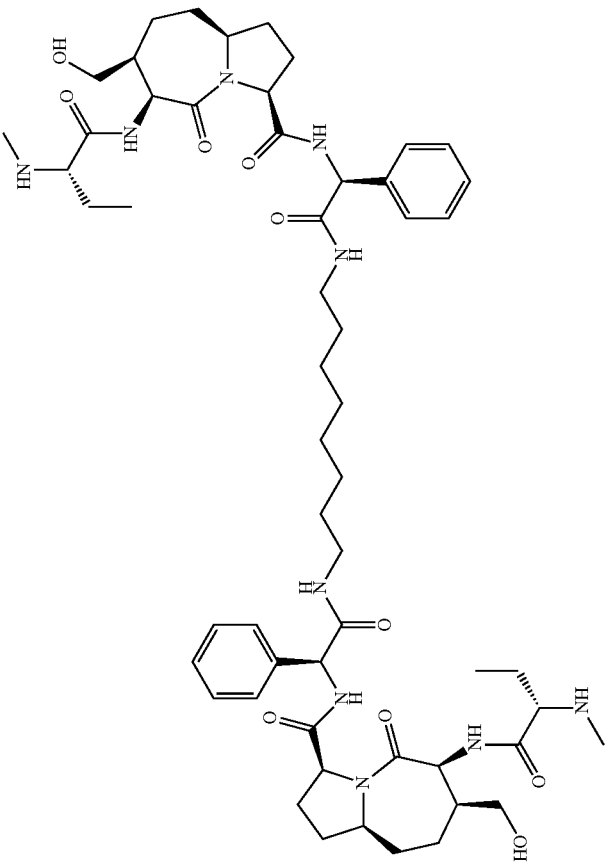
P3
Compound 30a

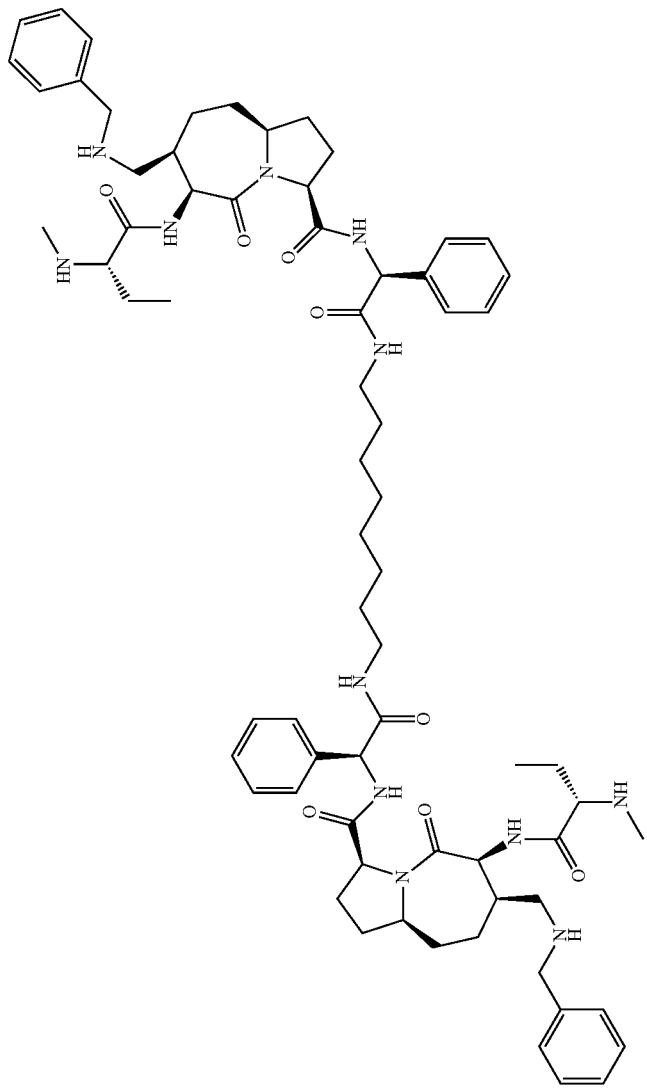

P5
Compound 30d
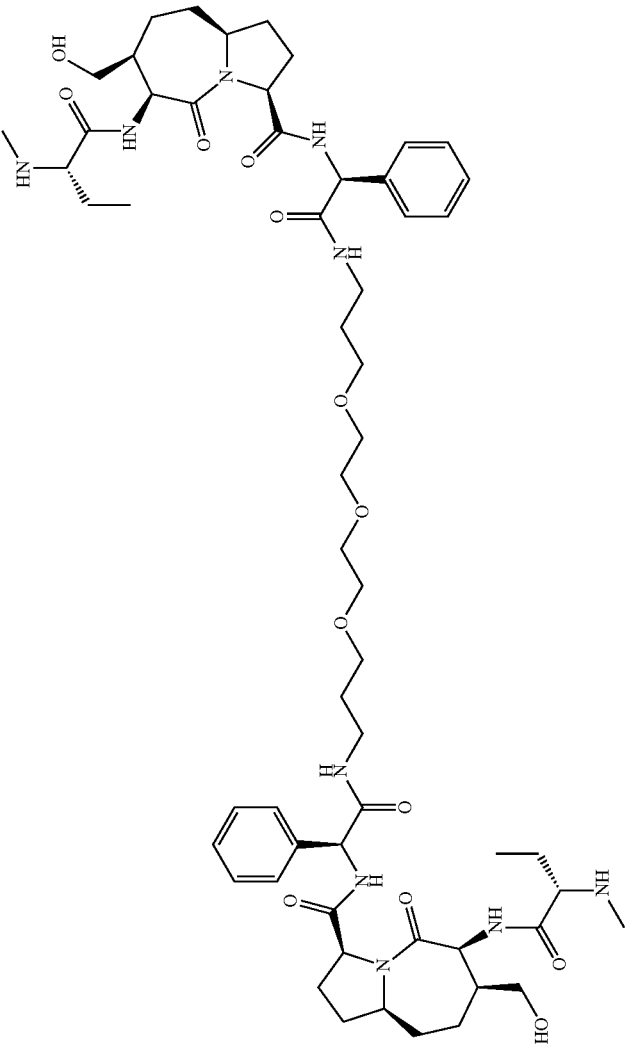

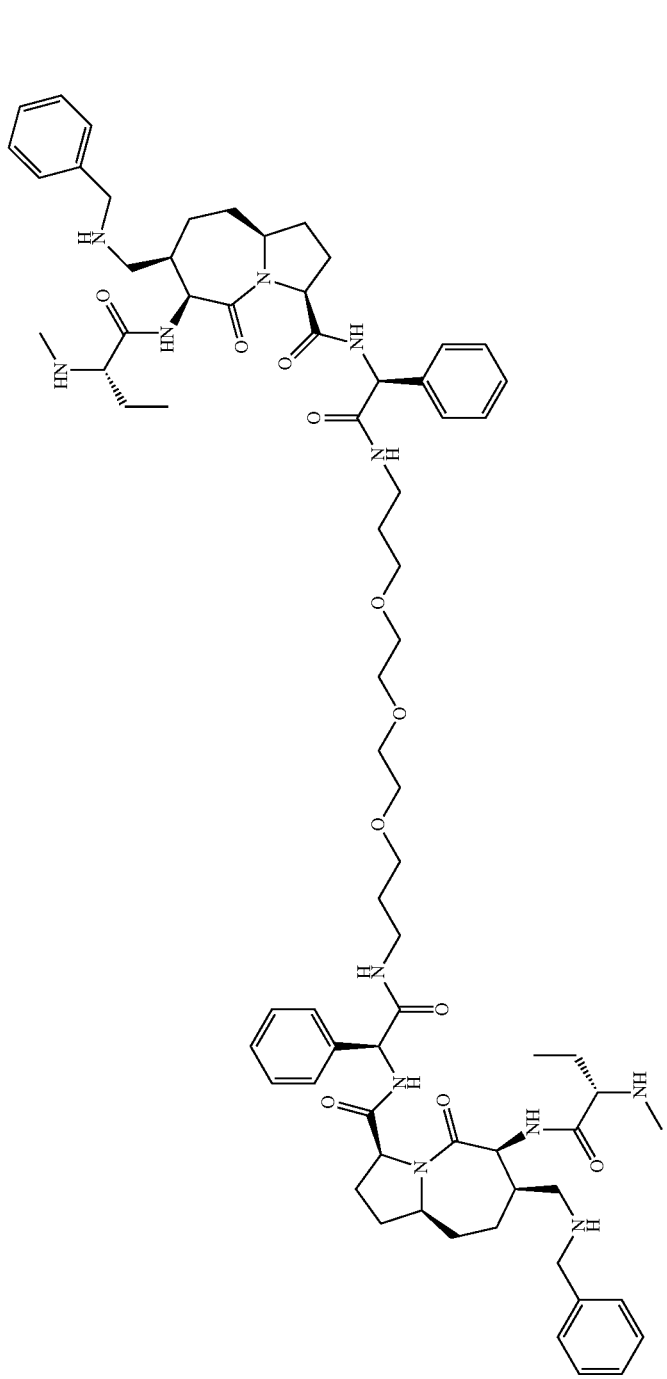
P6

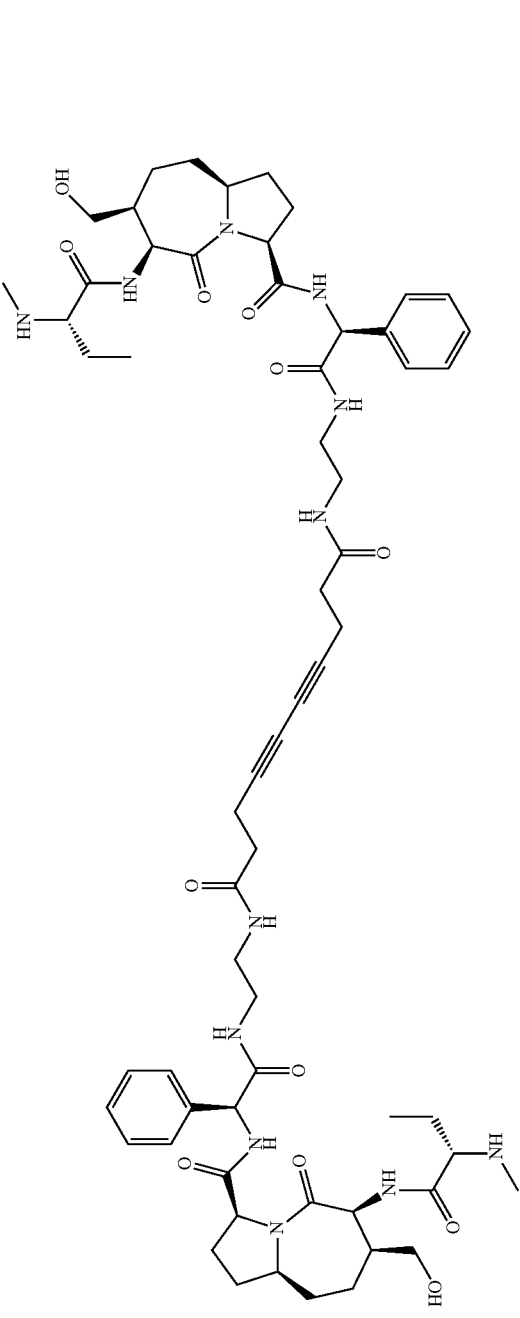
P7
Compound 30c
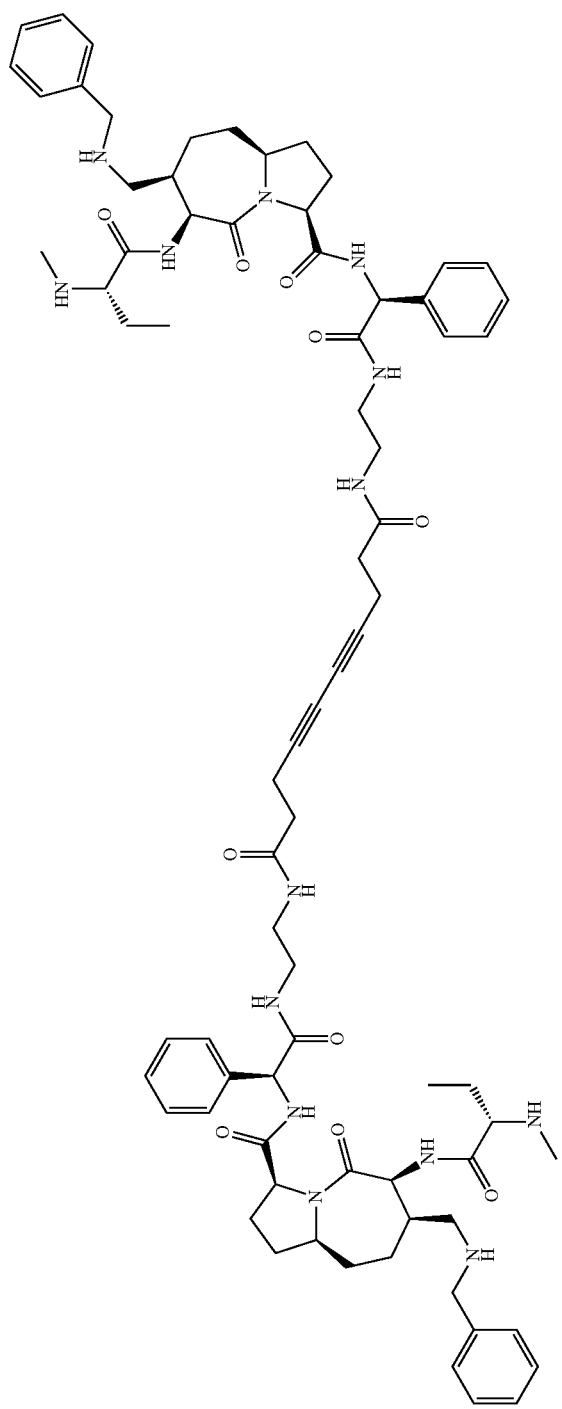
P8

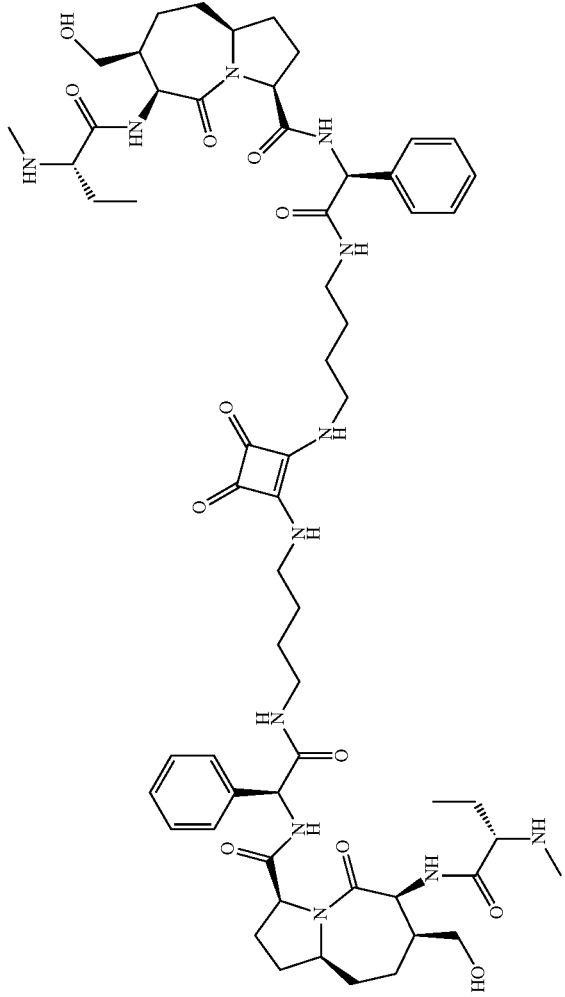
P9
Compound 30b

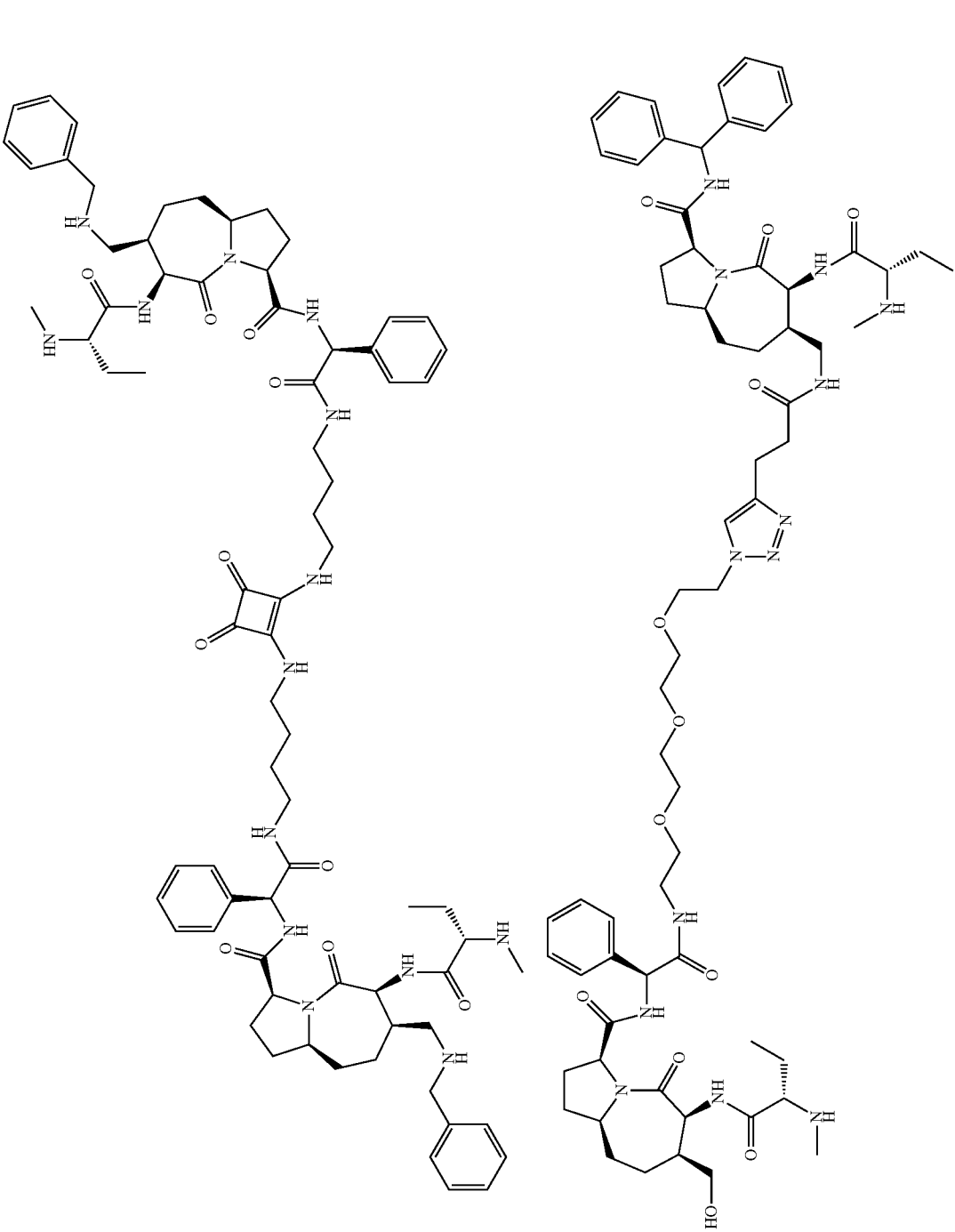
P10
P11
Compound 34a

-continued
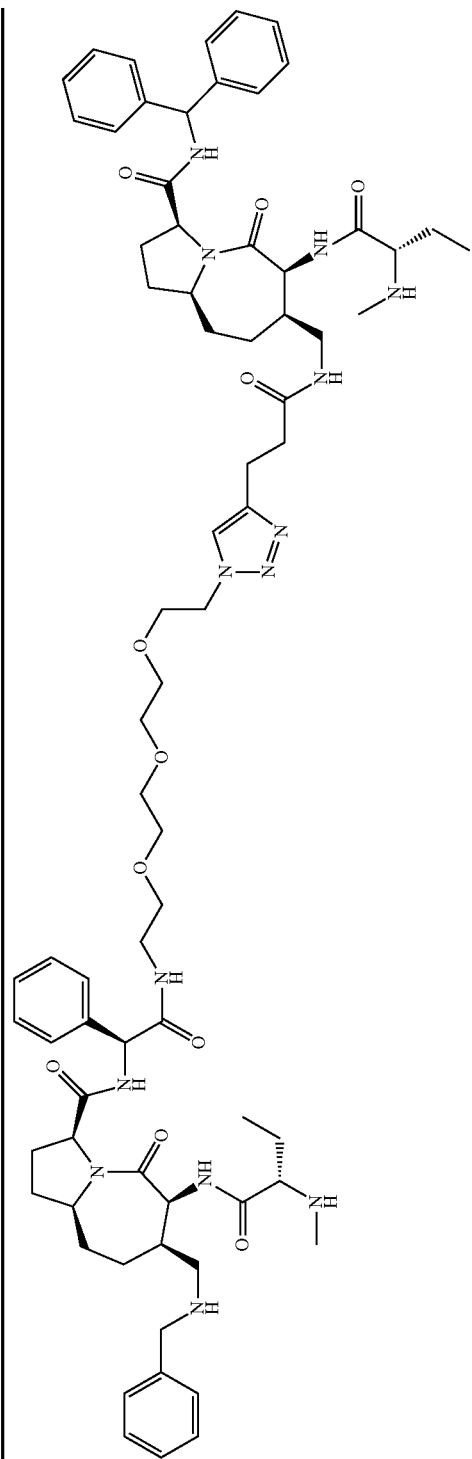
P12
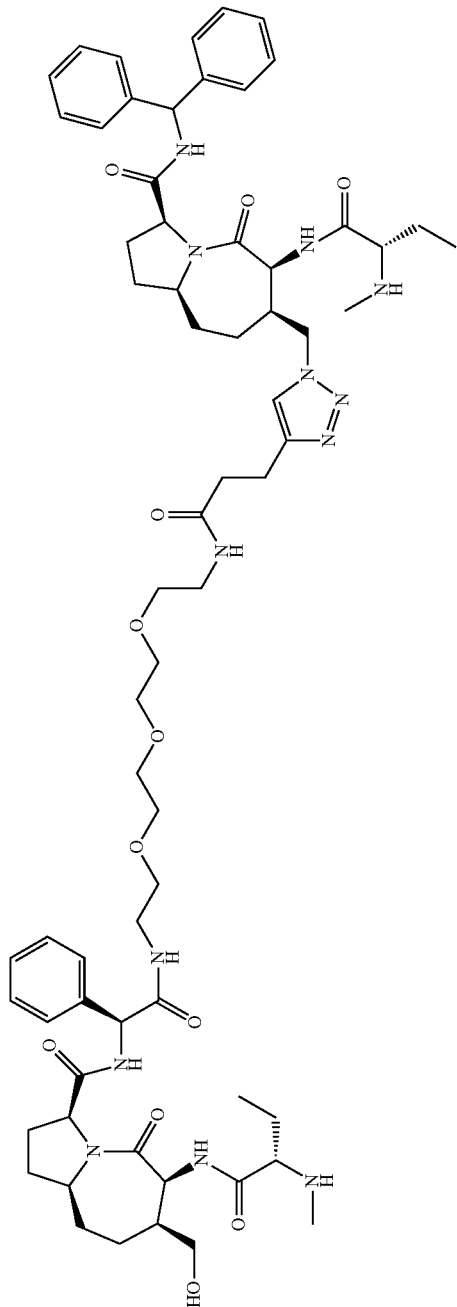
P13
Compound 35a

-continued
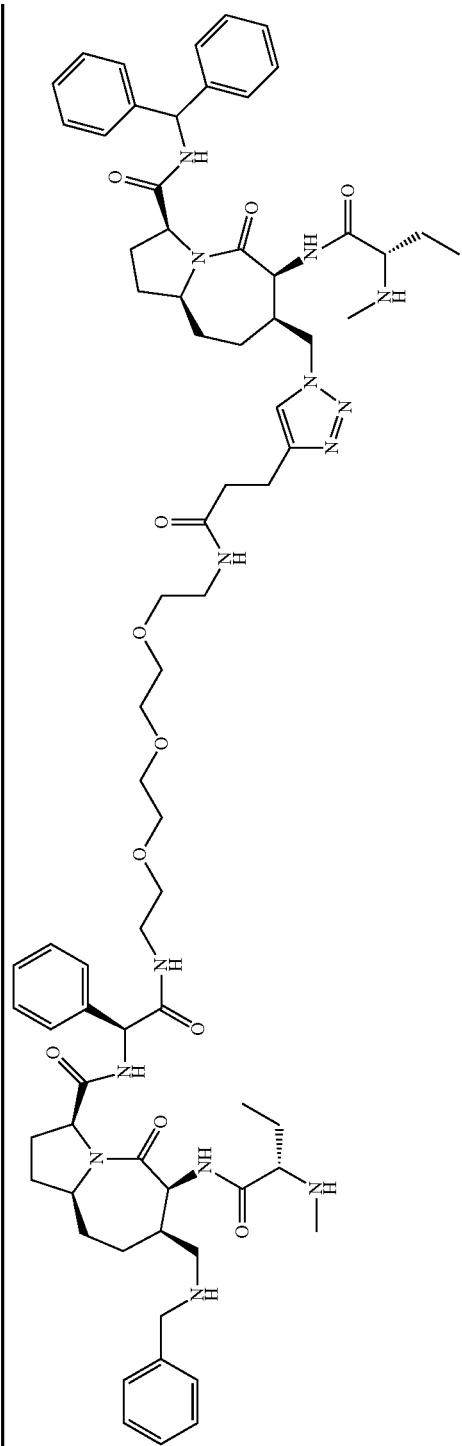
P14
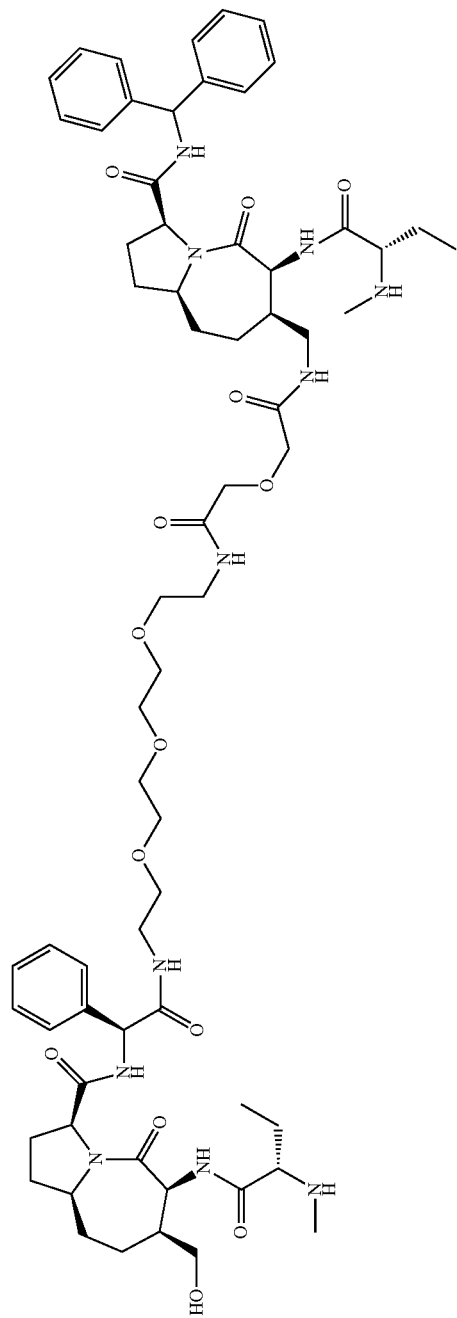
P15
Compound 36a

-continued
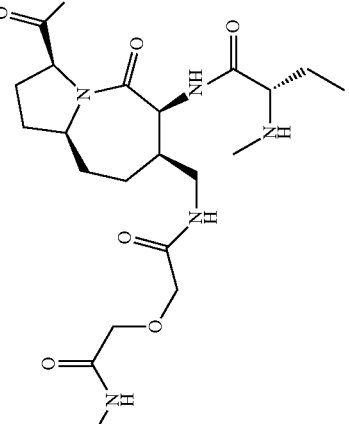
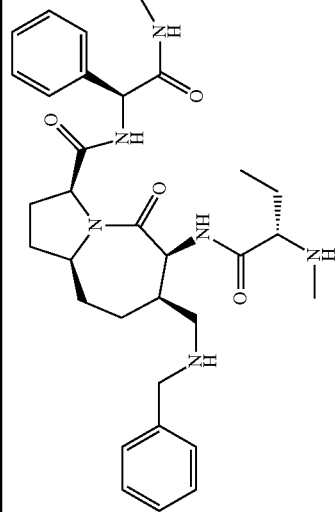
P16
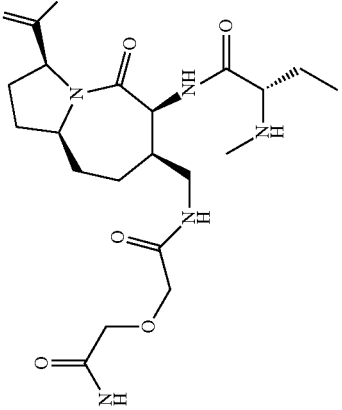
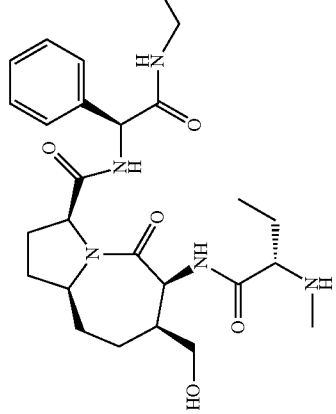
P17

-continued
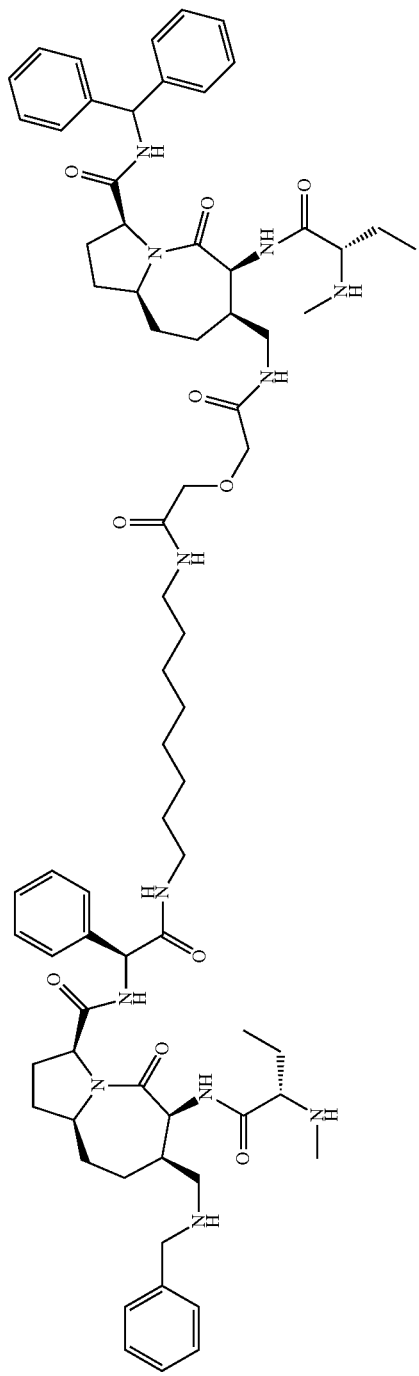
P18

Other preferred homodimeric compounds are those of the following table:
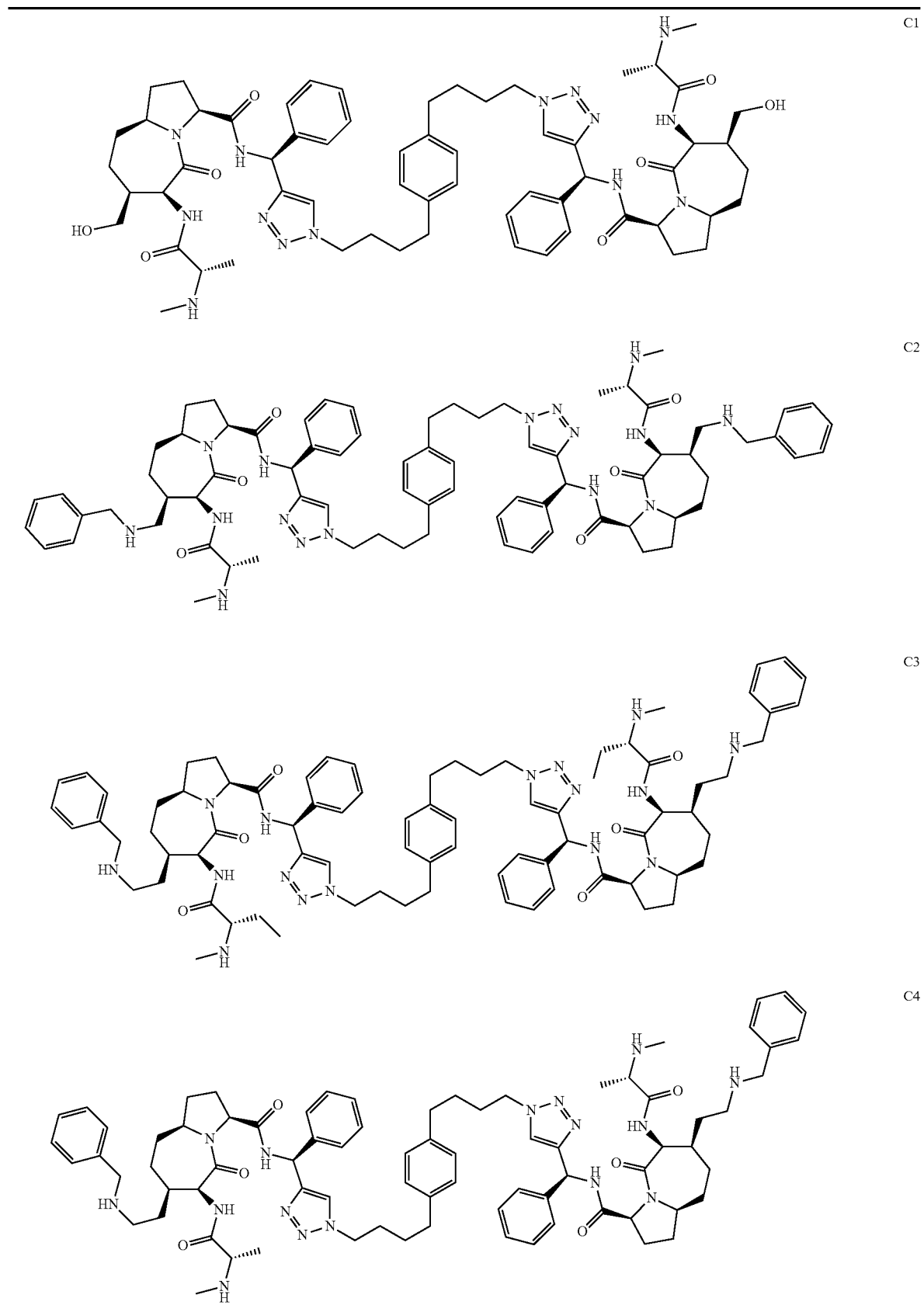

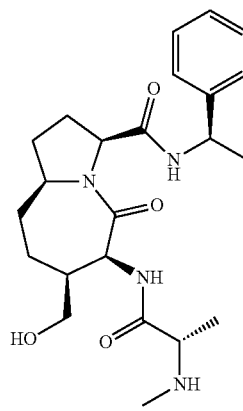
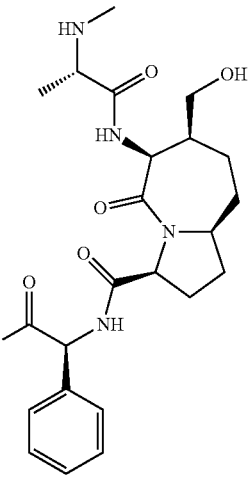
C5
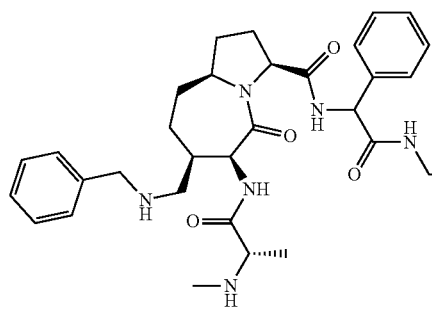
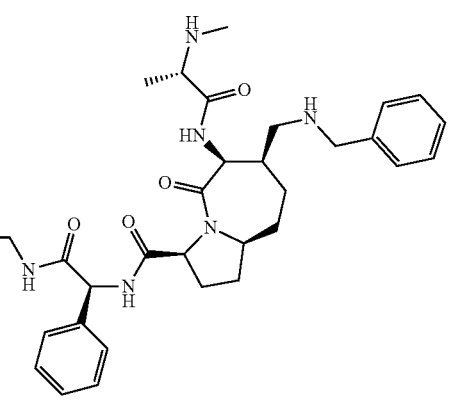
C6
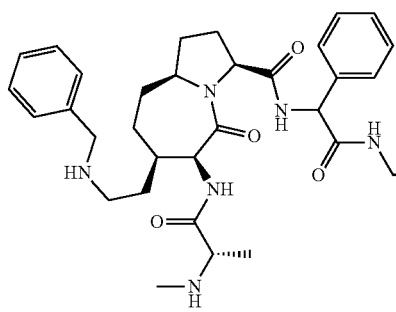
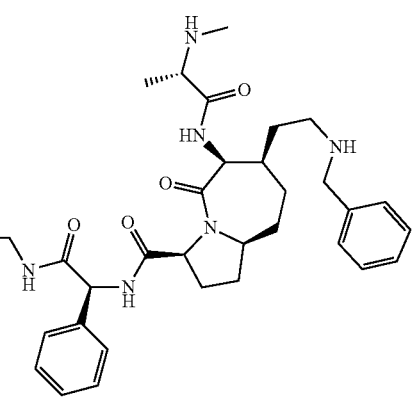
C7

-continued
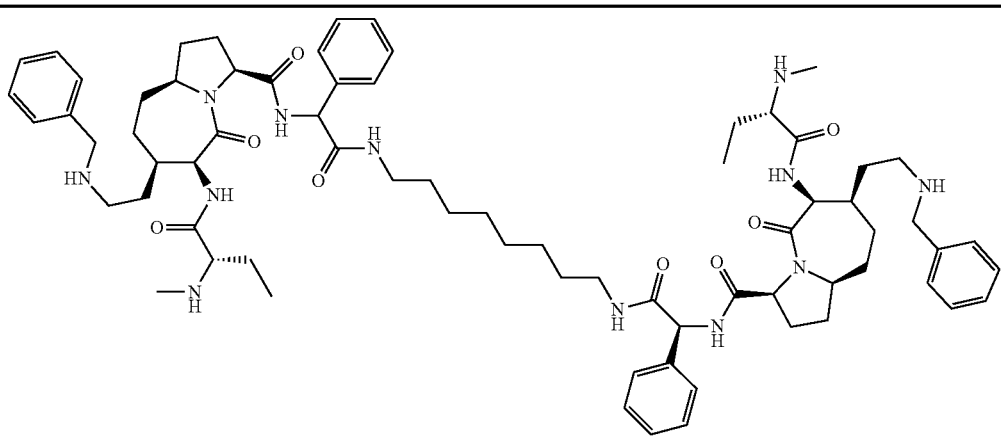
C8
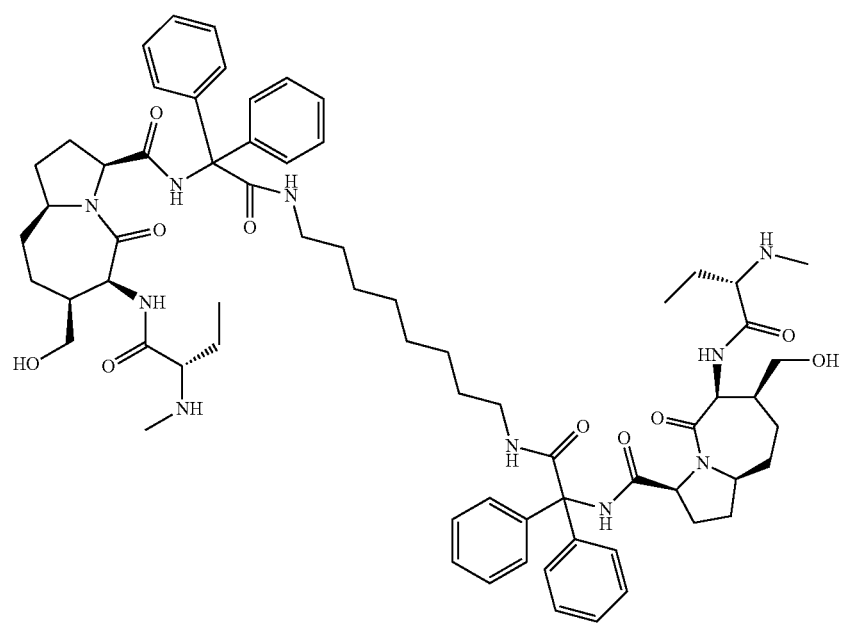 [SMILES: CC[C@H](NC)C(=O)N[C@@H]1C(=O)N2[C@@H](CC[C@@H]1CO)CC[C@H]2C(=O)NC(C(=O)NCCCCCCCCNC(=O)C(NC(=O)[C@@H]1CC[C@@H]2CC[C@H](CO)[C@H](NC(=O)[C@H](CC)NC)C(=O)N21)(c1ccccc1)c1ccccc1)(c1ccccc1)c1ccccc1]
C9
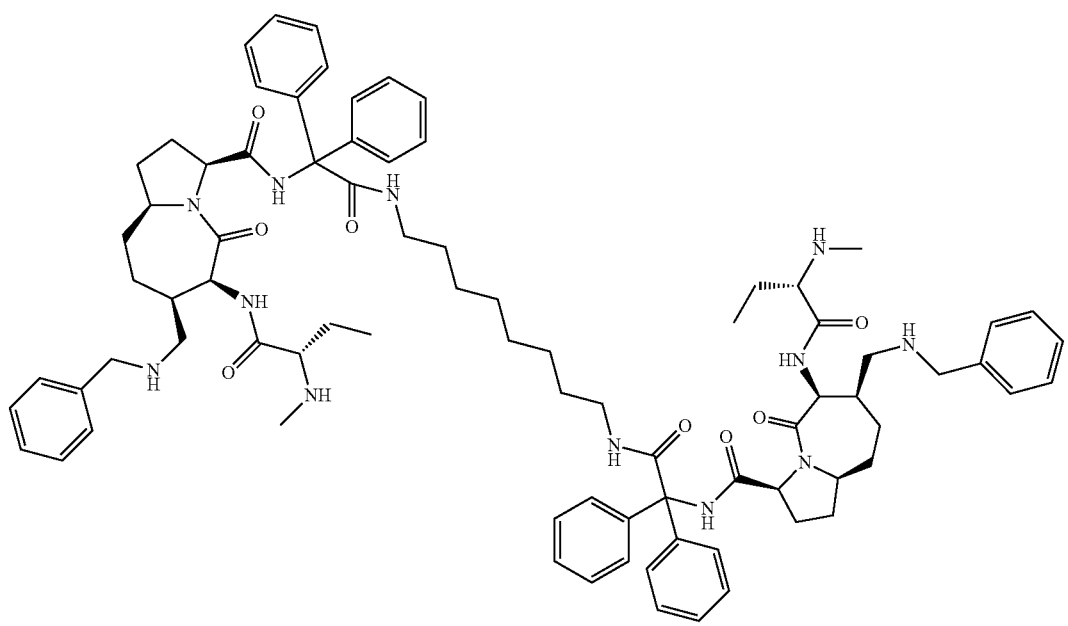 [SMILES: CC[C@H](NC)C(=O)N[C@@H]1C(=O)N2[C@@H](CC[C@@H]1CNCc1ccccc1)CC[C@H]2C(=O)NC(C(=O)NCCCCCCCCNC(=O)C(NC(=O)[C@@H]1CC[C@@H]2CC[C@H](CNCc3ccccc3)[C@H](NC(=O)[C@H](CC)NC)C(=O)N21)(c1ccccc1)c1ccccc1)(c1ccccc1)c1ccccc1]
C10

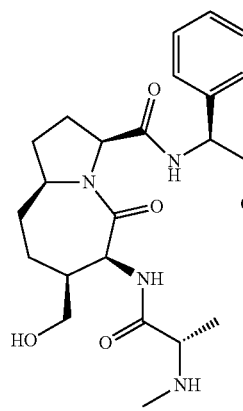
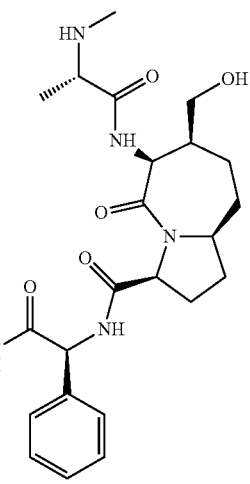
C11
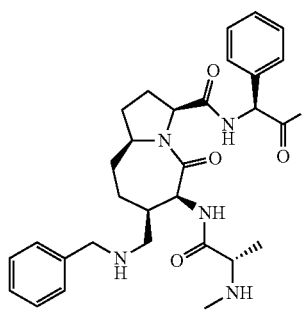
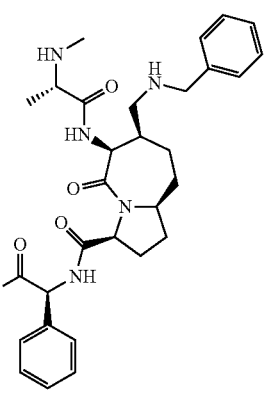
C12
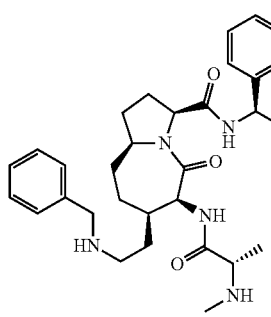
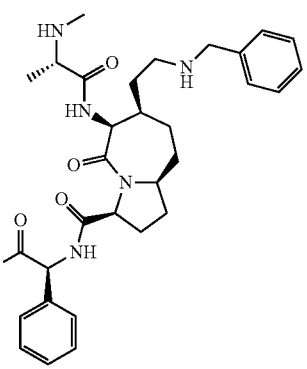
C13

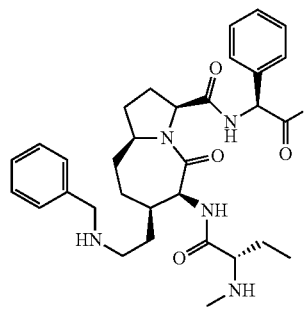
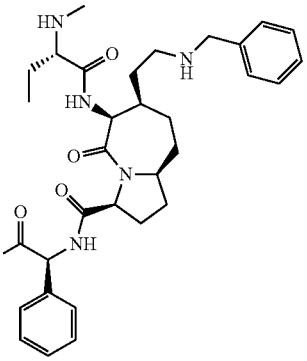
C14
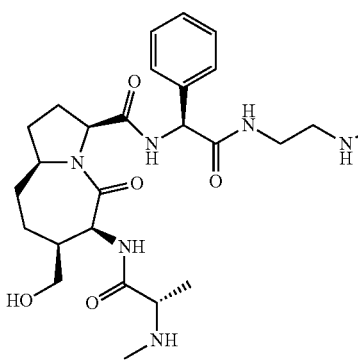
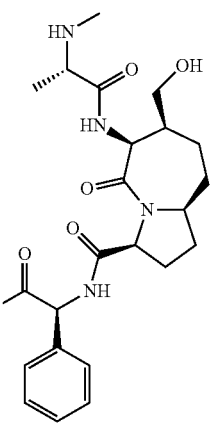
C15
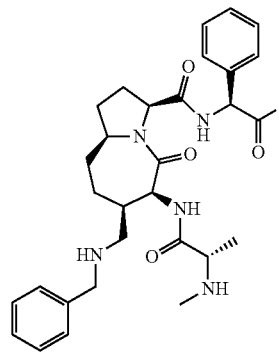
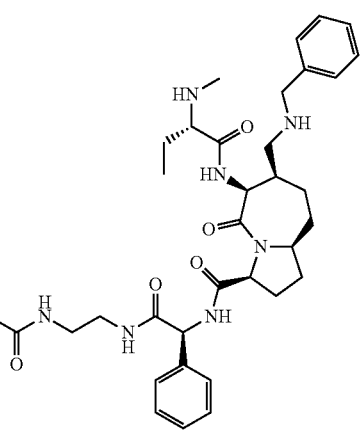
C16

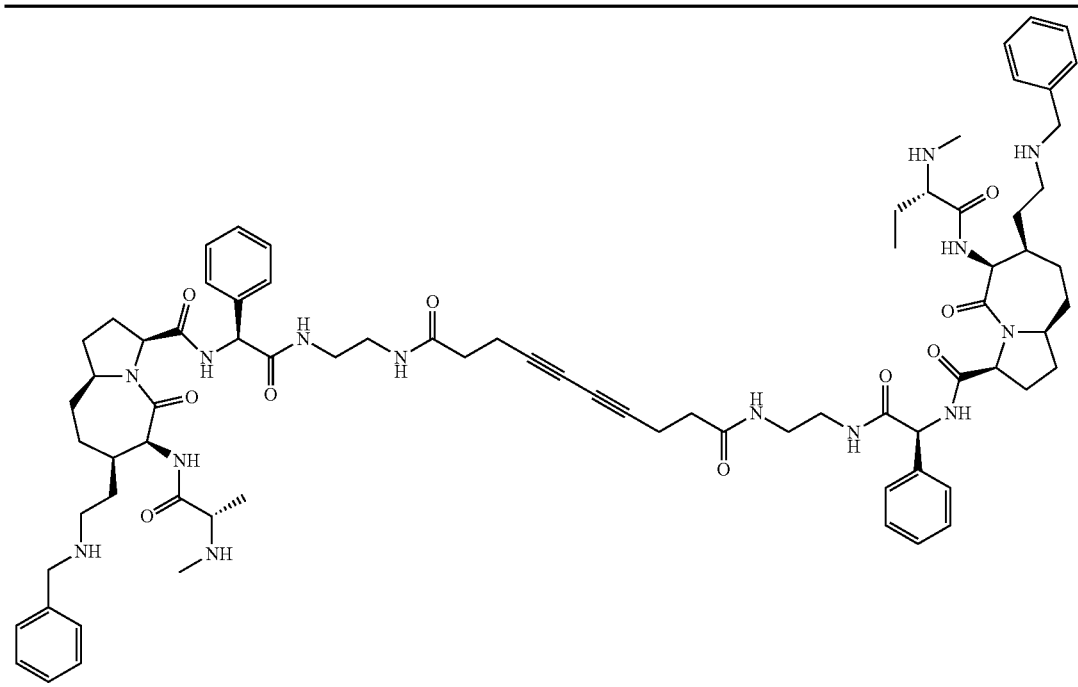
C17
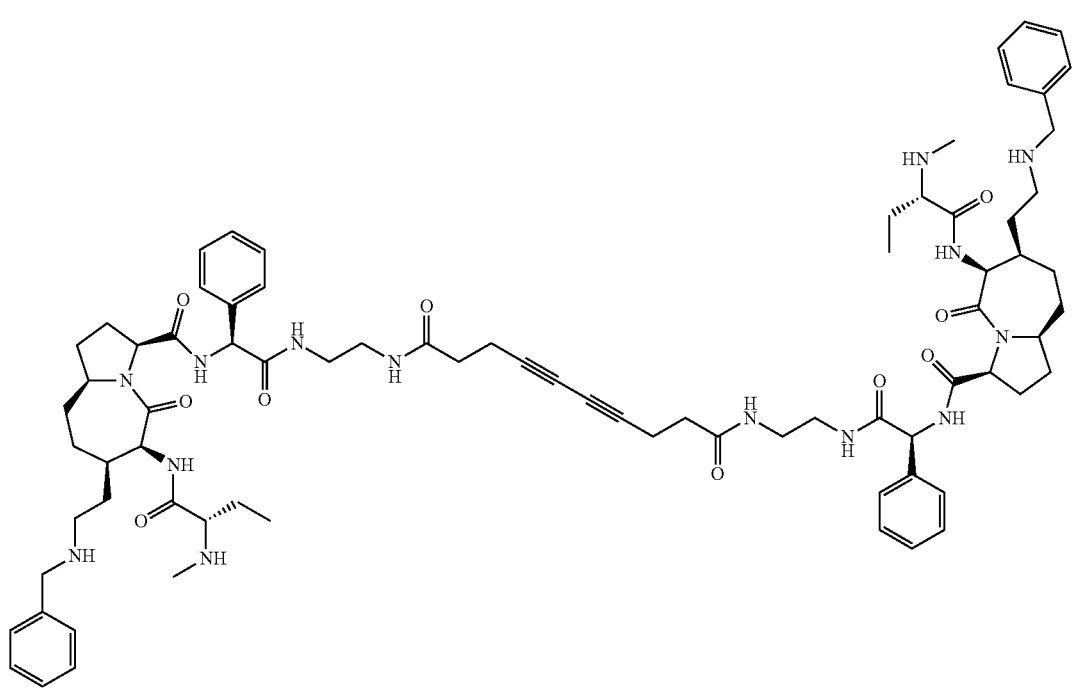 [SMILES: CC[C@H](NC)C(=O)N[C@@H]1C(=O)N2[C@@H](CC[C@@H]1CCNCc1ccccc1)CC[C@H]2C(=O)N[C@H](C(=O)NCCNC(=O)CCC#CC#CCCC(=O)NCCNC(=O)[C@@H](NC(=O)[C@@H]1CC[C@@H]2CC[C@H](CCNCc3ccccc3)[C@H](NC(=O)[C@H](CC)NC)C(=O)N21)c1ccccc1)c1ccccc1]
C18

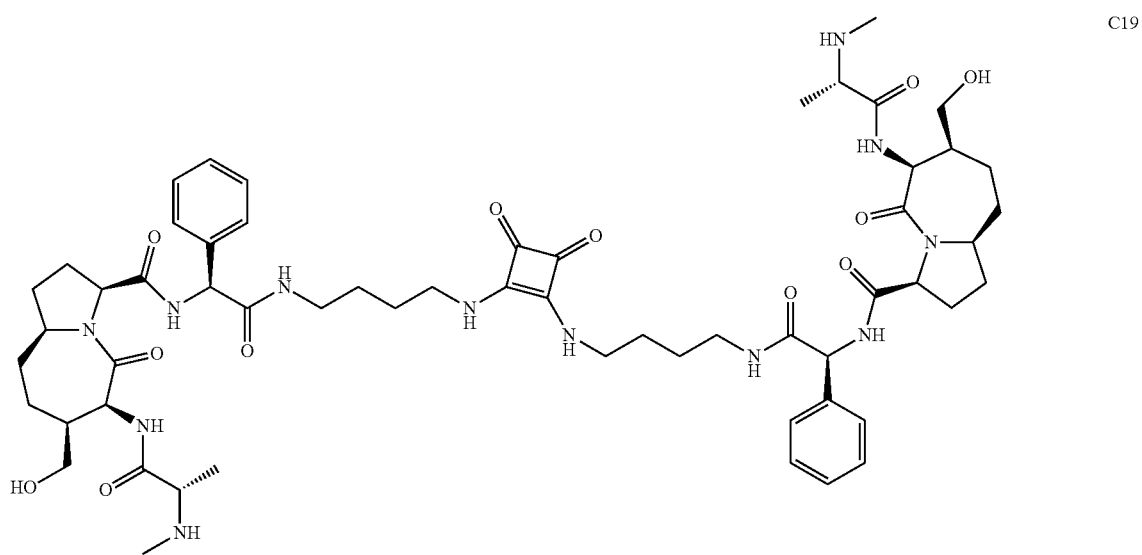
C19
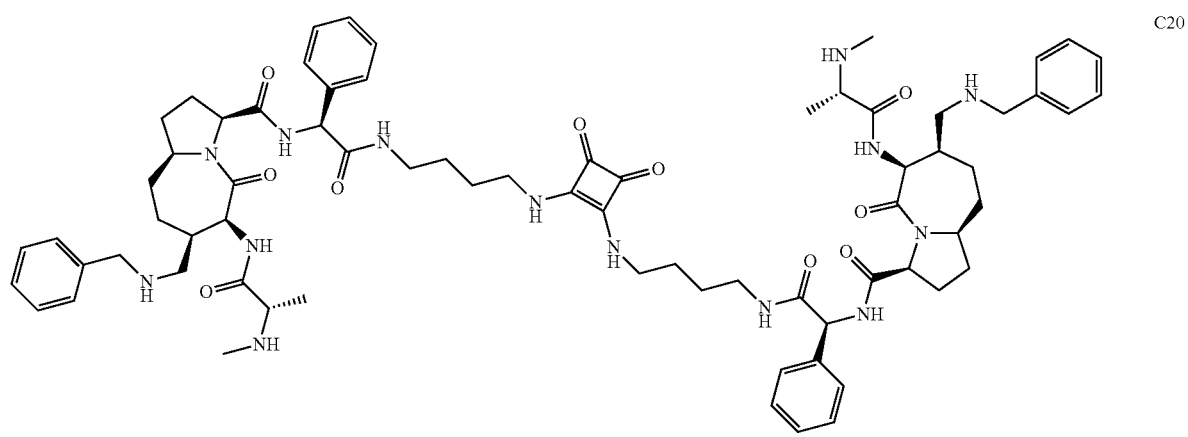
C20
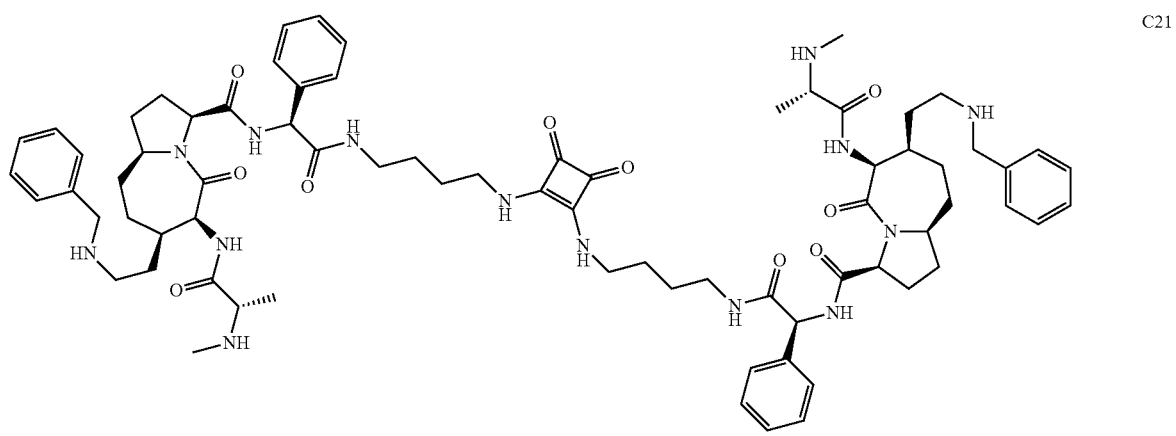
C21

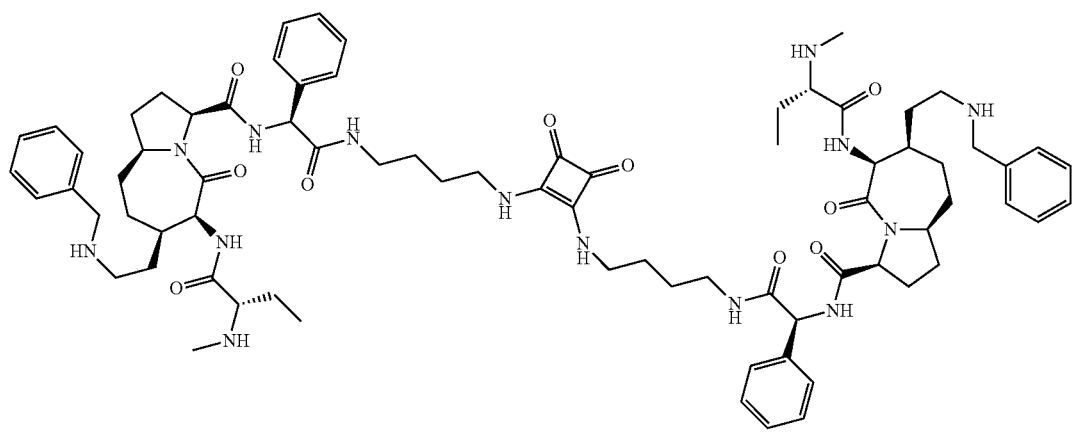 [SMILES: CC[C@H](NC)C(=O)N[C@@H]1C(=O)N2[C@@H](CC[C@@H]1CCNCc1ccccc1)CC[C@H]2C(=O)N[C@H](C(=O)NCCCCNc1c(NCCCCNC(=O)[C@@H](NC(=O)[C@@H]2CC[C@@H]3CC[C@H](CCNCc4ccccc4)[C@H](NC(=O)[C@H](CC)NC)C(=O)N32)c2ccccc2)c(=O)c1=O)c1ccccc1]
C22
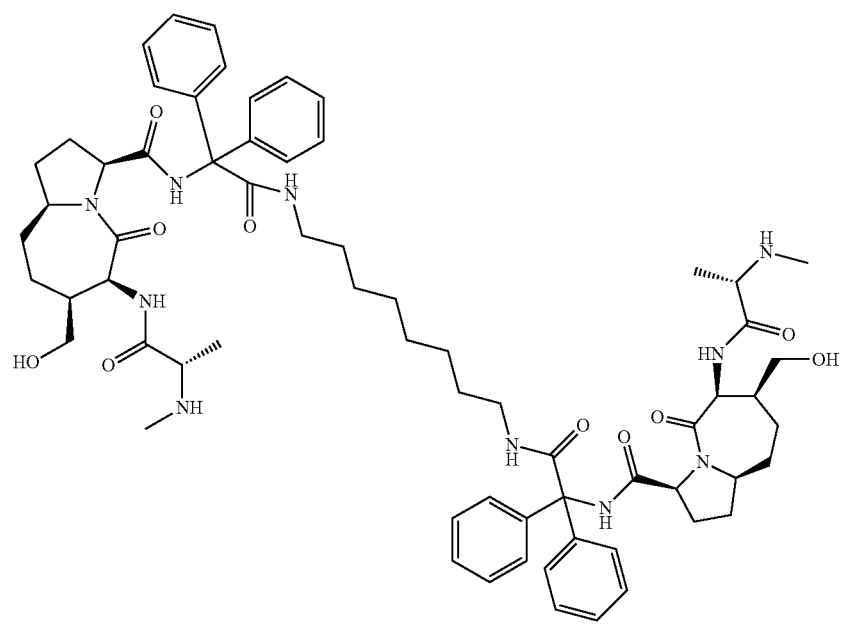 [SMILES: CN[C@@H](C)C(=O)N[C@@H]1C(=O)N2[C@@H](CC[C@@H]1CO)CC[C@H]2C(=O)NC(C(=O)NCCCCCCCCNC(=O)C(NC(=O)[C@@H]1CC[C@@H]2CC[C@H](CO)[C@H](NC(=O)[C@H](C)NC)C(=O)N21)(c1ccccc1)c1ccccc1)(c1ccccc1)c1ccccc1]
C23
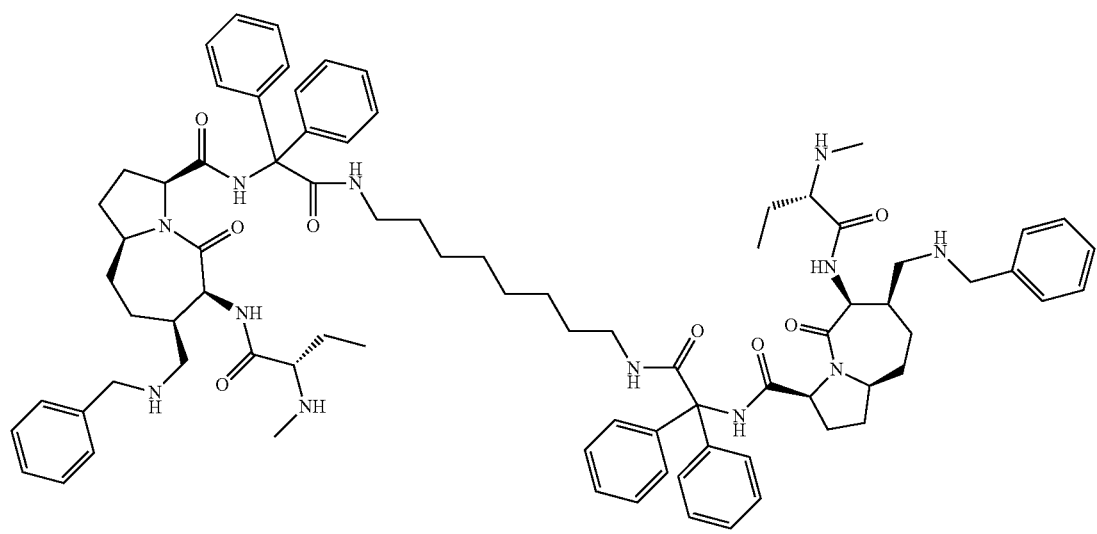 [SMILES: CC[C@H](NC)C(=O)N[C@@H]1C(=O)N2[C@@H](CC[C@@H]1CNCc1ccccc1)CC[C@H]2C(=O)NC(C(=O)NCCCCCCCCNC(=O)C(NC(=O)[C@@H]1CC[C@@H]2CC[C@H](CNCc3ccccc3)[C@H](NC(=O)[C@H](CC)NC)C(=O)N21)(c1ccccc1)c1ccccc1)(c1ccccc1)c1ccccc1]
C24

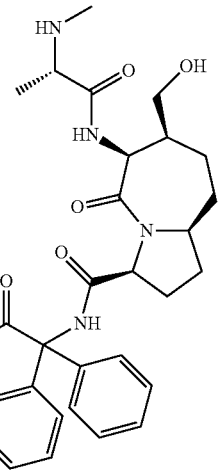
C25
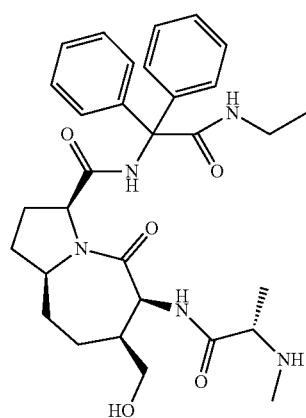
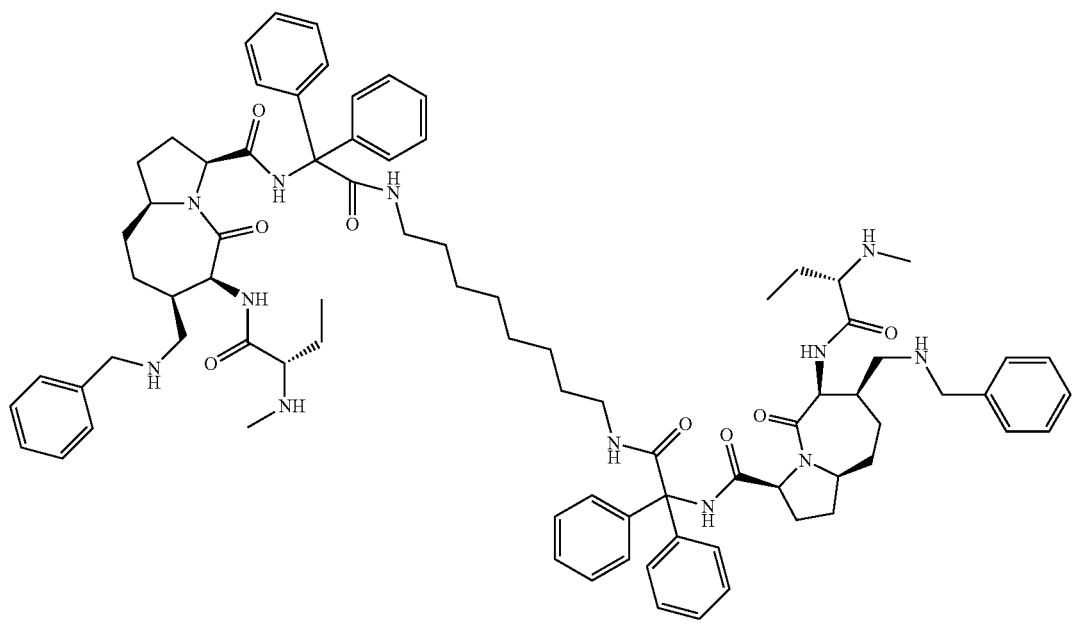 [SMILES: CC[C@H](NC)C(=O)N[C@@H]1C(=O)N2[C@@H](CC[C@@H]1CNCc1ccccc1)CC[C@H]2C(=O)NC(C(=O)NCCCCCCCCNC(=O)C(NC(=O)[C@@H]1CC[C@@H]2CC[C@H](CNCc3ccccc3)[C@H](NC(=O)[C@H](CC)NC)C(=O)N21)(c1ccccc1)c1ccccc1)(c1ccccc1)c1ccccc1]
C26

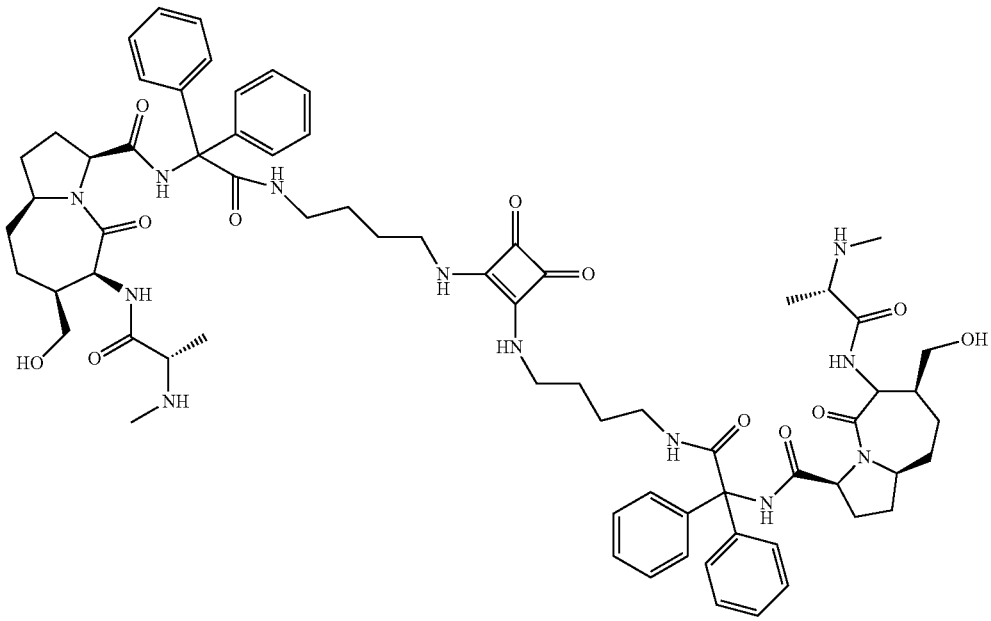
C27
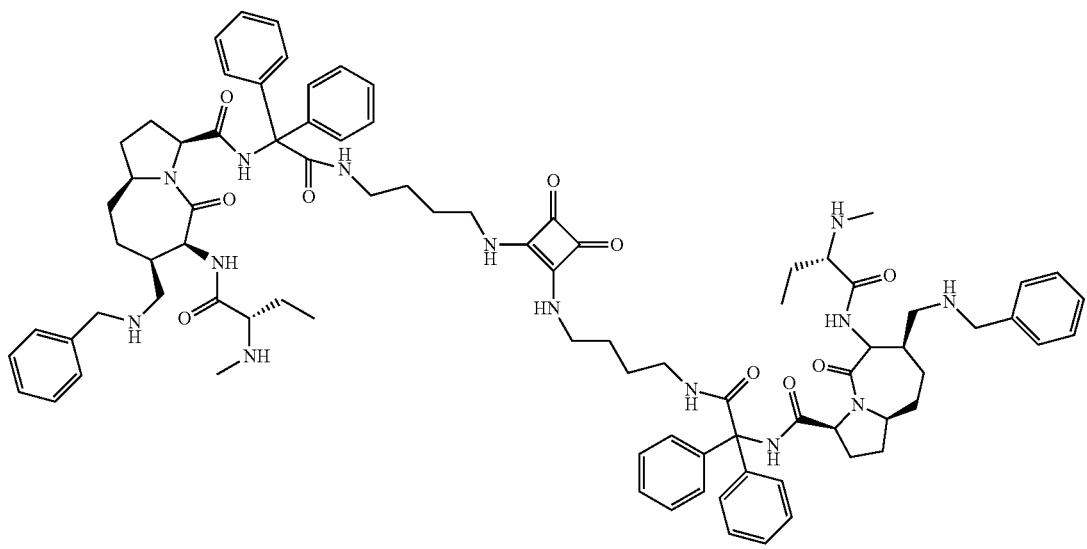
C28

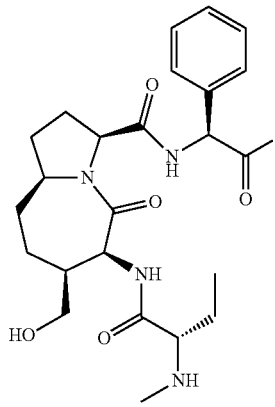
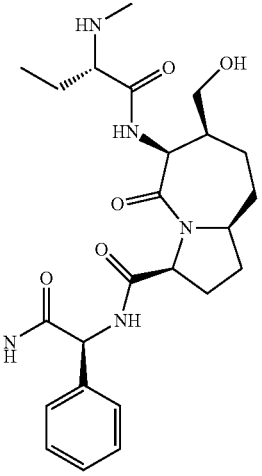
C29
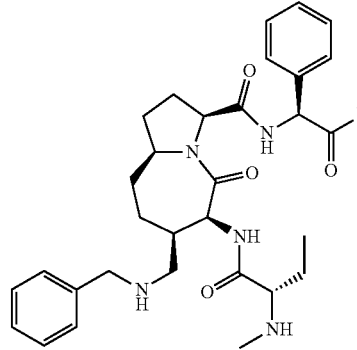
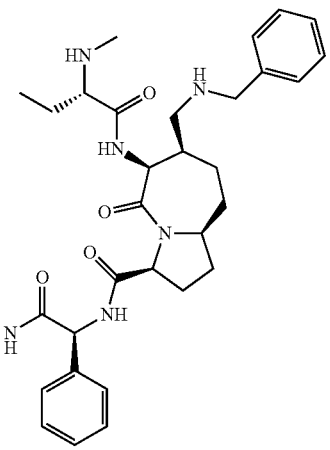
C30
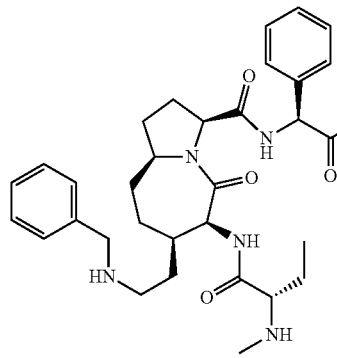
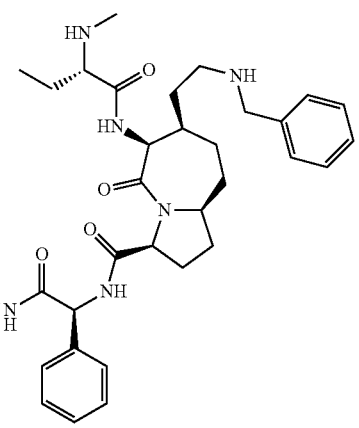
C31

-continued
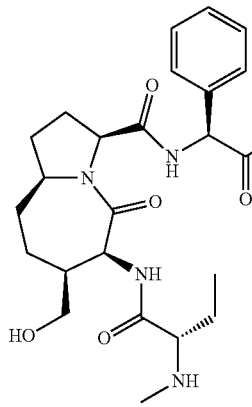
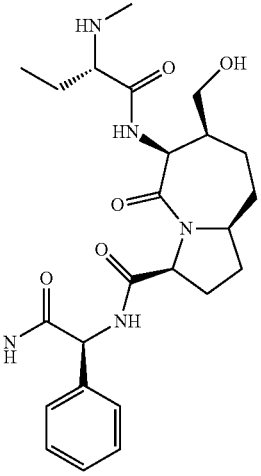
C32
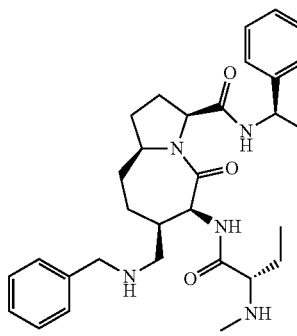
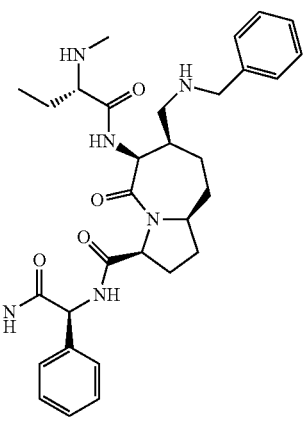
C33
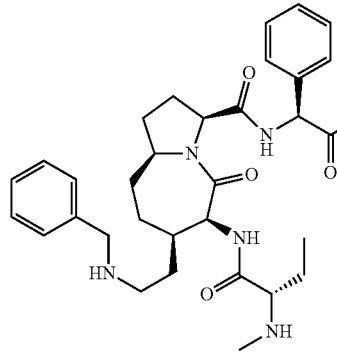
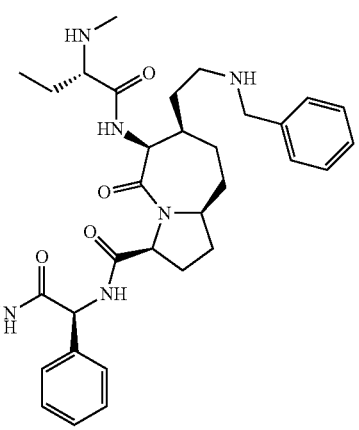
C34

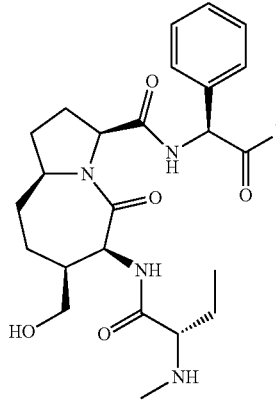
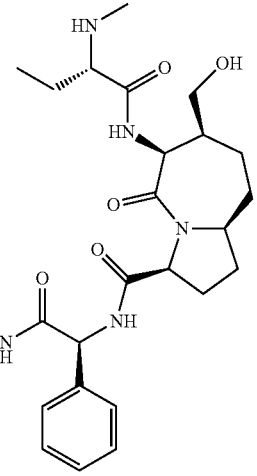
C35
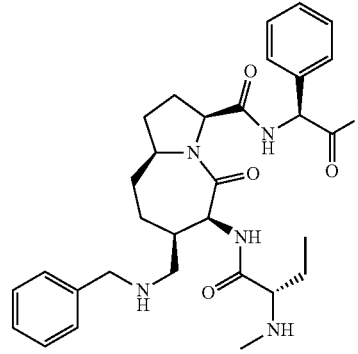
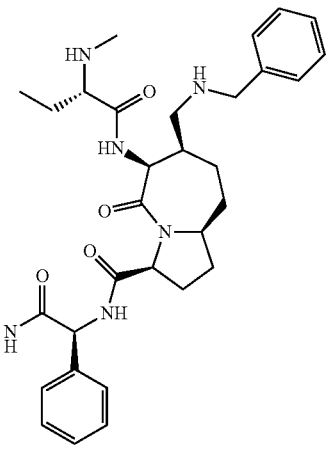
C36
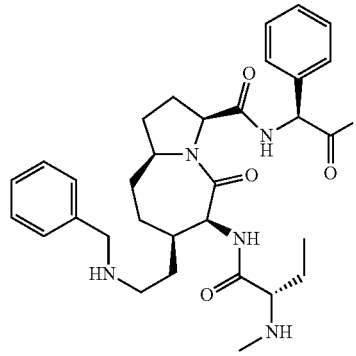
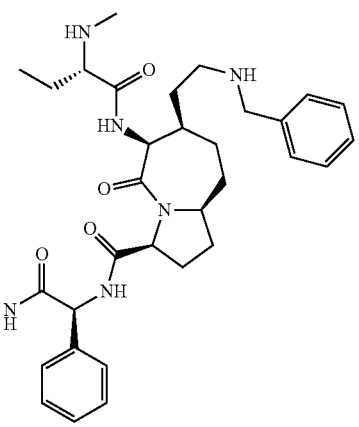
C37

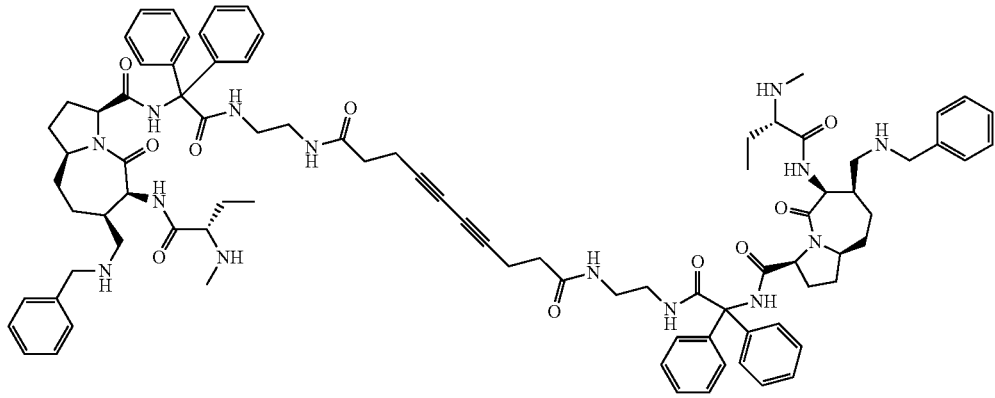 [SMILES: CC[C@H](NC)C(=O)N[C@@H]1C(=O)N2[C@@H](CC[C@@H]1CNCc1ccccc1)CC[C@H]2C(=O)NC(C(=O)NCCNC(=O)CCC#CC#CCCC(=O)NCCNC(=O)C(NC(=O)[C@@H]1CC[C@@H]2CC[C@H](CNCc3ccccc3)[C@H](NC(=O)[C@H](CC)NC)C(=O)N21)(c1ccccc1)c1ccccc1)(c1ccccc1)c1ccccc1]
C38
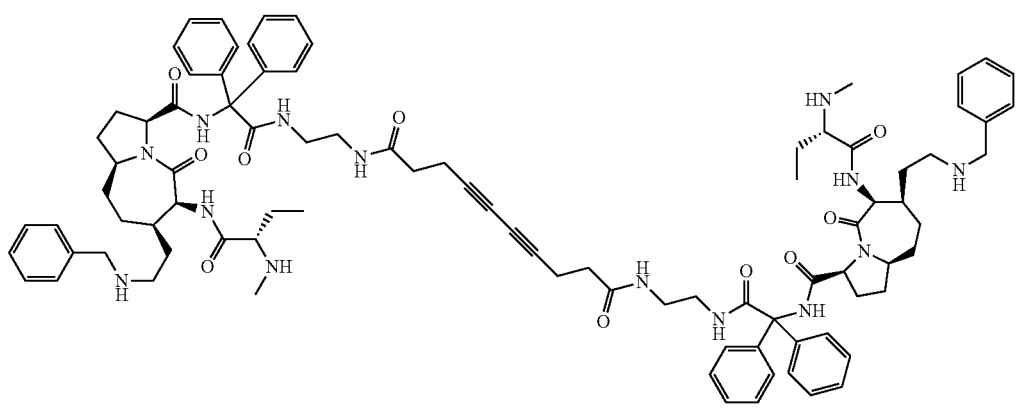 [SMILES: CC[C@H](NC)C(=O)N[C@@H]1C(=O)N2[C@@H](CC[C@@H]1CCNCc1ccccc1)CC[C@H]2C(=O)NC(C(=O)NCCNC(=O)CCC#CC#CCCC(=O)NCCNC(=O)C(NC(=O)[C@@H]1CC[C@@H]2CC[C@H](CCNCc3ccccc3)[C@H](NC(=O)[C@H](CC)NC)C(=O)N21)(c1ccccc1)c1ccccc1)(c1ccccc1)c1ccccc1]
C39
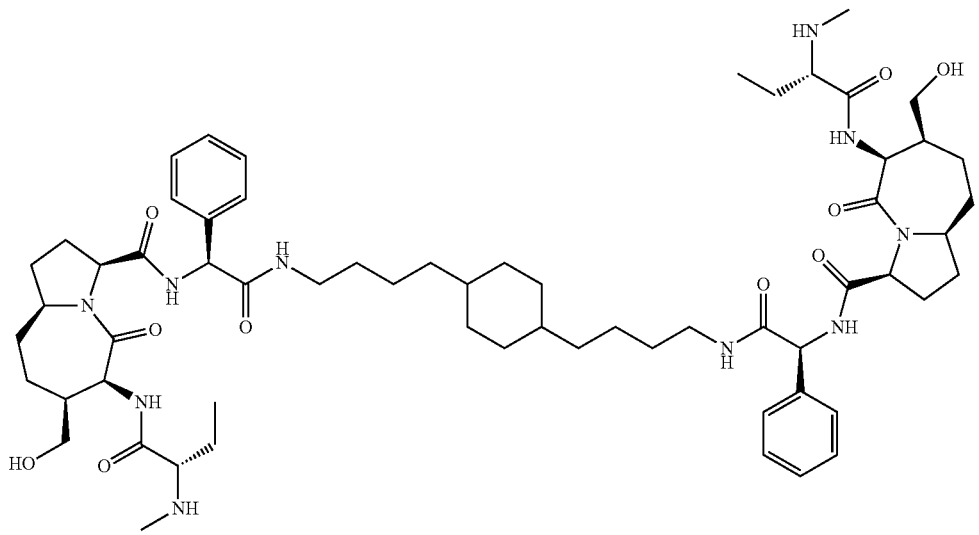
C40

-continued
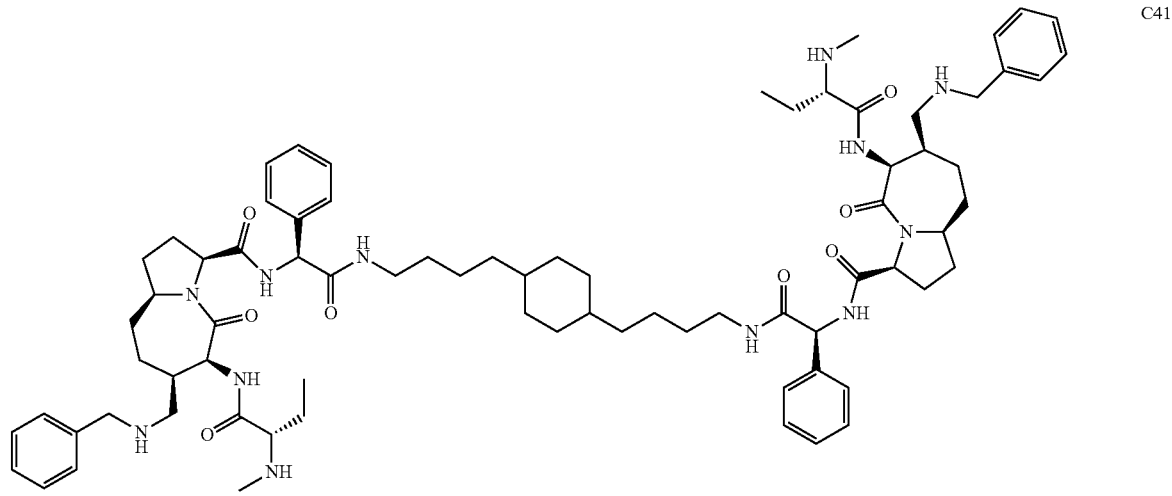
C41
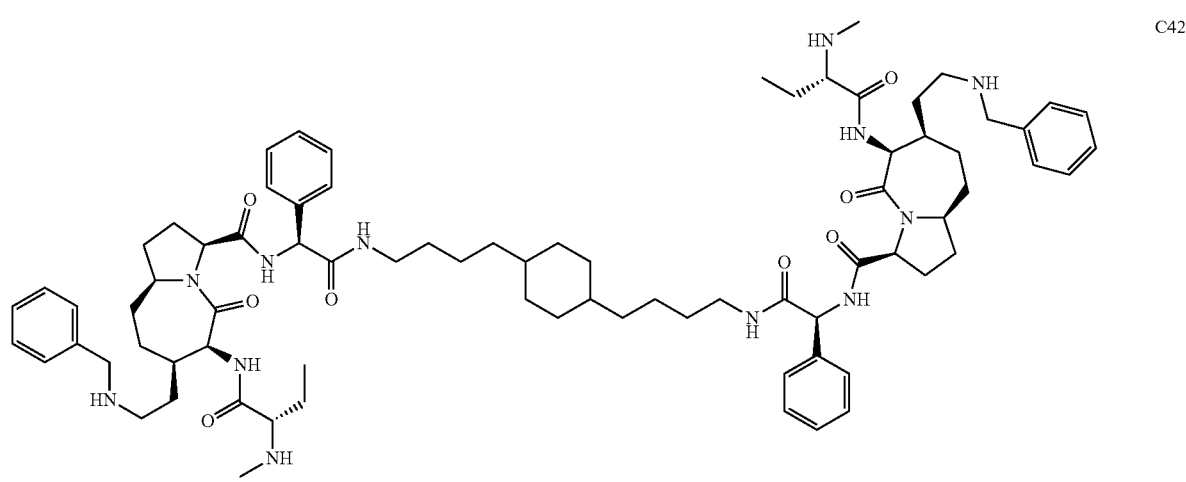
C42
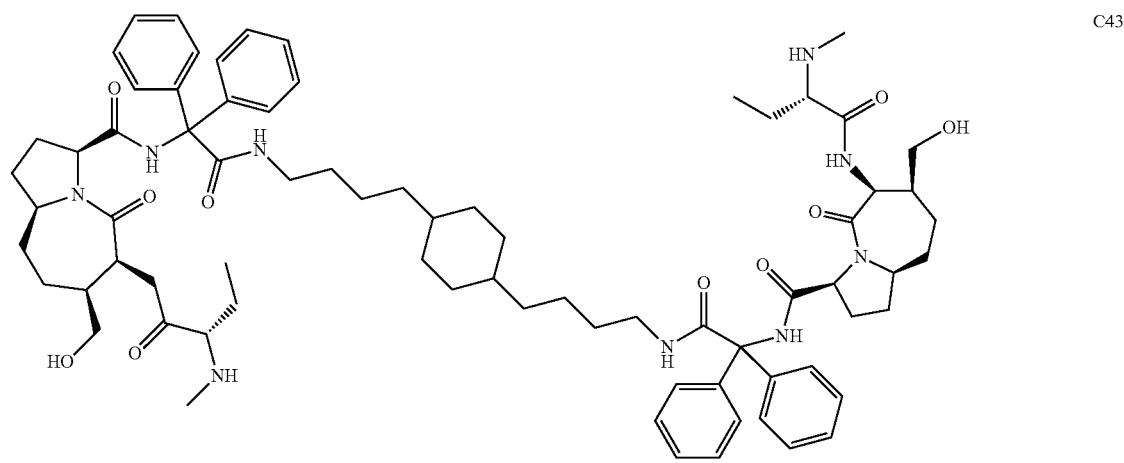
C43

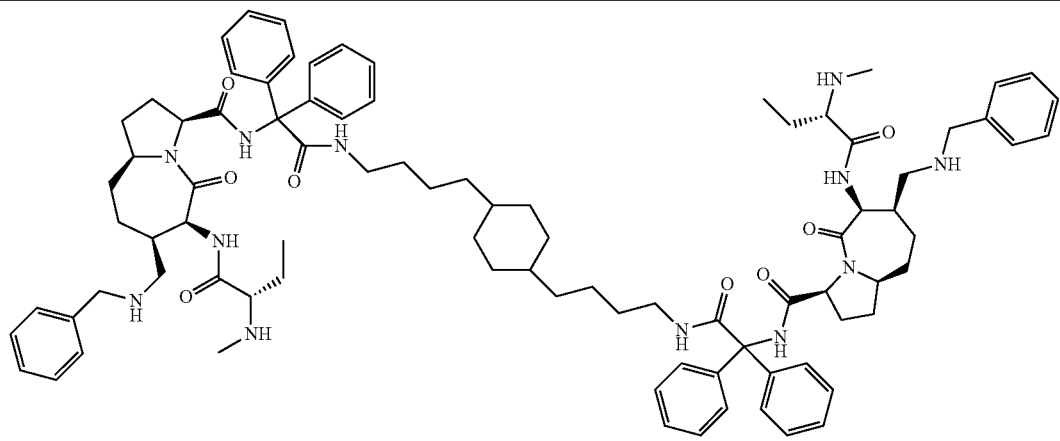
C44
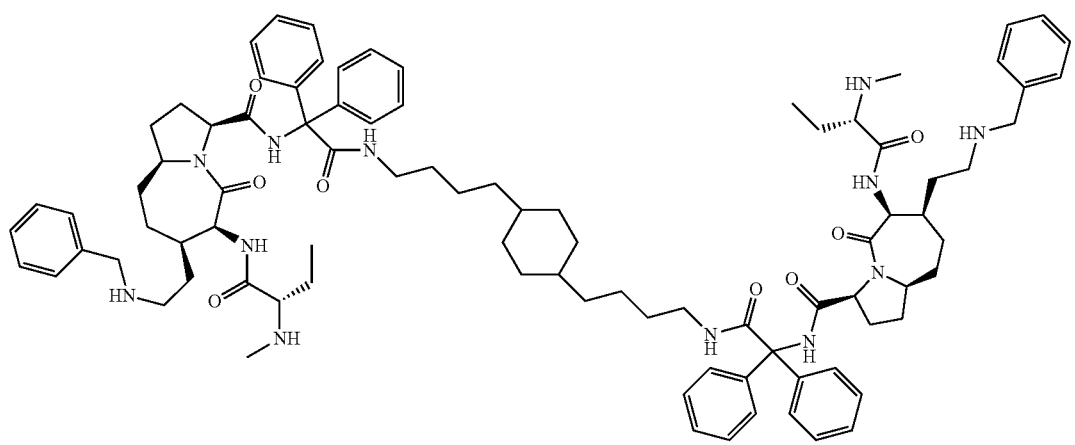 [SMILES: CC[C@H](NC)C(=O)N[C@@H]1C(=O)N2[C@@H](CC[C@@H]1CCNCc1ccccc1)CC[C@H]2C(=O)NC(C(=O)NCCCCC1CCC(CCCCNC(=O)C(NC(=O)[C@@H]2CC[C@@H]3CC[C@H](CCNCc4ccccc4)[C@H](NC(=O)[C@H](CC)NC)C(=O)N32)(c2ccccc2)c2ccccc2)CC1)(c1ccccc1)c1ccccc1]
C45
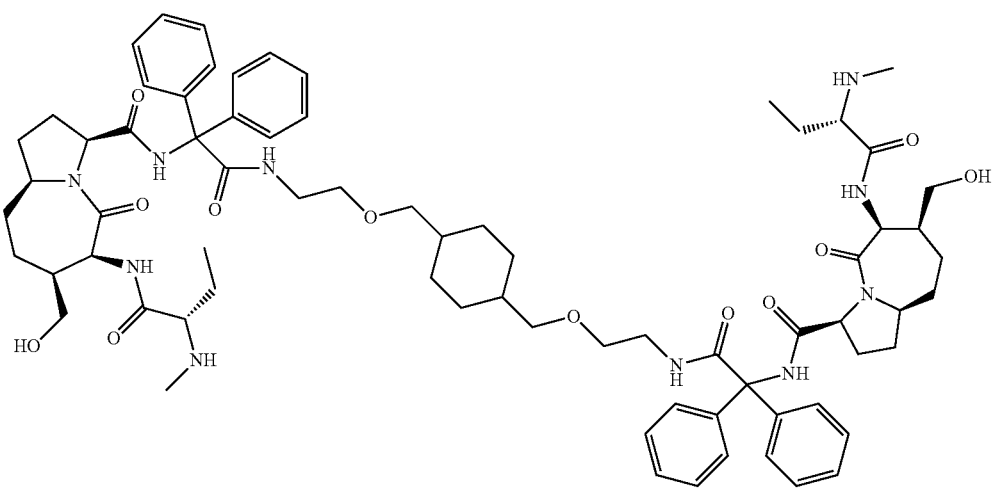 [SMILES: CC[C@H](NC)C(=O)N[C@@H]1C(=O)N2[C@@H](CC[C@@H]1CO)CC[C@H]2C(=O)NC(C(=O)NCCOCC1CCC(COCCNC(=O)C(NC(=O)[C@@H]2CC[C@@H]3CC[C@H](CO)[C@H](NC(=O)[C@H](CC)NC)C(=O)N32)(c2ccccc2)c2ccccc2)CC1)(c1ccccc1)c1ccccc1]
C46

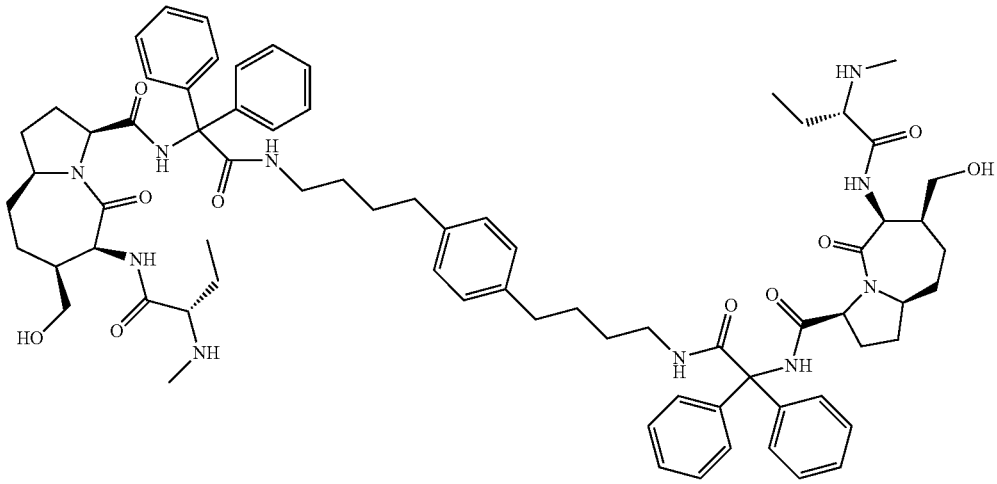 [SMILES: CC[C@H](NC)C(=O)N[C@@H]1C(=O)N2[C@@H](CC[C@@H]1CO)CC[C@H]2C(=O)NC(C(=O)NCCCCc1ccc(CCCCNC(=O)C(NC(=O)[C@@H]2CC[C@@H]3CC[C@H](CO)[C@H](NC(=O)[C@H](CC)NC)C(=O)N32)(c2ccccc2)c2ccccc2)cc1)(c1ccccc1)c1ccccc1]
C47
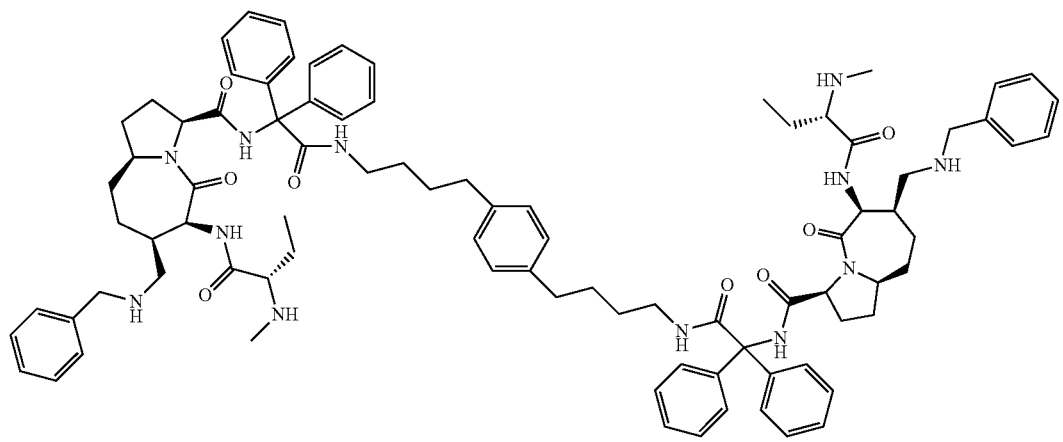 [SMILES: CC[C@H](NC)C(=O)N[C@@H]1C(=O)N2[C@@H](CC[C@@H]1CNCc1ccccc1)CC[C@H]2C(=O)NC(C(=O)NCCCCc1ccc(CCCCNC(=O)C(NC(=O)[C@@H]2CC[C@@H]3CC[C@H](CNCc4ccccc4)[C@H](NC(=O)[C@H](CC)NC)C(=O)N32)(c2ccccc2)c2ccccc2)cc1)(c1ccccc1)c1ccccc1]
C48
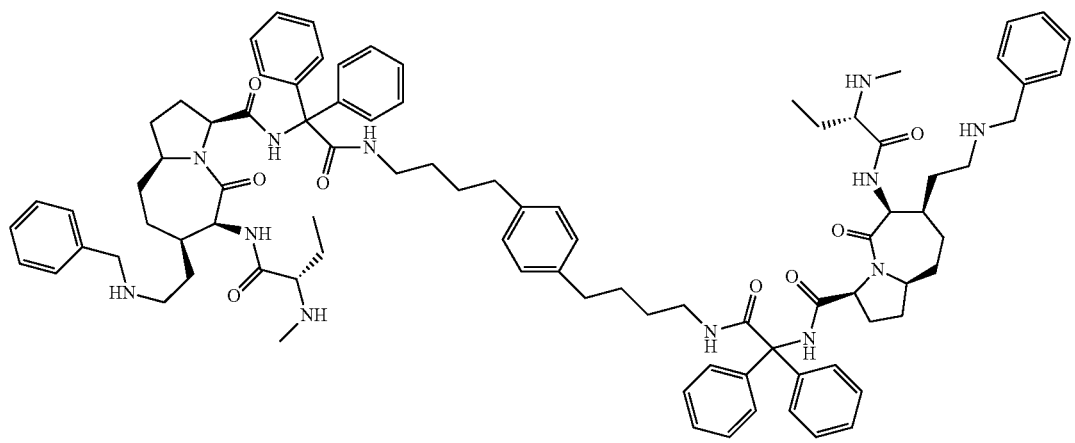 [SMILES: CC[C@H](NC)C(=O)N[C@@H]1C(=O)N2[C@@H](CC[C@@H]1CCNCc1ccccc1)CC[C@H]2C(=O)NC(C(=O)NCCCCc1ccc(CCCCNC(=O)C(NC(=O)[C@@H]2CC[C@@H]3CC[C@H](CCNCc4ccccc4)[C@H](NC(=O)[C@H](CC)NC)C(=O)N32)(c2ccccc2)c2ccccc2)cc1)(c1ccccc1)c1ccccc1]
C49

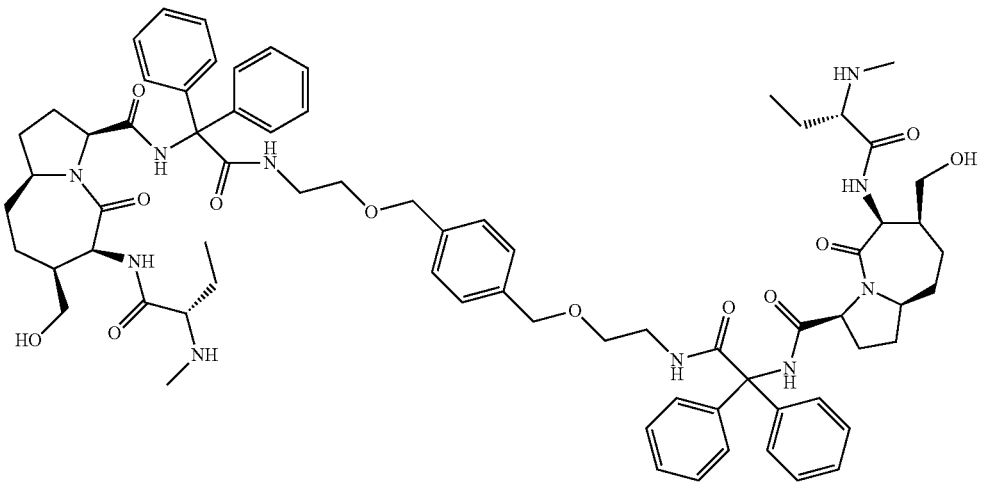 [SMILES: CC[C@H](NC)C(=O)N[C@@H]1C(=O)N2[C@@H](CC[C@@H]1CO)CC[C@H]2C(=O)NC(C(=O)NCCOCc1ccc(COCCNC(=O)C(NC(=O)[C@@H]2CC[C@@H]3CC[C@H](CO)[C@H](NC(=O)[C@H](CC)NC)C(=O)N32)(c2ccccc2)c2ccccc2)cc1)(c1ccccc1)c1ccccc1]
C50
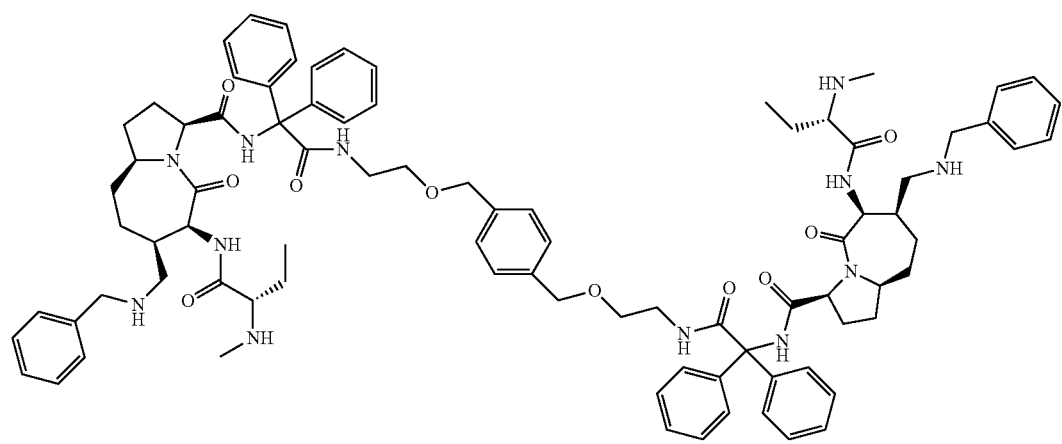 [SMILES: CC[C@H](NC)C(=O)N[C@@H]1C(=O)N2[C@@H](CC[C@@H]1CNCc1ccccc1)CC[C@H]2C(=O)NC(C(=O)NCCOCc1ccc(COCCNC(=O)C(NC(=O)[C@@H]2CC[C@@H]3CC[C@H](CNCc4ccccc4)[C@H](NC(=O)[C@H](CC)NC)C(=O)N32)(c2ccccc2)c2ccccc2)cc1)(c1ccccc1)c1ccccc1]
C51
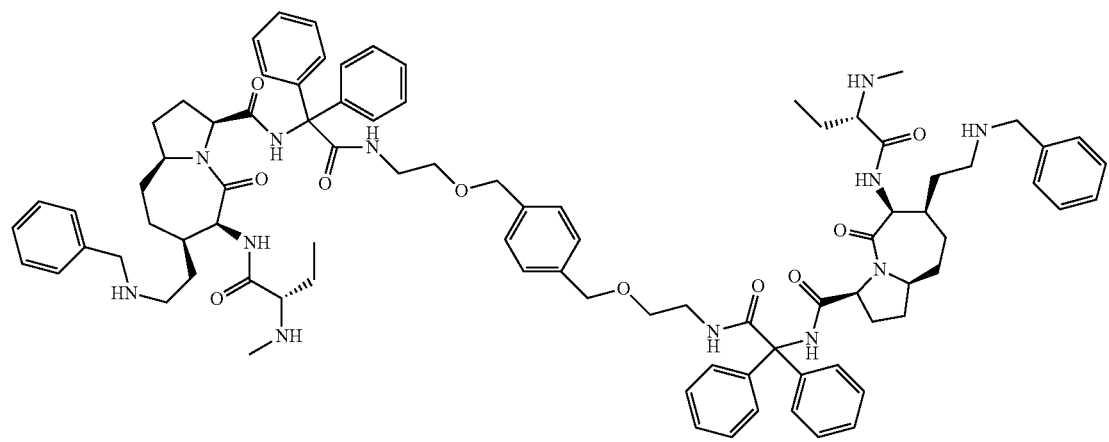 [SMILES: CC[C@H](NC)C(=O)N[C@@H]1C(=O)N2[C@@H](CC[C@@H]1CCNCc1ccccc1)CC[C@H]2C(=O)NC(C(=O)NCCOCc1ccc(COCCNC(=O)C(NC(=O)[C@@H]2CC[C@@H]3CC[C@H](CCNCc4ccccc4)[C@H](NC(=O)[C@H](CC)NC)C(=O)N32)(c2ccccc2)c2ccccc2)cc1)(c1ccccc1)c1ccccc1]
C52
Other preferred heterodimeric compounds of the invention are the following:

C53
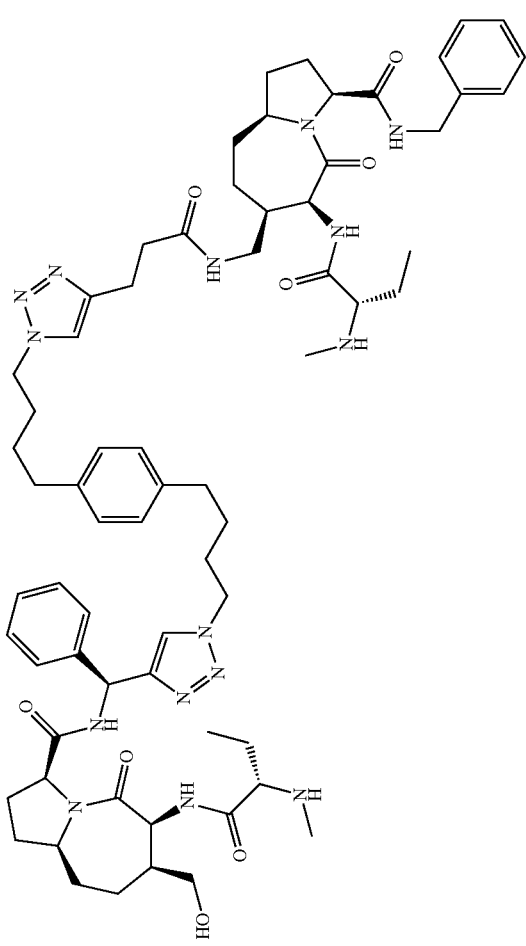
C54
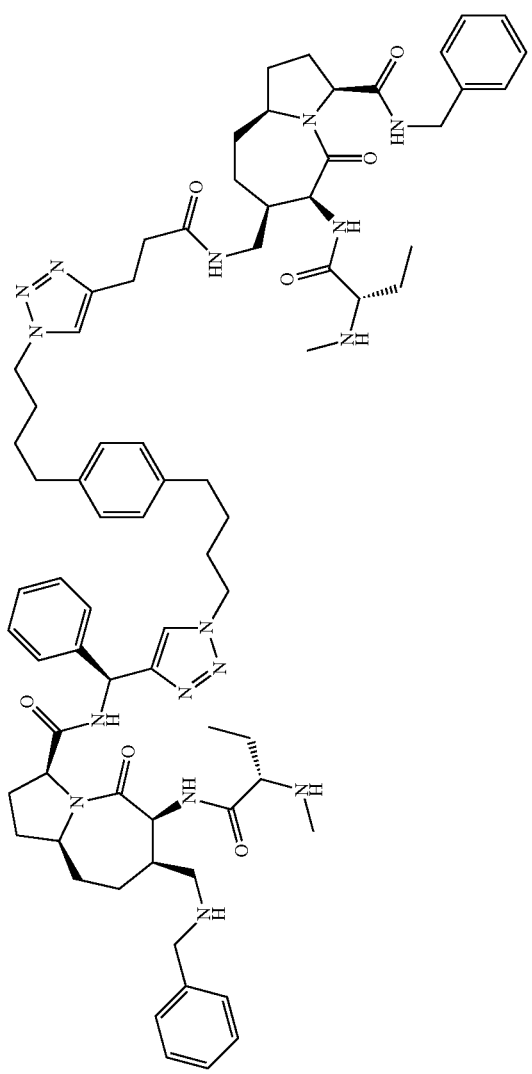

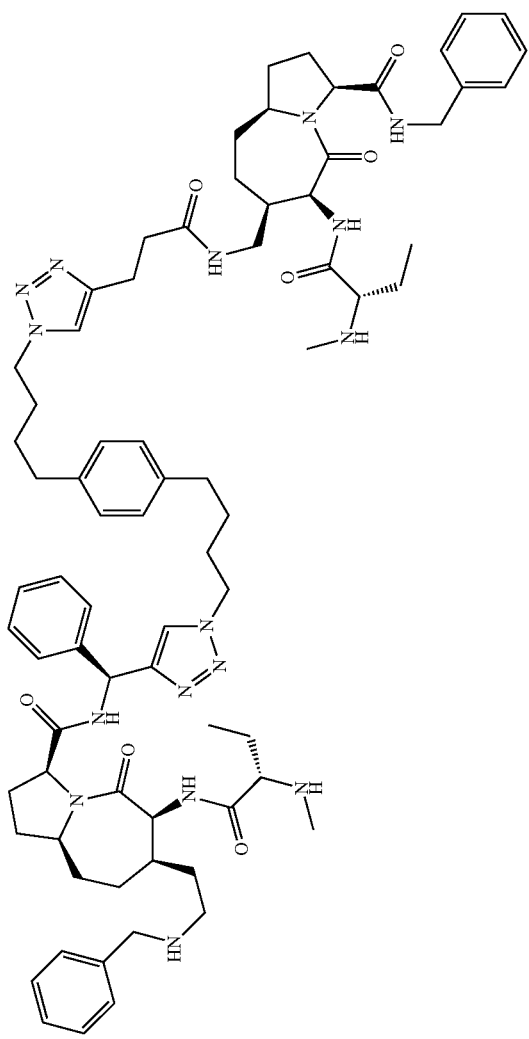
C55
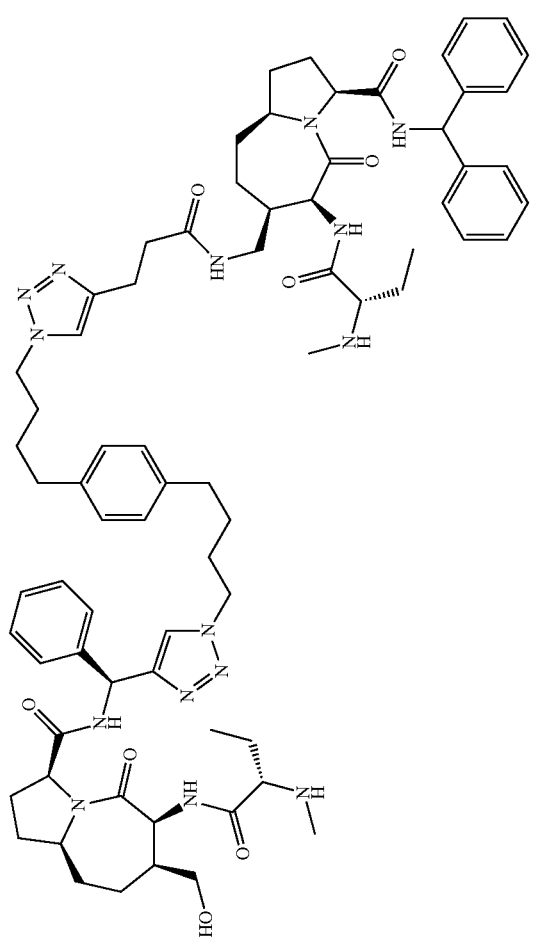
C56

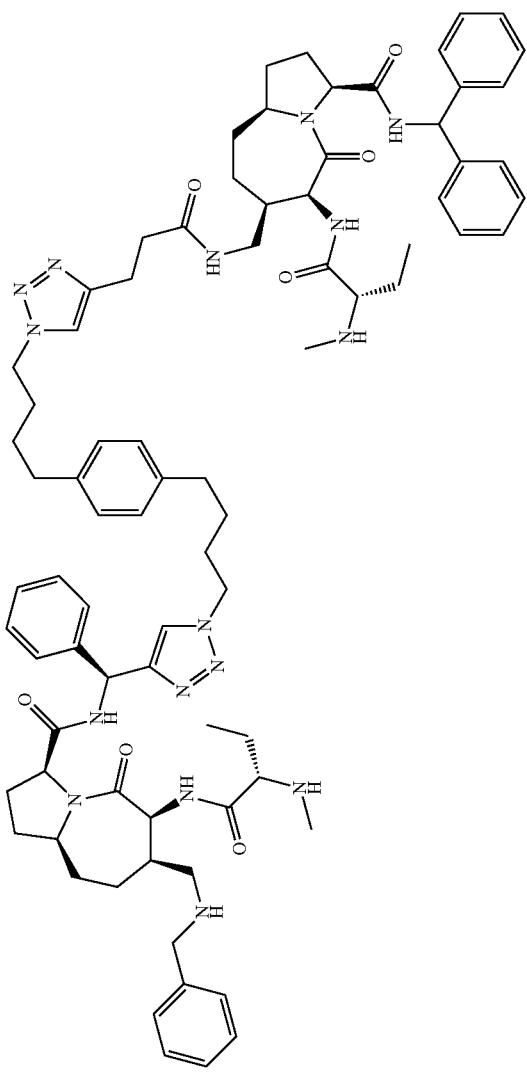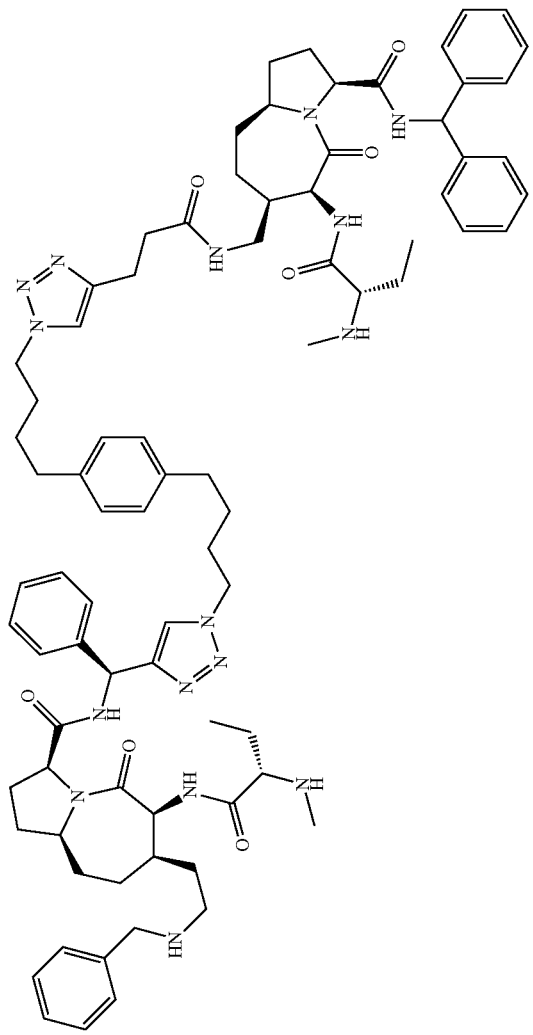

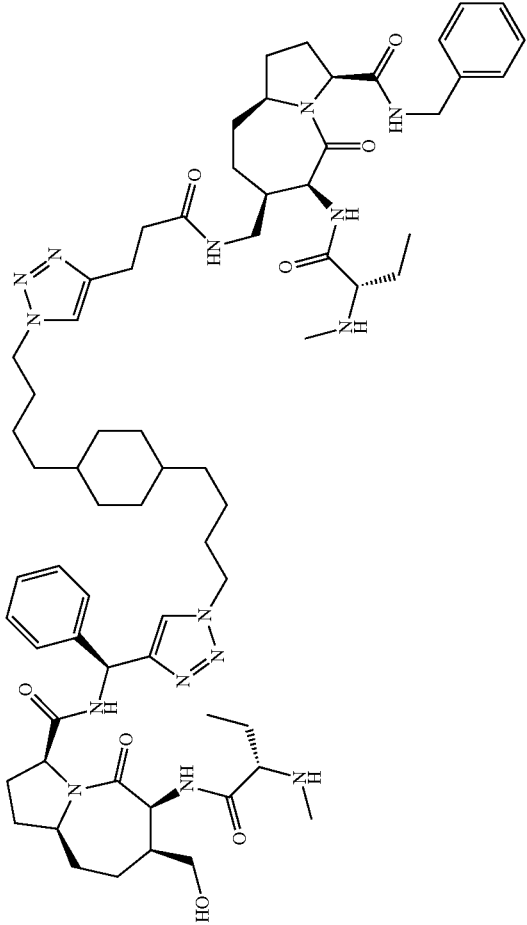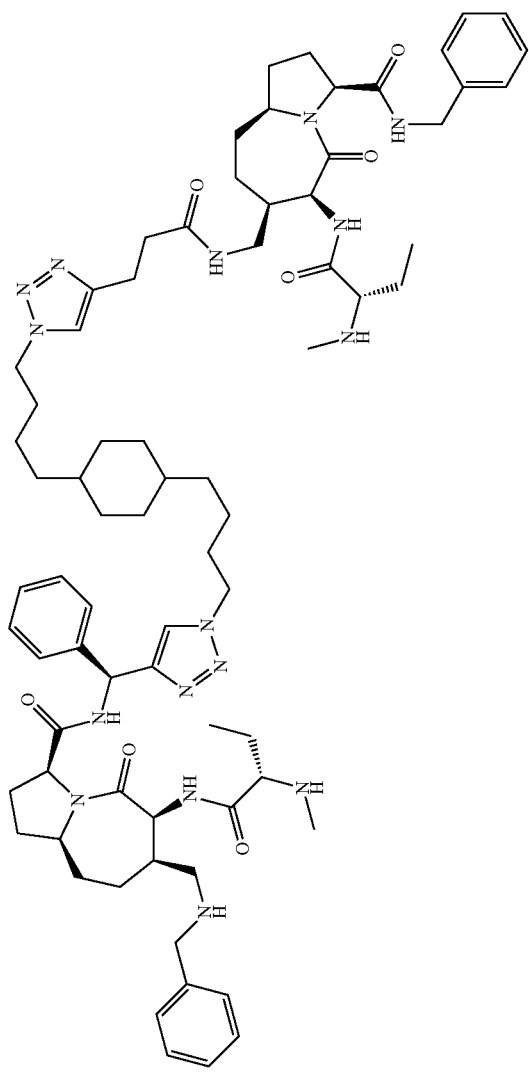

-continued
C61
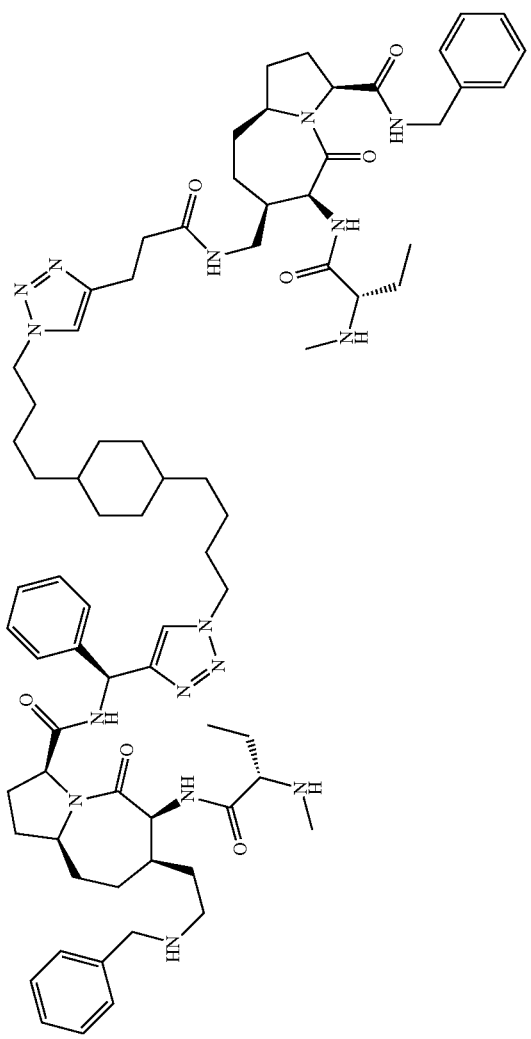
C62
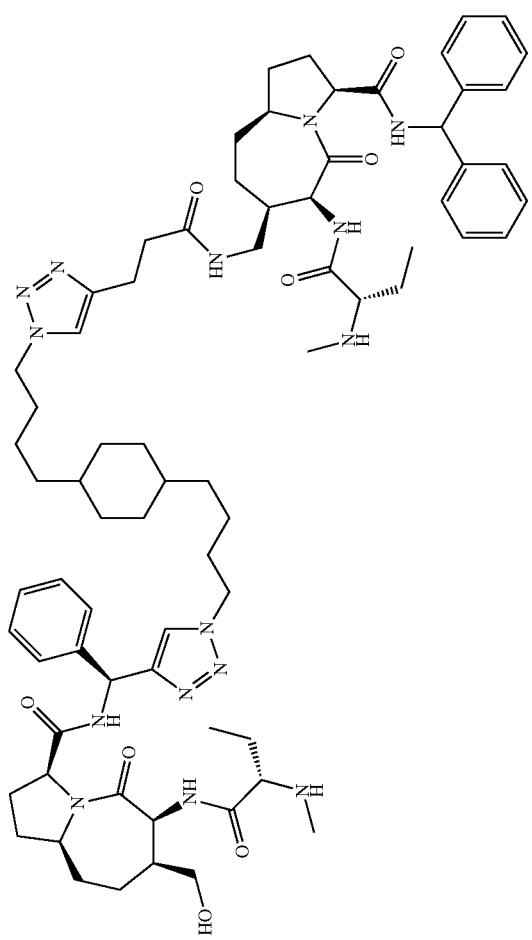

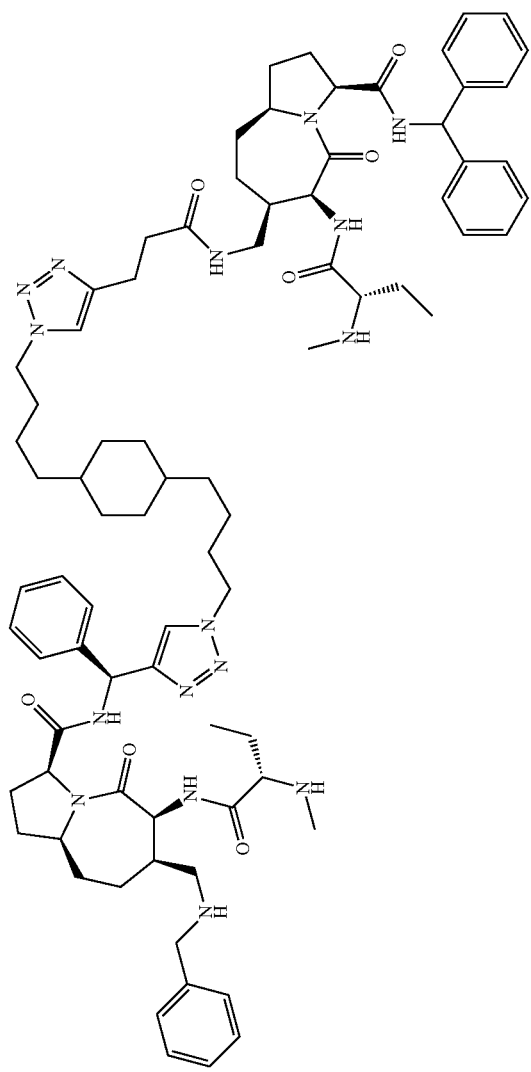
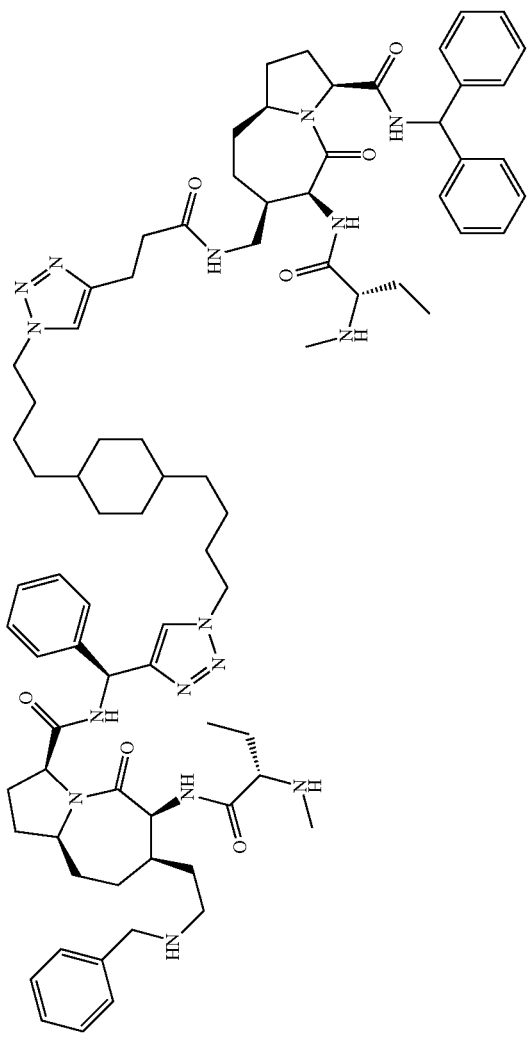

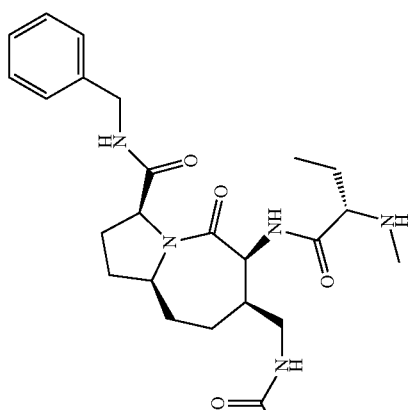
C65
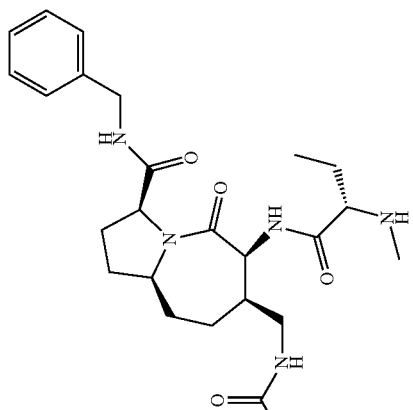
C66
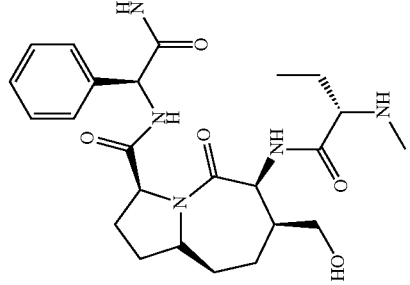
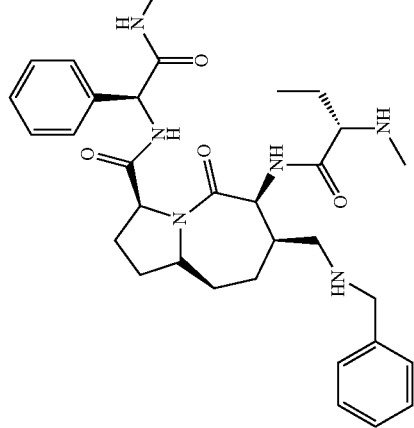

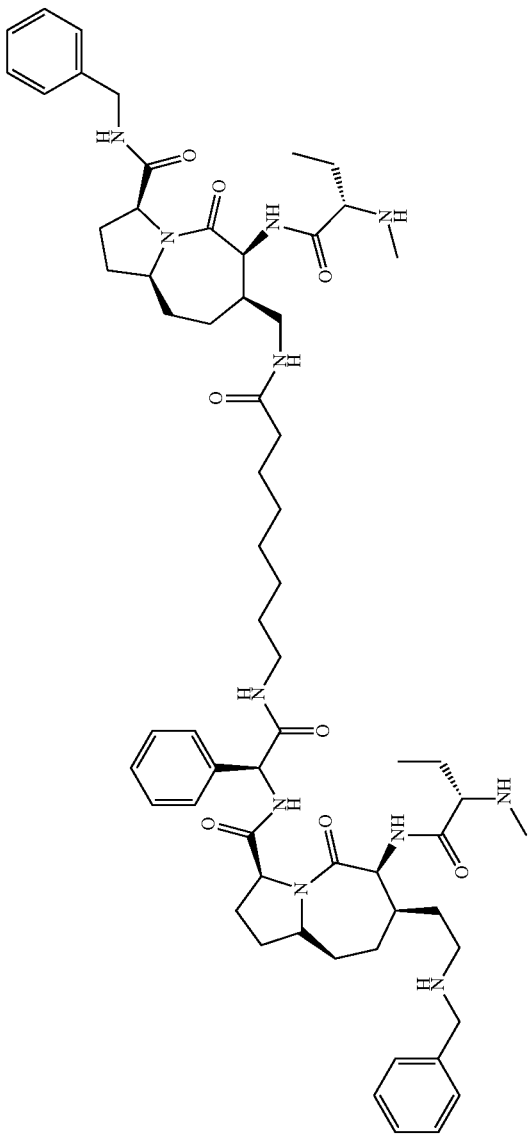
C67
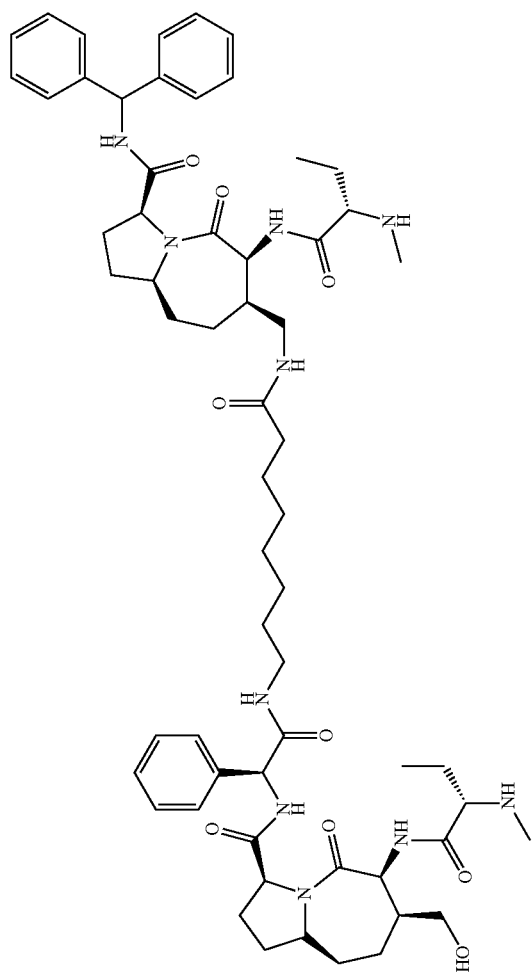
C68

-continued
C69
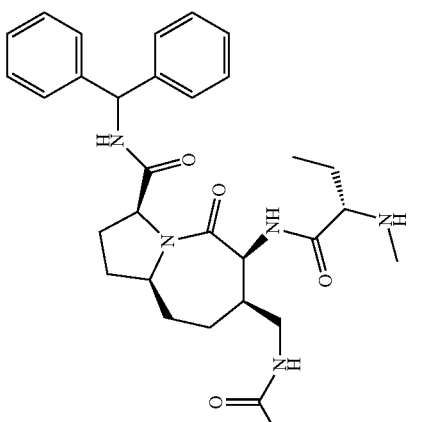
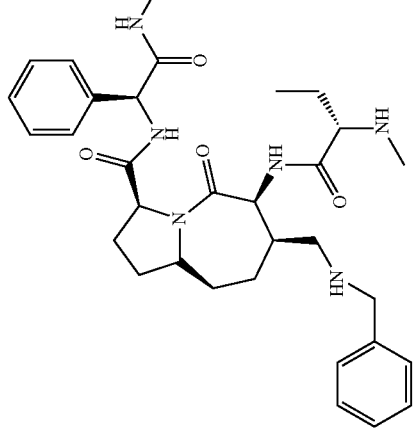
C70
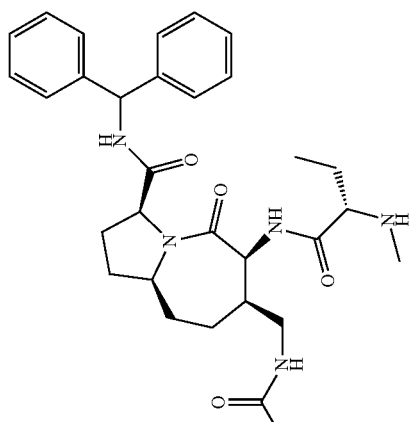
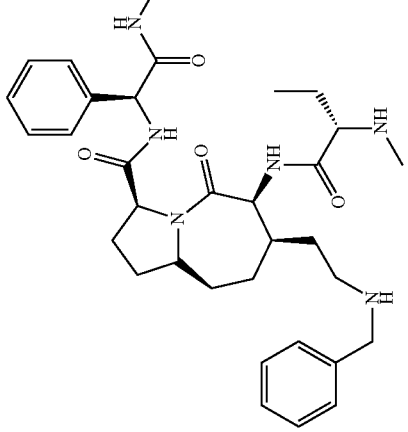

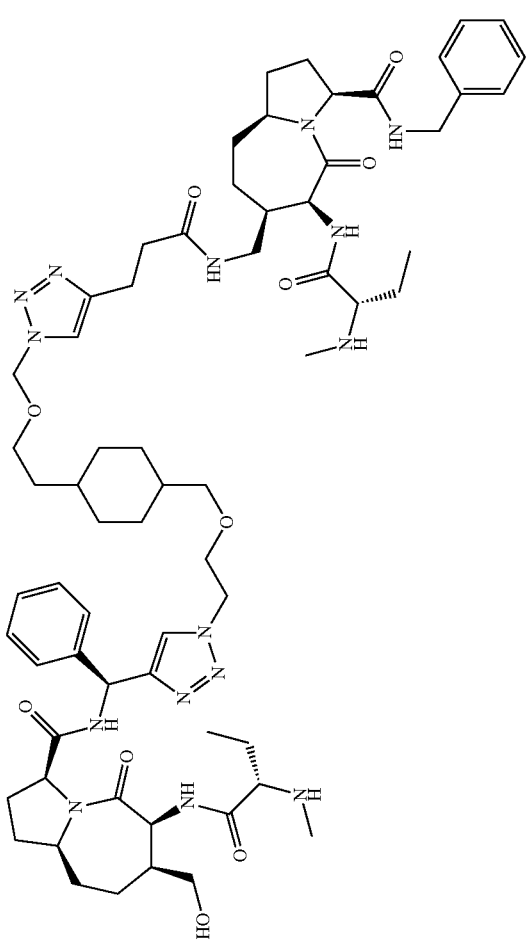
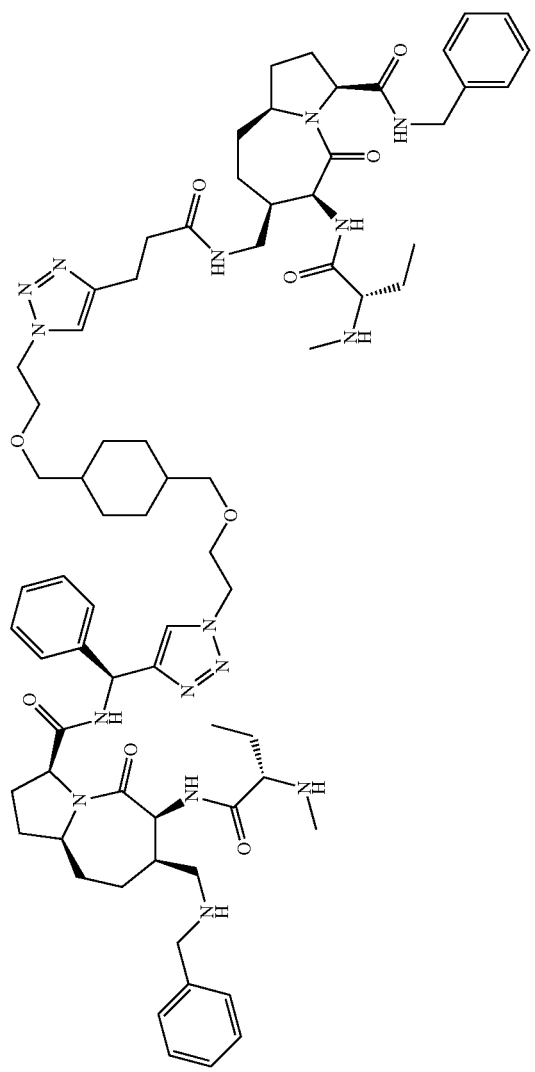

-continued
C73
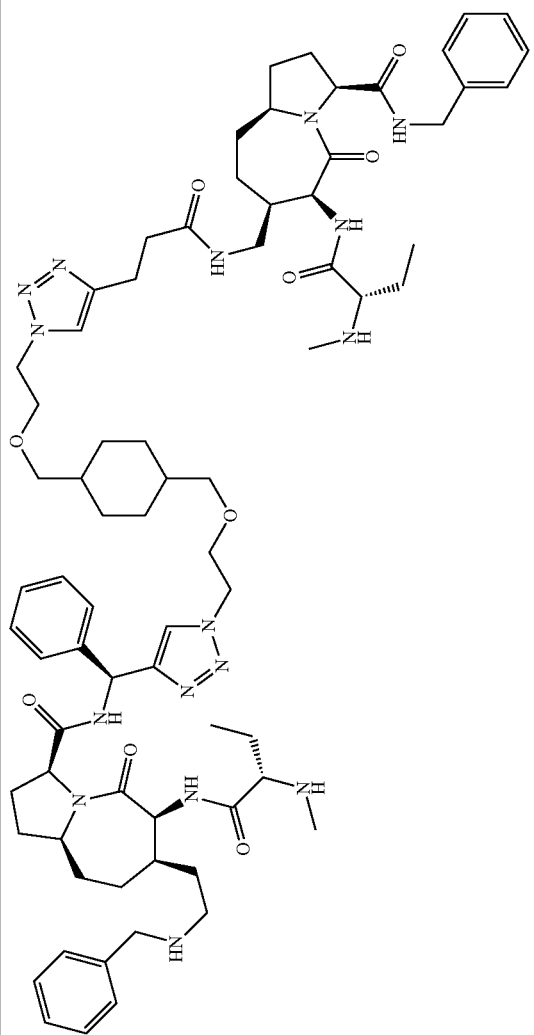
C74
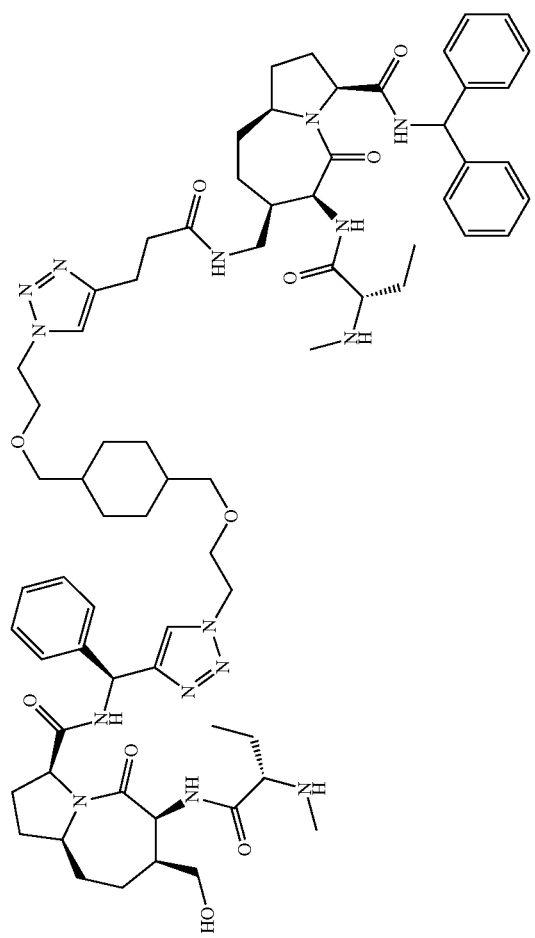

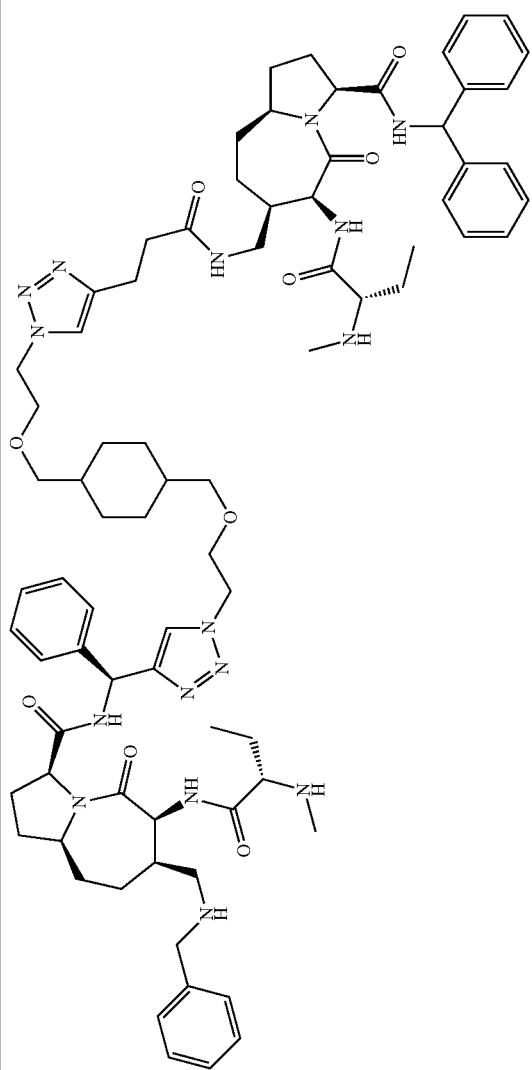
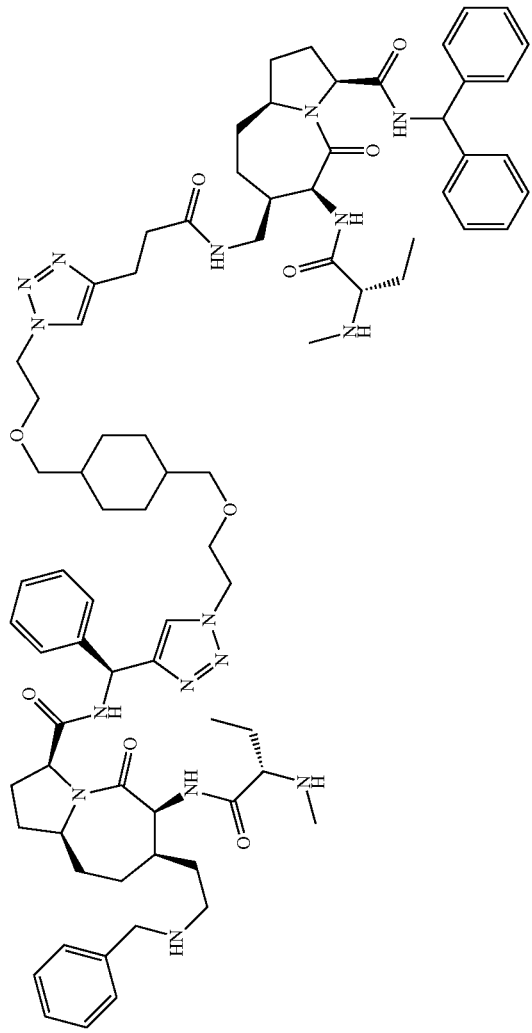

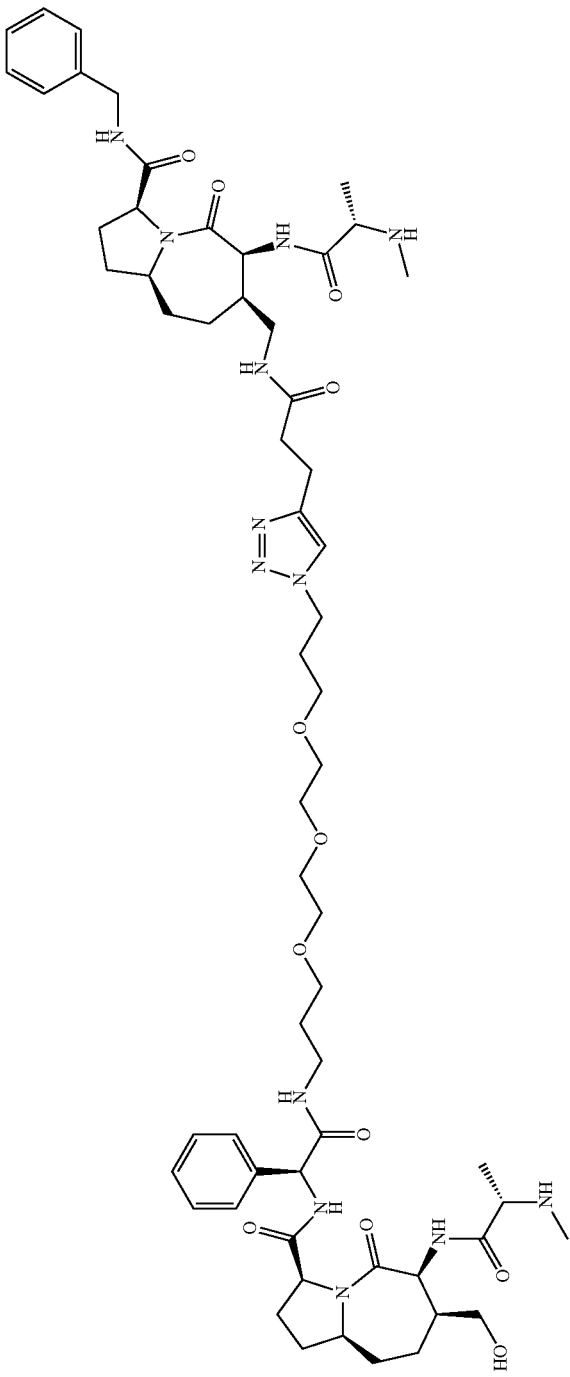

C78
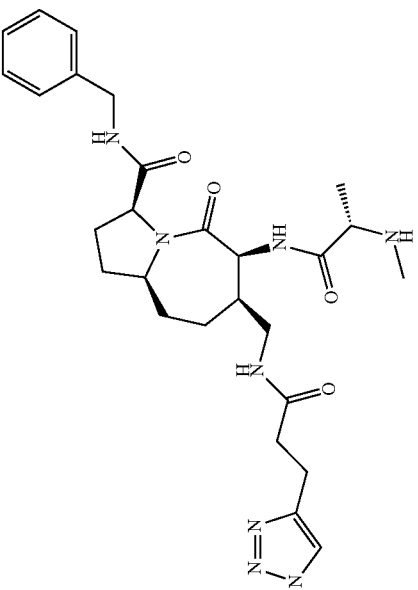
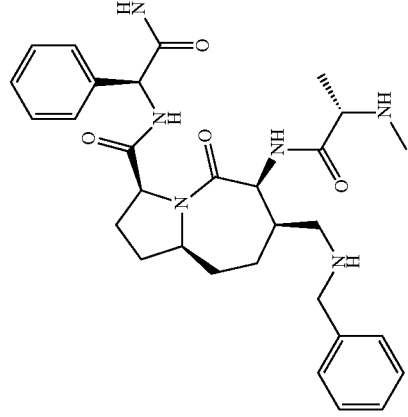

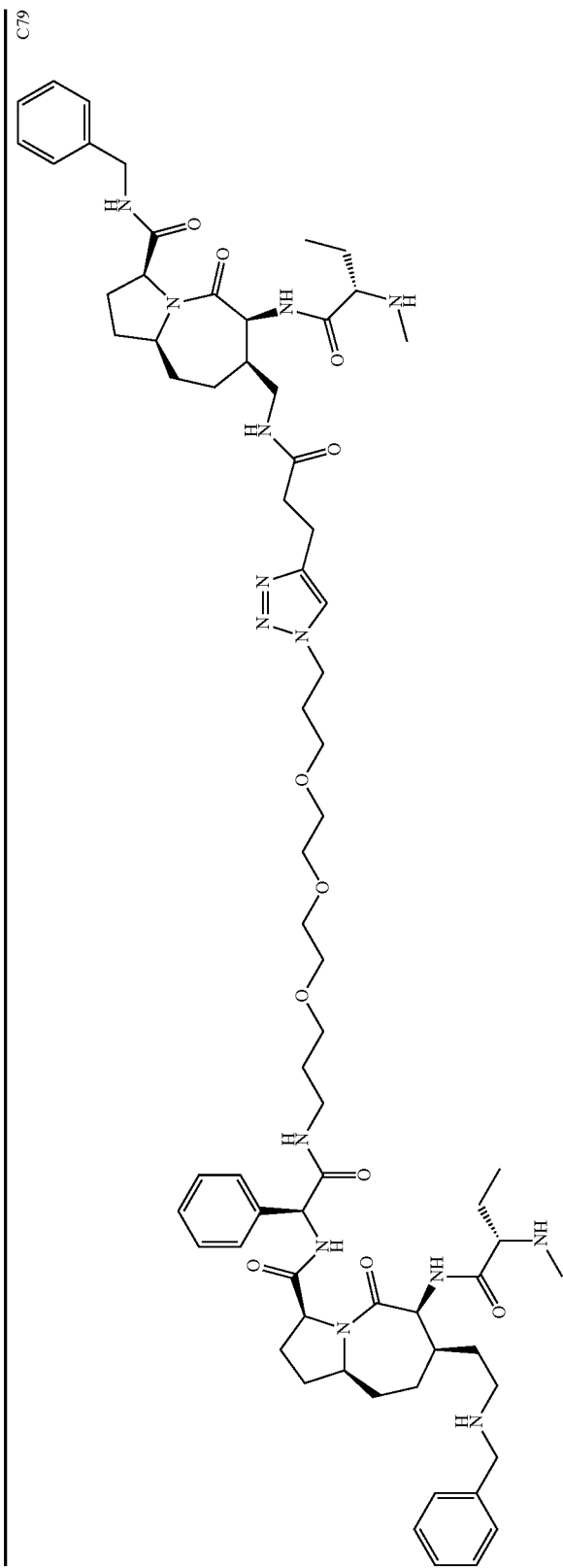

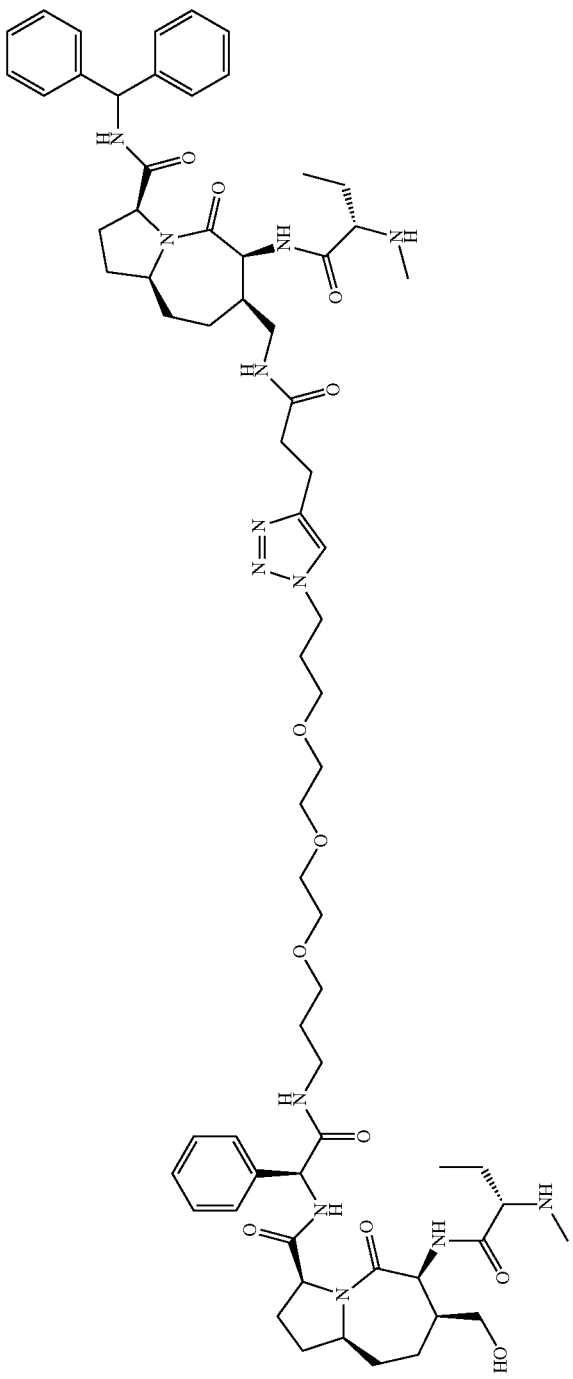

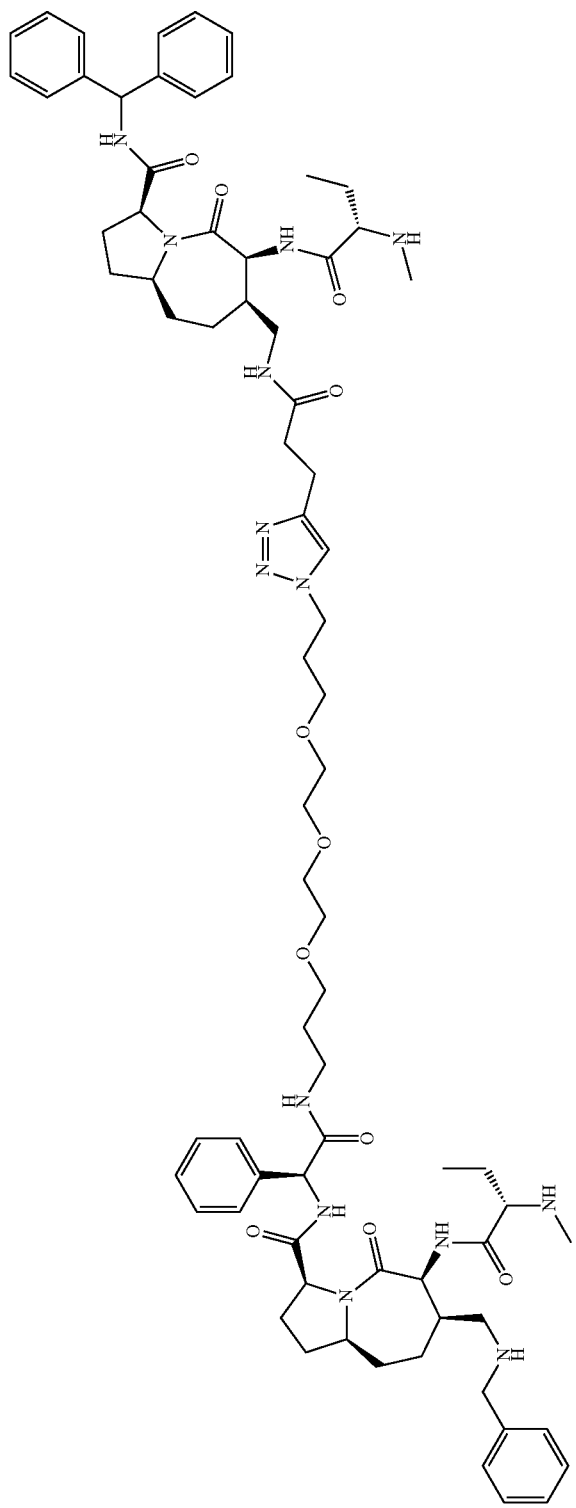

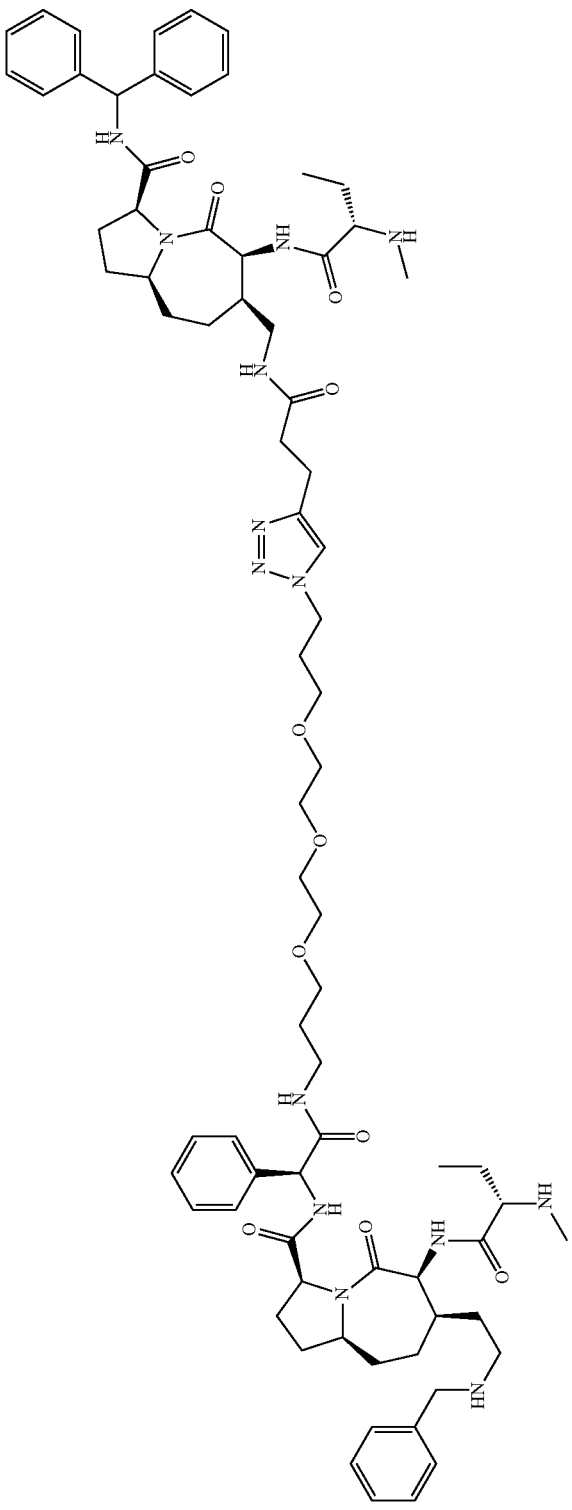
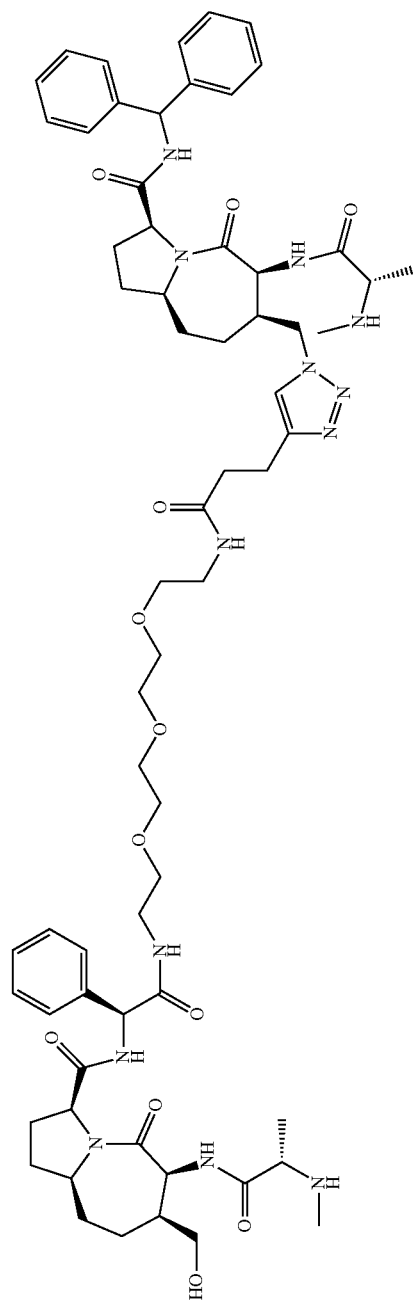

C84
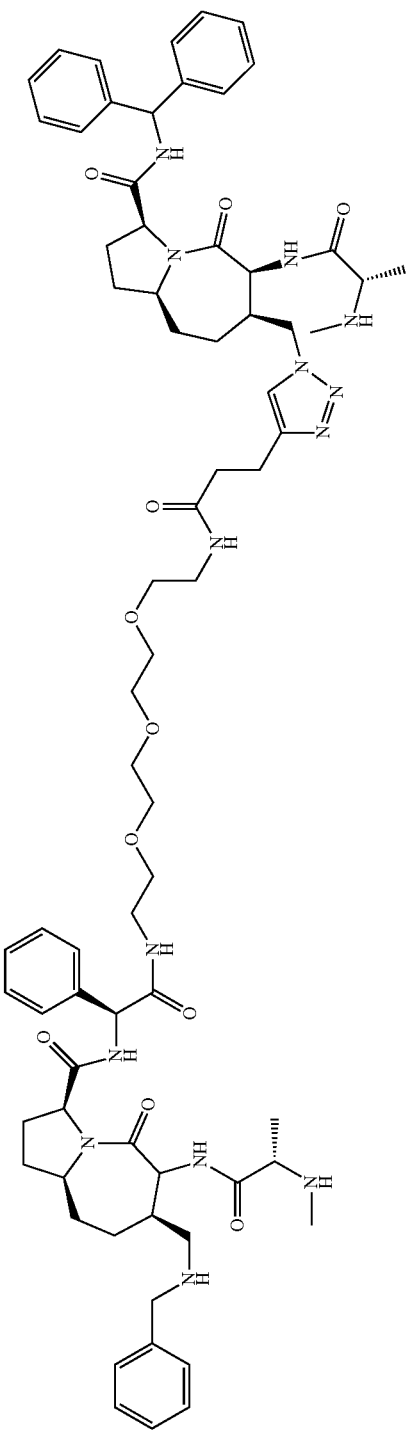
C85
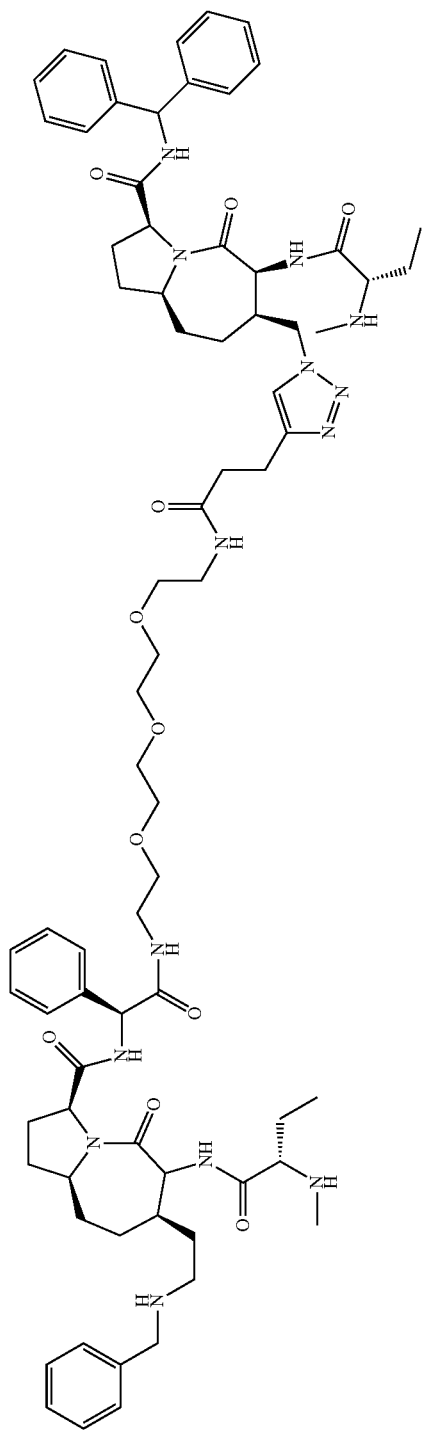

-continued
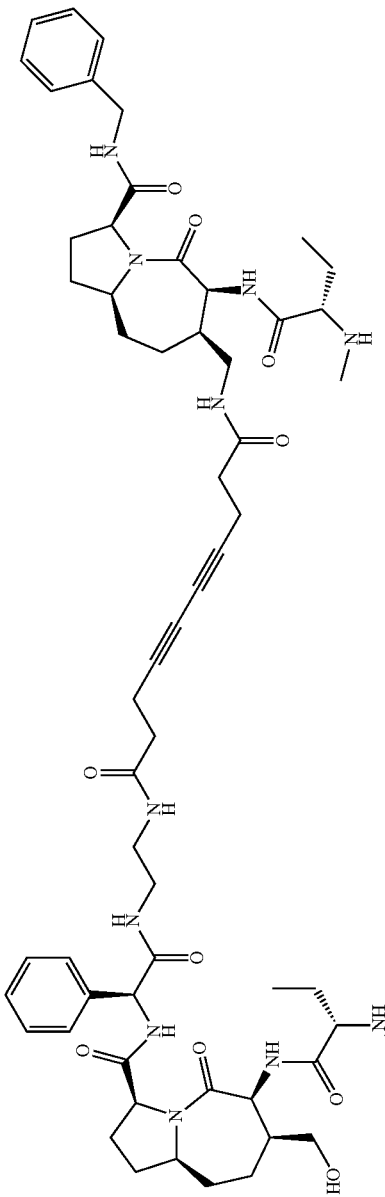
C86
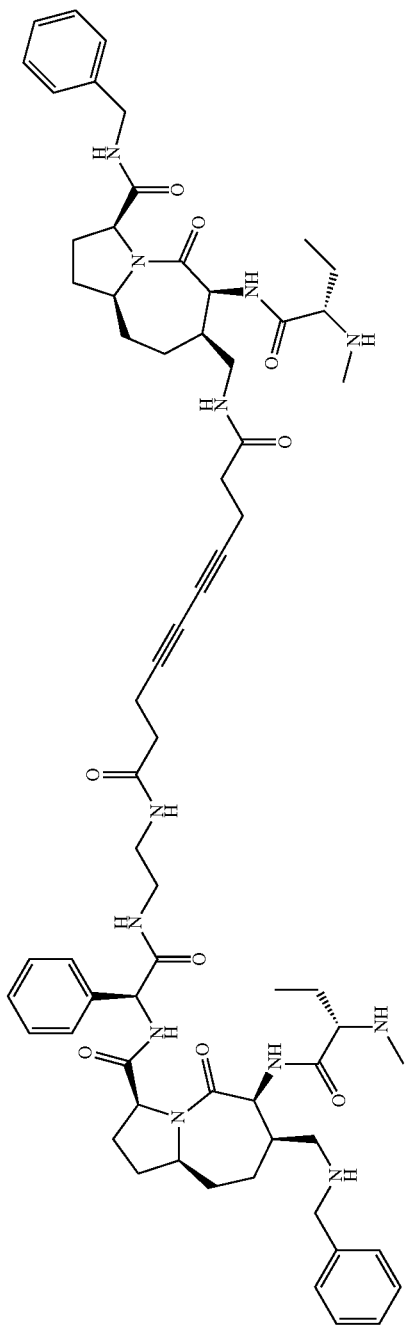
C87

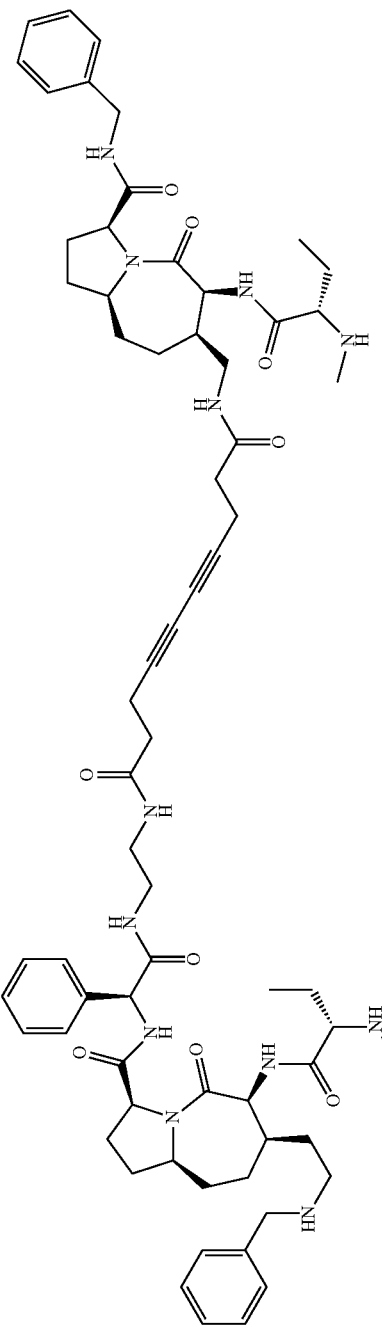
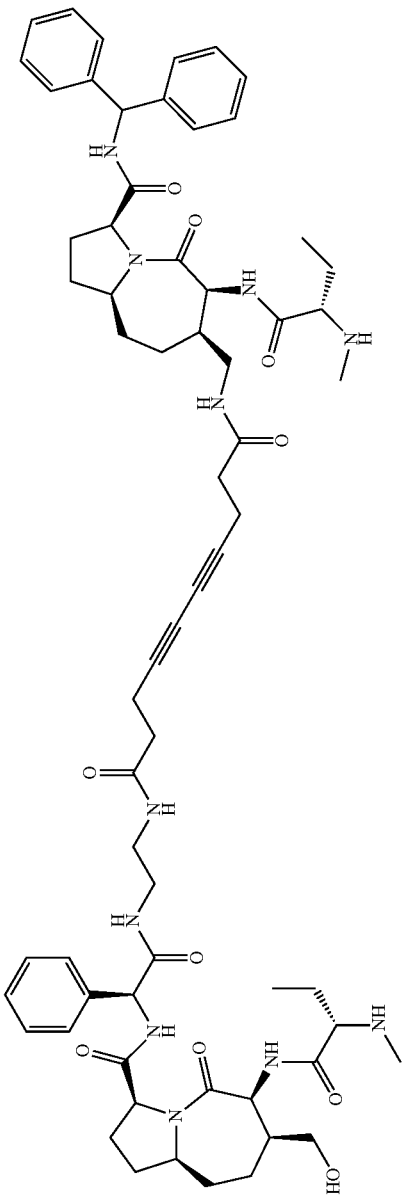

C90
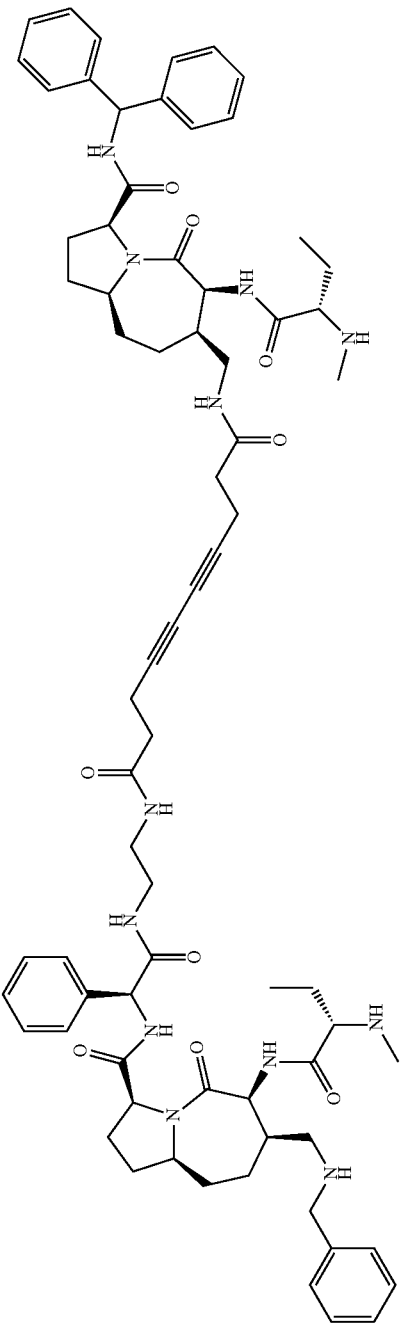
C91
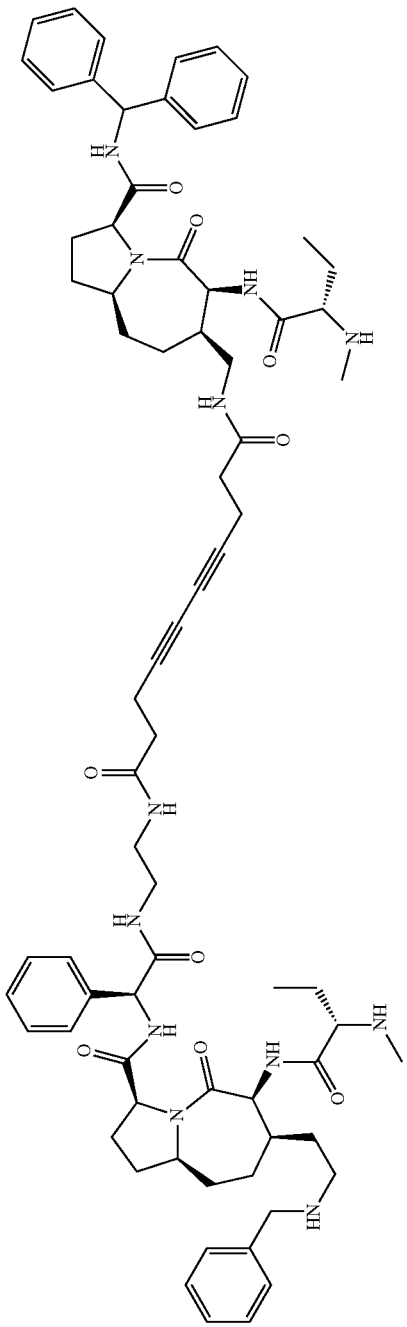

-continued
C92
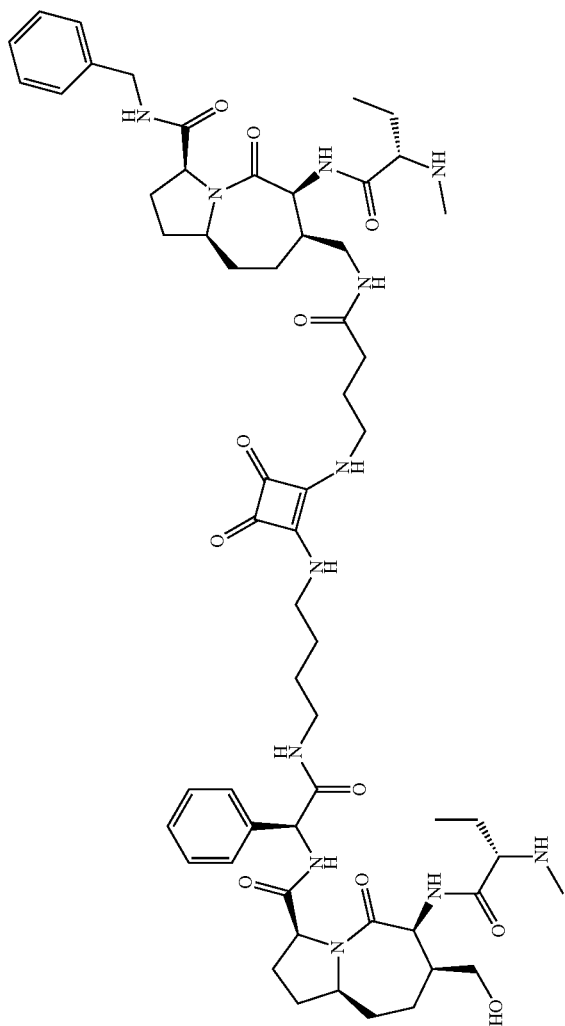

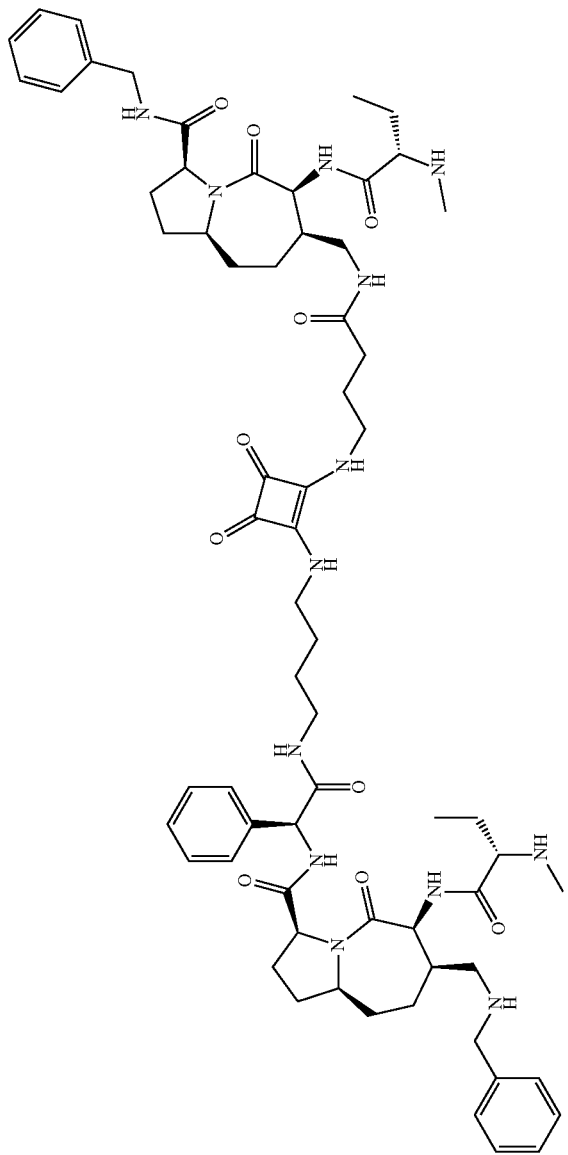

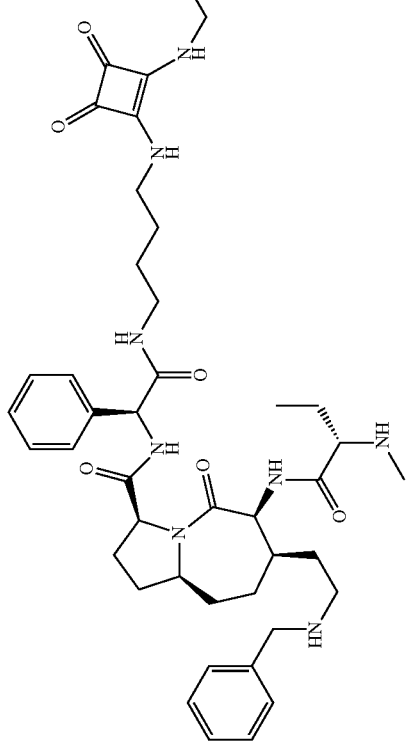

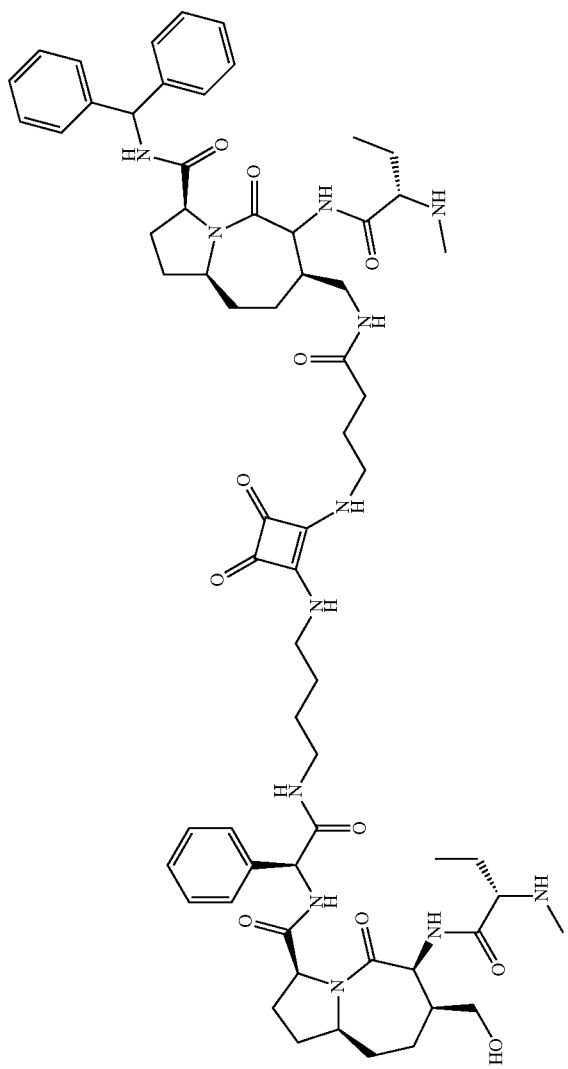

-continued
C96
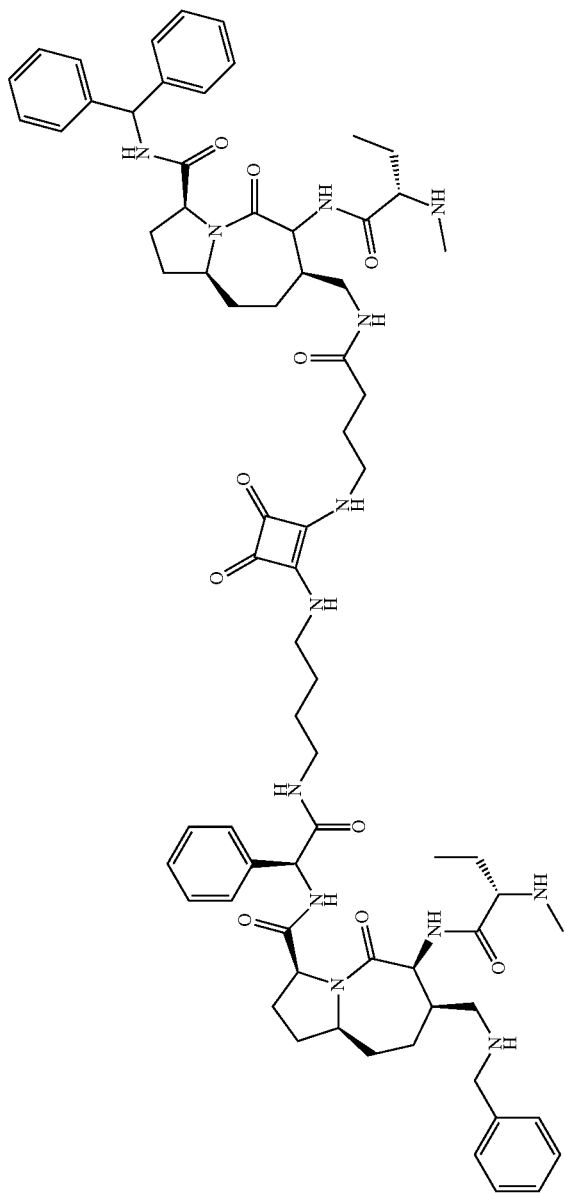

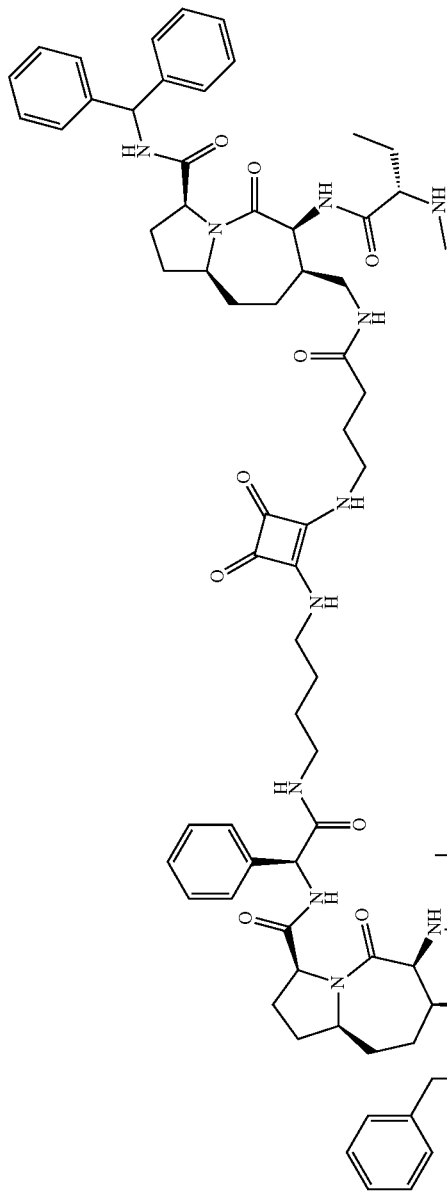
C97
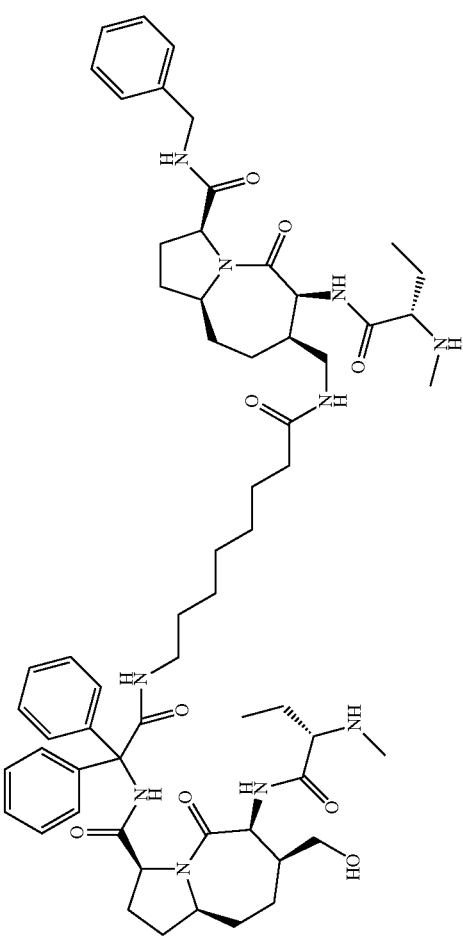
C98

-continued
C99
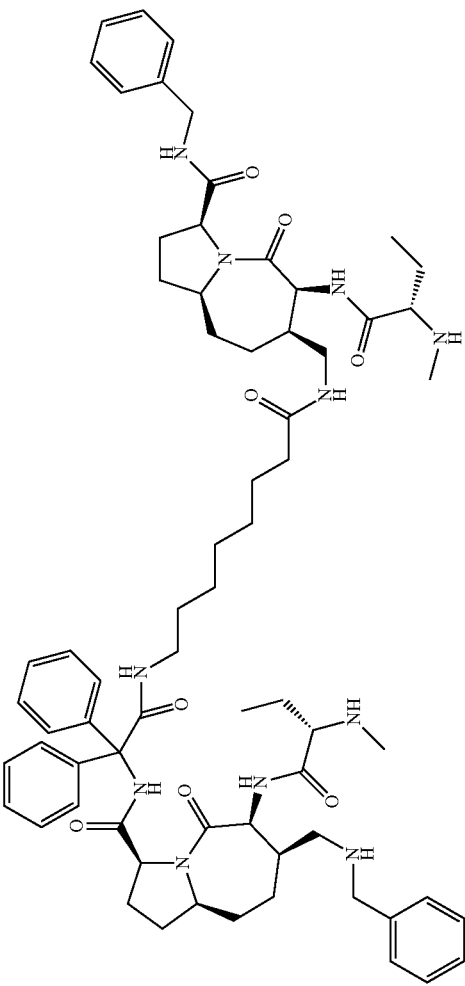
C100
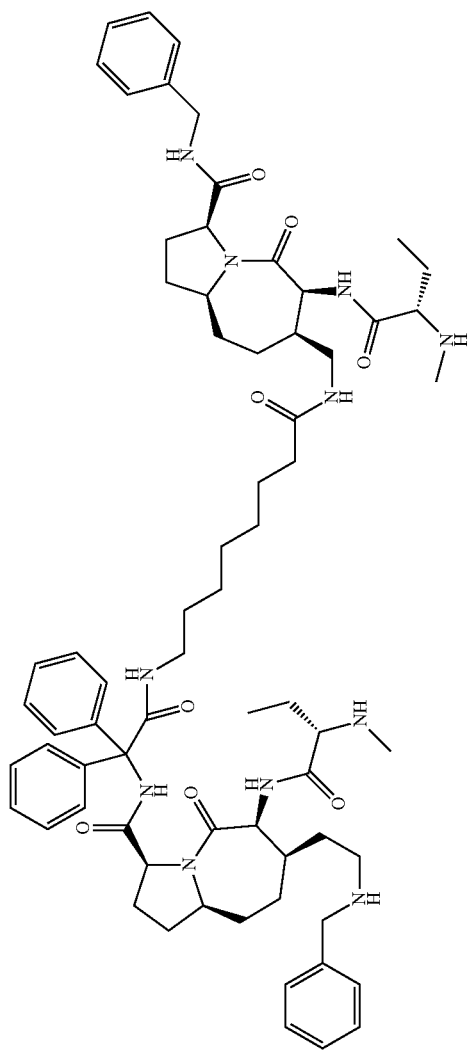

C101
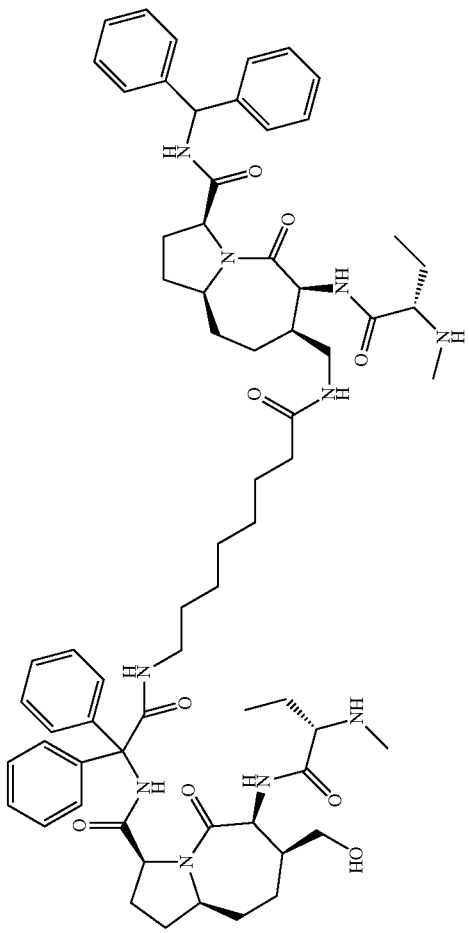
C102
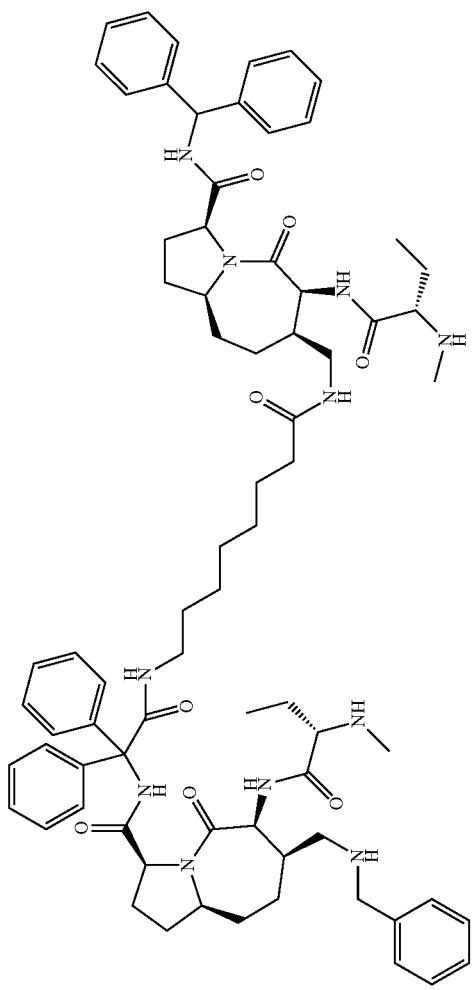

C103
C104
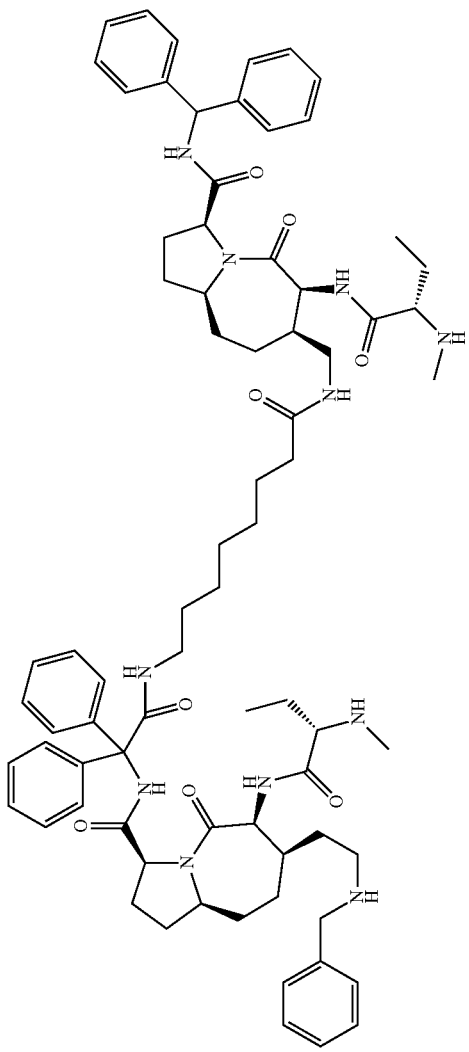
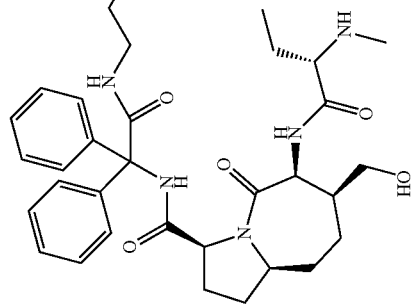

C105
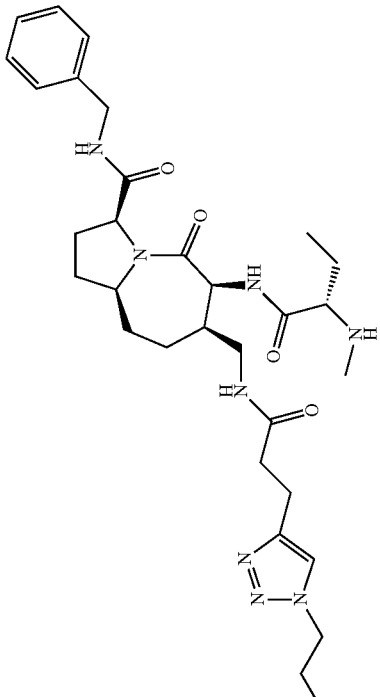
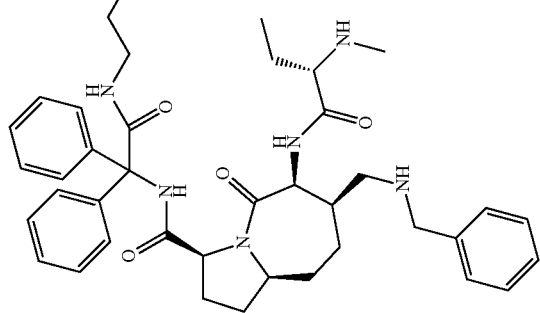

C106
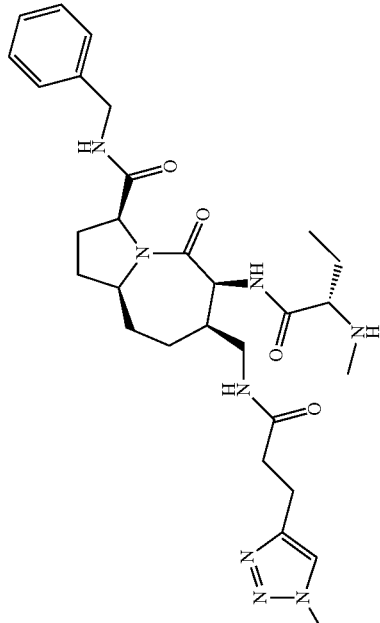
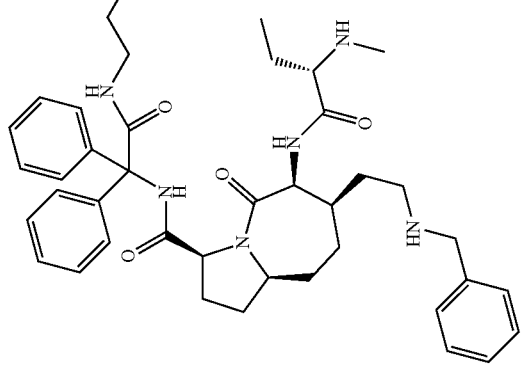

C107
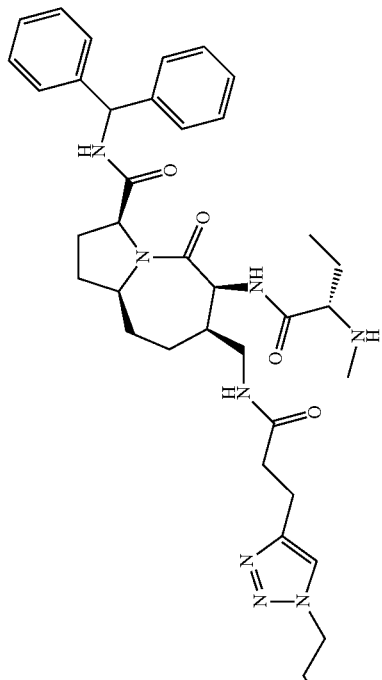
C108
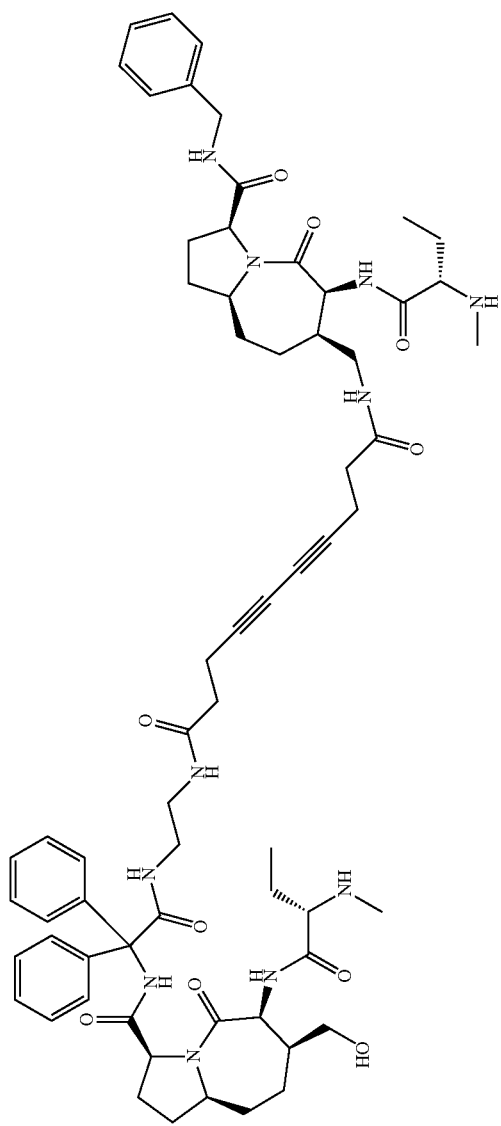

C109 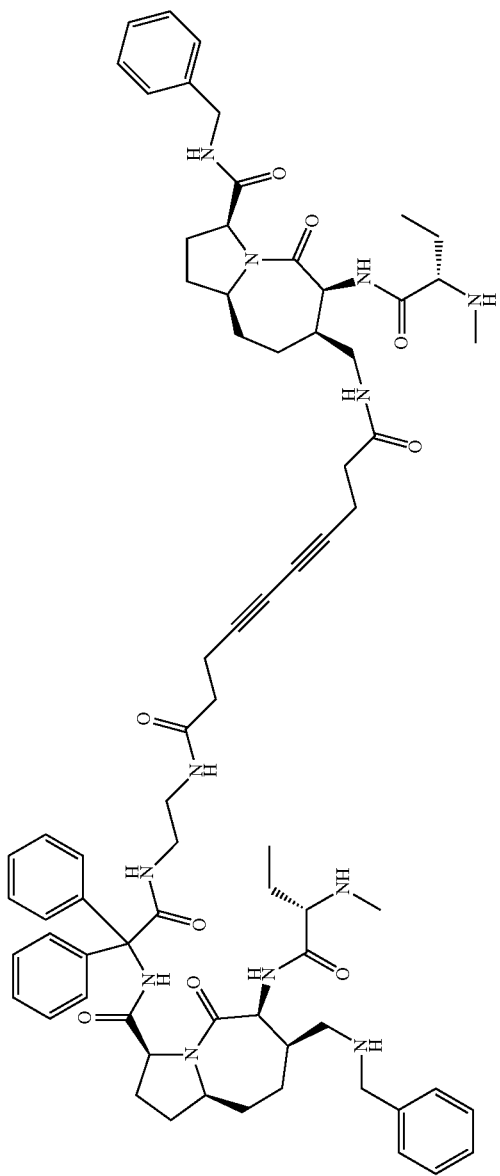
C110 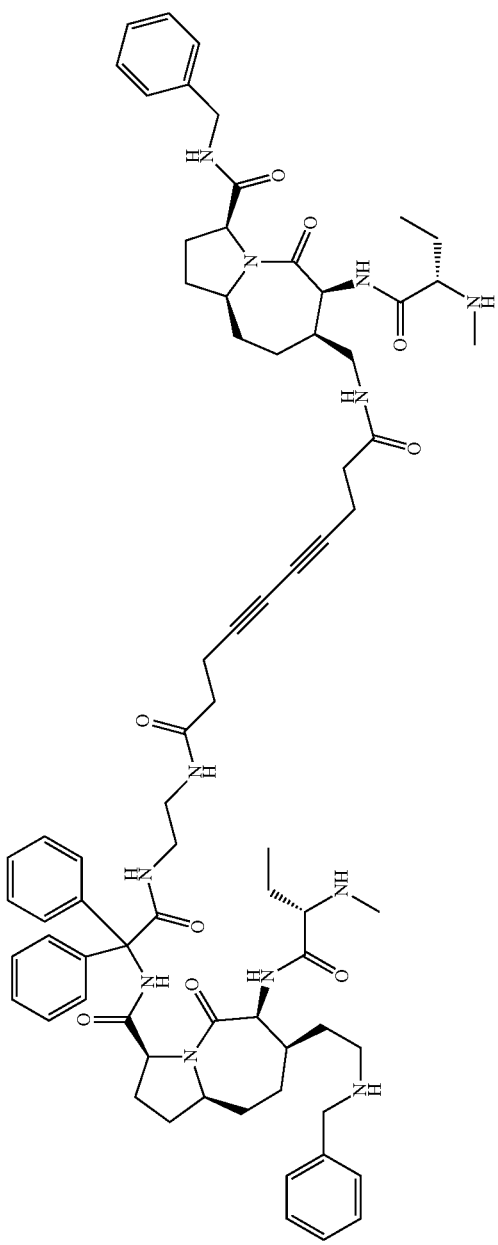

C111
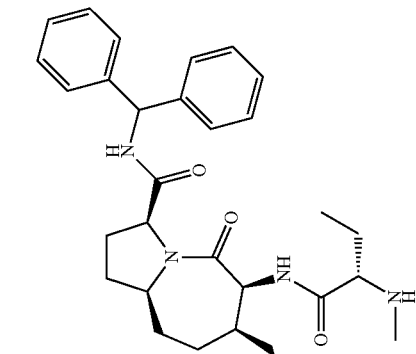
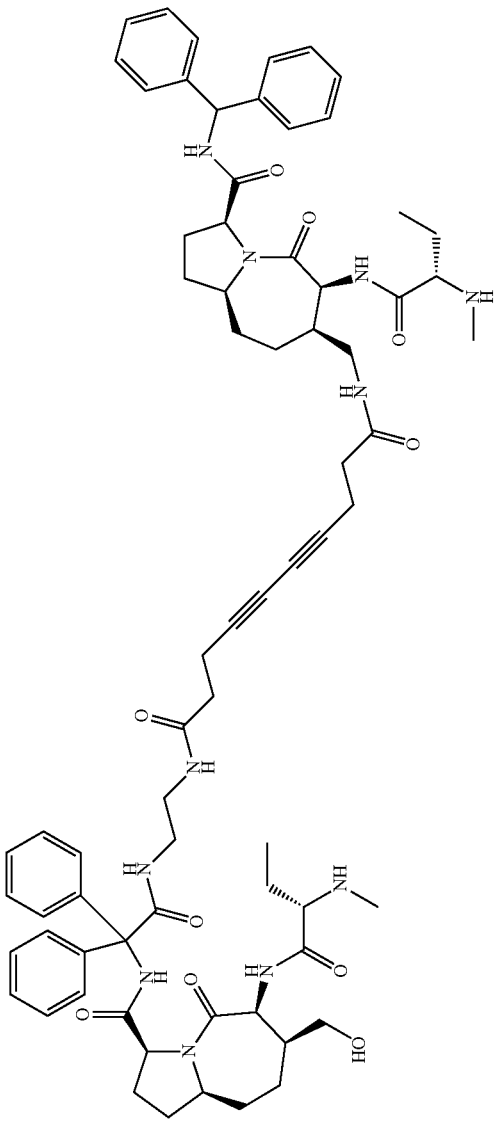

C112
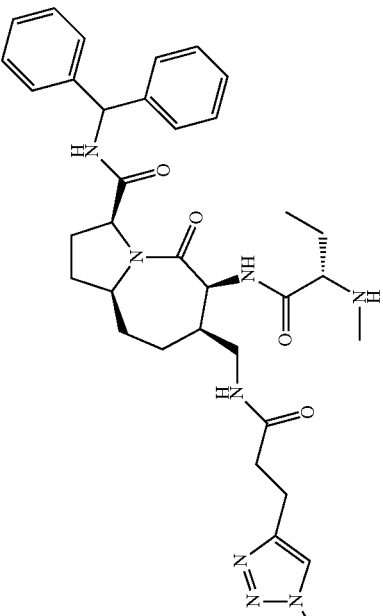
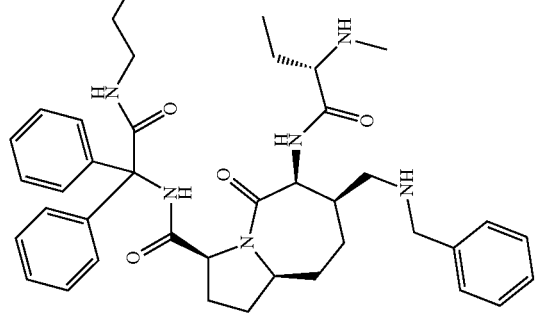

C113
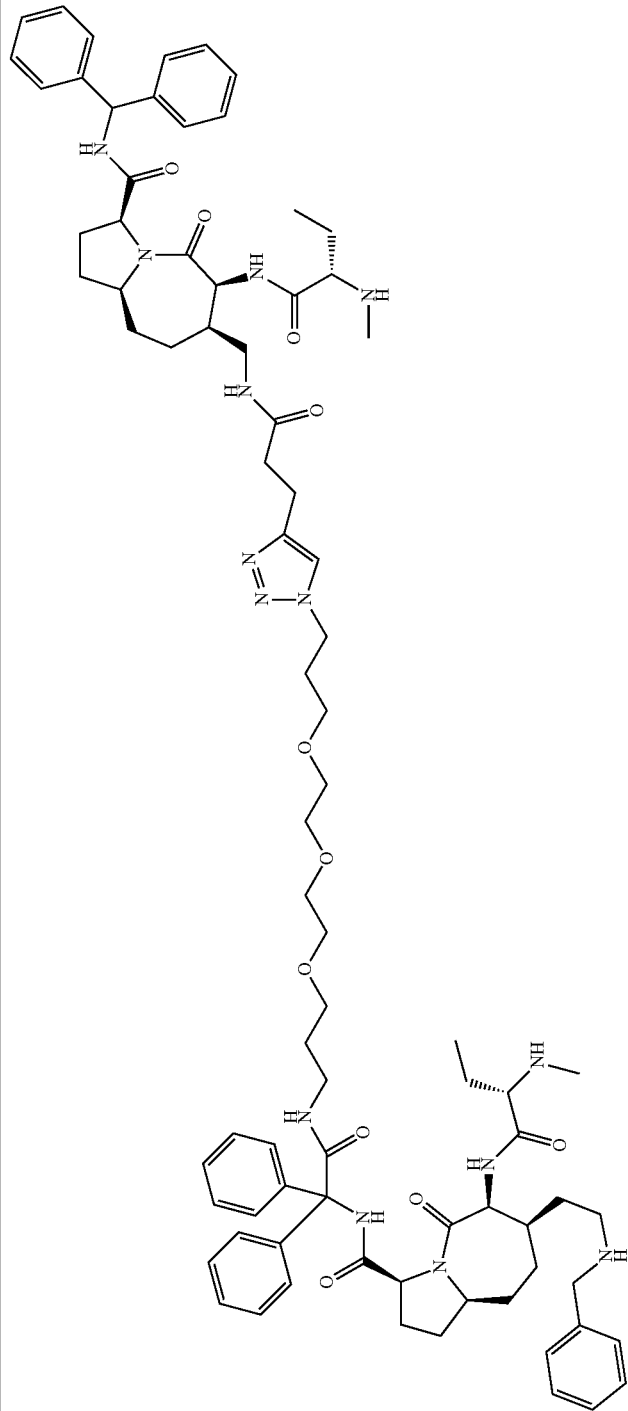

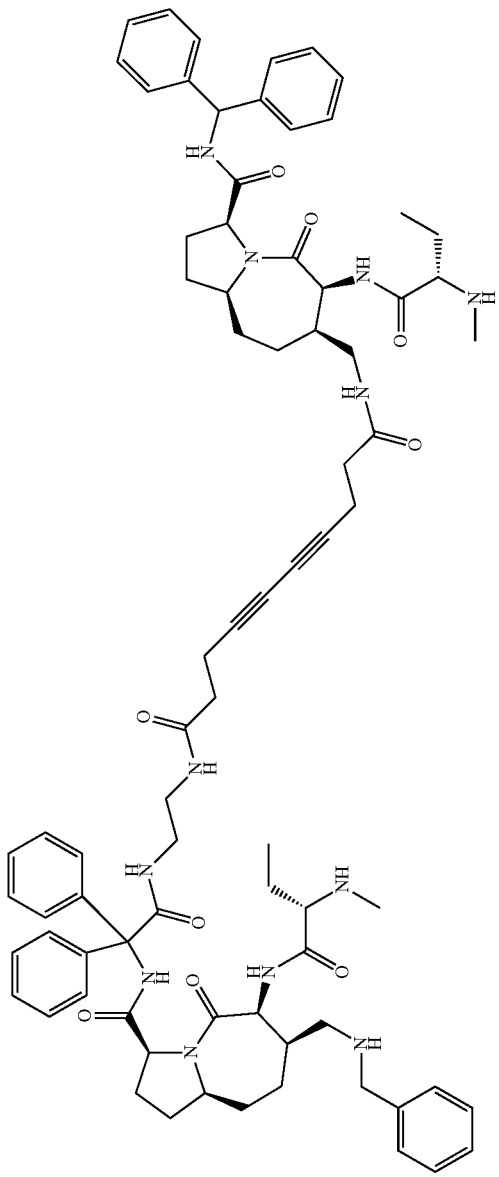
C114
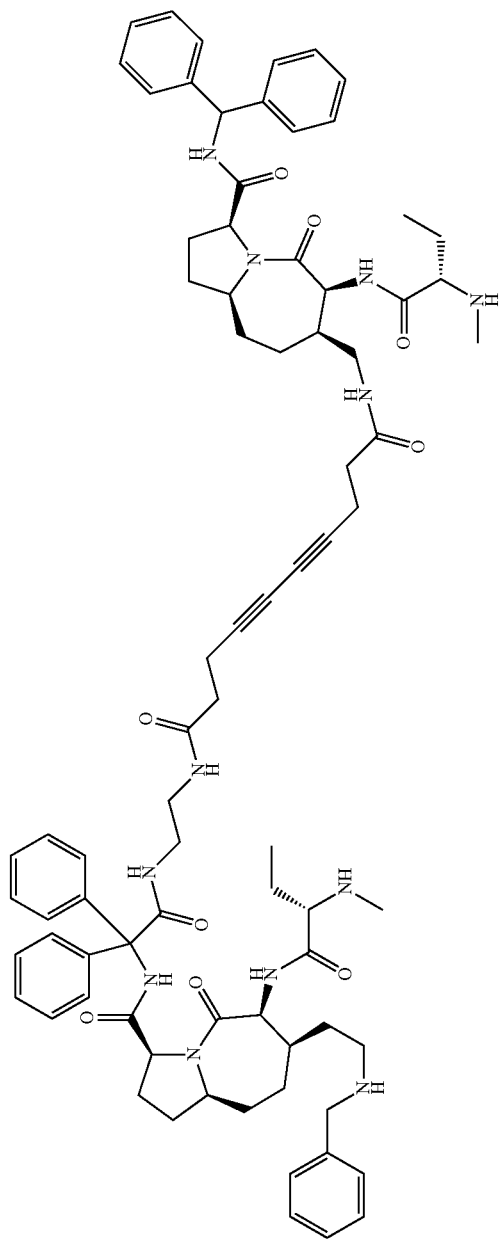
C115

C116
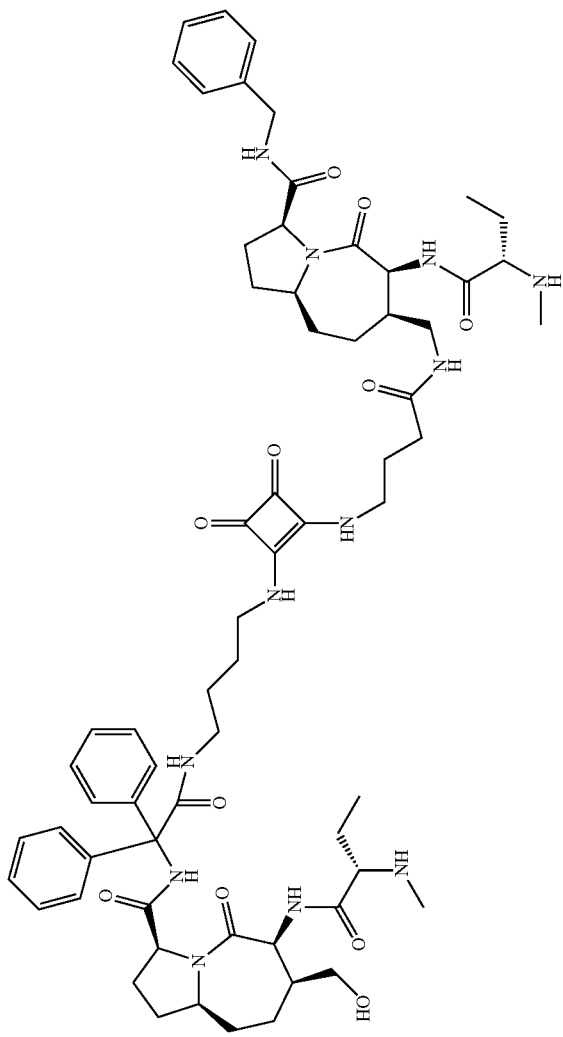

C117
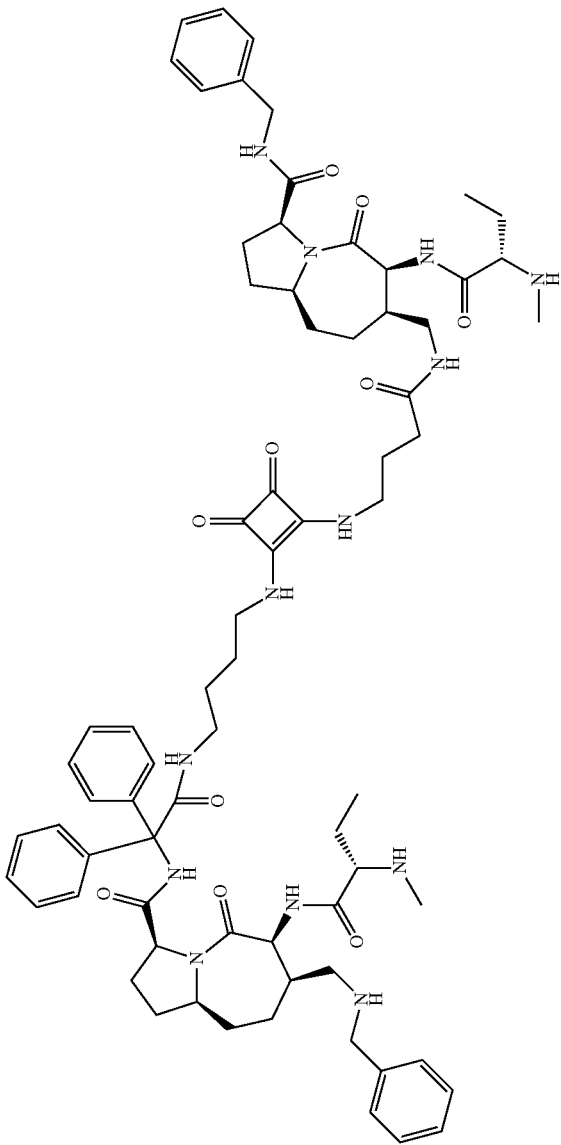

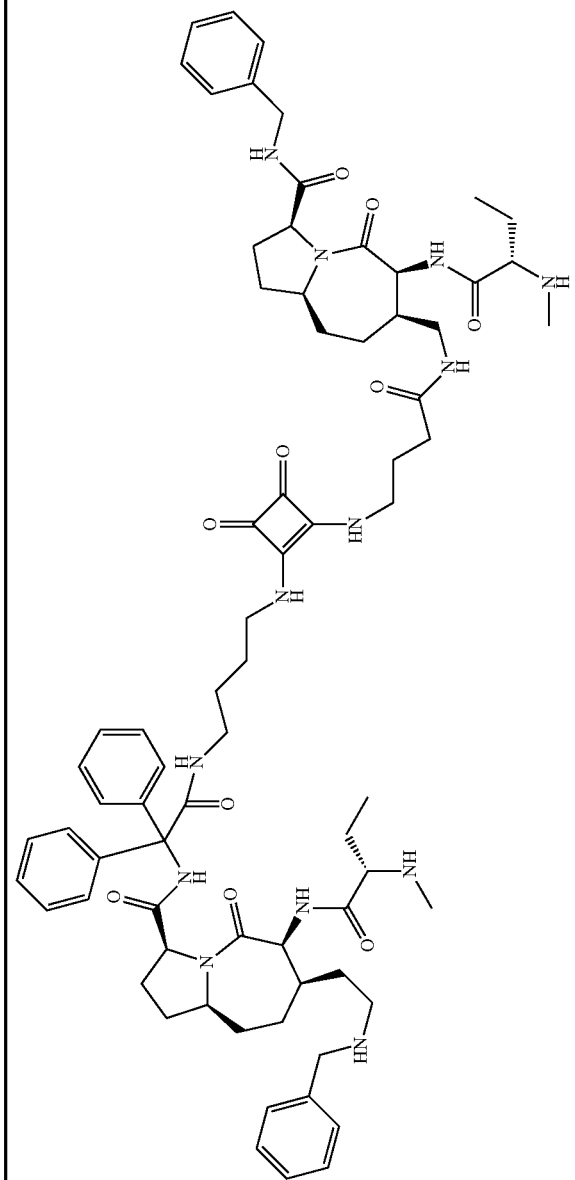

C119
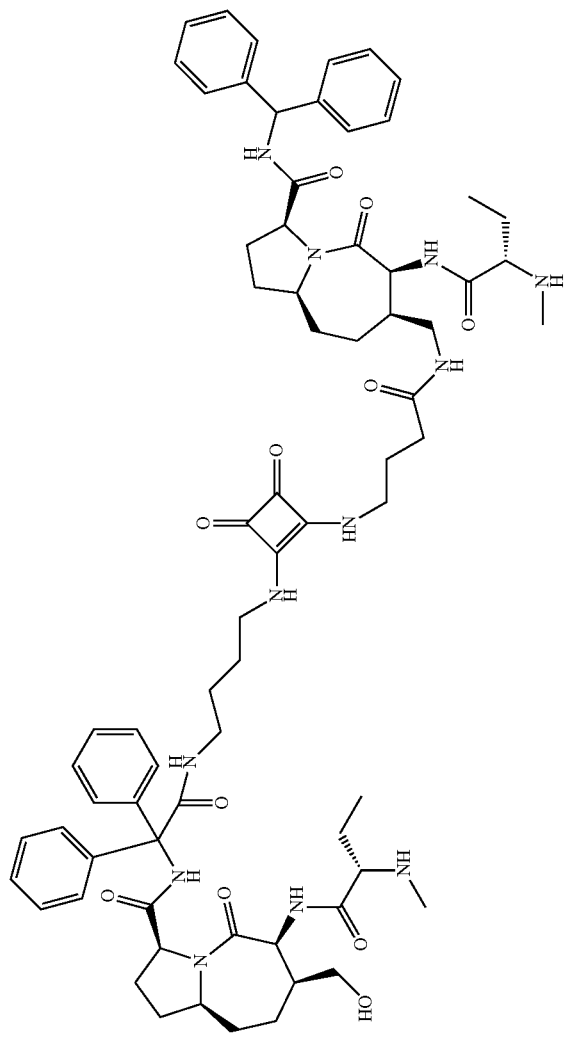

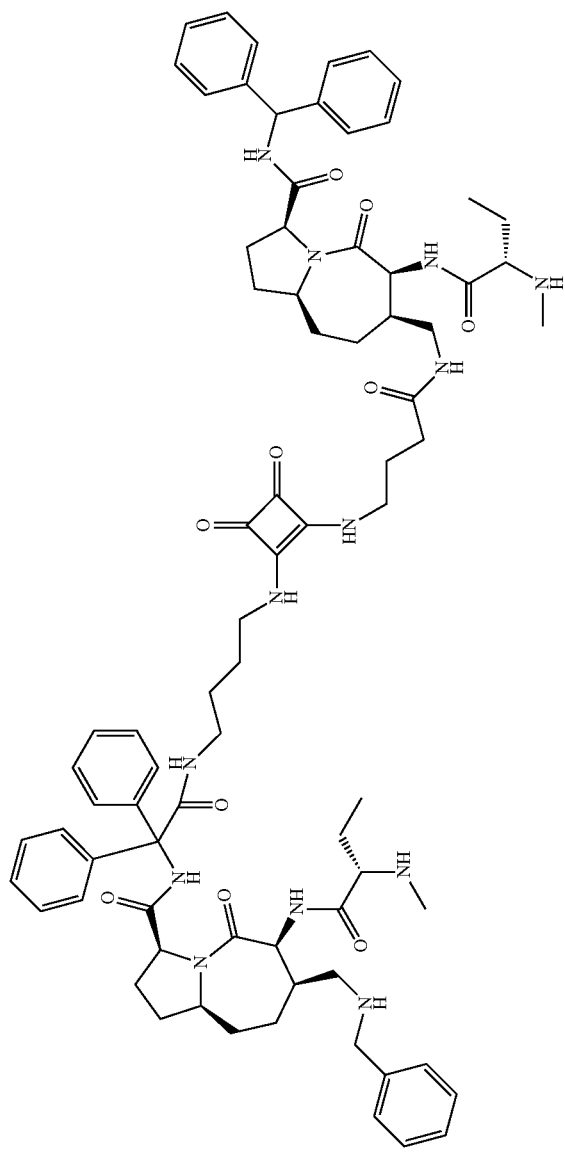

C121
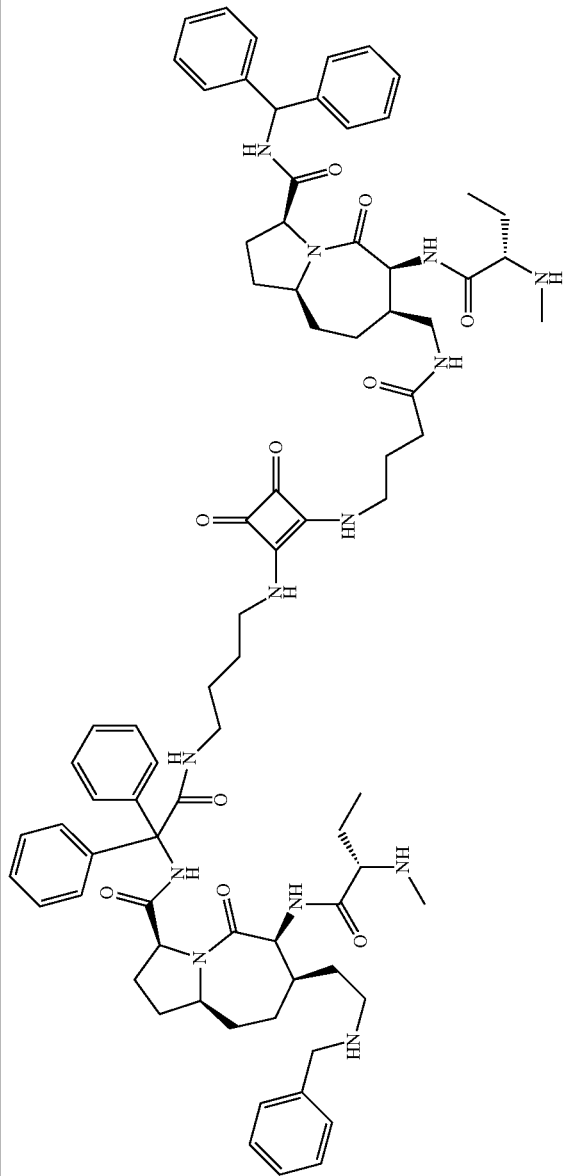
C122
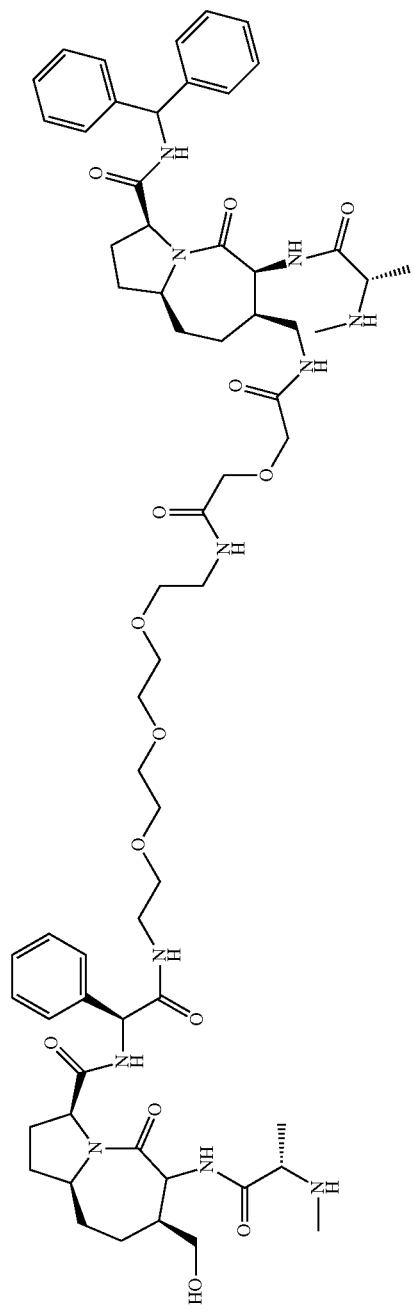

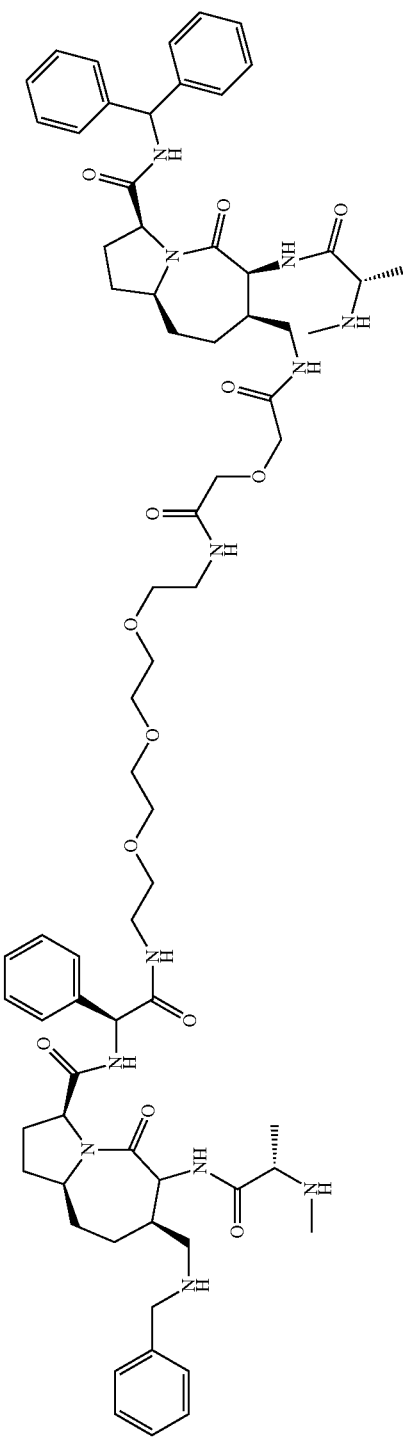
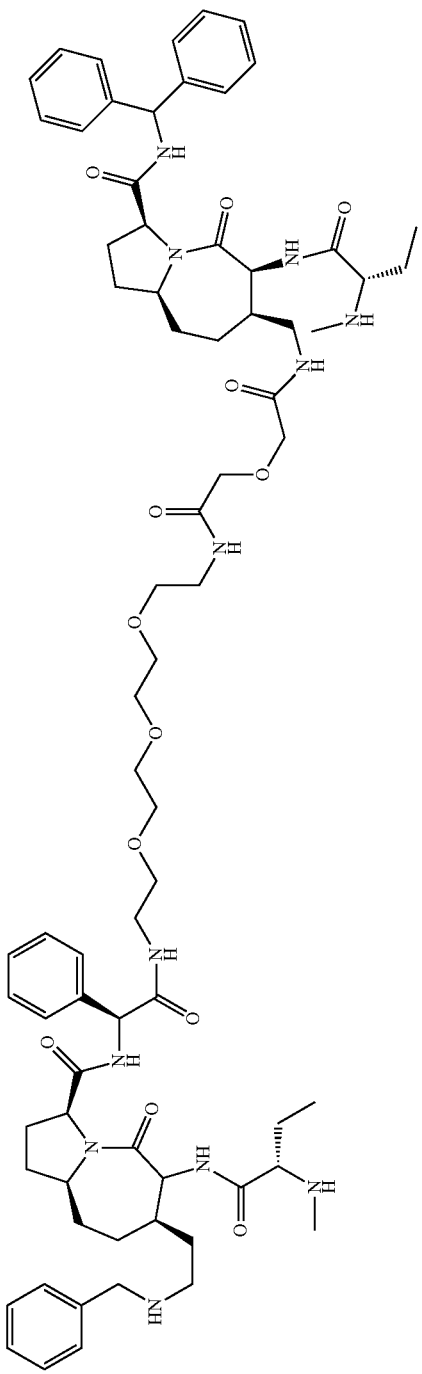

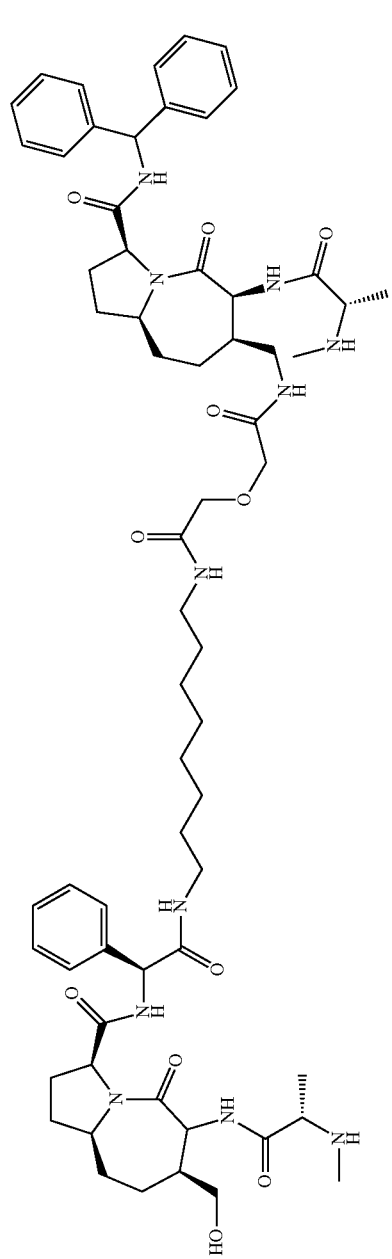
C125
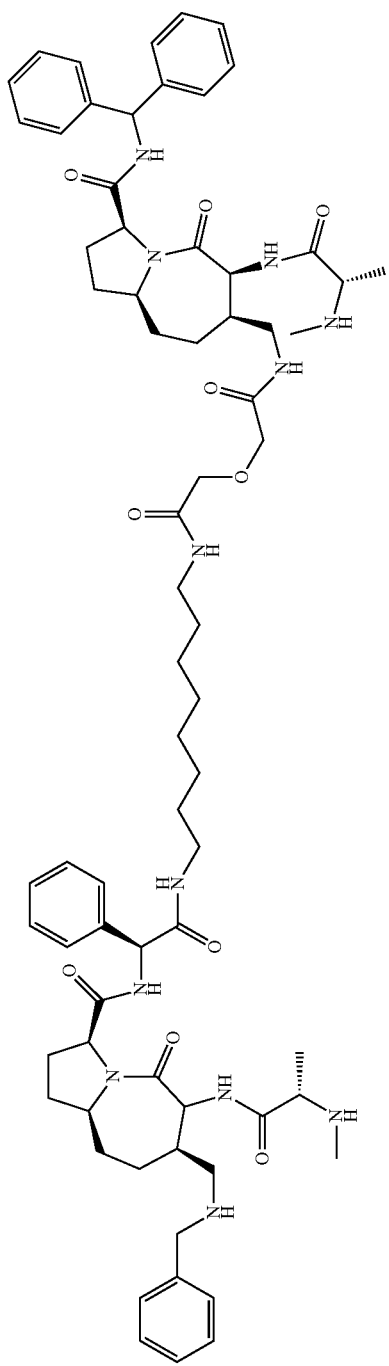
C126

C127
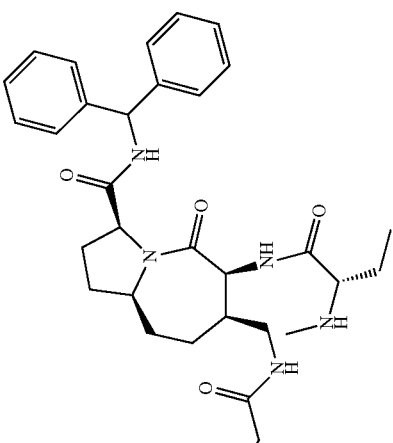
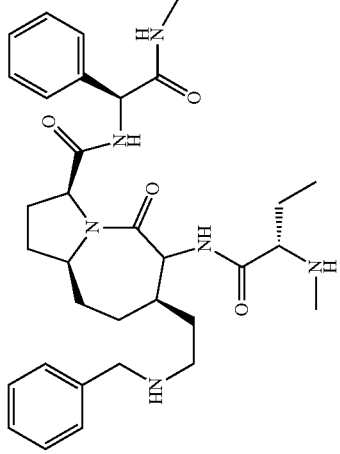

Preferred compounds of the invention are here below indicated and also disclosed in the examples.

Compound 28a (P1) where:
L is selected as linker L5 with n=2 taken from Table 1
$R_4$ is selected as hydrogen
m=1, n=2
Y is selected as OH
A is selected as $NR_1R_2$ where $R_1$ is hydrogen and $R_2$ is $C_1$ alkyl
B is selected as $C_2$ alkyl.

Compound 29a (P2) where:
L is selected as linker L5 with n=2 taken from Table 1
$R_4$ is selected as hydrogen
m=1, n=2
Y is selected as $NR_5R_6$ where $R_5$ is hydrogen and $R_6$ is $CH_2$Phe
A is selected as $NR_1R_2$ where $R_1$ is hydrogen and $R_2$ is $C_1$ alkyl
B is selected as $C_2$ alkyl.

Compound 30a (P3) where:
L is selected as linker L19 taken from Table 1
$R_4$ is selected as hydrogen
m=1, n=2
Y is selected as OH
A is selected as $NR_1R_2$ where $R_1$ is hydrogen and $R_2$ is $C_1$ alkyl ($CH_3$)
B is selected as $C_2$ alkyl.

Compound 30b (P9) where:
L is selected as linker L55 taken from Table 1
$R_4$ is selected as hydrogen
m=1, n=2
Y is selected as OH
A is selected as $NR_1R_2$ where $R_1$ is hydrogen and $R_2$ is $C_1$ alkyl ($CH_3$)
B is selected as $C_2$ alkyl.

Compound 30c (P7) where:
L is selected as linker L51 taken from Table 1
$R_4$ is selected as hydrogen
m=1, n=2
Y is selected as OH
A is selected as $NR_1R_2$ where $R_1$ is hydrogen and $R_2$ is $C_1$ alkyl ($CH_3$)
B is selected as $C_2$ alkyl.

Compound 30d (P5) where:
L is selected as linker L27 with n=2 taken from Table 1
$R_4$ is selected as hydrogen
m=1, n=2
Y is selected as OH
A is selected as $NR_1R_2$ where $R_1$ is hydrogen and $R_2$ is $C_1$ alkyl ($CH_3$)
B is selected as $C_2$ alkyl.

Compound 34a (P11) where:
LL is selected as L95
A is selected as $NR_1R_2$ where $R_1$ is selected as hydrogen and $R_2$ is selected as $C_1$ alkyl ($CH_3$)
B is selected as $C_2$ alkyl
$R_4$ is selected as hydrogen
Y is selected as OH
m=1, n=2
X is selected as $NR_7R_8$ with $R_7$ selected as hydrogen and $R_8$ selected as substituted C1 alkyl with two aryl groups
Z is selected as Compound 35a (P13) where:
LL is selected as L95
A is selected as $NR_1R_2$ where $R_1$ is selected as hydrogen and $R_2$ is selected as $C_1$ alkyl ($CH_3$)
B is selected as $C_2$ alkyl
$R_4$ is selected as hydrogen
Y is selected as OH
m=1, n=2
X is selected as $NR_7R_8$ with $R_7$ selected as hydrogen and $R_8$ selected as substituted C1 alkyl with two aryl groups
Z is selected as Compound 36a (P15) where:
LL is selected as L88 where n=3
A is selected as $NR_1R_2$ where $R_1$ is selected as hydrogen and $R_2$ is selected as $C_1$ alkyl ($CH_3$)
B is selected as $C_2$ alkyl
$R_4$ is selected as hydrogen
Y is selected as OH
m=1, n=2
X is selected as $NR_7R_8$ with $R_7$ selected as hydrogen and $R_8$ selected as substituted C1 alkyl with two aryl groups
Z is selected as $NR_7$ with $R_7$ selected as hydrogen.

The compounds of this invention may be prepared using experimental methods known to those skilled in the art, and according to the methods and reactions described in details in the experimental section of the present description.

The compounds of formula (I) and (II) induce apoptosis as standalone treatments, and also potentiate the induction of apoptosis as a response to proapoptotic signals.

Thus, the compounds may sensitize cells to inducers of apoptosis, including cells that are resistant to these inducers.

These compounds can be used to induce or restore apoptosis in any disease that can be prevented, ameliorated or fully treated by induction or restoration of apoptosis.

Thus, the present invention also provides compositions and methods for targeting mammals characterized as overexpressing an IAP family protein member. In some embodiments, the diseased cells (such as cancer cells) show elevated expression levels of IAP proteins as compared to non-pathological counterparts (such as non-cancerous cells).

In other embodiments, the cells operationally confirm to possess elevated expression levels of IAP proteins due to their entering the apoptosis program and dying in response to an inhibiting effective amount of a compound of the invention, such response being at least in part due to their IAP protein function-dependent survival.

In another embodiment, the invention pertains to modulating an apoptosis associated state which is connected with one or more apoptosis modulators. Examples of apoptosis modulating agents include, but are not limited to, Fas/CD95, TRAMP, TNF R1, DR1, DR2, DR3, DR4, DR5, DR6, FADD, RIP, TNFa, Fas ligand, TRAIL, antibodies to TRAILR1 or TRAILR2, Bcl-2, p53, BAX, BAD, Akt, CAD, PI3 kinase, PP1, and caspase proteins in general. Preferred apoptosing modulators are inducers of apoptosis such as TNF or a TNF-related ligand, particularly a TRAMP ligand, a Fas/CD95 ligand, a TNFR-1 ligand, or TRAIL.

The compounds of formula (I) and (II) prevent or inhibit angiogenesis and disrupt blood vessel homeostasis during vascular development in pathological conditions as standalone treatments.

So according to another of its aspects, the present invention relates to the use of the compounds of formula for the preparation of medicaments to treat diseased cells, tissues, organs, or pathological conditions and/or disease states in an animal (for example, a mammalian subject including, but not limited to, humans and veterinary mammals), more specifically for the treatment and/or prophylaxis of cancer and related conditions, such as lymphoma, melanoma, glioma, glioblastoma, myeloma, insulinoma, hypercalcemia, leukaemia, neuroblastoma, sarcoma, polycythemia, thrombocytosis, Hodgkin's disease, macroglobulinemia; autoimmune diseases; inflammatory diseases; infections; hyperproliferative diseases; AIDS; neurodegenerative diseases; vascular diseases. In some embodiments, treated cancer cells are metastatic.

In other embodiments, treated cancer cells are resistant to common anticancer agents. Infections suitable for treatment with the compounds of the invention include, but are not limited to, infections caused by viruses, bacteria, fungi, mycoplasma, prions.

Endothelial cell-associated diseases suitable for treatment with the compounds of the invention include, but are not limited to, macular degeneration, rheumatoid arthritis, psoriasis, diabetic retinopathycorneal graft rejection, myocardial angiogenesis, telangiectasia, angiofibroma, wound granulation, atherosclerosis, scleroderma and hypertrophic scars.

According to another of its aspects, the present invention relates to pharmaceutical compositions comprising at least one of the compounds of formula (I) and (II).

According to another of its aspects, the present invention relates to combinations of an effective amount of a compound of formula (I) and (II) and at least one additional therapeutic agent (including, but not limited to, chemotherapeutics, apoptosis modulators, anti-angiogenetics, antimicrobials, antivirals, antifungals and anti-inflammatory agents).

A number of suitable anticancer agents are contemplated for use in the method of the present invention. Examples of chemotherapeutic compounds and anticancer therapies suitable for co-administration with compounds of formula (I) and (II) are known to those skilled in the art.

In preferred embodiments, anticancer agents comprise agents that induce or stimulate apoptosis. They include, but are not limited to, radiation therapies; TNF-related factors; kinase inhibitors; antisense molecules; antibodies; anti-estrogens; antiandrogens; COX-2 inhibitors; anti-inflammatory drugs; cancer chemotherapeutic drugs; cellular signalling molecules; ceramides and cytokines; staurosporine, and the like. Specific examples of anticancer agents suitable for co-administration with compounds of Formula (I) and (II) are known to those skilled in the art.

In still other embodiments, the composition and methods of the present invention provide a compound of Formula (I) and (II) and at least one anti-hyperproliferative or antineoplastic agent selected from alkylating agents, antimetabolites, and natural products (for example, plant- and/or animal-derived compounds).

In some embodiments, alkylating agents suitable for use in the present compositions and methods include, but are not limited to, nitrogen mustards; ethyleneimines and methylmelamines; alkyl sulfonates; nitrosoureas; triazenes. Specific examples of alkylating agents suitable for co-administration with compounds of Formula (I) and (II) are known to those skilled in the art.

In other embodiments, antimetabolites suitable for use in the present compositions and methods include, but are not limited to, folic acid analogues; pyrimidine analogues; purine analogues. Specific examples of antimetabolites suitable for co-administration with compounds of Formula (I) and (II) are known to those skilled in the art.

In still further embodiments, chemotherapeutic agents suitable for use in the present compositions and methods include, but are not limited to, vinca alkaloids; epipodophyllotoxins; antibiotics; enzymes; biological response modifiers; platinum coordinating complexes; anthracenediones; methylhydrazine derivatives; adrenocortical suppressants; adrenocorticosteroids; progestins; estrogens; androgens; antiandrogens; gonadotropin-releasing hormone analogues. Specific examples of chemotherapeutic agents suitable for co-administration with compounds of Formula (I) and (II) are known to those skilled in the art.

Any oncolytic agent that is routinely used in a cancer therapy context finds use in the composition and methods of the present invention. The U.S. FDA and international counterpart agencies to the U.S. FDA maintain formularies of oncolytic agents approved for use, whose listed members are for example suitable for co-administration with compounds of Formula (I and (II). Those skilled in the art will appreciate that the "product labels" required on all approved chemotherapeutics describe approved indications, dosing information, toxicity data, and the like, for the agents.

For a more detailed description of anticancer agents and other therapeutic agents suitable, for example, to be co-administered or associated with the compounds according to formula (I) and (II) of the present invention, those skilled in the art are referred to any number of instructive manuals including, but not limited to, the Physician's Desk Reference and to Goodman and Gilman's "Pharmaceutical Basis of Therapeutics" 11$^{th}$ Edition, Eds. Hardman et al., 2005.

According to another of its aspects, the present invention relates to a combination of an effective amount of a compound of formula (I) and (II) and at least one treatment for cancer, for instance, surgical intervention or radiotherapy.

Therefore the present invention also provides methods for administering a compound of formula (I) and (II) with radiation therapy. The invention is not limited by the types, amounts, or delivery and administration systems used to deliver the therapeutic dose of radiation to an animal.

The source of radiation can be external or internal to the animal. External radiation therapy is most common and involves directing a beam of high-energy radiation to a tumour site through the skin using, for instance, a linear accelerator. Internal radiation therapy involves implanting a radiation-emitting source inside the body at or near the tumour site, including the use of delivery systems that specifically target cancer cells.

The animal may optionally receive radiosensitizers or radioprotectors. Radiosensitizers enhance the killing of tumour cells. Radioprotectors protect healthy tissues from the harmful effect of radiation.

Any type of radiation may be administered to a patient, as long as its dosage is tolerated without unacceptable side effects. Suitable radiotherapies include ionizing/electromagnetic radiotherapy and particle beam radiation therapy.

The total dose of radiation administered to an animal is preferably about 0.01 Gray (Gy) to about 100 Gy. More preferably, about 10 Gy to about 65 Gy are administered during the course of the treatment. While in some embodiments a complete dose of radiation can be administered over the course of one day, the total dose is ideally fractionated and administered over several days. Desirably, radiotherapy is administered at intervals of at least about 3 days, in a period of 1 to 8 weeks.

Accordingly, a daily dose of radiation will comprise approximately 1-5 Gy, and preferably 1-2 Gy. The daily dose of radiation should be sufficient to induce destruction of the targeted cells, but days of rest from therapy should be included. For example, radiation desirably is administered on 5 consecutive days, and not administered for 2 days, for each week of treatment, thereby allowing 2 days of rest per week. These exemplary radiotherapy administration schedules are not intended, however, to limit the present invention.

In some embodiments of the present invention, a compound of Formula (I) and (II) and one or more therapeutic or anticancer agents are administered to an animal under one or more of the following conditions: at different periodicities, at different durations, at different concentrations, by different administration routers, and so on. In some embodiments, the compound is administered prior to the therapeutic or anticancer agent, i. e. 0.5, 1, 2, 3, 4, 5, 10, 12, or 18 hours, 1, 2, 3, 4, 5, or 6 days, 1, 2, 3 or 4 weeks prior to the administration of the therapeutic or anticancer agent. In other embodiments, the compound is administered after the therapeutic or anticancer agent, i.e. 0.5, 1, 2, 3, 4, 5, 10, 12, or 18 hours, 1, 2, 3, 4, 5, or 6 days, 1, 2, 3 or 4 weeks after the administration of the therapeutic or anticancer agent. In some embodiments, the compound and the therapeutic or anticancer agent are administered concurrently but on different schedules, i.e. the compound is administered daily while the therapeutic or anticancer agent is administered once a week, once every two weeks, once every three weeks, or once every four weeks. In other embodiments, the compound is administered once a week while the therapeutic or anticancer agent is administered daily, once a week, once every two weeks, once every three weeks, or once every four weeks.

Pharmaceutical compositions within the scope of this invention include all compositions wherein the compounds of the present invention are comprised in an amount which is effective to achieve its intended purpose. While individual needs vary, determination of optimal ranges of effective amounts of each component is within the skill of the art. Typically, the compounds may be administered to mammals, and in particular humans, orally at a dose of 0.0025 to 50 mg/kg, or an equivalent amount of the pharmaceutically acceptable salt thereof, per day of the body weight of the mammal being treated for disorders responsive to induction or restoration of apoptosis. Preferably, about 0.01 to about 10 mg/kg is orally administered to treat, ameliorate, or prevent such disorders. For intramolecular injections, the dose is generally one half of the oral dose. For example, a suitable i.m. dose would be about 0.0025 to about 25 mg/kg, and most preferably, from about 0.01 to about 5 mg/kg. In a topical formulation, the compound may be present at a concentration of about 0.01 to 100 mg per gram of carrier. In a preferred embodiment, the compound is present at a concentration of about 0.07-1.0 mg/mL, more preferably, about 0.1-0.5 mg/mL, most preferably, about 0.4 mg/mL.

In addition to administering the compound as a raw chemical, the compounds of the invention may be administered as part of a pharmaceutical preparation containing suitable pharmaceutically acceptable carriers comprising excipients and auxiliaries which facilitate processing of the compounds into preparations which can be used pharmaceutically. Preferably, the preparations, particularly those preparations which can be administered orally or topically and which can be used for the preferred type of administration, such as tablets, dragées, slow release lozenges and capsules, mouth rinses and washes, gels, liquid suspensions, hair rinses, hair gels, shampoos and other preparations which can be administered rectally, such as suppositories, as well as suitable solutions for administration by injection, topically or orally, contain from about 0.01 to 99 percent, preferably from 0.25 to 75 percent of active compound(s), together with the excipient.

The compounds and pharmaceutical compositions thereof may be administered by any means that achieve their intended purpose. For example, administration may be by parenteral, subcutaneous, intravenous, intramuscular, intraperitoneal, transdermal, buccal, intratechal, intracranial, intranasal or topical routes. Alternatively, or concurrently, administration may be by the oral route. The dosage administered will be dependent upon the age, health, and weight of the recipient, kind of concerned treatment, if any, frequency of treatment, and the nature of the desired effect.

The pharmaceutical preparations of the present invention are manufactured in a manner which is itself known, for example, by means of conventional mixing, granulating, dragée-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragée cores.

Suitable excipients are, in particular, filters such as saccharides, cellulose preparations and/or calcium phosphates, as well as binders as starch paste, using, for example, starch, gelatine, cellulose, and/or polyvinyl pyrrolidone. If desired, disintegrating agents may be added such as the above mentioned starches, cross-linked polyvinyl pyrrolidone, agar, or alginic acid or a salt thereof. Auxiliaries are, above all, flow-regulating agents and lubricants, for example, silica, talc, stearic acid or salts thereof, and/or polyethylene glycol. Dragée cores are provided with suitable coatings which, if desired, are resistant to gastric juices. In order to produce coatings resistant to gastric juices, solutions of suitable cellulose are used.

Other pharmaceutical preparations which can be used orally include push-fit capsule made of gelatine, as well as soft, sealed capsules made of gelatine and a plasticizer such as glycerol or sorbitol. The push-fit capsules can contain the active compounds in the form of granules which may be mixed with fillers, binders and/or lubricants and, optionally, stabilizers. In soft capsules, the active compounds are preferably dissolved or suspended in suitable liquids, such as fatty oils, or liquid paraffin. In addition, stabilizers may be added.

Possible pharmaceutical preparations which can be used rectally include, for example, suppositories, which consist of a combination of one or more active compounds with a suppository base. Suitable suppository bases are, for example, natural or synthetic triglycerides, or paraffin hydrocarbons.

Suitable formulations for parenteral administration include aqueous solutions of the active compounds in water-soluble form. In addition, suspensions of the active compounds as appropriate oily injection suspensions may be administered. Suitable lipophilic solvents or vehicles include fatty oils or synthetic fatty acid esters. Aqueous injections may contain substances which increase the viscosity of the suspension, such as sorbitol and/or dextran. Optionally, the suspension may also contain stabilizers.

The topical compositions of this invention are formulated preferably as oils, creams, lotions, ointments and the like by choice of appropriate carriers. Suitable carriers include vegetable or mineral oils, white soft paraffin, fats and high molecular weight alcohol. The preferred carriers are those in which the active ingredient is soluble.

Creams are preferably formulated from a mixture of mineral oil, self-emulsifying beeswax and water in which mixture the active ingredient, dissolved in a small amount of an oil is admixed. A typical example includes about 40 parts water, about 20 parts beeswax, about 40 parts mineral oil and about 1 part almond oil.

Ointments may be formulated by mixing a solution of the active ingredient in a vegetable oil with warm soft paraffin and allowing the mixture to cool. A typical example of such an ointment includes about 30% almond oil and about 70% white soft paraffin by weight.

Lotions may be conveniently prepared by dissolving the active ingredient, in a suitable high molecular weight alcohol.

The following examples are illustrative, but not limiting, of the method and compositions of the present invention. Other suitable modifications and adaptations of the variety of conditions and parameters normally encountered in clinical therapy and which are obvious to the those skilled in the art are within the scope and the spirit of the invention.

The invention is now disclosed by way of non-limiting examples.

EXPERIMENTAL SECTION

Example 1

Synthesis of Monomeric Intermediates with [4.3.0] and [5.3.0] Bicyclic Lactam Systems Title intermediates may be in general prepared according to a synthetic process outlined in Scheme 1.

b) hydrogenation of the isoxazolidine ring and coupling with the suitable protected aminoacid derivative, compounds 4;
c) hydrolysis of the methyl ester, compounds 5.

Intermediates 5 are the synthetic gateway to functionalized homodimeric and heterodimeric bivalent Smac mimetics.

1.1 General Methods:

$^1$H-NMR spectra were recorded on Bruker Avance in $CDCl_3$, $CD_3OD$ or $D_2O$ as solvent at 400 MHz or 600 MHz. $^{13}$C-NMR spectra were recorded in $CDCl_3$, $CD_3OD$ or $D_2O$ as solvent at 100 MHz or 125 MHz. Coupling constants are given in hertz and are rounded to the nearest 0.1 Hz. Purifications were carried out either by flash chromatography on silica gel (particle size 60 μm, 230-400 mesh), Kieselgel, or by Biotage™ flash chromatography [Biotage columns Si-12-M (150×12 mm; silica gel (40-63 μm), flow rate 12 ml/min; and Si-25-M columns (150×25 mm; silica gel (40-63 μm), flow rate 25 ml/min], or by Biotage™ $C_{18}$ reverse phase chromatography [Biotage columns $C_{18}$HS (150×12 mm; KP—$C_{18}$—HS (35-70 μm), flow rate 25 ml/min]. Final products were purified by $C_{18}$ reverse phase semi-preparative HPLC using either a Waters X-Terra $RP_{18}$

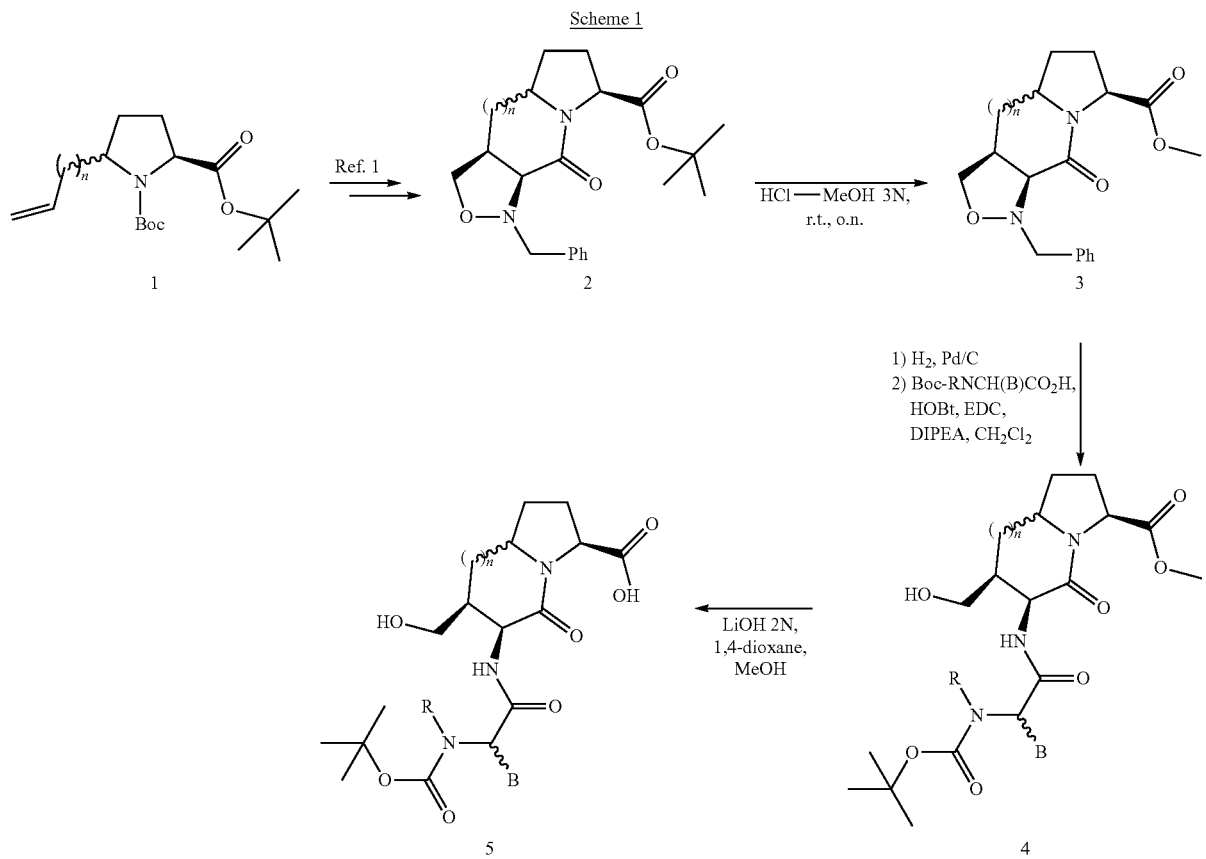

Scheme 1

Intermediates 2 are easily prepared using a procedure already reported in the literature (Leonardo Manzoni, et. al., *J. Org. Chem.* 2005, 70, 4124). Compounds of general structure 5 were prepared efficiently using standard methods, comprising the following stages:

a) Trans-esterification from tert-butyl-ester to methyl ester, compounds 3;

ODB column (19 mm×10.0 cm, 5 μm) or a Supelco Ascentis $C_{18}$ column (21.2 mm×15.0 cm, 5 pin). Solvents were distilled and dried according to standard procedures, and reactions requiring anhydrous conditions were performed under nitrogen or argon. Solvents for the reactions were used directly from the bottle if not specified. Optical rotations $[\alpha]_D^{20}$ were measured in cells of 1 dm pathlength and 1 mL capacity with Perkin Elmer 241 polarimeter. LC-MS data were collected with an Agilent 1100 HPLC connected to a Brucker Esquire 3000+ ion trap nass spectrometer through an ES interface.

1.2 General Procedure for the Synthesis of Compounds 3

Compounds 2 (5.3 mmol) were dissolved in 26.5 mL of a 3N methanolic HCl solution. The resulting mixture was stirred at room temperature for 48 hours and then condensed under reduced pressure. The crude product was redissolved in $CH_2Cl_2$ and washed once with a saturated solution of $NaHCO_3$. The organic layer was dried over $Na_2SO_4$, filtered and the solvent was removed under reduced pressure. Finally, the crude product was purified by flash chromatography.

Compound 3a was synthesized by the general procedure described above.

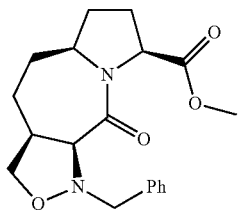

3a

3a. Biotage™ $C_{18}$ reverse phase eluant conditions: from 90% $H_2O$ and 10% $CH_3CN$ to 100% $CH_3CN$. Yield 90% (1.65 g, MW 344.17, 4.79 mmol) of pure 3a as an amorphous white solid. Analytical characterization: $[\alpha]_D^{20}$ −142.0 (c 1.15, MeOH); $^1$H-NMR (400 MHz, $CDCl_3$): δ: 7.44 (d, J=6.8 Hz, 2H), 7.35-7.23 (m, 3H), 4.74 (dd, J=7.2, 4.4 Hz, 1H), 4.46 (d, J=13.6 Hz, 1H), 4.13 (dd, J=9.2, 7.6 Hz, 1H), 3.87 (m, 1H), 3.74, (s, 3H), 3.65 (d, J=13.6 Hz, 1H), 3.52 (dd, J=7.6, 6.0 Hz, 1H), 3.18 (d, J=10.0 Hz, 1H), 2.78 (m, 1H), 2.30 (m, 1H), 2.14-2.01 (m, 3H), 1.95-1.63 (m, 4H); $^{13}$C-NMR (100 MHz, $CDCl_3$): δ: 172.6, 168.8, 137.4, 129.0, 128.2, 127.2, 73.2, 71.4, 61.4, 59.9, 58.8, 52.4, 44.9, 33.9, 33.3, 32.2, 27.4; ESI-MS: m/z 344.9 [M+H]$^+$, 711.0 [M+Na]$^+$.

1.3 General Procedure for the Synthesis of Compounds 4

Simultaneous N—O hydrogenolytic cleavage and benzyl deprotection on compounds 3 was performed using H-Cube™ continuous-flow hydrogenation reactor. The methyl ester 3 (4.8 mmol) was dissolved in 85:15 EtOH/$H_2O$ (190 mL, ~0.025 M final concentration) and reduced over 10% Pd/C catalyst (hydrogen pressure: 10 bar, T=85° C., flow: 0.7 mL/min). The reaction was monitored by LC-MS. After reaction completion the solvent was evaporated under reduced pressure. The crude aminoalcohol was obtained in quantitative yield and used without any further purification.

Dry DIPEA (2 equiv) was added to a solution of N-Boc protected aminoacid (1.2 equiv), EDC*HCl (1.2 equiv) and HOBt (1.2 equiv) in dry $CH_2Cl_2$ at room temperature under a nitrogen atmosphere. The solution was stirred for 10 min before adding a solution of the aminoalcohol (1 equiv) in $CH_2Cl_2$ (final concentration of aminoalcohol: 0.1 M). The reaction mixture was stirred at room temperature and monitored by LC-MS. After reaction completion, the solution was diluted with $CH_2Cl_2$ and washed once with 5% citric acid and saturated $NaHCO_3$. The organic layer was dried over $Na_2SO_4$ and evaporated under reduced pressure. The crude product was purified by flash chromatography.

Compound 4a was synthesized by the general procedure described above starting from compound 3a (1.65 g, 4.79 mmol) and N-Boc, N-Me ethylglycine.

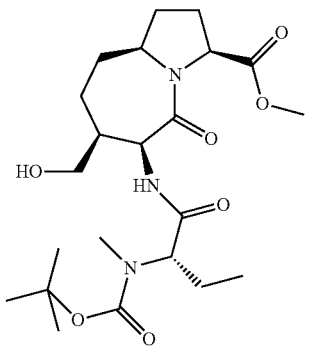

4a

4a. Biotage™ $C_{18}$ reverse phase eluant conditions: from 90% $H_2O$ and 10% $CH_3CN$ to 100% $CH_3CN$. Yield 82% (1.78 g, MW 455.55, 3.91 mmol) of pure 4a as an amorphous white solid. Analytical characterization: $[\alpha]_D^{20}$ −88.2 (c 0.5, $CHCl_3$). $^1$H-NMR (400 MHz, $CDCl_3$): δ: 7.51 (d, J=5.2 Hz, 1H), 4.62 (dd, J=3.8, 4.1 Hz, 1H), 4.50 (t, J=7.6 Hz, 1H), 4.42 (bs, 1H), 3.92 (dd, J=6.6, 14.5 Hz, 1H), 3.77 (s, 3H), 3.70 (d, J=12.3 Hz, 1H), 3.39 (dd, J=3.2, 12.3 Hz, 1H), 2.86 (s, 3H), 2.30 (m, 1H), 2.14-1.73 (m, 9H), 1.63 (m, 1H), 1.49 (s, 9H), 0.94 (t, J=7.3 Hz, 3H); $^{13}$C-NMR (100 MHz, $CDCl_3$): δ: 173.1, 172.4, 170.3, 80.5, 64.4, 60.9, 60.6, 58.8, 54.0, 52.4, 41.6, 33.6, 32.8, 31.3, 30.4, 28.4, 27.7, 21.6, 10.7; ESI-MS: m/z 456.6 [M+H]$^+$, 478.5 [M+Na]$^+$.

Compound 4b was synthesized by the general procedure described above starting from compound 3a (1.65 g, 4.79 mmol) and N-Boc ethylglycine.

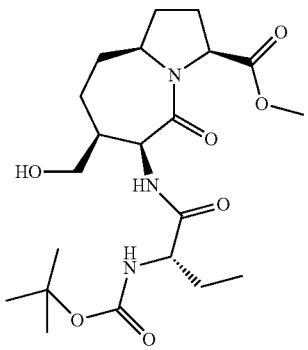

4b

4b. Biotage™ $C_{18}$ reverse phase eluant conditions: from 90% $H_2O$ and 10% $CH_3CN$ to 100% $CH_3CN$. Yield 70% (1.48 g, MW 441.25, 3.35 mmol) of pure 4b as an amorphous white solid. Analytical characterization: $[\alpha]_D^{20}$: −146.5 (c 0.71, MeOH); $^1$H-NMR (400 MHz, $CDCl_3$): δ: 7.53 (d, J=3.5 Hz, 1H), 5.07 (d, J=7.6 Hz, 1H), 4.56 (dd, J=8.5, 4.0 Hz, 1H), 4.48 (dd, J=10.0 Hz, 7.5, 1H), 4.03 (m, 1H), 3.89 (m, 1H), 3.73 (s, 3H), 3.66 (m, 1H), 3.31 (dd, J=12.0, 3.0 Hz, 1H), 2.30-2.23 (m, 1H), 2.15-1.97 (m, 4H), 1.90-1.75 (m, 4H), 1.69-1.58 (m, 2H), 1.43 (s, 9H), 0.95 (t, 7.5 Hz, 3H); $^{13}$C-NMR (100 MHz, $CDCl_3$): δ: 173.9, 172.4, 170.2, 155.6, 80.2, 64.3, 60.6, 58.8, 56.6, 54.1, 52.3, 41.5, 32.8, 28.2, 25.7, 10.1; ESI-MS: m/z 441.9 [M+H]$^+$, 463.9 [M+Na]$^+$.

1.4 General Procedure for the Synthesis of Compounds 5

A 2 N aqueous LiOH solution (7.0 equiv) was slowly added to an iced cooled, stirred solutions of methyl esters 4 (1.0 equiv) in 1,4-dioxane (0.25 M concentration for 4). The reaction mixture was then stirred at room temperature until complete hydrolysis of the starting material. After reaction completion, the cloudy solution was concentrated, the residue was taken up in CH$_2$Cl$_2$ and water, and acidified to pH≈3 with aqueous 2N solution of HCl. The mixture was extracted with CH$_2$Cl$_2$, the combined organic layer was dried over Na$_2$SO$_4$, and then the solvent was removed under reduced pressure. The crude carboxylic acid, obtained as amorphous white solids, did not require further purification.

Compound 5a was synthesized by the general procedure described above starting from compound 4a (4.55 g, 10.0 mmol).

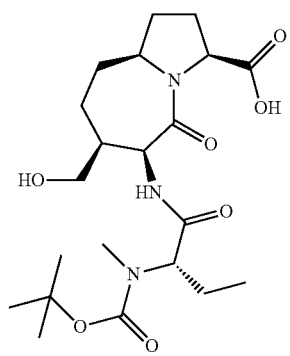

5a

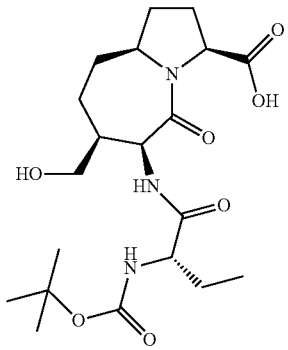

5b

5a. Quantitative yield (4.41 g, MW 441.20, 10.0 mmol). Analytical characterization: [α]$_D^{20}$ −95.0 (c 0.50, MeOH); $^1$H-NMR (400 MHz, CDCl$_3$): δ: 7.59 (bs, 1H), 4.56 (d, J=7.7 Hz, 1H), 4.45 (m, 2H), 3.84 (dd, J=8.2, 17.5 Hz, 1H), 3.59 (d, J=12.9 Hz, 1H), 3.35 (dd, J=3.1, 11.8 Hz, 1H), 2.79 (s, 3H), 2.23-1.58 (m, 11H), 1.41 (s, 9H), 0.85 (t, J=7.2 Hz, 3H); $^{13}$C-NMR (100 MHz, CDCl$_3$): δ: 173.5, 173.0, 171.8, 80.8, 64.4, 61.1, 60.5, 59.2, 54.2, 41.2, 33.8, 33.0, 31.1, 27.0, 21.6, 10.7; ESI-MS: m/z 442.3 [M+H]$^+$, 464.3 [M+Na]$^+$.

Compound 5b was synthesized by the general procedure described above starting from compound 4b (4.41 g, 10.0 mmol).

5b. Quantitative yield (4.27 g, MW 427.23, 10.0 mmol). Analytical characterization: [α]$_D^{20}$ −123.0 (c 0.61, MeOH); $^1$H-NMR (400 MHz, CDCl$_3$): δ: 7.76 (d, J=6.5 Hz, 1H), 7.20 (bs, 1H), 5.33 (m, 1H), 4.56 (m, 2H), 4.09 (m, 1H), 3.91 (d, J=7.5 Hz, 1H), 3.43 (d, J=9.5 Hz, 1H), 2.26 (d, J=6.5 Hz, 1H), 2.12-1.62 (m, 10H), 1.42 (s, 9H), 0.95 (t, J=6.5 Hz, 3H); $^{13}$C-NMR (100 MHz, CDCl$_3$): δ: 173.8, 173.5, 171.0, 156.0, 80.4, 64.3, 60.8, 60.4, 59.0, 56.5, 54.0, 41.2, 33.4, 32.9, 31.0, 28.2, 27.6, 25.7, 10.1; ESI-MS: m/z 427.9 [M+H]$^+$, 877.8 [2M+Na]$^+$.

Example 2

Synthesis of Monomeric, Linker-Functionalized [4.3.0] and [5.3.0] Bicyclic Lactam Intermediates Some title intermediates may be prepared according to a synthetic process outlined in Scheme 2, comprising the following reactions:
  a) coupling of the free acid of compounds 5 with suitable amines;
  b) transformation of the 4-hydroxy group into an azide, followed by reduction to afford a 4-amino compounds 11;
  c) coupling of compounds 11 with acids or N-protected aminoacids.

The general synthesis of key intermediates is showed in Scheme 2.

Scheme 2

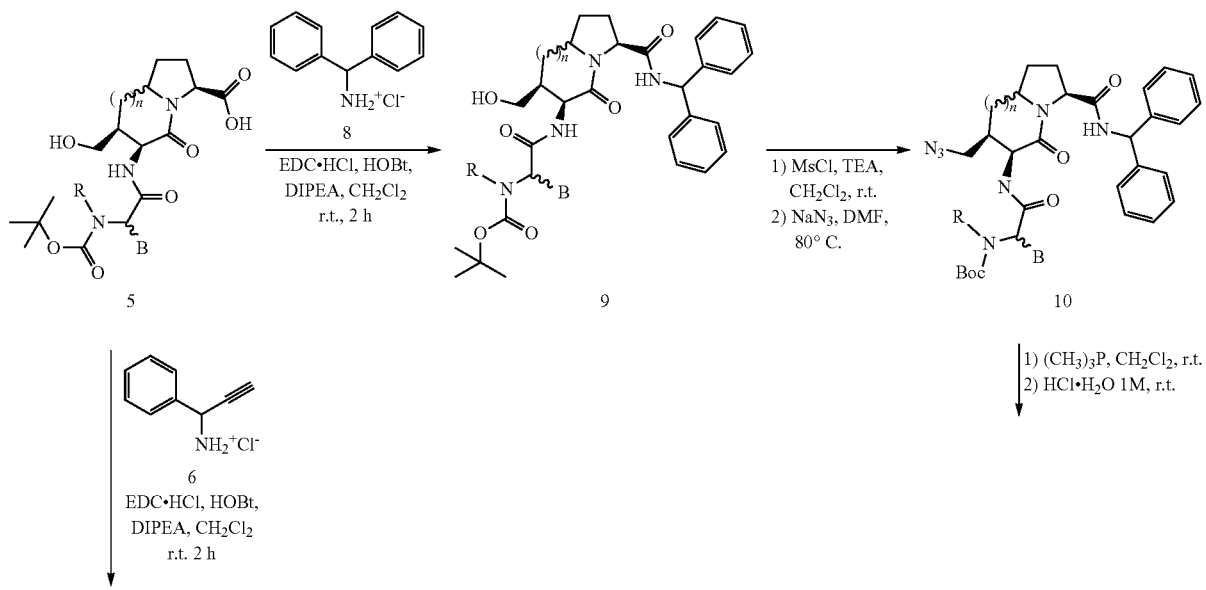

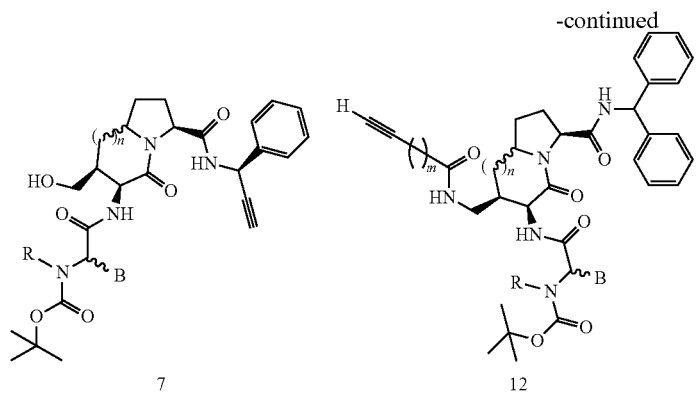
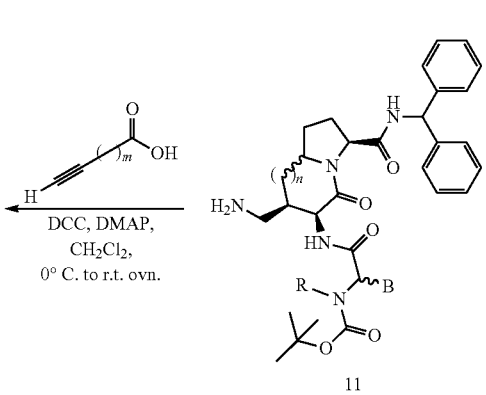

2.1 General Procedure for the Synthesis of Compounds 7

EDC*HCl (1.2 equiv), HOBt (1.2 equiv) and DIPEA (4.0 equiv) were sequentially added to a stirred solution of 5 (1 equiv) in CH$_2$Cl$_2$. The reaction mixture was left stirring at room temperature for 15 min, and then added to a stirred solution of 6 (1.25 equiv) in dry CH$_2$Cl$_2$ (final concentration of 5~0.05 M). The reaction mixture was stirred at room temperature overnight and then, after reaction completion, the solvent was removed under reduced pressure. The crude product was diluted with EtOAc and sequentially washed with 5% aqueous citric acid, saturated aqueous sodium bicarbonate and brine. The organic layer was dried over Na$_2$SO$_4$, and then the solvent removed under reduced pressure. The residue was purified by Biotage™ flash chromatography.

Compound 7a was synthesized by the general procedure described above starting from compound 5a (500 mg, 1.14 mmol).

2.2 General Procedure for the Synthesis of Compounds 9

EDC*HCl (1.2 equiv), HOBt (1.2 equiv) and DIPEA (4.0 equiv) were sequentially added to a stirred solution of 5 (1 equiv) in CH$_2$Cl$_2$. The reaction mixture was left stirring at room temperature for 15 min, and then added to a stirred solution of 8 (1.25 equiv) in dry CH$_2$Cl$_2$ (final concentration of 5~0.1 M). The reaction mixture was stirred at room temperature overnight and then, after reaction completion, the solvent was removed under reduced pressure. The crude product was diluted with EtOAc and sequentially washed with 5% aqueous citric acid, saturated aqueous sodium bicarbonate and brine. The organic layer was dried over Na$_2$SO$_4$, and then the solvent removed under reduced pressure. The residue was purified by Biotage™ flash chromatography.

Compound 9a was synthesized by the general procedure described above starting from compound 5a (4.41 g, 10.0 mmol).

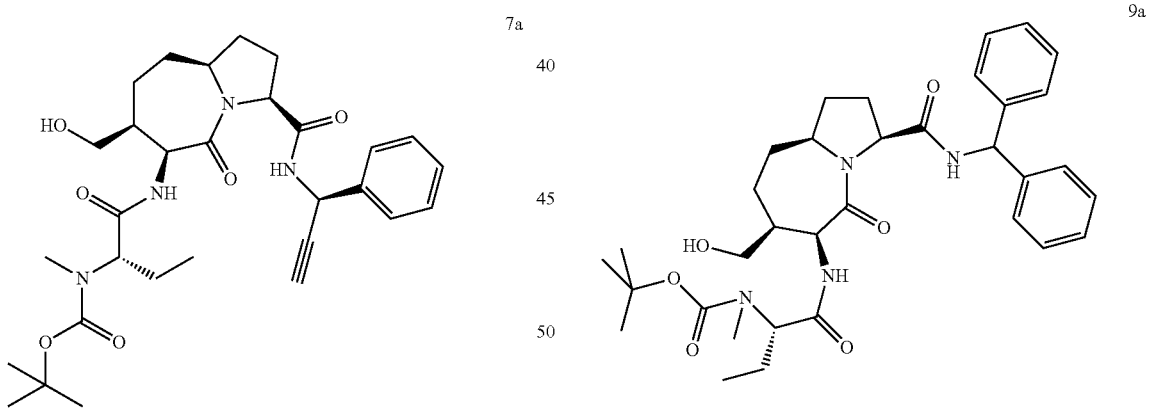

7a. Biotage™ eluant conditions: 50% of EtOAc and 50% of petroleum ether to 100% of EtOAc. Yield 94% (592 mg, MW 554.69, 1.07 mmol) of pure 7a. Analytical characterization: $[\alpha]_D^{20}$ −116 (c 1.5, CHCl$_3$); $^1$H-NMR (400 MHz, CDCl$_3$): δ: 7.65 (d, J=7.6 Hz, 1H), 7.36 (m, 3H), 7.20 (m, 3H), 5.87 (d, J=6.8 Hz, 1H), 4.61 (d, J=6.0 Hz, 1H), 4.42-4.30 (m, 2H), 3.67 (m, 1H), 3.47 (d, J=11.6 Hz, 1H), 3.14 (d, J=12.0 Hz, 1H), 2.78 (s, 3H), 2.42 (s, 1H), 2.36 (m, 1H), 2.18 (m, 1H), 2.00-1.70 (m, 4H), 1.70-1.55 (m, 3H), 1.44 (s, 9H), 0.97 (m, 1H), 0.84 (m, 4H); $^{13}$C-NMR (100 MHz, CDCl$_3$): δ: 171.7, 138.9, 128.9, 126.8, 73.0, 64.1, 60.8, 60.2, 58.7, 53.6, 44.4, 41.5, 34.6, 33.2, 31.0, 30.0, 28.4, 25.4, 21.4, 10.6. ESI-MS: m/z 555.4 [M+H]$^+$, 577.3 [M+Na]$^+$.

9a Biotage™ eluant conditions: from 90% of H$_2$O and 10% CH$_3$CN to 100% of CH$_3$CN. Yield 83% (5.04 g, MW 606.75, 8.30 mmol) of pure 9a. Analytical characterization: $[\alpha]_D^{20}$ −85.3 (c 1.00, CHCl$_3$). $^1$H-NMR (400 MHz, CDCl$_3$): δ: 7.87 (d, J=6.8 Hz, 1H), 7.45 (bs, 1H), 7.29-7.10 (m, 10H), 6.15 (d, J=8.6 Hz, 1H), 4.68 (d, J=7.5 Hz, 1H), 4.46 (bs, 1H), 4.39 (t, J=8.2 Hz, 1H), 3.71 (dd, J=17.3, 8.6 Hz, 1H), 3.53 (d, J=12.2 Hz, 1H), 3.20 (dd, J=3.2, 12.2 Hz, 1H), 2.79 (s, 3H), 2.38 (m, 1H), 2.20 (m, 1H), 1.98-1.67 (m, 7H), 1.42 (s, 9H), 1.10-1.02 (m, 2H), 0.85 (t, J=7.1 Hz, 3H); $^{13}$C-NMR (100 MHz, CDCl$_3$): δ: 173.1, 171.9, 169.5, 142.2, 141.2, 128.7, 128.5, 127.4, 127.3, 80.5, 64.2, 61.2, 60.2, 58.9, 56.8, 53.7, 41.7, 34.6, 33.2, 31.1, 30.2, 28.4, 25.6, 21.4, 10.7. ESI-MS: m/z 607.5 [M+H]$^+$, 629.5 [M+Na]$^+$.

Compound 9b was synthesized by the general procedure described above starting from compound 5b (4.27 g, 10.0 mmol).

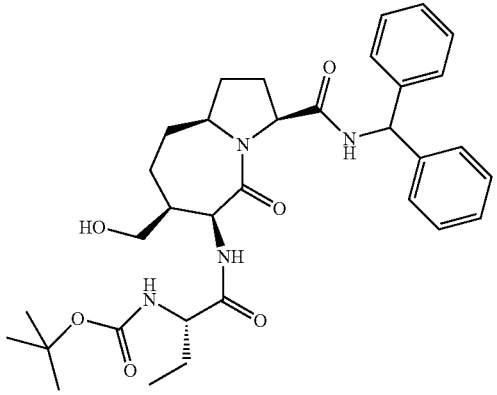

9b

9b Biotage™ eluant conditions: from 90% of H₂O and 10% CH₃CN to 100% of CH₃CN. Yield 76% (4.5 g, MW 592.73, 7.6 mmol) of pure 9b. Analytical characterization: $[\alpha]_D^{20}$ −125.0 (c 1.48, MeOH); ¹H-NMR (400 MHz, CDCl₃): δ: 7.97 (d, J=8.4 Hz, 1H), 7.62 (d, J=7.2 Hz, 1H), 7.35-7.15 (m, 10H), 6.21 (d, J=8.8 Hz, 1H), 5.17 (d, J=7.2 Hz, 1H), 4.73 (d, J=7.6 Hz, 1H), 4.49 (m, 1H), 4.10 (m, 1H), 3.77 (dd, J=17.6, 8.5 Hz, 1H), 3.67 (d, J=10.8 Hz, 1H), 3.28 (dd, J=12.0, 3.2 Hz, 1H), 2.38 (dd, J=12.0, 6.8 Hz, 1H), 2.23 (m, 1H), 2.10-1.95 (m, 2H), 1.89-1.55 (m, 5H), 1.43 (s, 9H), 1.30-1.10 (m, 2H), 0.96 (t, 7.2 Hz, 3H); ¹³C-NMR (100 MHz, CDCl₃): δ: 173.9, 171.7, 171.1, 169.6, 155.8, 142.0, 141.2, 128.6, 128.4, 127.4, 127.2, 126.9, 80.3, 64.2, 61.2, 58.9, 56.8, 53.9, 41.5, 34.0, 33.2, 31.1, 28.3, 25.8, 25.6, 21.0, 14.2, 10.2. ESI-MS: m/z 593.1 [M+H]⁺, 615.1 [M+Na]⁺.

2.3 General Procedure for the Synthesis of Compounds 10

Dry TEA (4.0 equiv) and MsCl (4.0 equiv) were sequentially added to a stirred solution of compounds 9 (1.0 equiv) in dry CH₂Cl₂ (≈0.25 M concentration for 9) under argon at 0° C. The reaction mixture was stirred at room temperature overnight.

After reaction completion, the resulting mixture was diluted with CH₂Cl₂ and washed with a saturated NH₄Cl solution. The organic layer was dried over Na₂SO₄, and then the solvent removed under reduced pressure. The crude product was dissolved in dry DMF (≈0.1 M concentration) under argon at room temperature, and then NaN₃ (10.0 equiv) was added. The reaction mixture was stirred at 80° C. overnight. After reaction completion, the solvent was removed under reduced pressure, the crude product was diluted with CH₂Cl₂ and washed with water. The organic layer was dried over Na₂SO₄, and then the solvent removed under reduced pressure. The crude product was purified by flash chromatography.

Compound 10a was synthesized by the general procedure described above starting from compound 9a (1.21 g, 2.0 mmol).

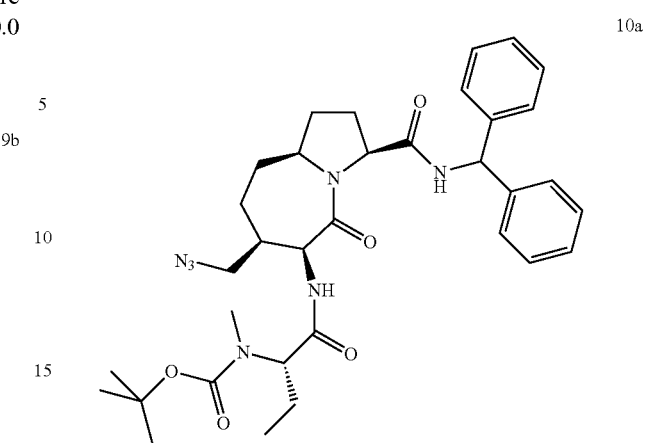

10a

10a. Eluant mixture: Petroleum ether/EtOAc 30:70. Yield 64% (810 mg, MW 631.75, 1.28 mmol) of pure 10a. Analytical characterization: $[\alpha]_D^{20}$ −101.7 (c 0.75, CHCl₃); ¹H-NMR (400 MHz, CDCl₃): δ: 7.86 (d, J=8.7 Hz, 1H), 7.30-7.13 (m, 10H), 7.00 (bs, 1H), 6.15 (d, J=8.7 Hz, 1H), 4.65 (d, J=7.5 Hz, 1H), 4.51 (t, J=8.7 Hz, 1H), 4.41 (bs, 1H), 3.77 (m, 1H), 3.33 (bd, J=11.2, Hz, 1H), 3.07 (dd, J=11.2, 7.5 Hz, 1H), 2.78 (s, 3H), 2.37 (m, 1H), 2.18 (m, 1H), 1.95-1.75 (m, 4H), 1.50-1.20 (m, 3H), 1.45 (s, 9H), 1.30 (m, 1H), 1.05 (m, 1H), 0.84 (t, J=7.5 Hz, 3H); ¹³C-NMR (100 MHz, CDCl₃): δ: 171.3, 142.0, 141.1, 128.7, 128.6, 127.3, 127.2, 126.9, 80.3, 61.0, 60.2, 58.8, 56.8, 53.6, 53.3, 39.8, 34.3, 33.4, 32.1, 29.9, 28.4, 25.6, 21.2, 10.6. ESI-MS: m/z 632.5 [M+H]⁺, 654.5 [M+Na]⁺.

Compound 10b was synthesized by the general procedure described above starting from compound 9b (1.18 g, 2.0 mmol).

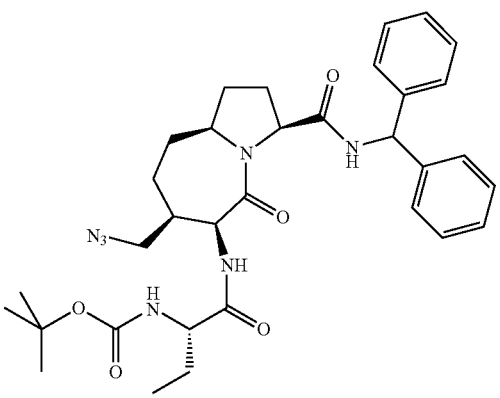

10b

10b. Eluant mixture: Petroleum ether/EtOAc 30:70. Yield 51% (635 mg, MW 617.74, 1.02 mmol) of pure 10b. Analytical characterization: $[\alpha]_D^{20}$ −109.9 (c 0.62, MeOH); ¹H-NMR (400 MHz, CDCl₃): δ: 7.82 (d, J=8.8 Hz, 1H), 7.30-7.13 (m, 10H), 7.21 (d, J=6.4 Hz, 2H), 7.11 (d, J=6.8 Hz, 1H), 6.14 (d, J=8.8 Hz, 1H), 4.92 (bd, J=7.2 Hz, 1H), 4.64 (d, J=7.6 Hz, 1H), 4.50 (dd, J=10.0 Hz, 8.0, 1H), 3.96 (dd, J=13.6, 7.2 Hz, 1H), 3.76 (dd, J=17.6, 9.2 Hz, 1H), 3.45 (dd, J=12.4, 3.6 Hz, 1H), 3.06 (dd, J=12.4, 9.2 Hz, 1H), 2.36 (dd, J=12.4, 6.8 Hz, 1H), 2.18 (m, 1H), 1.95 (m, 1H), 1.82-1.44 (m, 6H), 1.39 (s, 9H), 1.30-1.10 (m, 2H), 0.89 (t, J=7.2 Hz, 3H); $^{13}$C-NMR (100 MHz, CDCl$_3$): δ: 172.4, 171.3, 169.4, 155.8, 142.0, 141.1, 128.7, 128.6, 127.3, 127.2, 80.3, 61.0, 58.9, 56.8, 56.4, 53.6, 53.5, 40.0, 34.2, 33.3, 32.0, 28.3, 25.5, 21.0, 10.2. ESI-MS: m/z 618.1 [M+H]$^+$, 640.1 [M+Na]$^+$.

2.4 General Procedure for the Synthesis of Compounds 11

A 1 N solution of (CH$_3$)$_3$P in toluene (1.5 equiv) was added to a stirred solution of azides 10 (1.0 equiv) in dry CH$_2$Cl$_2$ (≈0.67 M concentration for 10) under argon at room temperature. After complete conversion of the azide to the corresponding iminophosphorane, 1N aqueous HCl was added to the reaction mixture, which was stirred at room temperature for further 10-20 min. After reaction completion, the reaction mixture was extracted with CH$_2$Cl$_2$, the organic layer was dried over Na$_2$SO$_4$, and the solvent was removed under reduced pressure. The crude hydrochloride salt was used without further purification.

Compound 11a was synthesized by the general procedure described above starting from compound 10a (632 mg, 1.0 mmol).

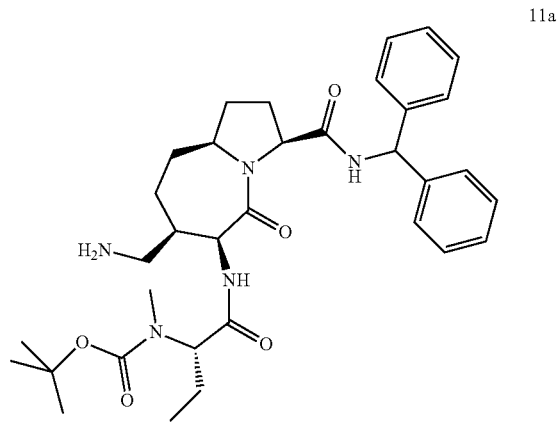 [SMILES: CC[C@@H](C(=O)N[C@@H]1C(=O)N2[C@@H](CC[C@@H]1CN)CC[C@H]2C(=O)NC(c1ccccc1)c1ccccc1)N(C)C(=O)OC(C)(C)C]

11a

11a. Yield 50% (321 mg, MW 642.23, 0.50 mmol) of pure hydrochloride salt of 11a. Analytical characterization: [α]$_D^{20}$ −96.5 (c=1.10, CHCl$_3$); $^1$H-NMR (400 MHz, CDCl$_3$): δ: 7.90 (bs, 1H), 7.64 (bs, 1H), 7.30-7.10 (m, 10H), 6.12 (d, J=8.3 Hz, 1H), 4.63 (d, J=6.9 Hz, 1H), 4.40 (bs, 1H), 4.34 (bs, 1H); 3.70 (m, 1H); 2.81 (bd, 5H); 2.31 (m, 1H), 2.17 (m, 1H), 1.95-1.60 (m, 7H), 1.45 (m, 1H), 1.40 (s, 9H), 1.13 (m, 1H), 0.85 (m, 3H); $^{13}$C-NMR (100 MHz, CDCl$_3$): δ: 174.3, 170.3, 169.5, 142.1, 141.4, 128.7, 128.6, 127.5, 127.4, 127.3, 80.7, 61.4, 61.0, 58.7, 57.0, 53.8, 42.3, 38.1, 34.0, 33.0, 31.8, 28.3, 25.9, 21.1, 10.6; ESI-MS: ink 606.6 [M+H]$^+$, 628.6 [M+Na]$^+$.

Compound 11b was synthesized by the general procedure described above starting from compound 10b (617 mg, 1.0 mmol).

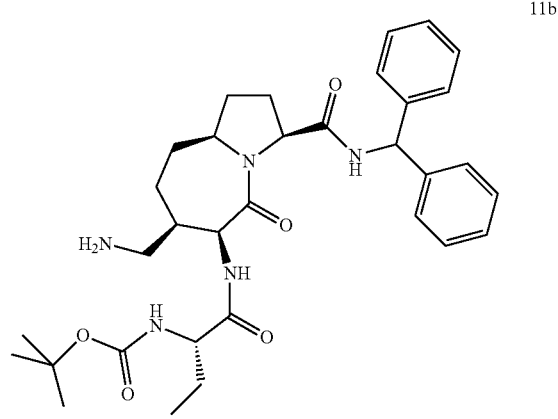 [SMILES: CC[C@H](NC(=O)OC(C)(C)C)C(=O)N[C@@H]1C(=O)N2[C@@H](CC[C@@H]1CN)CC[C@H]2C(=O)NC(c1ccccc1)c1ccccc1]

11b

11b. Yield 92% (578 mg, MW 628.20, 0.92 mmol) of pure hydrochloride salt of 11b. Analytical characterization: [α]$_D^{20}$ −68.5 (c 1.31, MeOH); $^1$H-NMR (400 MHz, CDCl$_3$): δ: 8.39 (bs, 3H), 8.04 (d, J=7.2 Hz, 1H), 7.82 (d, J=8.4 Hz, 1H), 7.40-7.20 (m, 10H), 6.18 (d, J=8.4 Hz, 1H), 5.12 (d, J=6.4 Hz, 1H), 4.71 (d, J=7.2 Hz, 1H), 4.49 (t, J=8.0 Hz, 1H), 4.05 (q, J=7.2 Hz, 1H); 3.74 (q, J=8.4 Hz, 1H); 2.90 (bs, 2H); 2.40 (m, 1H), 2.21 (m, 1H), 2.05-1.55 (m, 7H), 1.47 (s, 9H), 1.33 (m, 1H), 1.22 (m, 1H), 0.99 (t, J=7.6 Hz, 3H); $^{13}$C-NMR (100 MHz, CDCl$_3$): δ: 175.9, 170.1, 169.4, 142.2, 141.1, 128.7, 127.5, 127.4, 127.3, 80.3, 61.3, 58.7, 57.1, 53.8, 42.8, 38.1, 34.0, 33.3, 28.3, 25.8, 25.0, 10.4. ESI-MS: m/z 592.1 [M+H]$^+$, 614.1 [M+Na]$^+$.

2.5 General Procedure for the Synthesis of Compounds 12

DCC (1.0 equiv) and DMAP (0.2 equiv) were sequentially added to a stirred solution of compounds 11 (1.0 equiv) and the appropriate terminal alkyne carboxylic acid (1.0 equiv) in dry CH$_2$Cl$_2$ at 0° C. The reaction mixture was warmed to room temperature over a period of 1 hour. After reaction completion, the reaction mixture was filtered, and washed with diethyl ether. The solvent was removed under reduced pressure, and the crude product was purified by Biotage™ flash chromatography.

Compound 12a was synthesized by the general procedure described above starting from compound 11a (60 mg, 0.1 mmol).

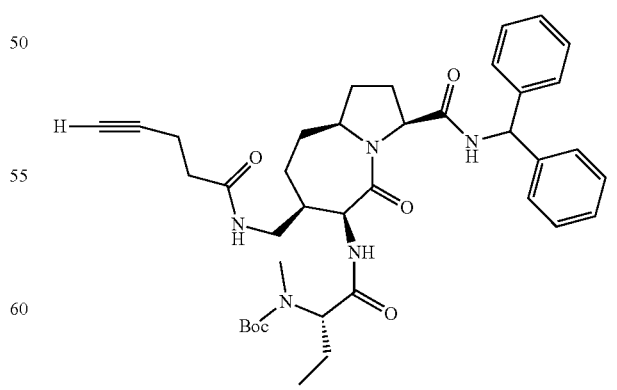

12a

12a. Biotage™ eluant conditions: from 1% of MeOH and 99% of CH$_2$Cl$_2$ to 10% of MeOH and 90% of CH$_2$Cl$_2$. Yield 93% (64 mg, MW 685.87, 0.093 mmol) of pure 12a. Analytical characterization: [α]$_D^{20}$ −116.0 (c 0.90, CHCl$_3$); $^1$H-NMR (400 MHz, CDCl$_3$): δ: 7.90 (d, J=6.8 Hz, 1H), 7.28-7.09 (m, 11H), 6.13 (d, J=8.0 Hz, 1H), 4.64 (d, J=7.0 Hz, 1H), 4.45 (bs, 1H), 4.34 (m, 1H), 3.67 (m, 1H), 3.35 (m, 1H), 3.00-2.60 (m, 4H), 2.50-2.30 (m, 5H), 2.15 (m, 1H), 2.00-1.50 (m, 9H), 1.45 (m, 1H), 1.40 (s, 9H), 1.35-1.05 (m, 1H), 0.91 (t, J=7.6 Hz, 3H); $^{13}$C-NMR (100 MHz, CDCl$_3$): δ: 172.8, 171.7, 171.3, 169.3, 142.0, 141.2, 128.7, 128.6, 127.5, 127.4, 127.3, 127.2, 80.7, 69.0, 62.0, 58.9, 56.8, 54.0, 41.8, 39.9, 35.4, 34.5, 33.3, 33.0, 32.0, 28.3, 27.5, 25.5, 21.9, 15.1, 10.8. ESI-MS: m/z 686.5 [M+H]$^+$, 703.5 [M+Na]$^+$.

Compound 12b was synthesized by the general procedure described above starting from compound 11b (63 mg, 0.1 mmol).

12b. Biotage™ eluant conditions: from 1% of MeOH and 99% of CH$_2$Cl$_2$ to 10% of MeOH and 90% of CH$_2$Cl$_2$. Yield 87% (57 mg, MW 657.35, 0.087 mmol) of pure 12b. Analytical characterization: [α]$_D^{20}$ −95.0 (c 0.93, CHCl$_3$); $^1$H-NMR (400 MHz, CDCl$_3$): δ: 7.90 (d, J=6.8 Hz, 1H), 7.36-7.16 (m, 11H), 6.21 (d, J=8.0 Hz, 1H), 5.07 (bs, 1H), 4.71 (d, J=8.0 Hz, 1H), 4.58 (t, J=9.2 Hz, 1H), 3.98 (d, J=6.4, 1H), 3.77 (m, 1H), 3.40 (m, 1H), 3.13 (m, 1H), 2.60-2.40 (m, 6H), 2.22 (m, 1H), 2.10-1.40 (m, 7H), 1.45 (s, 9H), 1.35-1.10 (m, 2H), 0.91 (t, J=7.6 Hz, 3H); $^{13}$C-NMR (100 MHz, CDCl$_3$): δ: 173.5, 171.8, 171.4, 169.3, 156.1, 141.9, 141.2, 128.7, 128.6, 127.5, 127.4, 127.3, 127.2, 80.6, 69.1, 61.2, 58.9, 57.2, 56.9, 54.4, 42.1, 39.9, 35.4, 34.5, 33.3, 33.0, 32.2, 28.3, 25.6, 25.1, 15.1, 10.4. ESI-MS: m/z 658.4 [M+H]$^+$, 680.4 [M+Na]$^+$.

Some other title intermediates may be prepared according to a synthetic process outlined in Scheme 3, comprising the following reactions:

a) coupling of linker 13 with suitable amino acids to provide intermediates 15;

b) condensation of N-deprotected compounds 15 with compounds 5;

c) azide reduction to provide amines 17;

d) coupling of amines 17 with suitable acid derivatives to provide amides 18 and 19.

The general synthesis of key intermediates is showed in Scheme 3.

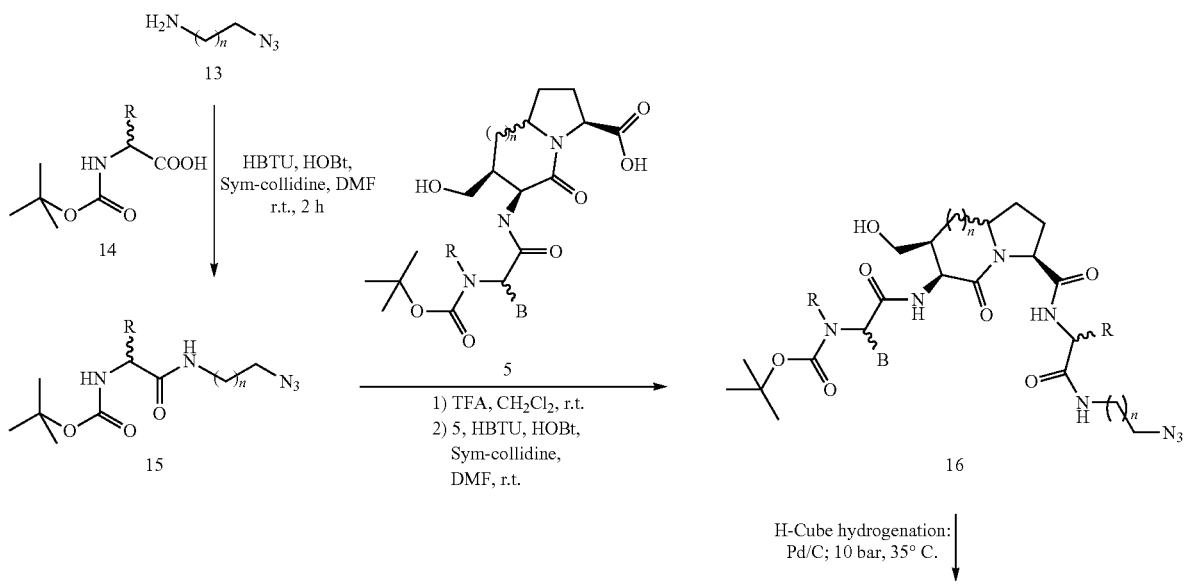

Scheme 3

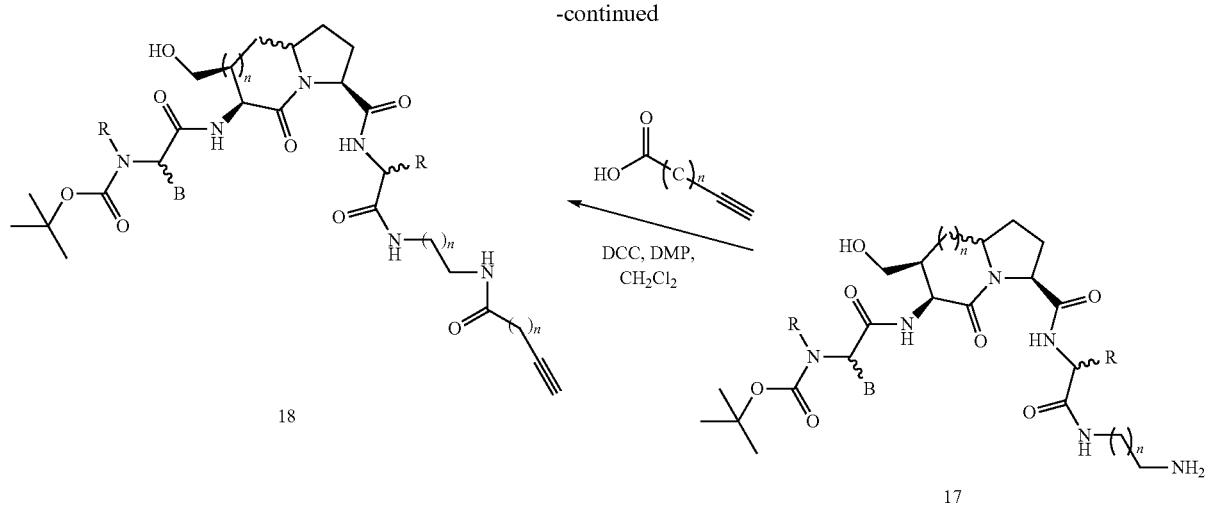

18

17

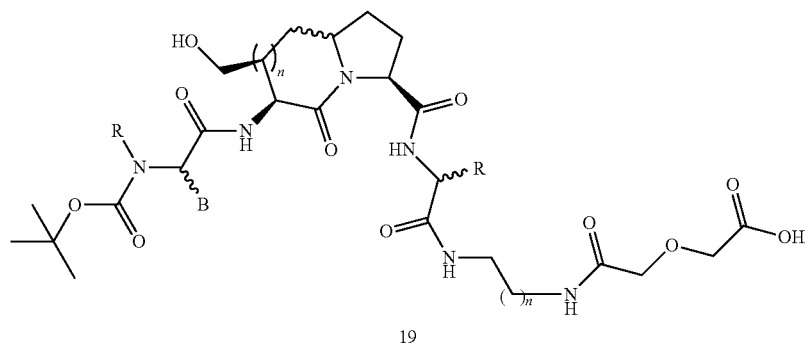

19

2.6 General Procedure for the Synthesis of Compounds 15

HOBt (1.2 equiv), HBTU (1.2 equiv) and Sym-collidine (2.0 equiv) were sequentially added to a stirred solution of azides 13 (1.0 equiv) and N-Boc protected aminoacids 14 (1.25 equiv) in dry DMF (≈0.15 M concentration for 13) at 0° C. The reaction mixture was left stirring and monitored by LC-MS. After reaction completion, the mixture was diluted with EtOAc and sequentially washed with 5% aqueous citric acid, saturated aqueous sodium bicarbonate and brine. The organic layer was dried over $Na_2SO_4$, and then the solvent removed under reduced pressure. The residue was purified by Biotage™ flash chromatography.

Compound 15a was synthesized by the general procedure described above starting from 11-azido-3,6,9-trioxaundecan-1-amine 13a (110 mg, 0.503 mmol) and Boc-(S)-2-Phenylglycine 14a (158 mg, 0.630 mmol).

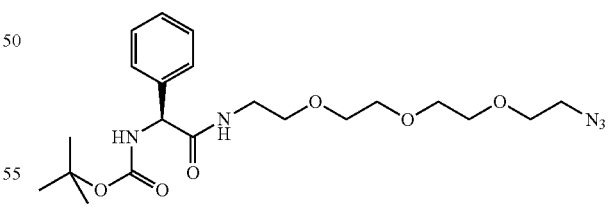

15a

15a. Biotage™ eluant conditions: from 1% of MeOH and 99% of $CH_2Cl_2$ to 10% of MeOH and 90% of $CH_2Cl_2$. Yield 74% (167 mg, MW 451.53, 0.37 mmol) of pure 15a. Analytical characterization: $^1$H-NMR (400 MHz, $CDCl_3$): δ: 7.32.7.20 (m, 5H), 6.28 (bs, 1H), 5.77 (bs, 1H), 5.07 (bs, 1H), 3.6-3.28 (m, 16H), 1.35 (s, 9H); $^{13}$C-NMR (100 MHz, $CDCl_3$): δ: 129.0, 128.3, 127.2, 70.7, 70.6, 70.5, 70.3, 70.0, 69.6, 68.8, 58.5, 50.7, 39.6, 28.3. ESI-MS: m/z 452.5 $[M+H]^+$, 474.5 $[M+Na]^+$.

2.7 General Procedure for the Synthesis of Compounds 16

TFA (50.0 equiv) was added to a stirred solution of compounds 15 (1.0 equiv) in $CH_2Cl_2$ (≈0.10 M concentration for 15). The reaction mixture was left stirring at room temperature and then concentrated under reduced pressure. The crude trifluoroacetate salts of the amines were used without further purification.

HOBt (1.2 equiv), HBTU (1.2 equiv) and sym-collidine (4.0 equiv) were sequentially added to a stirred solution of the crude residue (1.0 theoretical equiv) and compounds 5 (1.25 equiv) in dry DMF (≈0.10 M concentration for 5) at 0° C. The reaction mixture was left stirring and monitored by LC-MS. After reaction completion, the mixture was diluted with EtOAc and washed with 5% aqueous citric acid, saturated aqueous sodium bicarbonate and brine. The organic layer was dried over $Na_2SO_4$, and then the solvent removed under reduced pressure. The residue was purified by Biotage™ flash chromatography.

Compound 16a was synthesized by the general procedure described above starting from compound 15a (95 mg, 0.27 mmol) and 5a (150 mg, 0.34 mmol).

5H), 6.37 (bs, 1H), 5.38 (d, J=7 Hz, 1H), 4.71 (d, J=6.8 Hz, 1H), 4.48 (m, 2H), 3.68 (m, 1H), 3.65 (m, 8H), 3.55 (m, 4H), 3.45 (m, 4H), 3.38 (m, 2H), 3.32 (m, 1H), 2.87 (s, 3H), 2.32 (m 1H), 2.22 (m, 1H), 2.10-1.40 (m, 3H), 1.35-1.70 (m, 5H), 1.52 (s, 9H), 1.30 (m, 2H), 0.93 (t, J=7 Hz, 3H); $^{13}C$-NMR (100 MHz, $CDCl_3$): δ: 173.2, 172.4, 171.4, 170.0, 169.5, 138.2, 128.9, 128.2, 127.2, 70.7, 70.6, 70.5, 70.3, 70.0, 69.5, 64.3, 61.4, 61.0, 59.1, 58.8, 57.4, 53.9, 50.6, 41.6, 39.7, 34.4, 33.0, 32.8, 30.4, 28.4, 26.4, 21.6, 10.7. ESI-MS: m/z 775.5 $[M+H]^+$, 797.5 $[M+Na]^+$.

2.8 General Procedure for the Synthesis of Compounds 17

1.0 M aqueous citric acid (1.1 equiv) was added to a solution of azides 16 in $H_2O$/EtOH 1:9 (≈5.0 M concentration for 16). The solution was hydrogenated by flowing through a 10% Pd/C catalyst cartridge (hydrogen pressure 10 bar, temperature 35° C., flow rate 0.5 mL/min) using the H-Cube™ system by Thales Nanotechnology. After complete reduction to the corresponding amine, the solvent was removed under reduced pressure. The crude product was used without any further purification, and only an analytical sample was purified (semi-preparative HPLC reverse phase chromatography) and characterized.

Compound 17a was synthesized by the general procedure described above starting from compound 16a (170 mg, 0.220 mmol).

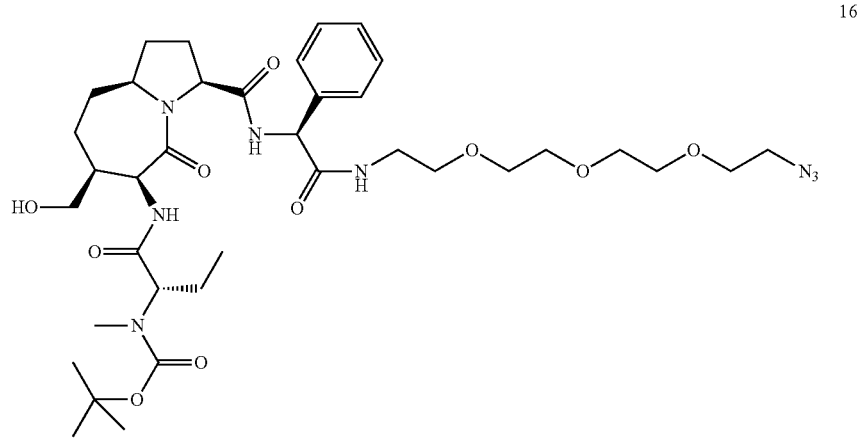 [SMILES: CC[C@@H](C(=O)N[C@@H]1C(=O)N2[C@@H](CC[C@@H]1CO)CC[C@H]2C(=O)N[C@H](C(=O)NCCOCCOCCOCCN=[N+]=[N-])c1ccccc1)N(C)C(=O)OC(C)(C)C]

16a

16a. Biotage™ eluant conditions: from 1% of MeOH and 99% of $CH_2Cl_2$ to 10% of MeOH and 90% of $CH_2Cl_2$. Yield 82% (170 mg, MW 774.92, 0.220 mmol) of pure 16a. Analytical characterization: $^1H$-NMR (400 MHz, $CDCl_3$): δ: 7.93 (d, J=6.8 Hz, 1H), 7.51 (d, J=8.0 Hz, 1H), 7.36-7.27 (m,

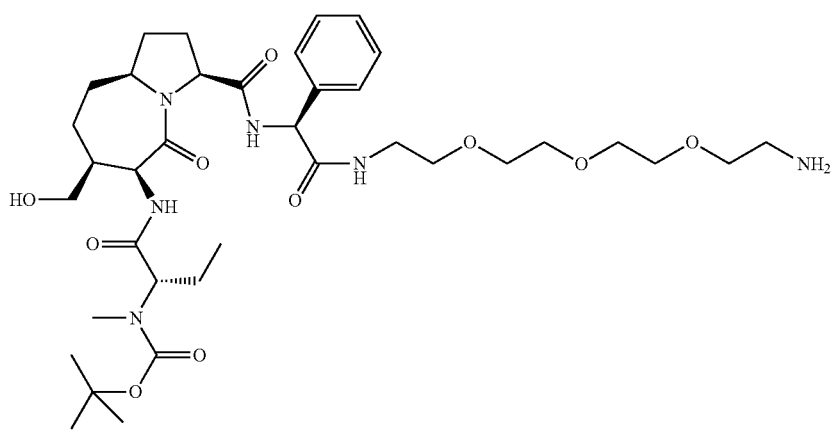

17a

17a. Biotage™ C$_{18}$ reverse phase eluant conditions: from 90% H$_2$O (1% CH$_3$COOH) and 10% CH$_3$CN (1% CH$_3$COOH) to 100% CH$_3$CN (1% CH$_3$COOH). Yield 98% (162 mg, MW 748.95, 0.219 mmol) of pure 17a. Analytical characterization: $^1$H-NMR (400 MHz, CD$_3$OD): δ: 8.6 (bs, 1H), 7.44-7.33 (m, 5H), 5.40 (s, 1H), 4.67 (dd, J=5.2, 2.8 Hz, 1H), 4.53 (m, 2H), 4.01 (m, 1H), 3.67 (m, 5H), 3.65-3.47 (m, 8H), 3.39 (m, 2H), 3.09 (bs, 2H), 2.85 (s, 3H), 2.27 (m, 1H), 2.16 (m, 1H), 2.10-1.88 (m, 4H), 1.82-1.65 (m, 4H), 1.55 (m, 1H), 1.50 (s, 9H), 1.42 (bs, 2H), 0.94 (t, J=7.2 Hz, 3H); $^{13}$C-NMR (100 MHz, CD$_3$OD): δ: 172.3, 171.8, 171.0, 137.6, 128.4, 127.9, 127.2, 70.1, 69.8, 69.0, 67.4, 63.9, 61.4, 58.5, 57.3, 40.3, 39.6, 39.2, 33.2, 32.8, 30.7, 29.5, 27.3, 27.2, 26.9, 9.6. ESI-MS: m/z 749.6 [M+H]$^+$, 771.7 [M+Na]$^+$.

2.9 General Procedure for the Synthesis of Compounds 18

DCC (1.0 equiv) and DMAP (0.2 equiv) were sequentially added to a stirred solution of compounds 17 (1.0 equiv) and the appropriate terminal alkyne carboxylic acid (1.0 mmol) in dry CH$_2$Cl$_2$ at 0° C. The reaction mixture was warmed to room temperature over a period of 1 hour. After reaction completion, the reaction mixture was filtered, and washed with diethyl ether. The solvent was removed under reduced pressure, and the crude product was purified by Biotage™ flash chromatography.

Compound 18a was synthesized by the general procedure described above starting from compound 17a (83 mg, 0.11 mmol).

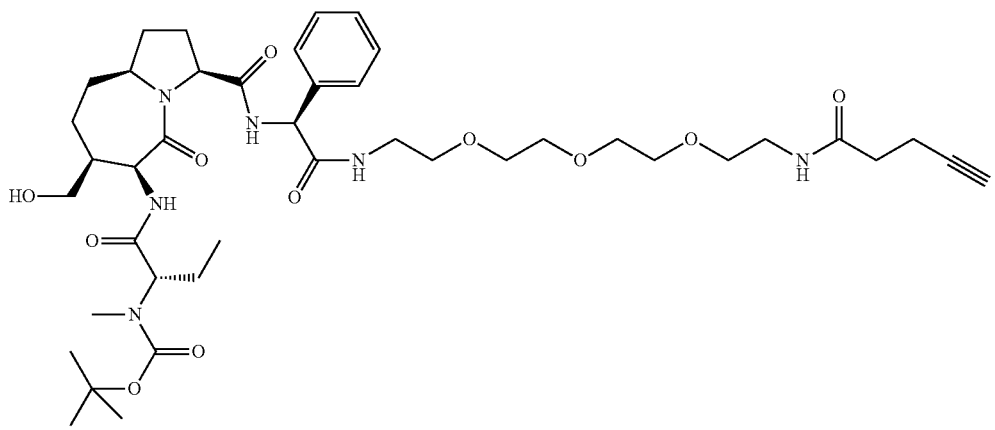

18a

18a. Biotage™ eluant conditions: from 1% of MeOH and 99% of CH$_2$Cl$_2$ to 10% of MeOH and 90% of CH$_2$Cl$_2$. Yield 74% (67 mg, MW 829.01, 0.081 mmol) of pure 18a. Analytical characterization: $^1$H-NMR (400 MHz, CDCl$_3$): δ: 7.98 (d, J=7.0 Hz, 1H), 7.51 (d, J=6.8 Hz, 1H), 7.45-7.25 (m, 5H), 6.68 (bs, 1H), 5.43 (d, J=7.2 Hz, 1H), 4.71 (d, J=6.8 Hz, 1H); 4.48 (bs, 2H), 3.8 (m, 1H), 3.70-3.30 (m, 18H), 2.87 (s. 3H), 2.48 (m, 2H), 2.40-2.15 (m, 4H), 2.15-1.65 (m, 9H), 1.52 (s, 9H), 1.40-1.25 (m, 2H), 0.93 (t, J=7.2 Hz, 3H); $^{13}$C-NMR (100 MHz, CDCl$_3$): δ: 173.4, 173.2, 171.4, 171.3, 170.1, 169.5, 138.2, 128.8, 128.2, 127.2, 83.2, 70.6, 70.5, 70.4, 70.3, 70.1, 69.8, 69.5, 69.2, 64.3, 61.4, 58.8, 57.2, 53.9, 41.6, 39.7, 39.6, 39.1, 35.1, 34.5, 33.0, 31.2, 28.4, 26.6, 21.6, 20.6, 14.8, 10.6. ESI-MS: m/z 829.6 [M+H]$^+$, 851.5 [M+Na]$^+$.

2.10 General Procedure for the Synthesis of Compounds 19

Diglycolic anydride (2.0 equiv) and pyridine (4.0 equiv) were sequentially added to a stirred solution of compounds 17 (1.0 equiv) in DMF. The reaction mixture was stirred at room temperature for 4 hours. After reaction completion, water was added to the reaction mixture. The mixture was diluted with EtOAc and washed with 5% aqueous citric acid, saturated aqueous sodium bicarbonate and brine. The organic layer was dried over Na$_2$SO$_4$, and then the solvent removed under reduced pressure. Finally, the crude product was purified by flash chromatography on Biotage using a C$_{18}$ reverse phase column.

Compound 19a was synthesized by the general procedure described above starting from compound 17a (83 mg, 0.11 mmol).

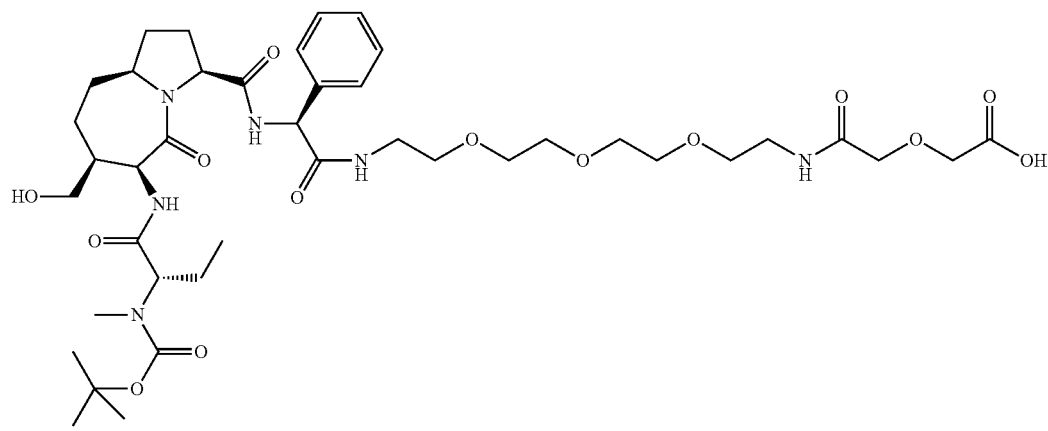

19a

19a. Biotage™ $C_{18}$ reverse phase eluant conditions: from 90% $H_2O$ (1% $CH_3COOH$) and 10% $CH_3CN$ (1% $CH_3COOH$) to 100% $CH_3CN$ (1% $CH_3COOH$). Yield 58% (55 mg, MW 865.00, 0.064 mmol) of pure 19a. Analytical characterization: $^1$H-NMR (400 MHz, $CDCl_3$): δ: 8.01 (d, J=7.0 Hz, 1H), 7.61 (bs, 1H), 7.53 (d, J=6.8 Hz, 1H), 7.40-7.28 (m, 5H), 6.98 (bs, 1H), 4.52 (d, J=7.2 Hz, 1H), 4.71 (d, J=6.8 Hz, 1H), 4.5 (m, 2H), 4.10 (m, 3H), 3.82 (m, 1H); 3.70-3.30 (m, 18H), 2.88 (s, 3H), 2.25 (m, 2H), 2.08 (s, 2H), 2.05-1.70 (m, 8H), 1.51 (s, 9H), 1.39 (m, 2H), 0.93 (t, J=7.2 Hz, 3H); $^{13}$C-NMR (100 MHz, $CDCl_3$): δ: 175.2, 173.0, 171.9, 171.4, 169.8, 169.8, 137.9, 128.8, 128.3, 127.2, 77.3, 77.0, 76.8, 71.4, 70.4, 70.0, 69.7, 69.5, 69.2, 64.3, 61.6, 58.9, 57.2, 54.0, 41.5, 39.7, 38.8, 34.3, 33.0, 31.2, 28.4, 26.7, 21.6, 20.6, 10.6. ESI-MS: m/z 865.4 $[M+H]^+$, 887.4 $[M+Na]^+$.

Example 3

Synthesis of Homodimeric Smac Mimetics with [4.3.0] and [5.3.0] Bicyclic Lactam Systems 3.1 General Procedure for the Synthesis of Compounds 21

Scheme 4

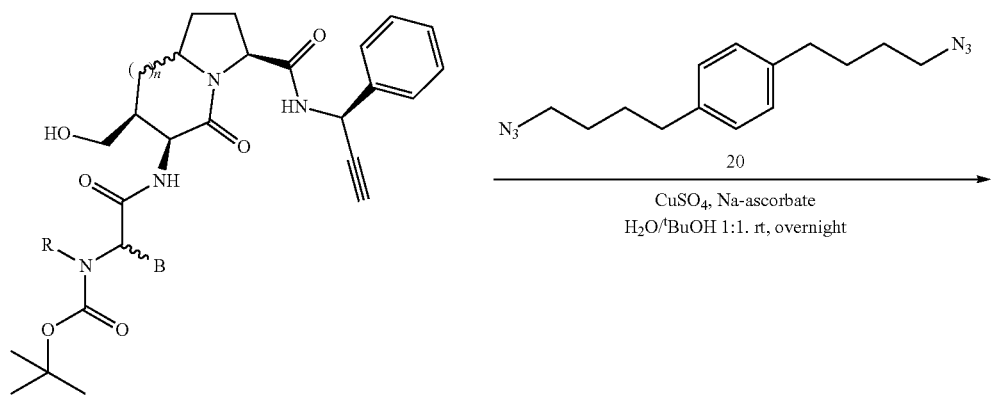

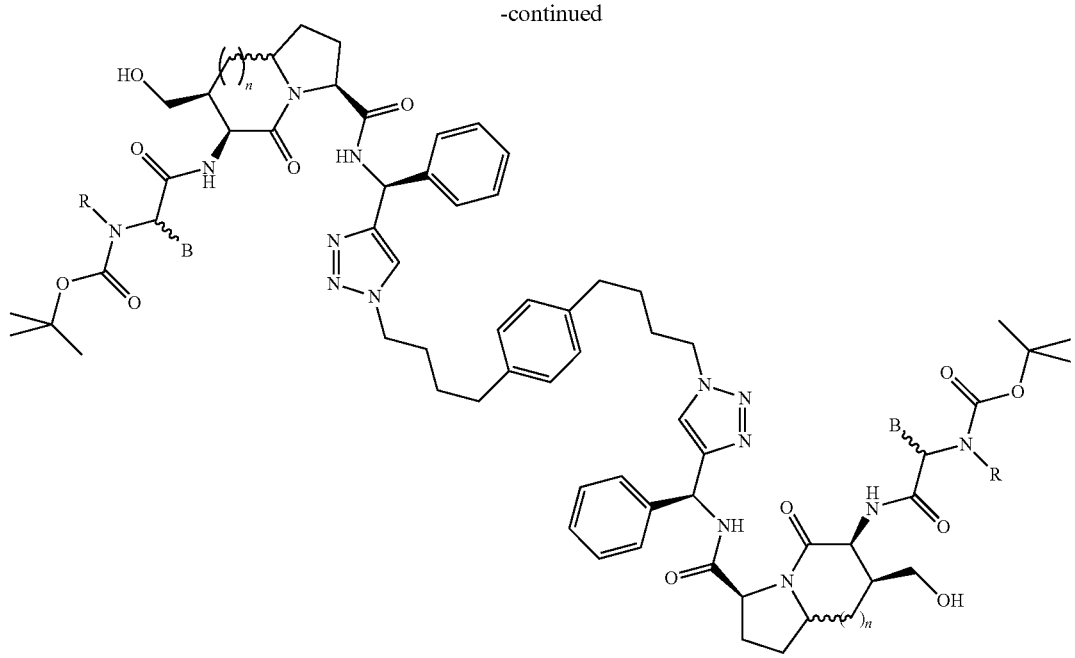

21

A 0.9 M aqueous solution of sodium ascorbate (0.55 equiv) and a 0.3 M aqueous solution of Cu(OAc)₂ (0.25 equiv) were sequentially added to a stirred solution of compounds 7 (1.1 equiv) and compound 20 (Yoshito Takeuchi, et. al., Journal of Organometallic Chemistry, 2003, 678, 61) (0.5 equiv) in a 1:1 mixture of H₂O/ⁿBuOH (final concentration of 7~0.05 M). The reaction mixture was stirred at room temperature and monitored by LC-MS. After reaction completion, the solvent was removed under reduced pressure, the crude product was taken up in CH₂Cl₂ and water and then extracted with CH₂Cl₂. The organic layer was dried over Na₂SO₄, and then the solvent removed under reduced pressure. Finally, the residue was purified by Biotage™ flash chromatography.

Compound 21a was synthesized by the general procedure described above starting from compound 7a (200 mg, 0.44 mmol).

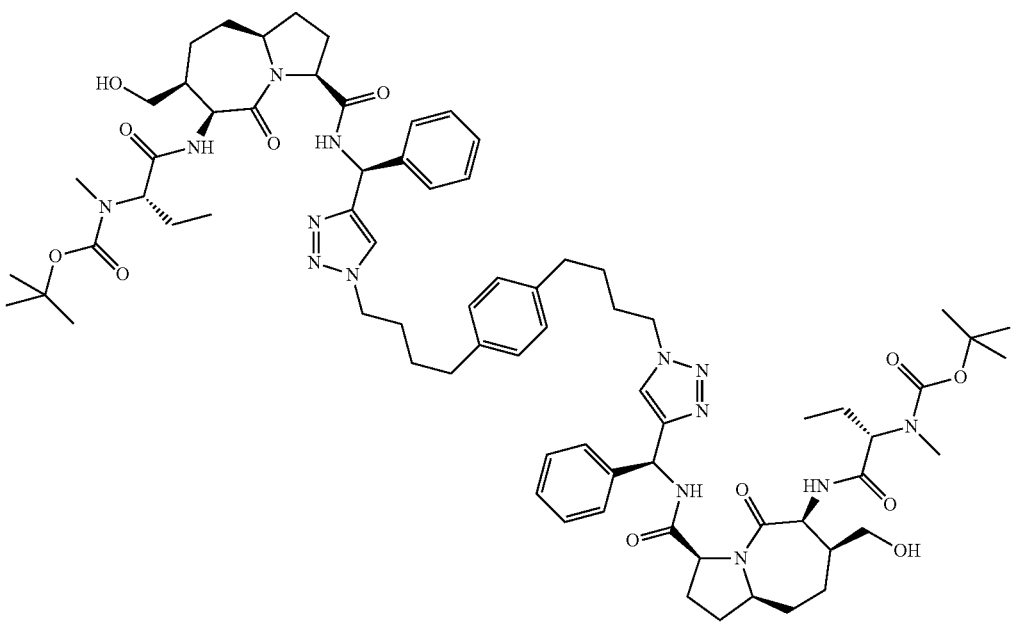

21a

21a. Biotage™ eluant conditions: from 20% of EtOAc and 80% of Petroleum ether to 100% of EtOAc. Yield 73% (221 mg, MW 1381.74, 0.160 mmol) of pure 21a. Analytical characterization: $[\alpha]_D^{20}$ −83 (c 1.15, CHCl$_3$); $^1$H-NMR (400 MHz, CDCl$_3$): δ: 7.94 (m, 2H), 7.42 (m, 2H), 7.30-7.10 (m, 12H), 6.96 (s, 4H), 6.20 (d, J=6.4 Hz, 2H), 4.64 (bs, 2H), 4.38 (m, 4H), 4.23 (bs, 4H), 3.70 (m, 2H), 3.53 (d, J=12.0 Hz, 2H), 3.21 (d, J=12.0 Hz, 2H), 2.79 (s, 6H), 2.53 (bs, 4H), 2.27 (m, 2H), 2.16 (m, 2H), 2.05-1.60 (m, 18H), 1.56 (m, 4H), 1.42 (s, 18H), 1.14 (m, 4H), 0.84 (bs, 6H); $^{13}$C-NMR (100 MHz, CDCl$_3$): δ: 173.0, 171.5, 169.6, 140.9, 139.0, 128.6, 128.4, 127.7, 127.1, 121.4, 80.0, 64.3, 61.2, 60.2, 58.8, 53.8, 50.2, 50.0, 41.6, 34.7, 34.5, 33.1, 31.1, 29.7, 28.4, 28.2, 26.0, 21.5, 10.7. ESI-MS: m/z 1382.1 [M+H]$^+$, 691.7 [M+2H]$^{2+}$.
3.2 General Procedure for the Synthesis of Compounds 22
Scheme 5
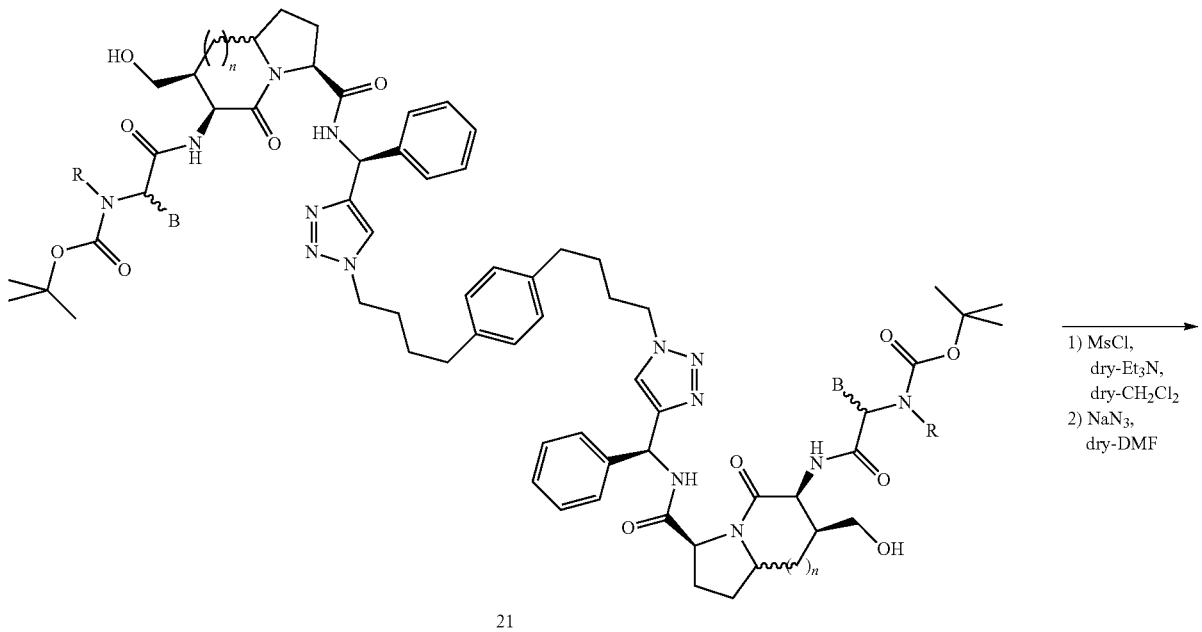
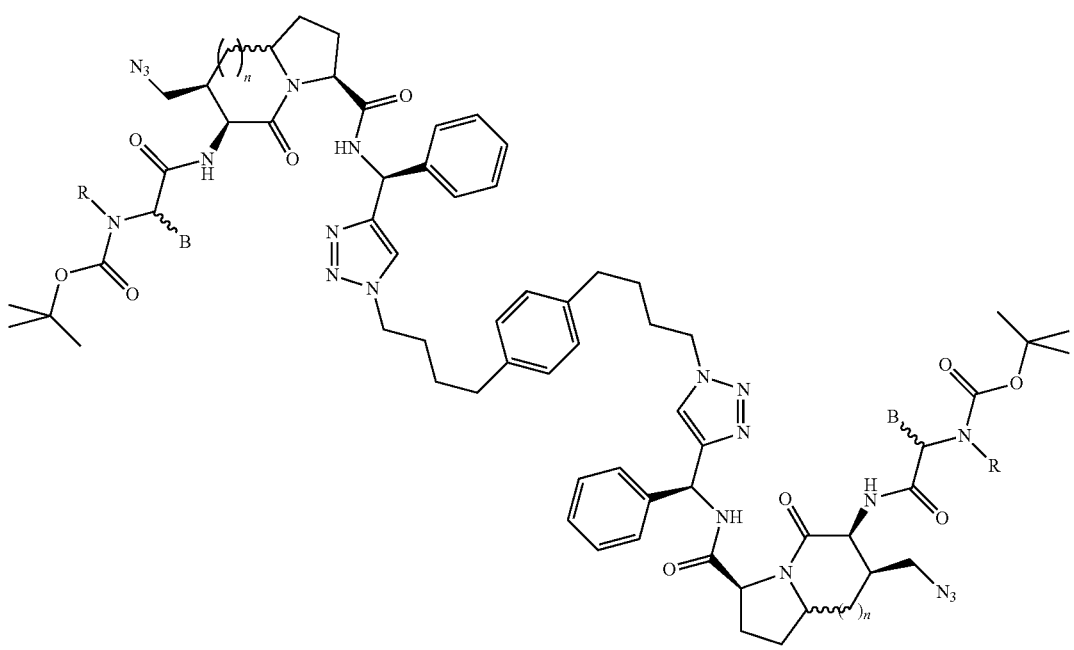

Dry TEA (4.0 equiv) and MsCl (4.0 equiv) were sequentially added to a stirred solution of compounds 21 (1.0 equiv) in dry $CH_2Cl_2$ (≈0.25 M concentration for 21) under argon at 0° C. The reaction mixture was stirred at room temperature for 2 hours. After reaction completion, the resulting mixture was diluted with $CH_2Cl_2$ and washed with a saturated aqueous solution of $NH_4Cl$. The organic layer was dried over $Na_2SO_4$, and then the solvent removed under reduced pressure. The crude product was dissolved in dry DMF (≈0.1 M concentration) under argon at room temperature, and then $NaN_3$ (20.0 equiv) was added. The reaction mixture was irradiated in a microwave reactor at 100° C. for 30 min. After reaction completion, the solvent was removed under reduced pressure, the crude product was diluted with EtOAc and washed with water. The organic layer was dried over $Na_2SO_4$, and then the solvent removed under reduced pressure. Finally, the crude product was purified by Biotage™ flash chromatography.

Compound 22a was synthesized by the general procedure described above starting from compound 21a (78 mg, 0.056 mmol).

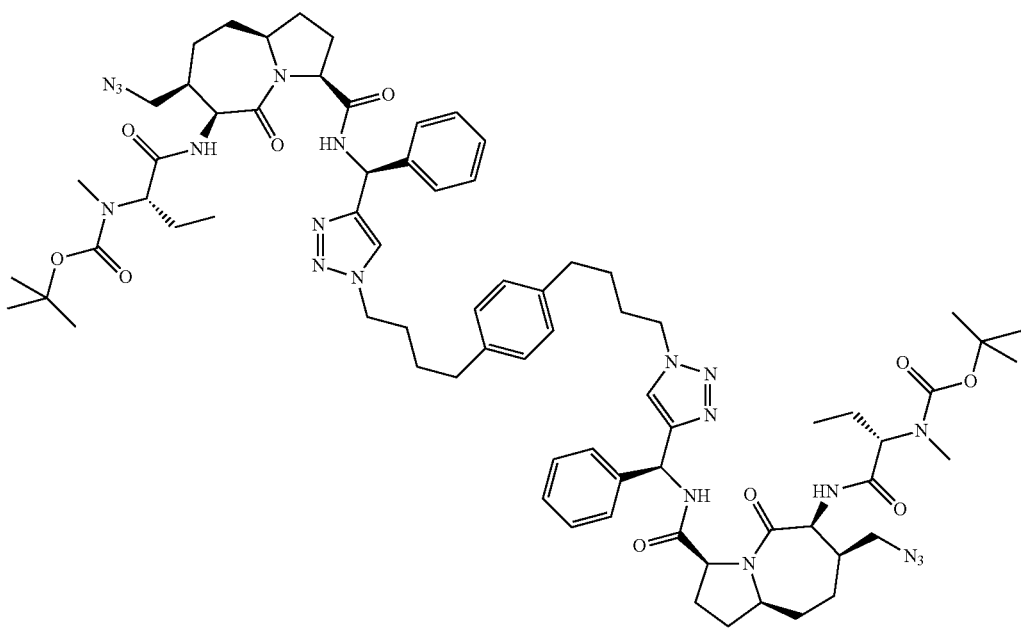

22a

22a. Biotage™ eluant conditions: from 1% of MeOH and 99% of $CH_2Cl_2$ to 10% of MeOH and 90% of $CH_2Cl_2$. Yield 58% (47 mg, MW 1431.77, 0.033 mmol) of pure 22a. Analytical characterization: $[\alpha]_D^{20}$ −105 (c 1.31, $CHCl_3$); $^1$H-NMR (400 MHz, $CDCl_3$): δ: 8.03 (m, 2H), 7.40-7.20 (m, 12H), 7.05 (m, 6H), 6.29 (d, J=7.6 Hz, 2H), 4.71 (d, J=6.4 Hz, 2H), 4.58 (m, 2H), 4.49 (m, 2H), 4.33 (bs, 4H), 3.83 (m, 2H), 3.42 (bd, J=11.6 Hz, 2H), 3.16 (t, J=12.8 Hz, 2H), 2.86 (s, 6H), 2.62 (m, 4H), 2.36 (m, 2H), 2.23 (m, 2H), 2.05-2.60 (m, 22H), 1.55 (bs, 20H), 1.22 (m, 2H), 0.85 (bs, 6H); $^{13}$C-NMR (100 MHz, $CDCl_3$): δ: 171.5, 171.0, 169.6, 140.7, 139.0, 128.7, 128.4, 127.9, 127.1, 121.6, 61.0, 59.0, 58.7, 53.6, 53.2, 50.3, 50.0, 34.7, 34.1, 33.3, 32.1, 29.7, 28.4, 28.2, 26.0, 21.4, 10.6. ESI-MS: ink 1433.1 $[M+H]^+$, 666.7 $[M+2H]^{2+}$.

3.3 General Procedure for the Synthesis of Compounds 23

Scheme 6

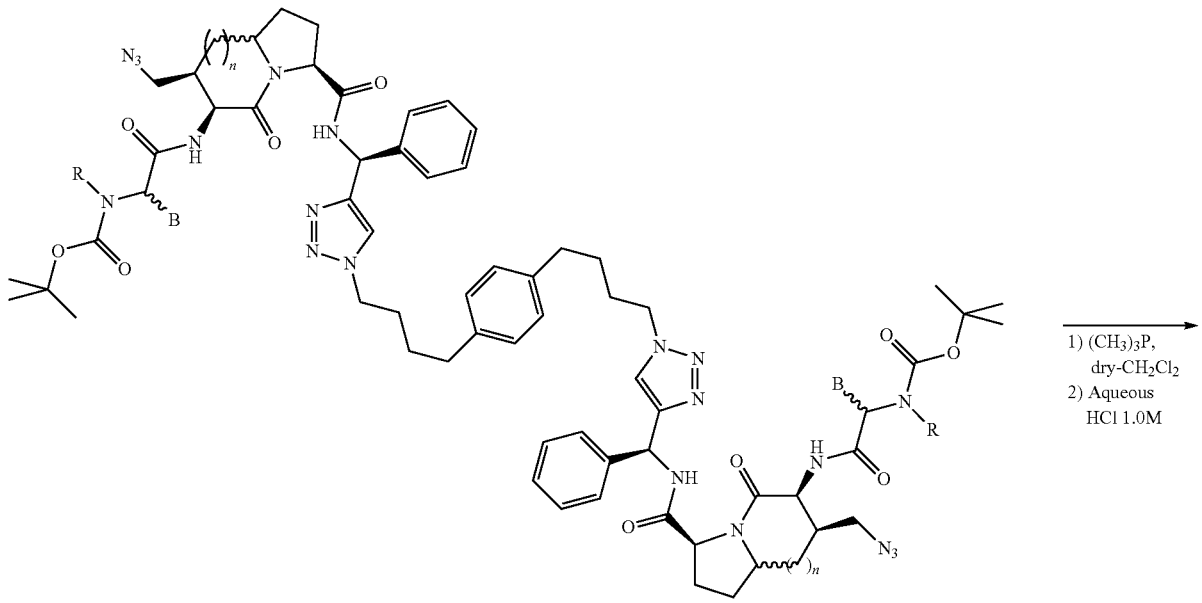

22

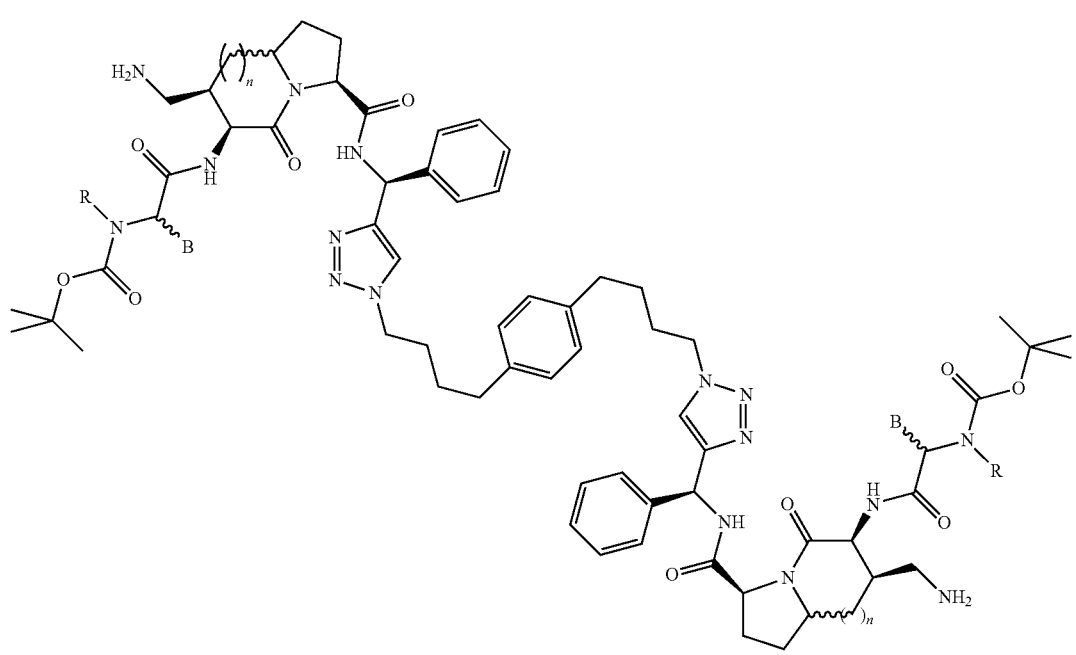

23

A 1N solution of (CH$_3$)$_3$P in toluene (3.0 equiv) was added to a stirred solution of compounds 22 (1.0 equiv) in dry CH$_2$Cl$_2$ (≈0.01 M concentration for 22) under argon at room temperature. After two hours, a 0.5 M HCl solution was added to the reaction mixture, which was stirred at room temperature for further 10-20 min. After reaction comple-tion, the mixture was extracted with CH$_2$Cl$_2$, the organic layer was combined and dried over Na$_2$SO$_4$, and then the solvent was removed under reduced pressure. The crude product was used without further purification.

Compound 23a was synthesized by the general procedure described above starting from compound 22a (36 mg, 0.026 mmol).

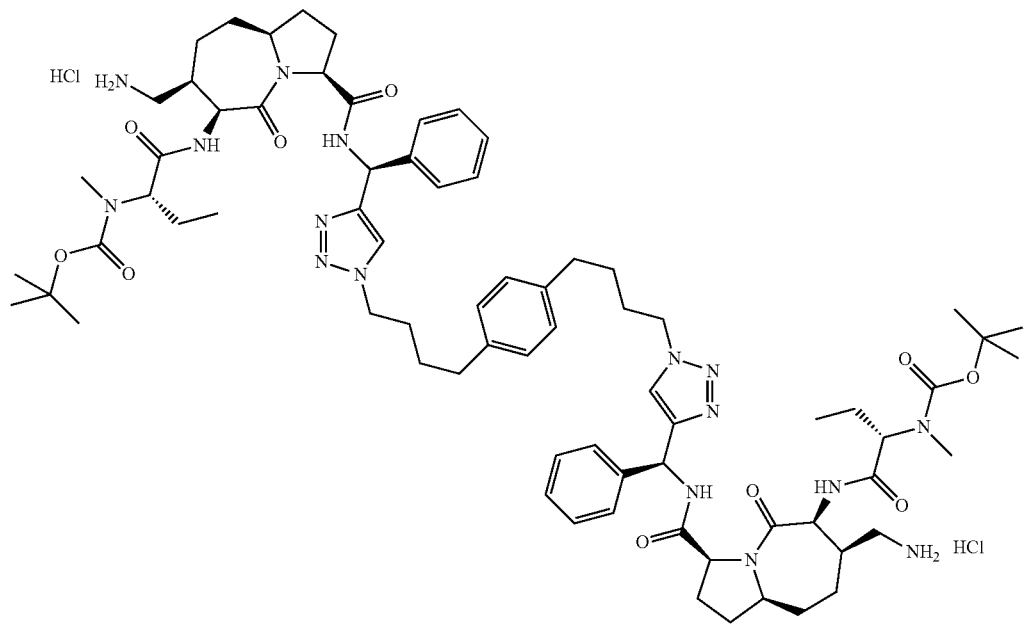
23a
23a. Yield 78% (28 mg, MW 1379.77, 0.020 mmol) of pure 23a. Analytical characterization: $[\alpha]_D^{20}$ −120 (c 0.48, CHCl$_3$); $^1$H-NMR (400 MHz, CDCl$_3$): δ: 8.35 (m, 4H), 7.88 (m, 2H), 7.35-7.15 (m, 12H), 6.93 (m, 4H), 6.14 (d, J=6.4 Hz, 2H), 4.62 (bs, 2H), 4.40 (m, 4H), 4.24 (bs, 4H), 3.70 (m, 2H), 3.00-2.65 (m, 10H), 2.52 (bs, 4H), 2.30-2.05 (m, 4H), 2.00-1.55 (m, 20H), 1.54 (m, 4H), 1.39 (s, 18H), 1.19 (m, 4H), 0.84 (bs, 6H); $^{13}$C-NMR (100 MHz, CDCl$_3$): δ: 173.2, 171.7, 169.2, 141.9, 139.3, 129.6, 128.2, 127.5, 127.4, 122.4, 81.0, 64.5, 61.4, 60.1, 58.8, 53.8, 50.2, 50.0, 41.6, 35.7, 33.5, 33.1, 31.5, 29.7, 28.4, 28.2, 26.0, 21.5, 10.4. ESI-MS: m/z 1380.1 [M+H]$^+$, 691.2 [M+2H]$^{2+}$.
3.4 General Procedure for the Synthesis of Compounds 24
Scheme 7
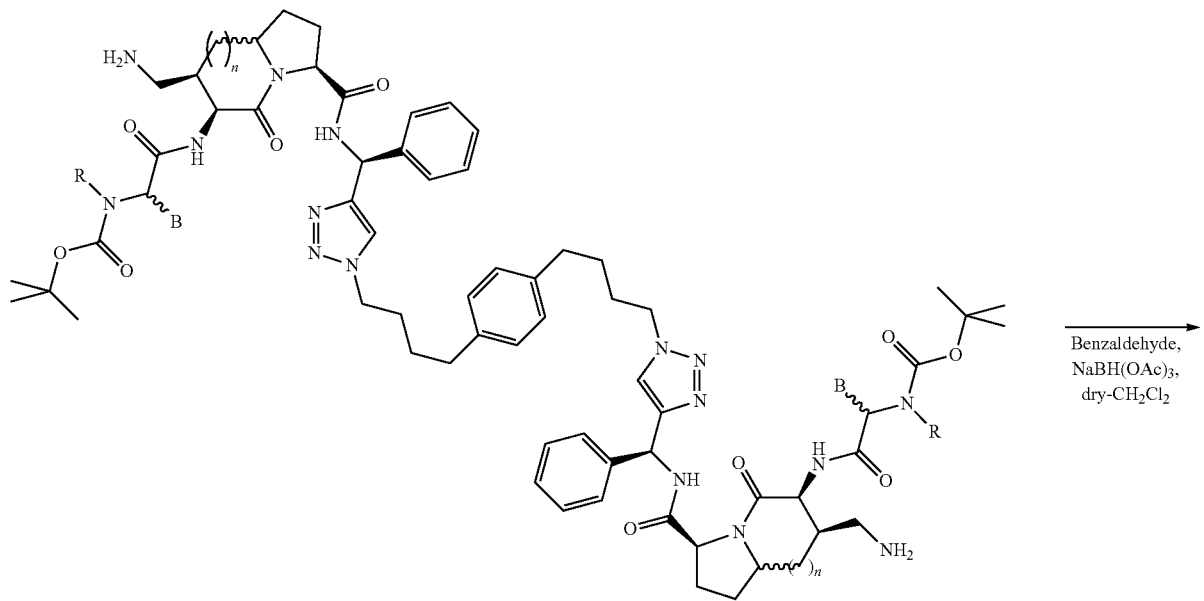
23

-continued

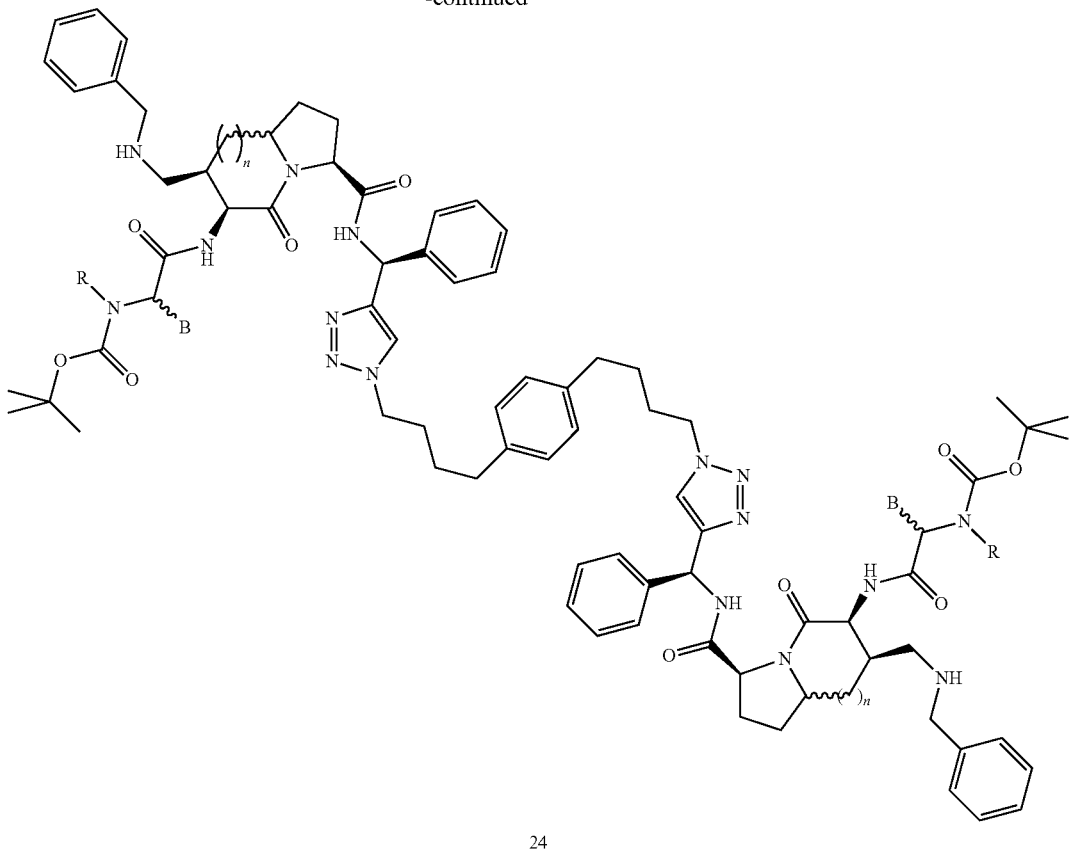

24

Solid NaBH(OAc)$_3$ (2.6 equiv) was added to a stirred solution of compounds 23 (1.0 equiv) and benzaldehyde (1.8 equiv) in dry CH$_2$Cl$_2$ (≈0.01 M concentration for 23).

The reaction mixture was stirred at room temperature and monitored by LC-MS. After reaction completion, the solution was diluted with CH$_2$Cl$_2$ and then washed with a saturated aqueous solution of NH$_4$Cl, then brine. The organic layer was dried over Na$_2$SO$_4$, and then the solvent removed under reduced pressure. The residue was purified by Biotage™ flash chromatography.

Compound 24a was synthesized by the general procedure described above starting from compound 23a (42 mg, 0.03 mmol).

24a

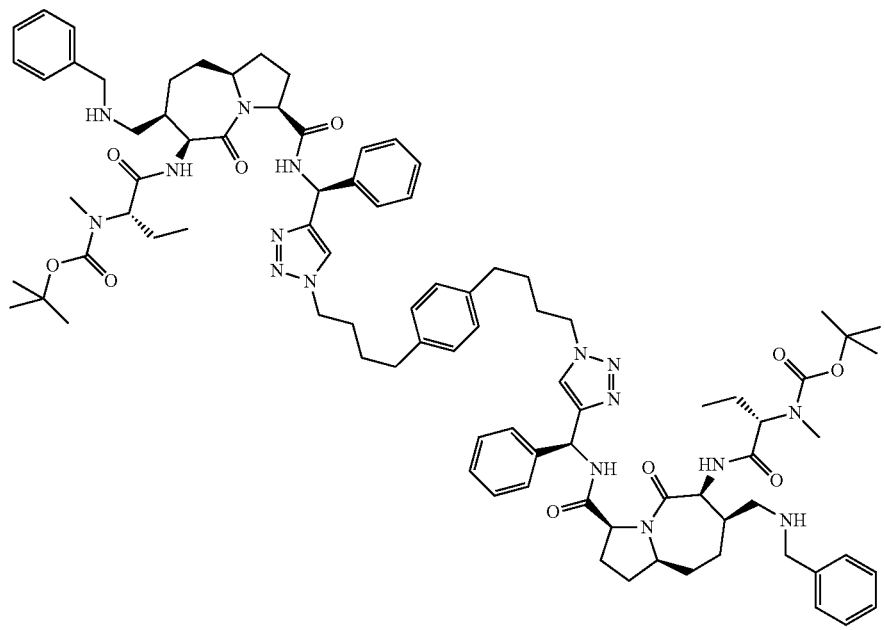

24a. Biotage™ eluant conditions: from 1% of MeOH and 99% of CH$_2$Cl$_2$ to 10% of MeOH and 90% of CH$_2$Cl$_2$. Yield 45% (21 mg, MW 1560.32, 0.0135 mmol) of pure 24a. Analytical characterization: $[\alpha]_D^{20}$ −150 (c 0.70, CHCl$_3$); $^1$H-NMR (400 MHz, CDCl$_3$): δ: 8.25 (bs, 2H), 8.03 (m, 2H), 7.40-7.24 (m, 20H), 7.18 (m, 2H), 7.05 (s, 4H), 6.28 (d, J=7.6 Hz, 2H), 4.73 (bs, 2H), 4.49 (m, 4H), 4.30 (s, 4H), 3.95-3.75 (m, 6H), 2.95-2.75 (m, 6H), 2.70-2.50 (m, 8H), 2.35 (m, 2H), 2.23 (m, 2H), 2.25-1.55 (m, 22H), 1.49 (m, 20H), 1.24 (m, 2H), 0.93 (bs, 6H); $^{13}$C-NMR (100 MHz, CDCl$_3$): δ: 169.9, 147.8, 141.0, 139.1, 128.8, 128.6, 127.6, 127.2, 127.0, 121.5, 61.0, 58.4, 50.2, 50.0, 38.1, 34.7, 33.3, 33.2, 29.7, 28.5, 28.2, 26.0, 22.1, 10.6. ESI-MS: m/z 1561.4 [M+H]$^+$, 781.0 [M+2H]$^{2+}$.

3.5 General Procedure for the Synthesis of Compounds 27

HOBt (2.4 equiv), HBTU (2.4 equiv) and Sym-collidine (4.0 equiv) were sequentially added at 0° C. to a stirred solution of commercially available diamines 25 (1.0 equiv) and N-Boc protected aminoacids 14 (2.5 equiv) in dry DMF (≈0.15 M concentration for 25). The reaction mixture was left stirring and monitored by LC-MS. After reaction completion, the mixture was diluted with EtOAc and sequentially washed with a saturated aqueous solution of NH$_4$Cl, saturated aqueous solution of sodium bicarbonate, and brine. The organic layer was dried over Na$_2$SO$_4$, and then the solvent removed under reduced pressure. The residue was purified by Biotage™ flash chromatography.

Compound 26a was synthesized by the general procedure described above starting from 1,8-diaminooctane 25a (46 mg, 0.32 mmol) and Boc-(S)-2-Phenylglycine 14a (200 mg, 0.80 mmol).

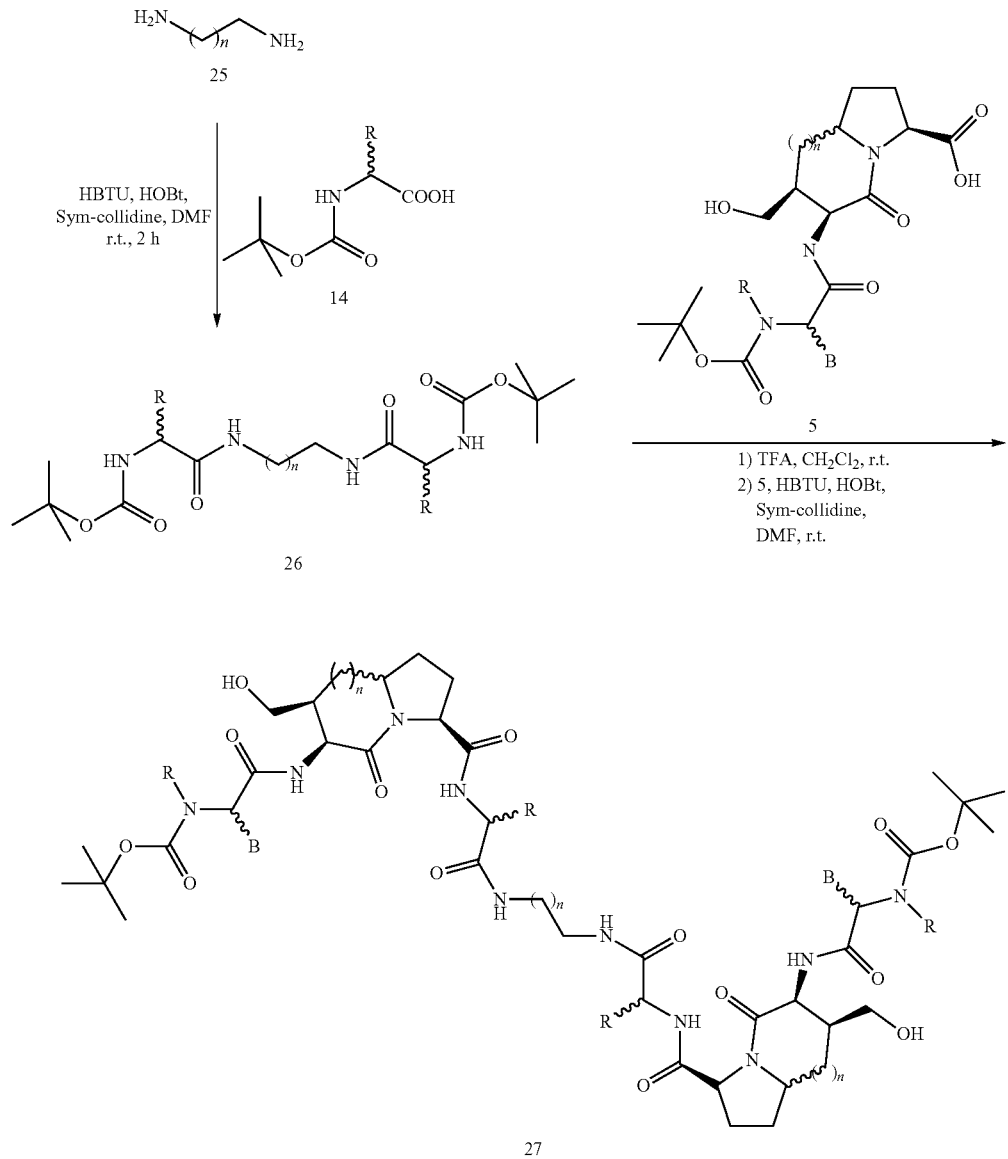

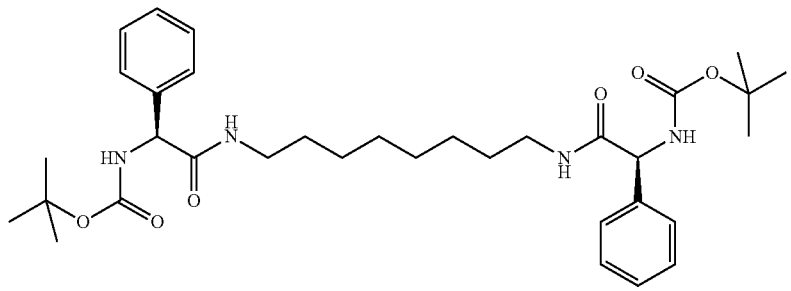

26a

26a. Biotage™ eluant conditions: from 1% of MeOH and 99% of CH$_2$Cl$_2$ to 10% of MeOH and 90% of CH$_2$Cl$_2$. Yield 94% (183 mg, MW 610.80, 0.30 mmol) of pure 26a. Analytical characterization: $^1$H-NMR (400 MHz, CDCl$_3$): δ: 7.38-7.25 (m, 10H), 5.76 (m, 2H), 5.25 (m, 2H), 3.32 (bs, 1H), 3.23 (m, 2H), 3.13 (bs, 1H), 1.57 (s, 4H), 1.42 (m, 18H), 1.21 (d, J=11.2 Hz, 6H); $^{13}$C-NMR (100 MHz, CDCl$_3$): δ: 129.0, 128.9, 128.3, 127.2, 39.7, 39.7, 29.2, 28.8, 28.3, 26.4. ESI-MS: m/z 611.4 [M+H]$^+$.

Compound 26b was synthesized by the general procedure described above starting from 3,4-Bis-(4-amino-butylamino)-cyclobut-3-ene-1,2-dione 25b (17 mg, 0.068 mmol) and Boc-(S)-2-Phenylglycine 14a (43 mg, 0.17 mmol).

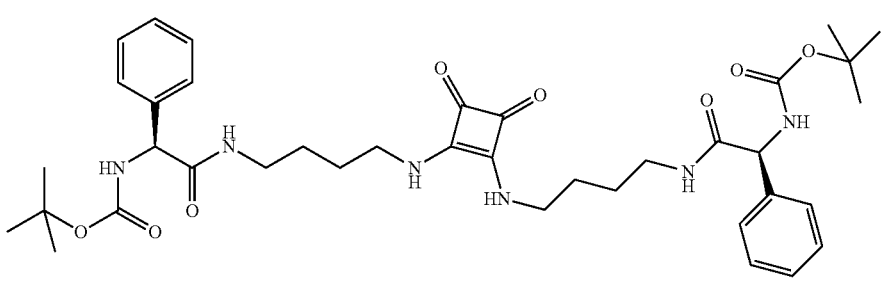

26b

26b. Biotage™ eluant conditions: from 1% of MeOH and 99% of CH$_2$Cl$_2$ to 10% of MeOH and 90% of CH$_2$Cl$_2$ 10 VC. Yield 88% (43 mg, MW 720.87, 0.60 mmol) of pure 26b. Analytical characterization: $^1$H-NMR (400 MHz, CD$_3$OD): δ: 7.41-7.31 (m, 10H), 5.11 (bs, 2H), 3.56 (bs, 4H), 3.30-3.19 (m, 4H), 1.55 (bs, 8H), 1.44 (s, 18H); $^{13}$C-NMR (100 MHz, CD$_3$OD): δ: 128.3, 127.8, 127.0, 43.4, 38.7, 28.1, 27.3, 25.8. ESI-MS: m/z 721.1 [M+H]$^+$.

Compound 26c was synthesized by the general procedure described above starting from deca-4,6-diynedioic acid bis-[(2-amino-ethyl)-amide] 25c (17 mg, 0.068 mmol) and Boc-(S)-2-Phenylglycine 14a (43 mg, 0.17 mmol).

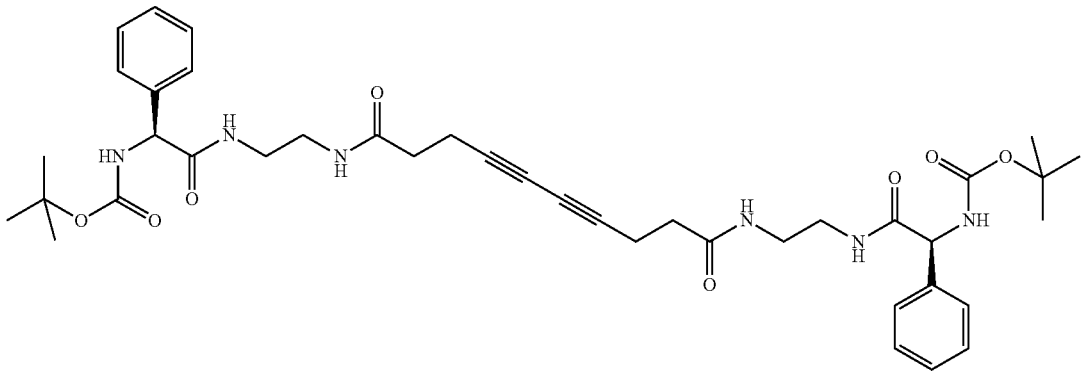

26c

26c. Biotage™ eluant conditions: from 1% of MeOH and 99% of CH$_2$Cl$_2$ to 10% of MeOH and 90% of CH$_2$Cl$_2$. Yield 83% (42 mg, MW 744.90, 0.56 mmol) of pure 26c. Analytical characterization: $^1$H-NMR (400 MHz, CDCl$_3$): δ: 7.32-7.19 (m, 10H), 6.81 (bs, 2H), 5.73 (d, J=6.4 Hz, 2H), 5.08 (bs, 2H), 3.32-3.19 (m, 8H), 2.43 (m, 4H), 2.19 (m, 4H), 1.33 (s, 18H); $^{13}$C-NMR (100 MHz, CDCl$_3$): δ: 171.3, 129.0, 128.3, 127.2, 80.2, 66.2, 59.0, 41.0, 38.7, 34.8, 28.3, 16.0. ESI-MS: m/z 745.6 [M+H]$^+$.

Compound 26d was synthesized by the general procedure described above starting from 4,7,10-trioxa-1,13-tridecanediamine 25d (50 mg, 0.227 mmol) and Boc-(5)-2-Phenylglycine 14a (142 mg, 0.567 mmol)

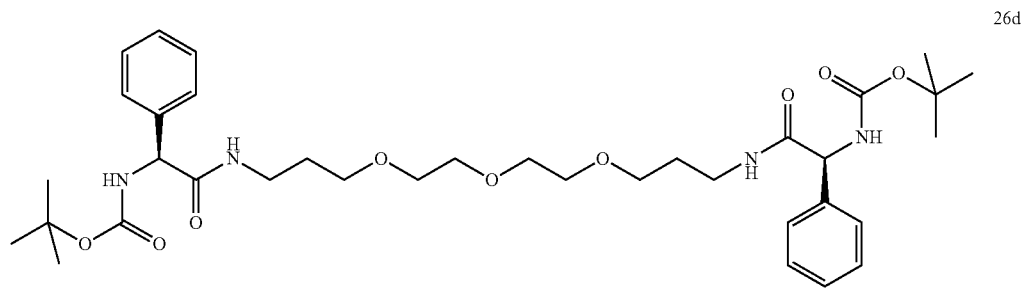 [SMILES: CC(C)(C)OC(=O)N[C@H](C(=O)NCCCOCCOCCOCCCNC(=O)[C@@H](NC(=O)OC(C)(C)C)c1ccccc1)c1ccccc1]

26d

26d. Biotage™ eluant conditions: from 1% of MeOH and 99% of CH$_2$Cl$_2$ to 10% of MeOH and 90% of CH$_2$Cl$_2$. Yield 94% (146 mg, MW 686.85, 0.212 mmol) of pure 26d. Analytical characterization: $^1$H-NMR (400 MHz, CDCl$_3$): δ: 7.39-7.28 (m, 10H), 6.55 (bs, 2H), 5.94 (bs, 2H), 5.10 (bs, 2H), 3.59-3.31 (m, 16H), 1.70 (t, J=6.0 Hz, 4H), 1.42 (s, 18H); $^{13}$C-NMR (100 MHz, CDCl$_3$): δ: 170.3, 138.9, 128.8, 128.1, 127.2, 79.8, 70.4, 70.1, 69.7, 38.1, 28.7, 28.3. ESI-MS: m/z 687.6 [M+H]$^+$, 709.5 [M+Na]$^+$.

TFA (50.0 equiv) was added to a stirred solution of compounds 26 (1.0 equiv) in CH$_2$Cl$_2$ (≈0.10 M concentration for 26). The reaction mixture was left stirring at room temperature and then concentrated under reduced pressure to give a crude residue which was used without purification.

HOBt (2.4 equiv), HBTU (2.4 equiv) and Sym-collidine (4.0 equiv) were sequentially added to a stirred solution of the crude residue (1.0 theoretical equiv) and compounds 5 (≈2.5 equiv) in dry DMF (≈0.10 M concentration for 5) at 0° C. The reaction mixture was left stirring and monitored by LC-MS. After reaction completion, the mixture was diluted with EtOAc and sequentially washed with 5% aqueous citric acid, saturated aqueous sodium bicarbonate and brine. The organic layer was dried over Na$_2$SO$_4$, and then the solvent removed under reduced pressure. The residue was purified by Biotage™ flash chromatography.

Compound 27a was synthesized by the general procedure described above starting from compound 26a (34 mg, 0.08 mmol) and 5a (91 mg, 0.200 mmol).

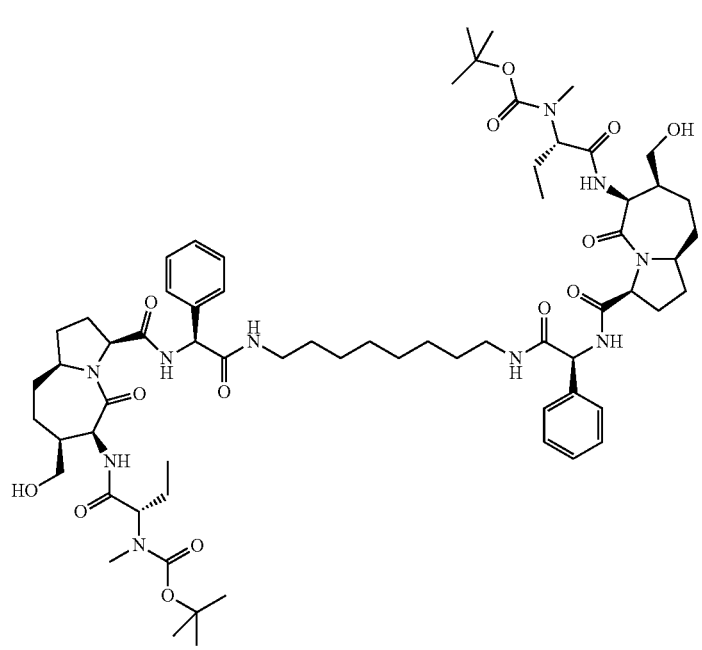

27a. Biotage™ eluant conditions: from 1% of MeOH and 99% of $CH_2Cl_2$ to 10% of MeOH and 90% of $CH_2Cl_2$. Yield 97% (98 mg, MW 1257.59, 0.078 mmol) of pure 27a. Analytical characterization: $[\alpha]_D^{20}$ −118 (c 1.23, $CHCl_3$); $^1$H-NMR (400 MHz, $CDCl_3$): δ: 8.43 (d, J=8 Hz, 2H), 8.17 (t, J=5.6 Hz, 2H), 7.86 (bs, 2H), 7.40-7.25 (m, 10H), 5.36 (d, J=8 Hz, 2H), 4.61 (dd, J=7.2, 4 Hz, 2H), 4.48-4.36 (m, 4H), 3.89 (m, 2H), 3.45 (bs, 2H), 3.25 (m, 2H), 3.00 (m, 4H), 2.70 (s, 6H), 2.16 (m, 2H), 2.14 (m, 2H), 2.00-1.75 (m, 8H), 1.70-1.45 (m, 10H), 1.40 (s, 18H), 1.35 (m, 4H), 1.15 (s, 8H), 0.80 (bs, 6H); $^{13}$C-NMR (100 MHz, $CDCl_3$): δ: 171.2, 170.3, 169.9, 139.4, 128.6, 127.8, 127.5, 79.5, 63.1, 61.1, 58.0, 56.8, 53.9, 41.0, 39.0, 33.2, 32.8, 30.2, 29.3, 29.0, 28.5, 28.1, 26.6, 11.2. ESI-MS: m/z 1257.9 $[M+H]^+$.

Compound 27b was synthesized by the general procedure described above starting from compound 26b (45 mg, 0.062 mmol) and 5a (68 mg, 0.153 mmol).

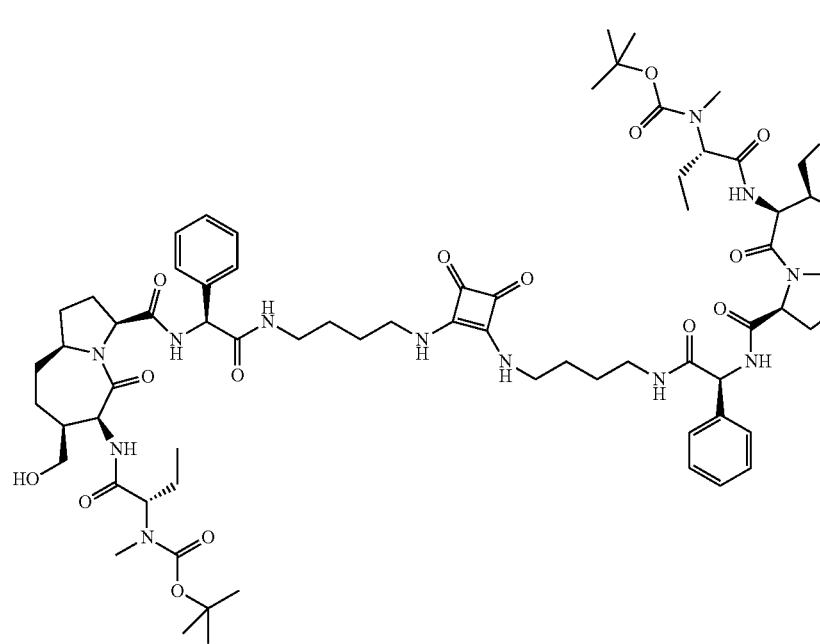

27b. Biotage™ eluant conditions: from 1% of MeOH and 99% of CH$_2$Cl$_2$ to 10% of MeOH and 90% of CH$_2$Cl$_2$. Yield 51% (42 mg, MW 1352.63, 0.031 mmol) of pure 27b. Analytical characterization: $^1$H-NMR (400 MHz, CD$_3$OD): δ: 7.31-7.18 (m, 10H), 5.24 (s, 2H), 4.54 (dd, J=8.0, 2.4 Hz, 2H), 4.41 (m, 4H), 3.87 (m, 2H), 3.43 (m, 8H), 3.21 (m, 4H), 2.73 (s, 6H), 2.14 (m, 2H), 2.01 (m, 2H), 1.95-1.75 (m, 8H), 1.61 (m, 8H), 1.43 (m, 10H), 1.38 (s, 18H), 0.81 (t, J=7.2 Hz, 6H); $^{13}$C-NMR (100 MHz, CD$_3$OD): δ: 171.8, 171.2, 170.9, 168.0, 137.6, 128.5, 127.9, 127.1, 63.9, 61.4, 58.5, 57.6, 54.8, 43.5, 40.3, 38.6, 33.2, 32.8, 30.8, 28.1, 27.3, 27.0, 25.8, 21.2, 9.7. ESI-MS: m/z 1367.9 [M+H]$^+$.

Compound 27c was synthesized by the general procedure described above starting from compound 26c (42 mg, 0.056 mmol) and 5a (67 mg, 0.152 mmol).

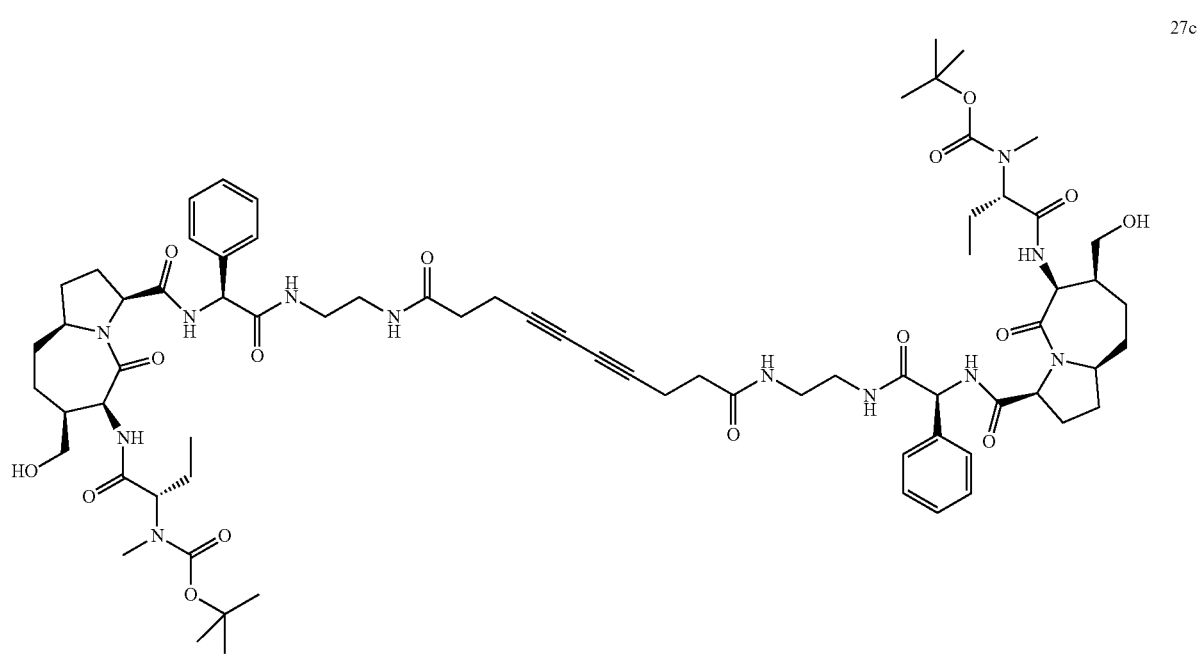 [SMILES: CC[C@@H](C(=O)N[C@@H]1C(=O)N2[C@@H](CC[C@@H]1CO)CC[C@H]2C(=O)N[C@H](C(=O)NCCNC(=O)CCC#CC#CCCC(=O)NCCNC(=O)[C@@H](NC(=O)[C@@H]1CC[C@@H]2CC[C@H](CO)[C@H](NC(=O)[C@H](CC)N(C)C(=O)OC(C)(C)C)C(=O)N21)c1ccccc1)c1ccccc1)N(C)C(=O)OC(C)(C)C]

27c. Biotage™ eluant conditions: from 1% of MeOH and 99% of CH$_2$Cl$_2$ to 10% of MeOH and 90% of CH$_2$Cl$_2$. Yield 74% (58 mg, MW 1391.69, 0.041 mmol) of pure 27c. Analytical characterization: $^1$H-NMR (400 MHz, CDCl$_3$): δ: 7.95 (bs, 2H), 7.55 (bs, 2H), 7.40-7.30 (m, 10H), 7.05 (bs, 2H), 6.95 (bs, 2H), 5.39 (d, J=7.2 Hz, 2H), 4.75 (d, J=6.4 Hz, 2H), 4.51 (bs, 4H), 3.82 (m, 2H), 3.64 (d, J=11.6, 2H), 3.42 (m, 4H), 3.35 (m, 6H), 2.88 (s, 6H), 2.60 (m, 4H), 2.45-2.15 (m, 8H), 2.15-1.60 (m, 14H), 1.51 (s, 18H), 1.35-1.25 (m, 4H) 0.93 (t, J=7.6 Hz, 6H); $^{13}$C-NMR (100 MHz, CDCl$_3$): δ: 173.0, 172.7, 171.7, 170.5, 137.8, 128.9, 128.3, 127.2, 66.2, 64.4, 61.4, 60.2, 58.9, 57.6, 54.0, 41.6, 41.0, 38.7, 34.7, 34.5, 33.1, 31.2, 28.4, 26.3, 21.6, 16.1, 10.7. ESI-MS: m/z 1392.0[M+H]$^+$.

Compound 27d was synthesized by the general procedure described above starting from compound 27d (30 mg, 0.044 mmol) and 5a (48 mg, 0.110 mmol).

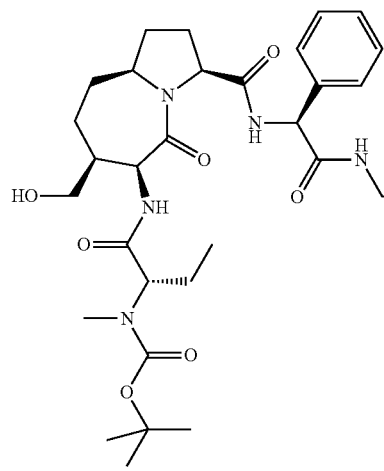
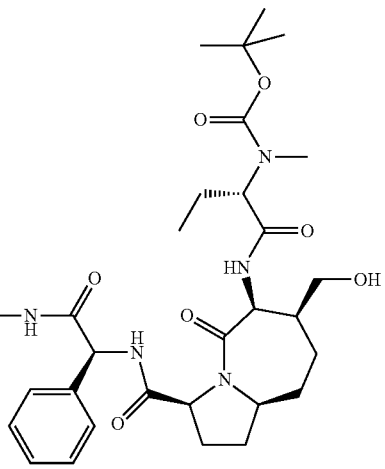

27d

27d. Biotage™ eluant conditions: from 1% of MeOH and 99% of CH$_2$Cl$_2$ to 10% of MeOH and 90% of CH$_2$Cl$_2$. Yield 80% (47 mg, MW 1333.64, 0.035 mmol) of pure 27d. Analytical characterization: $^1$H-NMR (400 MHz, CDCl$_3$): δ: 7.84 (d, J=7.8 Hz, 2H), 7.44 (d, J=6.8 Hz, 2H), 7.35-7.15 (m, 10H), 6.72 (bs, 2H), 5.25 (d, J=6.8 Hz, 2H), 4.60 (d, J=6.8 Hz, 2H), 4.40 (bs, 4H), 3.72 (d, J=12.0 Hz, 2H), 3.45 (m, 6H), 3.40-3.30 (m, 4H), 3.30-3.15 (m, 8H), 2.79 (s, 6H), 2.20-2.10 (m, 4H), 2.05-1.55 (m, 18H), 1.43 (s, 18H), 1.31-1.19 (m, 4H), 0.85 (t, J=7.2 Hz, 6H); $^{13}$C-NMR (100 MHz, CDCl$_3$): δ: 173.1, 171.4, 170.4, 169.4, 138.4, 128.9, 128.8, 128.1, 127.2, 80.5, 70.5, 70.0, 69.6, 64.4, 61.9, 60.3, 58.9, 57.4, 54.0, 41.6, 38.0, 34.4, 33.0, 31.2, 30.4, 28.4, 26.7, 21.6, 10.7. ESI-MS: m/z 1334.0[M+H]$^+$.

3.6 General Procedure for N-Boc Deprotection of Homodimeric Compounds 21, 24 and 27

TFA (50.0 equiv) was added to a stirred solution of compounds 21, 24, 27 (1.0 equiv) in CH$_2$Cl$_2$ (0.10 M concentration). The reaction mixtures were left stirring at room temperature and monitored by LC-MS. After reaction completion the solution was concentrated under reduced pressure. The residue was treated with water and vigorously stirred to hydrolyze any undesired trifluoroacetate ester, and finally the solution was concentrated under reduced pressure. The residues were purified by chromatography on a C$_{18}$ reverse phase semi-preparative HPLC column, and then lyophilized.

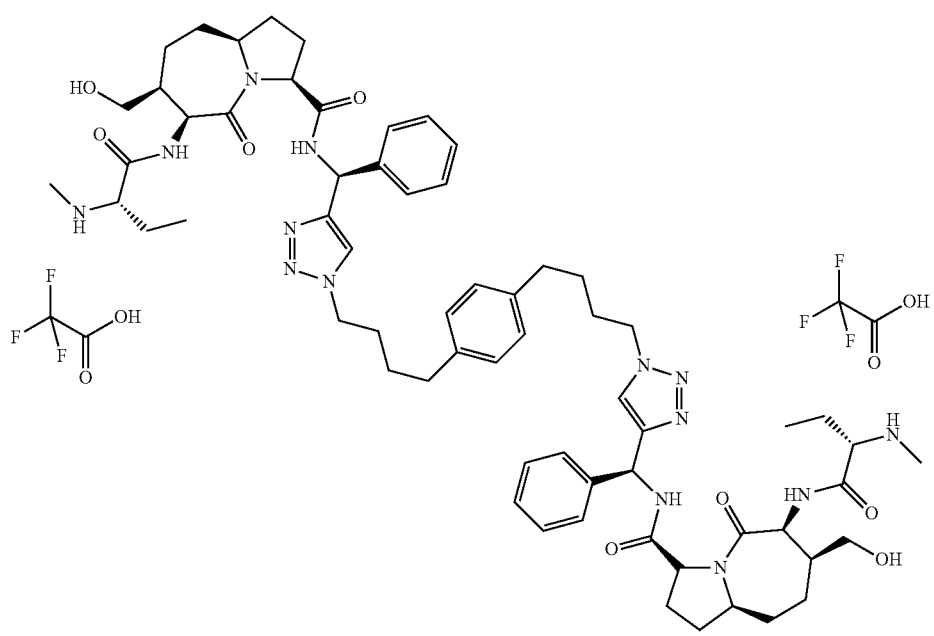

28a 28a, from 21a (30 mg, 0.022 mmol). HPLC eluant conditions: from 90% of H$_2$O (0.2% TFA) and 10% of MeOH/$^i$PrOH 6:4 (0.2% TFA) to 100% of MeOH/$^i$PrOH 6:4 (0.2% TFA), flow rate 12 ml/min., 20 min. runs. Yield 59% (18 mg, MW 1409.54, 0.013 mmol) of pure 28a. Analytical characterization: [α]$_D^{20}$ −110 (c 0.41, CH$_3$OH); $^1$H-NMR (400 MHz, D$_2$O): δ: 7.53 (s, 2H), 7.20-7.05 (m, 10H), 6.59 (s, 4H), 6.10 (s, 2H), 4.57 (d, J=9.2 Hz, 2H), 4.38 (bs, 2H), 3.96 (bs, 4H), 3.81 (m, 4H), 3-49 (bs, 4H), 2.62 (s, 6H), 2.08 (bs, 4H), 2.00-1.80 (m, 10H), 1.75-1.55 (m, 8H), 1.50-1.35 (m, 8H), 1.08 (bs, 4H), 0.88 (d, J=7.2 Hz, 6H); $^{13}$C-NMR (100 MHz, D$_2$O): δ: 172.3, 170.7, 168.0, 147.9, 139.4, 139.1, 128.8, 128.2, 128.0, 127.0, 123.0, 63.1, 62.7, 61.6, 58.5, 54.3, 50.0, 49.9, 39.0, 32.3, 31.5, 29.4, 28.9, 27.7, 27.5, 23.4, 8.3. ESI-MS: m/z 1181.9 [M+H]$^+$, 1204.2 [M+Na]$^+$, 591.8 [M+2H]$^{2+}$.

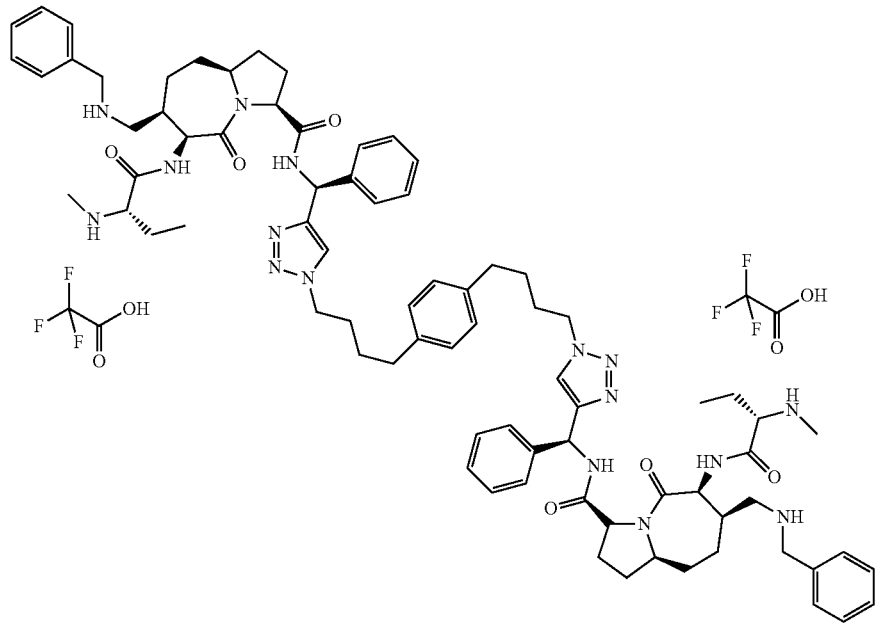

29a 29a, from 24a (21 mg, 0.013 mmol). HPLC eluant conditions: from 90% of H$_2$O (0.2% TFA) and 10% of MeOH/$^i$PrOH 6:4 (0.2% TFA) to 100% of MeOH/$^i$PrOH 6:4 (0.2% TFA), flow rate 12 ml/min., 20 min. runs. Yield 92% (19 mg, MW 1587.83, 0.012 mmol) of pure 29a. Analytical characterization: [α]$_D^{20}$ −121 (c 0.95, CH$_3$OH); $^1$H-NMR (400 MHz, D$_2$O): δ: 7.52 (s, 2H), 7.35 (s, 10H), 7.25-7.05 (m, 10H), 6.64 (s, 4H), 6.06 (s, 2H), 4.56 (d, J=9.2 Hz, 2H), 4.37 (bs, 2H), 4.14 (s, 4H), 4.045 (bs, 4H), 3.89 (bs, 2H), 3.76 (bs, 2H), 3.03 (d, J=12.0 Hz, 2H), 2.95 (t, J=11.2 Hz, 2H), 2.49 (s, 6H), 2.15 (bs, 4H), 2.12-1.90 (m, 8H), 1.90-1.70 (m, 8H), 1.70-1.65 (m, 2H), 1.50 (bs, 8H), 1.13 (bs, 4H), 0.84 (t, J=7.2 Hz, 6H); $^{13}$C-NMR (100 MHz, D$_2$O): δ: 172.5, 168.9, 168.7, 147.5, 139.3, 139.1, 130.1, 129.9, 129.8, 129.3, 128.9, 128.2, 128.1, 127.0, 132.2, 62.5, 61.7, 58.0, 54.1, 51.4, 50.2, 50.1, 47.8, 35.2, 33.7, 32.2, 31.5, 29.7, 28.7, 28.4, 27.9, 27.4, 23.4, 8.1. ESI-MS: m/z 1360.0 [M+H]$^+$, 680.6 [M+2H]$^{2+}$.

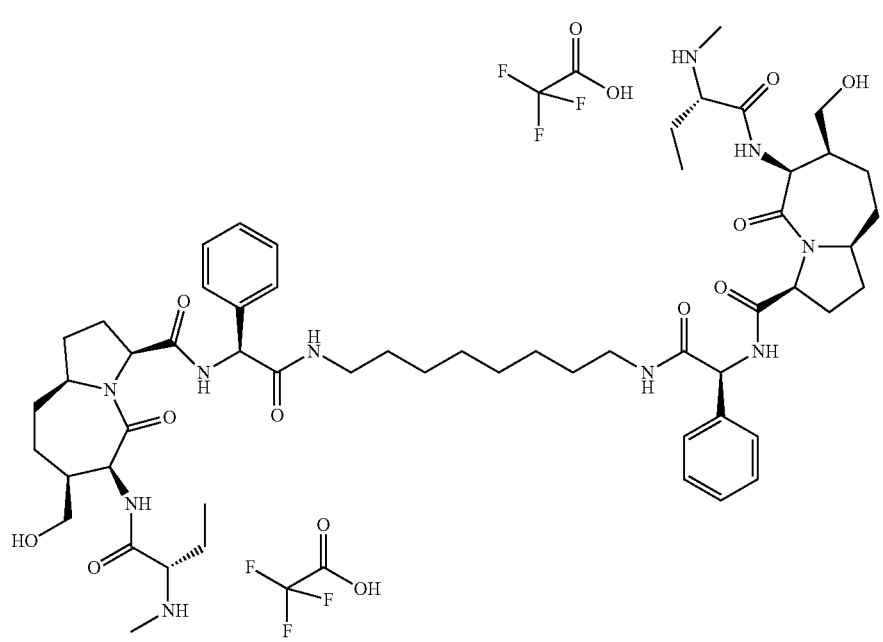
30a
30a, from 27a (93 mg, 0.074 mmol). HPLC eluant conditions: from 70% of H₂O (0.2% TFA) and 30% of CH₃CN (0.2% TFA) to 30% of H₂O (0.2% TFA) and 70% of CH₃CN (0.2% TFA), flow rate 12 ml/min., 20 min. runs. Yield 58% (55 mg, MW 1285.35, 0.043 mmol) of pure 30a. Analytical characterization: $[\alpha]_D^{20}$ −94 (c 1.44, CH₃OH); ¹H-NMR (400 MHz, D₂O): δ: 7.41 (m, 10H), 5.29 (s, 2H), 4.70 (m, 2H), 4.53 (dd, J=8.0, 4.4 Hz, 2H), 4.05 (m, 2H), 3.88 (dd, J=7.2, 5.2 Hz, 2H), 3.61 (m, 2H), 3.25 (m, 2H), 3.05 (m, 2H), 2.68 (s, 6H), 2.25 (m, 2H), 2.15 (m, 2H), 2.05 (m, 4H), 1.95 (m, 6H), 1.85 (m, 3H), 1.75 (m, 4H), 1.60 (m, 2H), 1.35 (m, 4H), 1.02 (bs, 8H), 0.96 (t, J=8.0 Hz, 6H); ¹³C-NMR (100 MHz, D₂O): δ: 173.2, 171.6, 171.2, 168.3, 136.1, 129.2, 129.0, 127.3, 63.2, 62.8, 61.8, 58.8, 58.2, 54.5, 39.3, 39.0, 32.4, 31.5, 31.4, 29.5, 28.1, 27.8, 25.6, 23.4, 8.2. ESI-MS: ink 1057.9 [M+H]⁺.
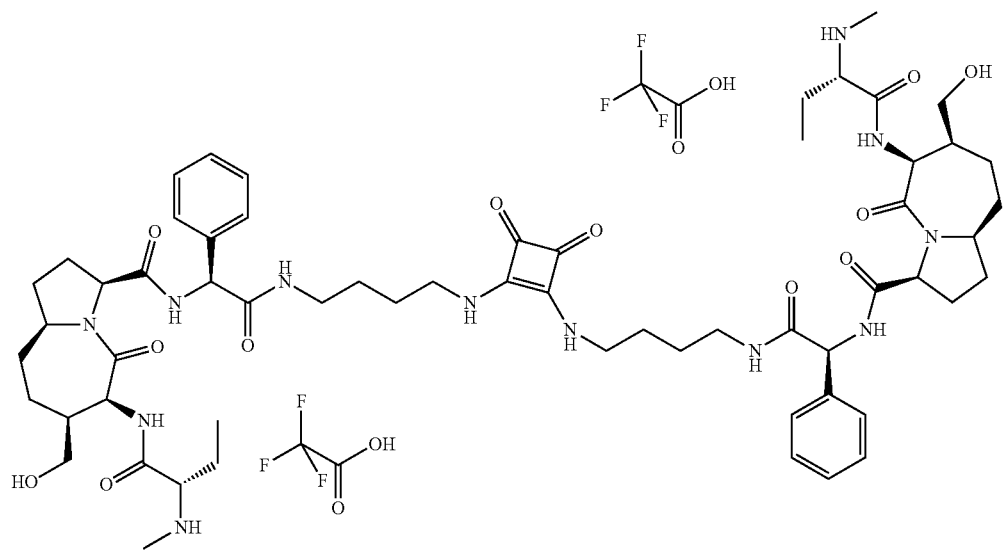
30b 30b, from 27b (22 mg, 0.016 mmol). HPLC eluant conditions: from 80% of H₂O (0.1% TFA) and 20% of CH₃CN (0.1% TFA) to 25% of H₂O (0.1% TFA) and 75% of CH₃CN (0.1% TFA), flow rate 12 ml/min., 25 min. runs. Yield 69% (16 mg, MW 1395.43, 0.011 mmol) of pure 30b. Analytical characterization: ¹H-NMR (600 MHz, D₂O): δ: 7.32-7.22 (m, 10H), 5.18 (s, 2H), 4.61 (d, J=10.2 Hz, 2H), 4.43 (dd, J=8.4, 4.8 Hz, 2H), 3.95 (m, 2H), 3.81 (dd, J=7.2, 5.4 Hz, 2H), 3.53 (dd, J=4.2, 1.8 Hz, 4H), 3.55-3.25 (m, 6H), 3.02 (m, 2H), 2.61 (s, 6H), 2.18 (m, 2H), 2.10 (m, 2H), 1.95-1.80 (m, 10H), 1.80-1.60 (m, 6H), 1.48 (m, 2H), 1.35 (m, 4H), 1.25 (m, 4H), 0.88 (t, J=7.8 Hz, 6H); ¹³C-NMR (125 MHz, D₂O): δ: 173.2, 171.8, 171.1, 168.2, 135.8, 129.0, 128.8, 127.2, 63.1, 62.6, 61.7, 58.7, 58.3, 54.3, 42.8, 38.9, 38.8, 32.4, 31.4, 29.4, 27.7, 25.3, 23.4, 8.1. ESI-MS: m/z 1167.6 [M+H]⁺.

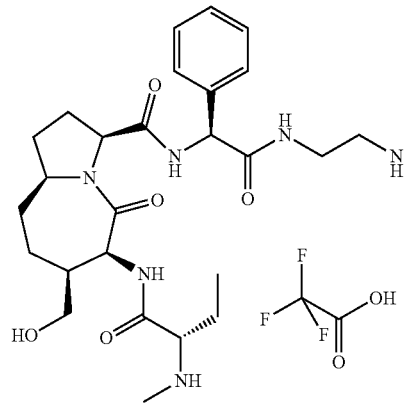
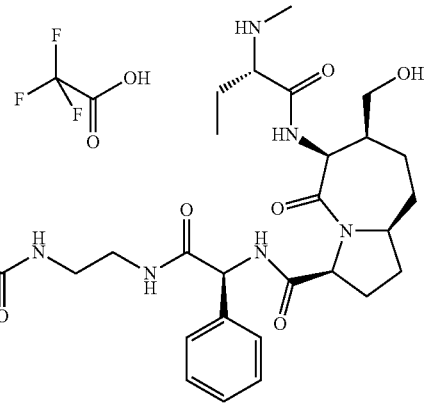

30c 30c, from 27c (57 mg, 0.041 mmol). HPLC eluant conditions: from 80% of H₂O (0.1% TFA) and 20% of CH₃CN (0.1% TFA) to 25% of H₂O (0.1% TFA) and 75% of CH₃CN (0.1% TFA), flow rate 12 ml/min., 25 min. runs. Yield 91% (53 mg, MW 1419.45, 0.037 mmol) of pure 30c. Analytical characterization: ¹H-NMR (600 MHz, D₂O): δ: 7.36-7.32 (m, 10H), 5.22 (s, 2H), 4.62 (d, J=10.2 Hz, 2H), 4.45 (dd, J=7.84, 4.8 Hz, 2H), 3.97 (m, 2H), 3.81 (dd, J=7.2, 5.4 Hz, 2H), 3.53 (dd, J=4.2, 1.8 Hz, 4H), 3.29 (m, 2H), 3.20 (m, 6H), 2.61 (s, 6H), 2.31 (dd, J=13.8, 6.6 Hz, 4H), 2.25-2.05 (m, 8H), 1.97 (m, 4H), 1.95-1.80 (m, 6H), 1.80-1.65 (m, 6H), 1.52 (m, 2H), 0.88 (t, J=7.8 Hz, 6H); ¹³C-NMR (125 MHz, D₂O): δ: 174.4, 173.3, 172.1, 171.1, 168.2, 135.8, 129.2, 129.0, 127.3, 76.7, 65.5, 63.1, 62.7, 58.7, 58.2, 54.4, 38.9, 38.8, 38.3, 33.9, 32.4, 31.4, 29.4, 27.7, 23.4, 15.2, 8.1. ESI-MS: m/z 1191.6 [M+H]⁺, 1213.5 [M+Na]⁺.

30d

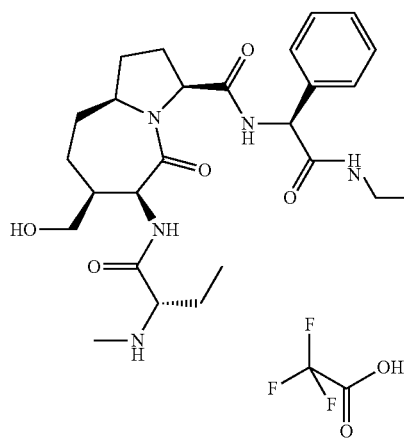
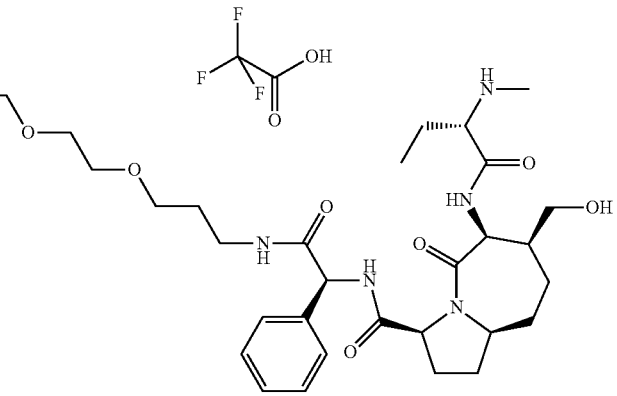

30d, from 27d (50 mg, 0.038 mmol). HPLC eluant conditions: from 80% of $H_2O$ (0.1% TFA) and 20% of $CH_3CN$ (0.1% TFA) to 25% of $H_2O$ (0.1% TFA) and 75% of $CH_3CN$ (0.1% TFA), flow rate 12 ml/min., 25 min. runs. Yield 97% (50 mg, MW 1361.41, 0.037 mmol) of pure 30d. Analytical characterization: $^1$H-NMR (600 MHz, $D_2O$): δ: 7.36-7.33 (m, 10H), 5.22 (s, 2H), 4.62 (d, J=9.6 Hz, 2H), 4.46 (dd, J=8.4, 4.8 Hz, 2H), 3.97 (m, 2H), 3.81 (dd, J=7.2, 5.4 Hz, 2H), 3.54 (dd, J=4.2, 1.8 Hz, 4H), 3.45 (m, 4H), 3.38 (m, 4H), 3.26 (m, 6H), 3.10 (m, 2H), 2.61 (s, 6H), 2.20 (m, 2H), 2.08 (m, 2H), 1.97 (m, 4H), 1.90-1.80 (m, 6H), 1.80-1.75 (m, 2H), 1.75-1.55 (m, 8H), 1.55-1.45 (m, 2H), 0.89 (t, J=7.8 Hz, 6H); $^{13}$C-NMR (125 MHz, $D_2O$): δ: 173.2, 171.7, 171.1, 168.2, 135.9, 129.2, 129.0, 127.3, 69.4, 68.0, 63.1, 62.7, 61.7, 58.7, 58.2, 54.4, 38.9, 36.3, 32.4, 31.5, 31.4, 29.4, 28.0, 27.7, 23.4, 8.1. ESI-MS: m/z 1133.6 [M+H]$^+$.

Example 4

Synthesis of Heterodimeric Smac Mimetics with [4.3.0] and [5.3.0] Bicyclic Lactam Systems 4.1 General Procedure for the Synthesis of Compounds 31

Scheme 9

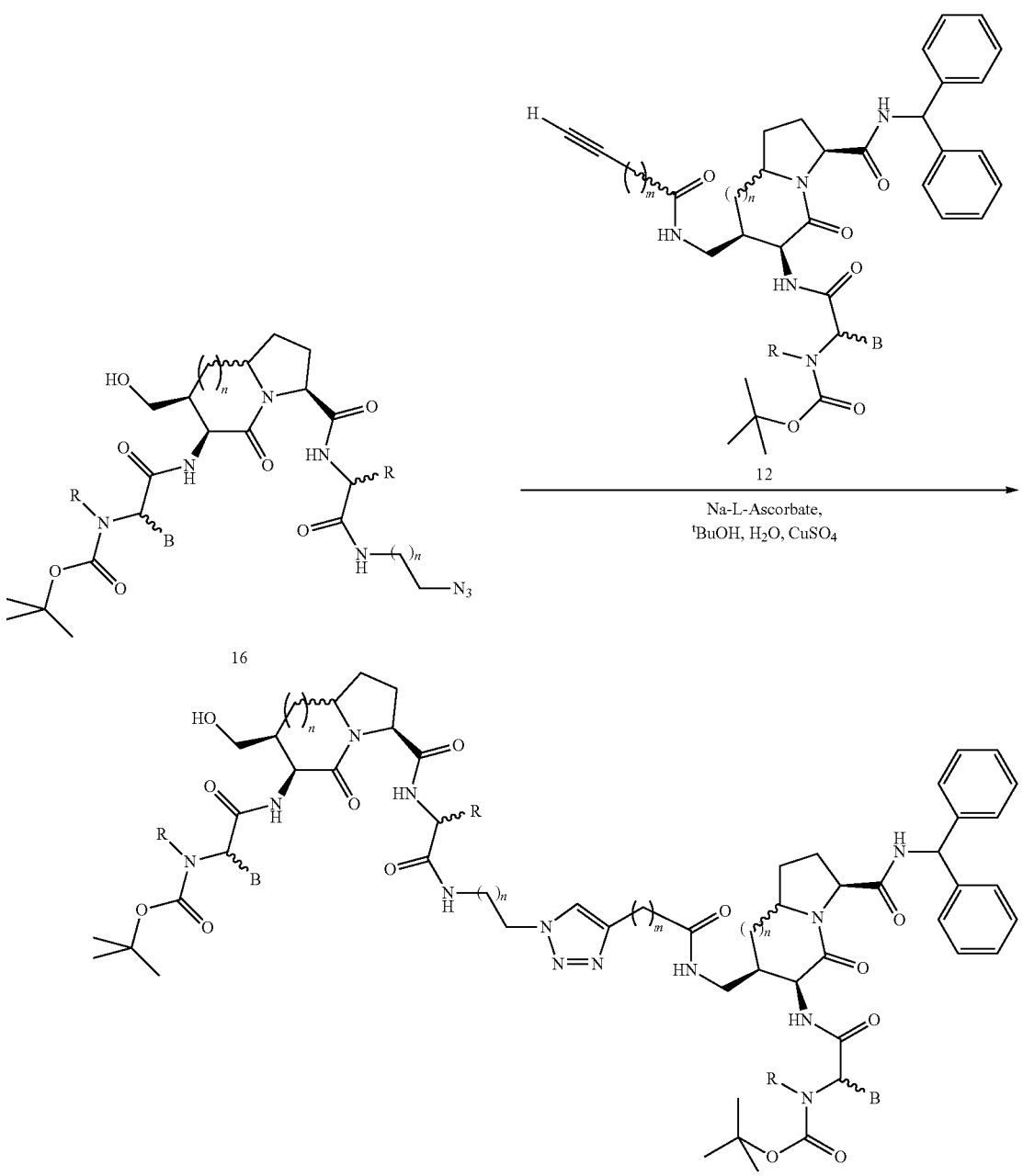

A 0.9 M aqueous solution of sodium ascorbate (0.55 equiv) and a 0.3 M aqueous solution of Cu(OAc)₂ (0.25 equiv) were sequentially added to a stirred solution of compounds 16 (1.0 equiv) and compounds 12 (1.0 equiv) in a 1:1 mixture of H₂O/ᵗBuOH (final concentration of 16~0.05 M). The reaction mixture was stirred overnight at room temperature and then the solvent was removed under reduced pressure. The residues were purified by Biotage™ flash chromatography.

Compound 31a was synthesized by the general procedure described above starting from compound 16a (44 mg, 0.057 mmol) and 12a (38 mg, 0.057 mmol).

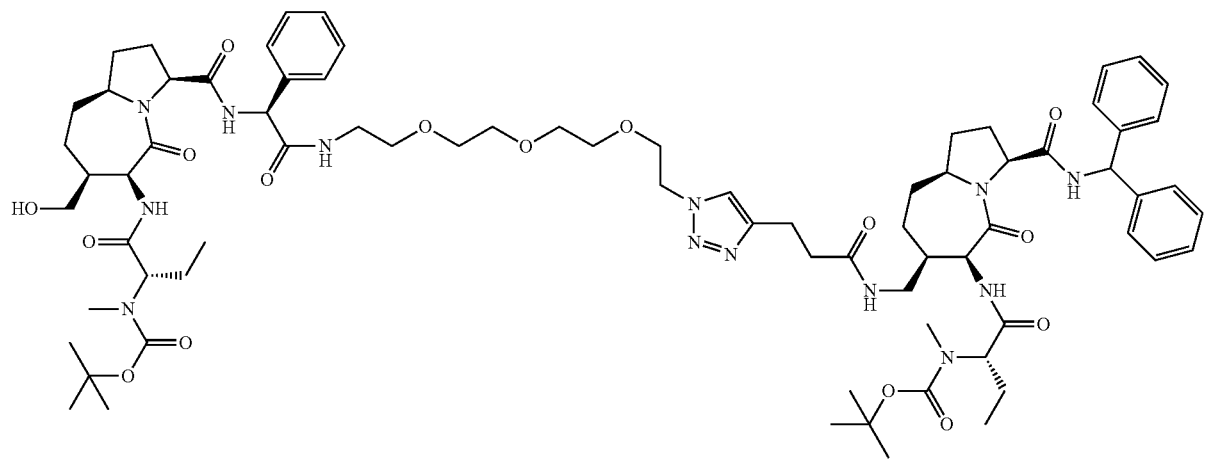

31a

31a. Biotage™ eluant conditions: from 1% of MeOH and 99% of CH₂Cl₂ to 10% of MeOH and 90% of CH₂Cl₂. Yield 61% (51 mg, MW 1460.79, 0.035 mmol) of pure 31a. Analytical characterization: $^1$H-NMR (400 MHz, CDCl₃): δ: 7.95 (d, J=6.8 Hz, 2H), 7.51 (m, 2H), 7.35-7.20 (m, 15H), 7.16 (d, J=9.2 Hz, 2H), 6.75 (bs, 1H), 6.22 (d, J=6.8 Hz, 1H), 5.43 (d, J=7.2 Hz, 1H), 4.72 (dd, J=16, 7.6 Hz, 2H), 4.48 (m, 6H), 3.82 (m, 4H), 3.70-3.30 (m, 15H), 3.07 (t, J=7.6 Hz, 2H), 2.85 (m, 6H), 2.67 (m, 3H), 2.48 (m, 1H), 2.25 (m, 3H), 2.05 (m, 1H), 2.00-1.80 (m, 5H), 1.80-1.65 (m, 7H), 1.52 (s, 9H), 1.48 (s, 9H), 1.35 (m, 1H), 1.25 (m, 2H), 1.10 (m, 1H), 0.94 (t, J=7.2 Hz, 6H); $^{13}$C-NMR (100 MHz, CDCl₃): δ: 173.1, 171.4, 169.6, 169.4, 146.1, 142.1, 138.4, 128.8, 128.7, 128.6, 127.3, 127.2, 127.1, 123.0, 70.5, 70.4, 70.2, 69.5, 69.3, 64.3, 61.4, 61.1, 58.8, 57.2, 56.8, 53.9, 53.7, 50.4, 41.7, 39.6, 35.5, 34.5, 33.2, 33.0, 31.2, 28.4, 28.3, 26.4, 25.6, 21.6, 21.3, 10.7. ESI-MS: ink 1461.7 [M+H]⁺, 1482.7 [M+Na]⁺.

4.2 General Procedure for the Synthesis of Compounds 32

Scheme 10

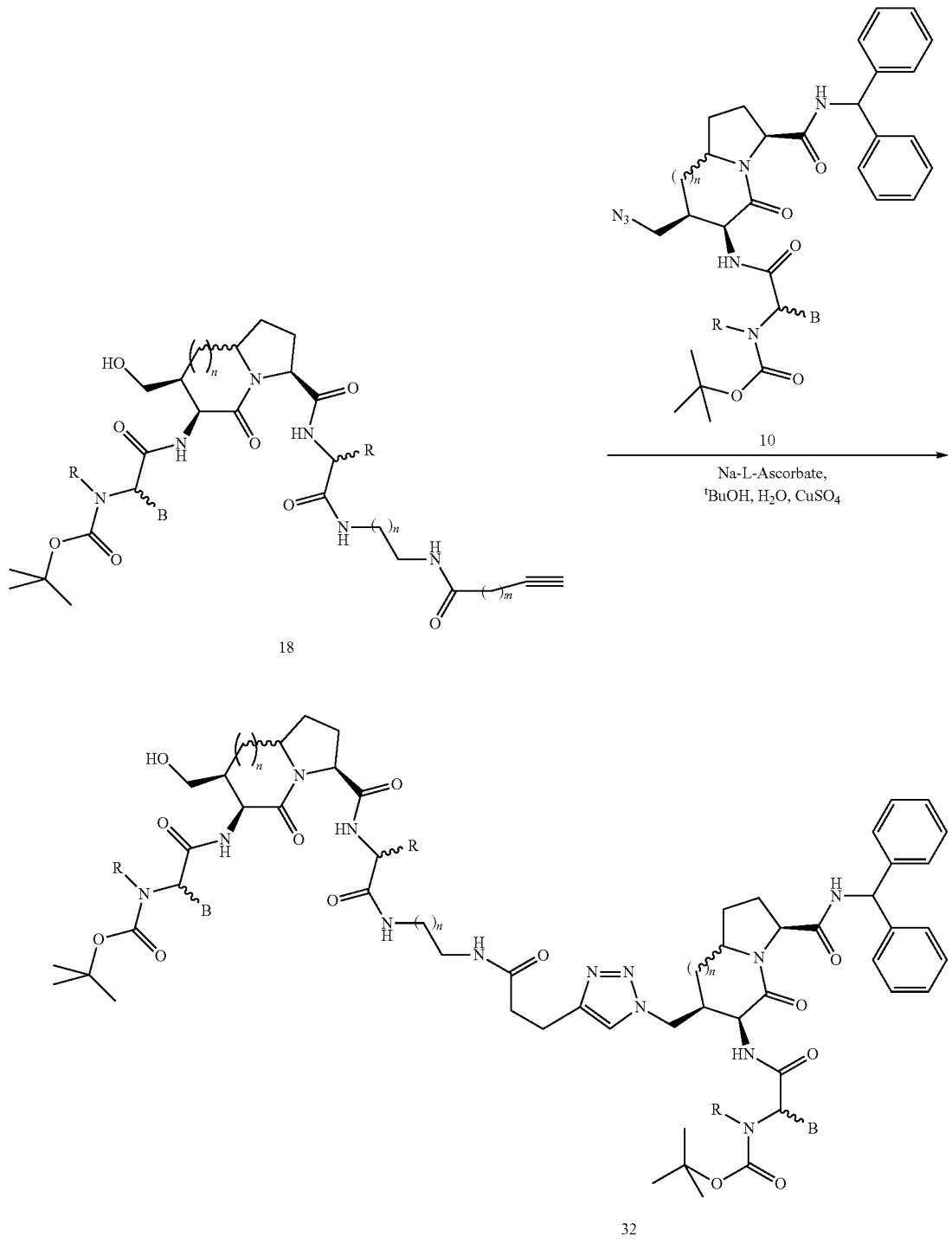

A 0.9 M aqueous solution of sodium ascorbate (0.55 equiv) and a 0.3 M aqueous solution of $Cu(OAc)_2$ (0.25 equiv) were sequentially added to a stirred solution of compounds 18 (1.0 equiv) and compounds 10 (1.0 equiv) in a 1:1 mixture of $H_2O$/$^tBuOH$ (final concentration of 18~0.05 M). The reaction mixture was stirred overnight at room temperature and then the solvent was removed under reduced pressure. The residues were purified by Biotage™ flash chromatography.

Compound 32a was synthesized by the general procedure described above starting from compound 18a (37 mg, 0.045 mmol) and 10a (29 mg, 0.045 mmol).

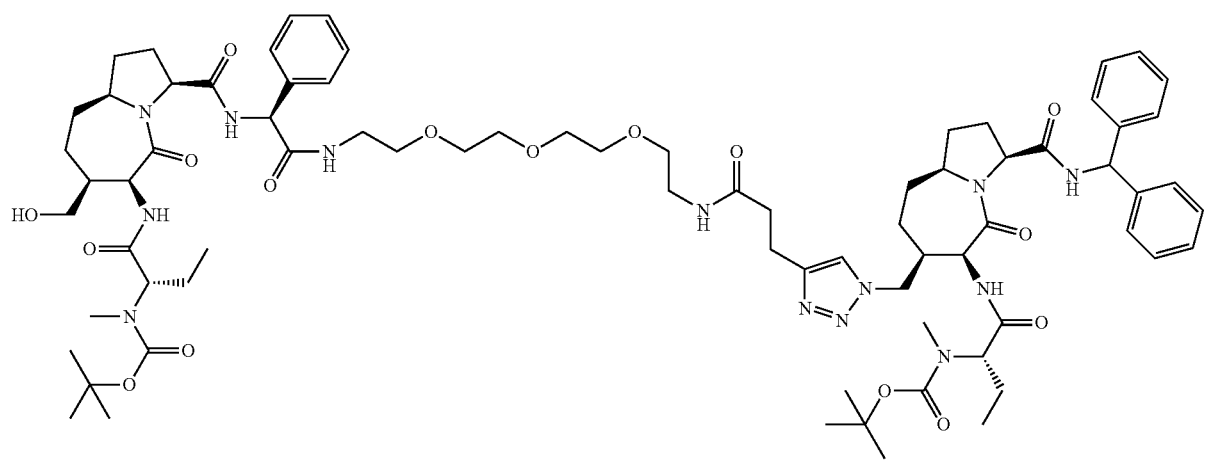

32a. Biotage™ eluant conditions: from 1% of MeOH and 99% of CH$_2$Cl$_2$ to 10% of MeOH and 90% of CH$_2$Cl$_2$. Yield 80% (52 mg, MW 1460.79, 0.036 mmol) of pure 32a. Analytical characterization: $^1$H-NMR (400 MHz, CDCl$_3$): δ: 7.89 (d, J=6.8 Hz, 1H), 7.71 (d, J=7.0 Hz, 1H), 7.47 (m, 1H), 7.35-7.12 (m, 15H), 7.08 (d, J=7.2 Hz, 1H), 6.85 (bs, 1H), 6.55 (bs, 1H), 6.10 (d, J=8.8 Hz, 1H), 5.36 (d, J=7.2 Hz, 1H), 4.56 (m, 3H), 4.38 (m, 4H), 4.10 (bs, 1H), 3.75 (m, 2H), 3.60-3.20 (m, 18H), 2.97 (bs, 2H), 2.75 (s, 6H), 2.55 (m, 3H), 2.32 (m, 1H), 2.15 (m, 3H), 1.95-1.60 (m, 13H), 1.43 (s, 9H), 1.38 (s, 9H); 1.35-1.15 (m, 3H), 1.02 (m, 1H), 0.85 (t, J=7.2 Hz, 6H); $^{13}$C-NMR (100 MHz, CDCl$_3$): δ: 171.9, 171.4, 170.7, 169.6, 141.8, 141.2, 138.4, 128.8, 128.7, 128.1, 127.6, 127.5, 127.3, 127.2, 127.1, 70.4, 70.1, 69.9, 69.8, 69.5, 64.3, 61.4, 61.3, 58.8, 57.2, 56.9, 53.9, 53.6, 41.6, 40.4, 39.6, 39.2, 34.4, 33.6, 33.3, 33.0, 31.1, 28.4, 28.3, 26.5, 25.9, 21.7, 21.2, 10.7. ESI-MS: m/z 681.2 [M+H]$^{2+}$, 1461.0 [M+H]$^+$, 1483.0 [M+Na]$^+$.

4.3 General Procedure for the Synthesis of Compounds 33

Scheme 11

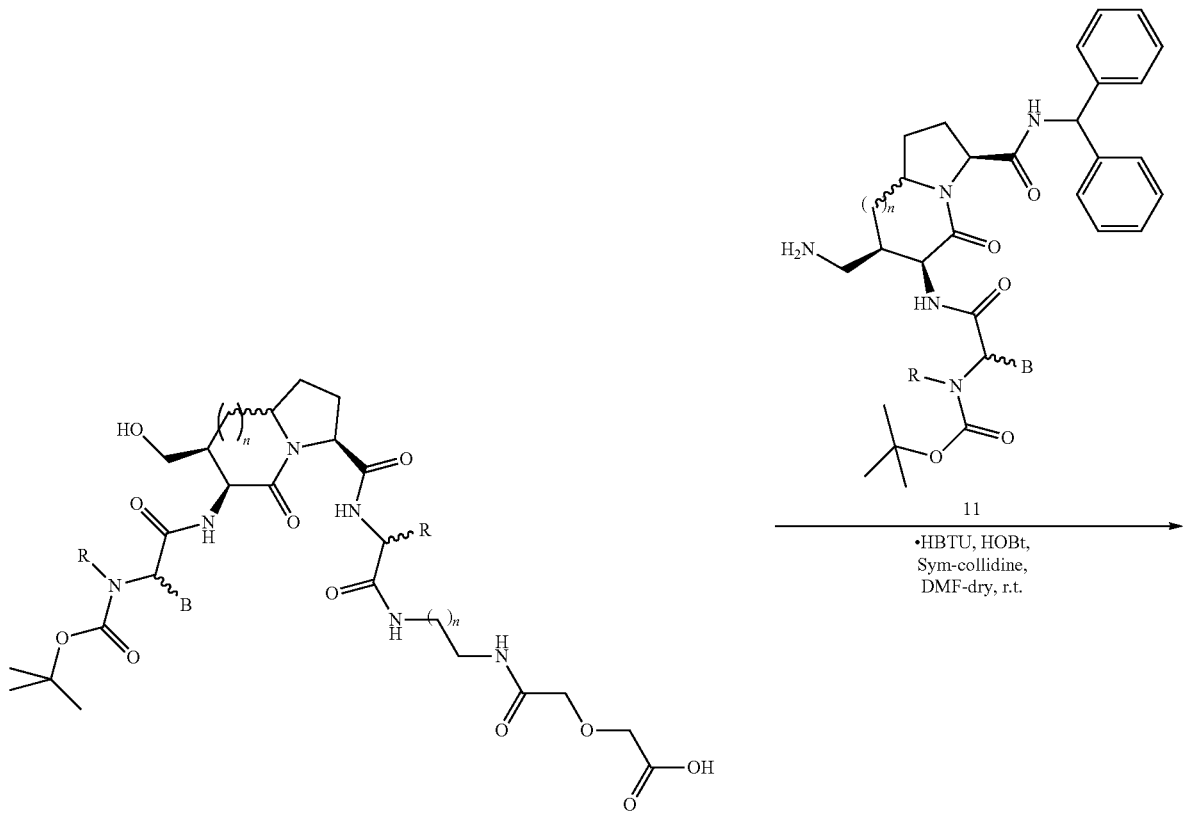

-continued

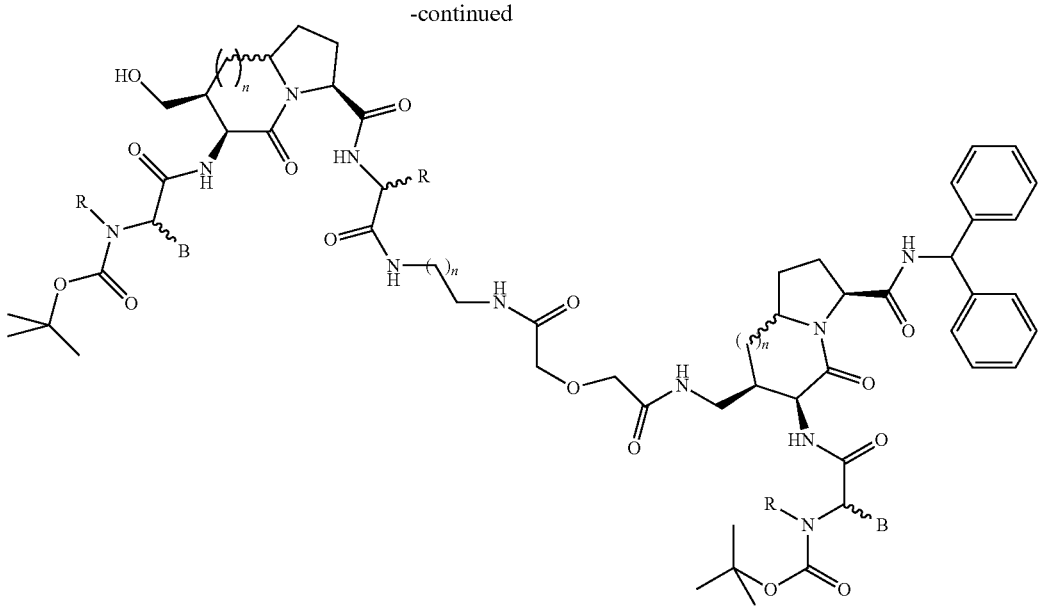

33

HOBt (1.2 equiv), HBTU (1.2 equiv) and sym-collidine (4.0 equiv) were sequentially added to a stirred solution of compounds 19 (1.0 equiv) and compounds 11 (1.25 equiv) in dry DMF (≈0.10 M concentration for 19) at 0° C. The reaction mixture was left stirring and monitored by LC-MS. After reaction completion, the mixture was diluted with EtOAc and washed with 5% aqueous citric acid, saturated aqueous sodium bicarbonate and brine. The organic layer was dried over $Na_2SO_4$, and then the solvent removed under reduced pressure. The residue was purified by Biotage™ flash chromatography.

Compound 33a was synthesized by the general procedure described above starting from compound 19a (54 mg, 0.063 mmol) and 11a (52 mg, 0.08 mmol).

33a. Biotage™ eluant conditions: from 1% of MeOH and 99% of $CH_2Cl_2$ to 10% of MeOH and 90% of $CH_2Cl_2$. Yield 67% (61 mg, MW 1457.77, 0.042 mmol) of pure 33a. Analytical characterization: $^1$H-NMR (400 MHz, $CDCl_3$): δ: 7.87 (d, J=7.2 Hz, 1H), 7.76 (d, J=6.8 Hz, 1H), 7.63 (d, J=6.0 Hz, 1H), 7.46 (m, 2H), 7.35-7.10 (m, 15H), 6.72 (bs, 1H), 6.15 (d, J=8.4 Hz, 1H), 5.35 (d, J=7.2 Hz, 1H), 4.64 (dd, J=19.2, 7.2 Hz, 2H), 4.40 (m, 4H), 3.95 (m, 4H), 3.72 (m, 3H), 3.6-3.20 (m, 18H), 2.79 (s, 3H), 2.75 (s, 3H), 2.52 (m, 2H), 2.35 (m, 1H), 2.18 (m, 2H), 1.90-1.55 (m, 14H), 1.43 (s, 9H), 1.41 (s, 9H), 1.30-1.10 (m, 4H), 0.85 (m, 6H); $^{13}$C-NMR (100 MHz, $CDCl_3$): δ: 172.7, 171.3, 169.6, 168.9, 168.9, 142.2, 138.4, 128.8, 128.6, 128.5, 128.1, 127.4, 127.3, 127.2, 70.7, 70.5, 70.4, 70.3, 70.1, 69.6, 69.5, 64.3, 61.7, 61.4, 61.3, 60.5, 58.9, 58.8, 57.2, 56.8, 53.9, 53.5, 41.6, 40.0, 39.7, 39.6, 38.7, 34.4, 34.3, 33.1, 33.0, 31.1, 28.4, 28.3, 26.4, 25.7, 21.7, 21.3, 10.7, 10.6. ESI-MS: m/z 1452.9 [M+H]$^+$, 1475.0 [M+Na]$^+$.

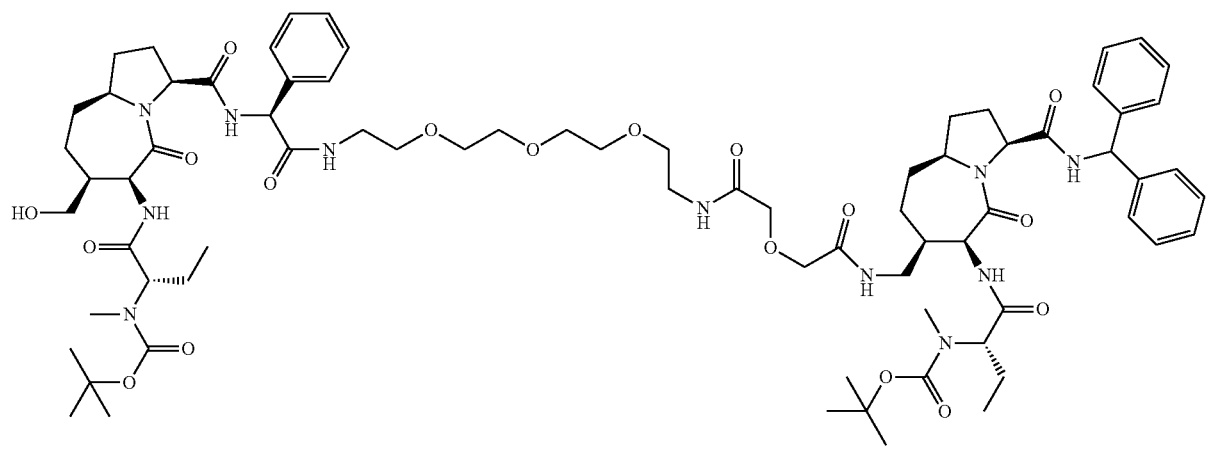

33a

4.4 General Procedure for the Boc-Deprotection of Compounds 31, 32 and 33

TFA (50.0 equiv) was added to a stirred solution of compounds 31, 32, 33 (1.0 equiv) in $CH_2Cl_2$ (≈0.10 M concentration). The reaction mixtures were left stirring at room temperature and monitored by LC-MS. After reaction completion the reaction mixture was concentrated under reduced pressure. The residue was treated with water and vigorously stirred to hydrolyze any undesired trifluoroacetate ester, then the mixture was concentrated under reduced pressure. The residue was purified by chromatography on a $C_{18}$ reverse phase semi-preparative HPLC column and then lyophilized.

34a, from 31a (0.035 mmol). HPLC eluant conditions: from 40% of $H_2O$ (0.1% TFA) and 60% of $CH_3CN$ (0.1% TFA) to 25% of $H_2O$ (0.1% TFA) and 75% of $CH_3CN$ (0.1% TFA), flow rate 15 ml/min., 22 min. runs. Yield 90% (47 mg, MW 1488.60, 0.032 mmol) of pure 34a. Analytical characterization; $^1$H-NMR (400 MHz, $D_2O$): δ: 8.77 (s, 1H), 7.39-7.29 (m, 15H), 6.04 (s, 1H), 5.33 (s, 1H), 4.67 (d, J=10.0 Hz, 2H), 4.60-4.40 (m, 5H), 4.00 (m, 2H), 3.90 (m, 2H), 3.79 (m, 2H), 3.58 (d, J=3.6 Hz, 2H), 3.55-38 (m, 11H), 3.35-3.20 (m, 2H), 2.96 (m, 3H), 2.67 (s, 6H), 2.57 (t, J=7.2 Hz, 2H), 2.23 (m, 2H), 2.12 (m, 2H), 2.07-1.85 (m, 8H), 1.85-1.62 (m, 7H), 1.55 (m, 1H), 1.50-1.30 (m, 2H), 0.95 (m, 6H); $^{13}$C-NMR (100 MHz, $D_2O$): δ: 174.8, 173.2, 172.7, 171.8, 171.1, 169.9, 168.4, 168.2, 146.0, 141.0, 140.8, 135.9, 129.2, 129.0, 128.8, 127.8, 127.3, 127.1, 123.9, 69.5, 69.4, 68.7, 68.6, 63.2, 62.7, 62.6, 61.7, 58.7, 58.3, 58.0, 57.6, 54.5, 54.4, 50.0, 40.7, 39.2, 38.9, 37.2, 35.1, 32.4, 31.5, 31.4, 30.1, 29.4, 27.9, 27.7, 23.4, 21.0, 8.2. ESI-MS: m/z 631.3 $[M+H]^{2+}$, 1260.8 $[M+H]^+$, 1282.7 $[M+Na]^+$.

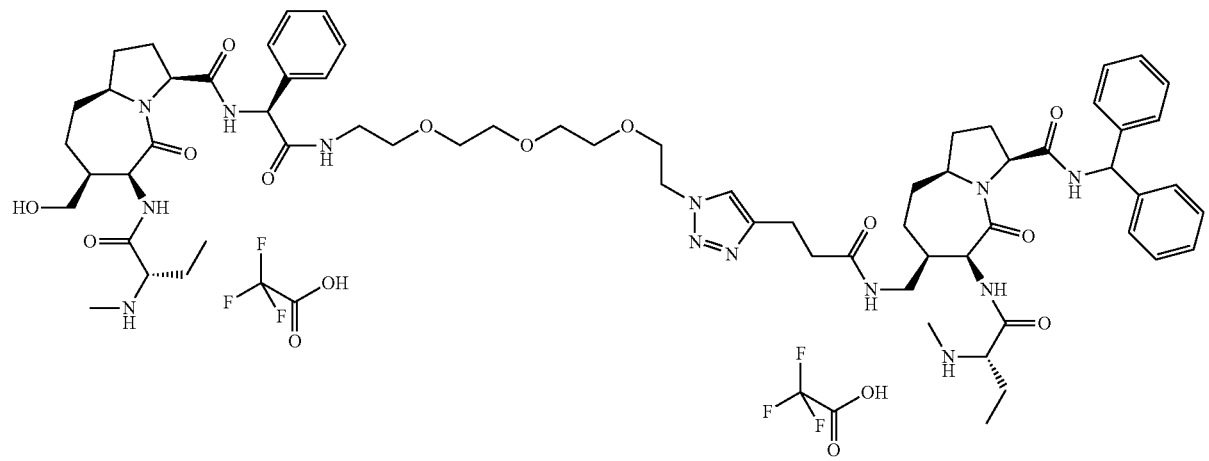

34a

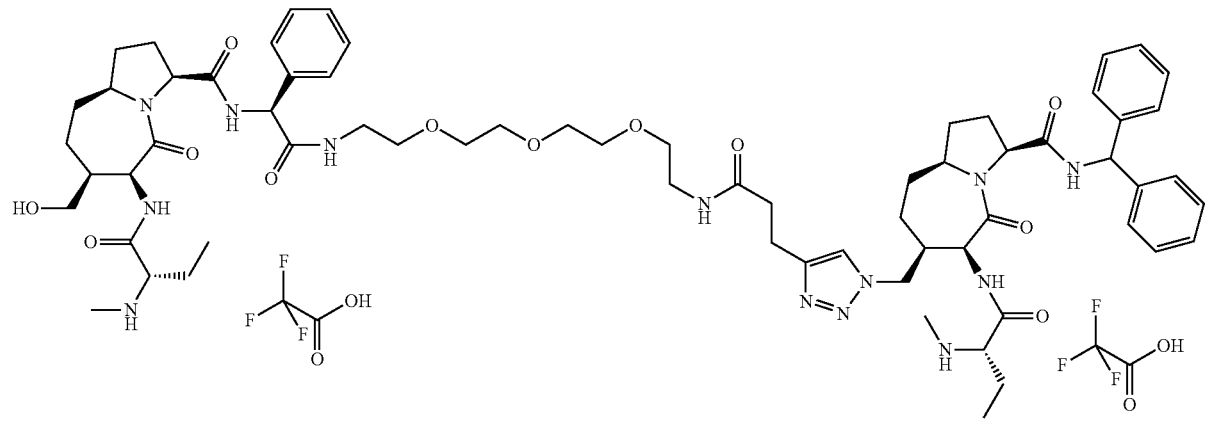

35a 35a, from 32a (0.022 mmol). HPLC eluant conditions: from 40% of $H_2O$ (0.1% TFA) and 60% of $CH_3CN$ (0.1% TFA) to 25% of $H_2O$ (0.1% TFA) and 75% of $CH_3CN$ (0.1% TFA), flow rate 15 ml/min., 22 min. runs. Yield 86% (28 mg, MW 1488.60, 0.019 mmol) of pure 35a. Analytical characterization: $^1$H-NMR (400 MHz, $D_2O$): δ: 7.78 (s, 1H), 7.37-7.28 (m, 15H), 6.04 (s, 1H), 5.34 (s, 1H), 4.78 (d, J=10.4 Hz, 1H), 4.66 (m, 1H), 4.53 (m, 3H), 4.36 (m, 1H), 4.03 (m, 2H), 3.88 (t, J=6.0 Hz, 2H), 3.60-3.25 (m, 16H), 3.28 (m, 3H), 2.94 (t, J=14.4 Hz, 2H), 2.70 (s, 3H), 2.58 (s, 3H), 2.56 (t, J=7.2 Hz, 2H), 2.35-2.05 (m, 5H), 2.05-1.88 (m, 9H), 1.85-1.65 (m, 6H), 1.62-1.46 (m, 3H), 0.95 (m, 6H); $^{13}$C-NMR (100 MHz, $D_2O$): δ: 174.9, 173.2, 172.7, 171.1, 169.5, 168.7, 146.5, 141.0, 140.9, 136.0, 129.2, 129.0, 128.9, 127.8, 127.4, 127.3, 127.1, 69.6, 69.4, 68.8, 68.7, 63.2, 62.8, 62.6, 61.9, 61.8, 58.7, 58.2, 58.0, 57.6, 54.5, 54.4, 52.0, 39.3, 39.0, 38.1, 35.0, 32.4, 32.3, 31.8, 31.5, 27.9, 27.7, 23.5, 23.4, 20.9, 8.2, 8.1. ESI-MS: m/z 631.1 $[M+H]^{2+}$, 1260.8 $[M+H]^+$, 1282.7 $[M+Na]^+$.

expression was induced by adding isopropyl-β-D-thiogalactopyranoside (IPTG) to a final concentration of 1 mM and 100 μM zinc acetate (ZnAc) for 3 hours at 37° C. Bacteria grown in LB medium plus kanamycin were harvested, resuspended in a buffer containing 50 mM Tris HCl pH 7.5, 200 mM NaCl, 50 μM ZnAc and protease inhibitors, treated with 100 μg/ml lysozyme for 30 minutes in ice and then lysed by sonication. After elimination of debris by centrifugation, recombinant protein was purified using Ni-NTA (His-trap Ffcrude, Ge-Healthcare) followed by gel filtration (Superdex 200, Ge-Healthcare). BIR3-His-tag was eluted with 250 mM imidazole and thereafter stored in 20 mM Tris pH 7.5, 200 mM NaCl, 50 μM ZnAc, and 10 mM Dithiothreitol.

5.2 Saturation Binding Experiment

Fluorescent polarization experiments were performed in black, flat-bottom 96-well microplates (PBI) and fluorescent polarization was measured by Ultra plate reader (Tecan). Fluorescent-labelled Smac peptide [AbuRPF-K(5-Fam)-

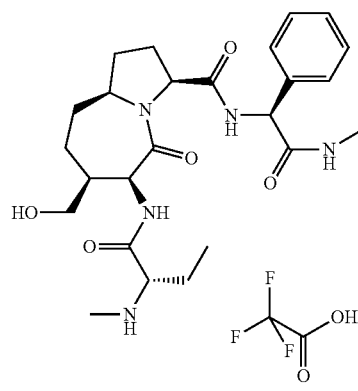
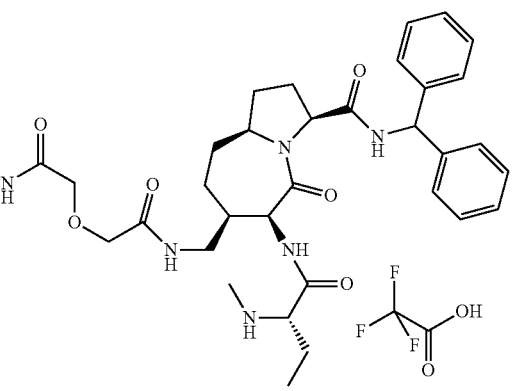

36a 36a, from 33a (0.042 mmol). HPLC eluant conditions: from 40% of $H_2O$ (0.1% TFA) and 60% of $CH_3CN$ (0.1% TFA) to 25% of $H_2O$ (0.1% TFA) and 75% of $CH_3CN$ (0.1% TFA), flow rate 15 ml/min., 22 min. runs. Yield 88% (55 mg, MW 1480.57, 0.037 mmol) of pure 36a. Analytical characterization; $^1$H-NMR (400 MHz, $D_2O$): δ: 7.41-7.30 (m, 15H), 6.06 (s, 1H), 5.36 (s, 1H), 4.67 (d, J=8.4 Hz, 2H), 4.55 (m, 2H), 4.10 (d, J=5.2 hz, 4H), 4.05 (m, 2H), 3.93 (t, J=6.4 Hz, 1H), 3.89 (t, J=5.6 Hz, 1H), 2.70 (s, 3H), 2.69 (s, 3H), 2.25 (m, 2H), 2.15 (m, 2H), 2.08-1-68 (m, 17H), 1.65-1.50 (m, 3H), 0.97 (m, 6H); $^{13}$C-NMR (100 MHz, $D_2O$): δ: 172.8, 171.8, 171.7, 171.1, 170.1, 168.5, 168.3, 141.0, 140.9, 129.2, 129.0, 128.9, 127.8, 127.4, 127.3, 127.2, 70.0, 69.9, 69.6, 69.4, 68.8, 68.7, 63.2, 62.8, 62.7, 61.9, 61.8, 58.8, 58.5, 58.0, 57.7, 54.6, 54.5, 40.7, 39.3, 39.0, 38.6, 37.4, 32.4, 31.6, 31.5, 30.5, 29.5, 29.0, 27.9, 27.7, 23.4, 8.2, 8.1. ESI-MS: m/z 627.1 $[M+H]^{2+}$, 1252.8 $[M+H]^+$, 1274.8 $[M+Na]^+$.

Example 5

Fluorescence Polarization Assay 5.1 Cloning, Expression and Purification of Human MAP BIR3

A pET28 vector (Novagen) with the cDNA coding for human XIAP BIR3 domain from residue 241 to 356 was used to transform *Escherichia coli* strain BL21. Protein $NH_2$] (FITC-SMAC) to a final concentration of 5 nM and increasing concentration of BIR3-His-tag from 0 to 20 μM were added to an assay buffer. The final volume in each well was 120 μl, with the assay buffer consisting of 100 mM potassium phosphate, pH 7.5; 100 μg/ml bovine γ-globulin; 0.02% sodium azide. After a 15 min shaking, the plate was incubated for 3 hours at room temperature. Fluorescence polarization was measured at an excitation and emission wavelengths of 485 nm and 530 nm respectively. The equilibrium binding graphs were constructed by plotting millipolarization units (mP) as function of the XIAP BIR3 concentration. Data were analyzed using Prism 4.0 software (Graphpad Software).

5.3 Competitive Binding Experiments

SMAC-mimic compounds were evaluated for their ability to displace FITC-SMAC probe from recombinant protein. 5 mM of FITC-SMAC, XIAP BIR3-His-tag and serial dilutions of the SMAC-mimic compounds (concentrations ranging from 4 μM to 0.4 nM) were added to each well to a final volume of 120 μl in the assay buffer described above. The concentration of BIR3-His-tag used was 60 nM, able to bind more than 50% of the ligand in the saturation binding experiment. After being mixed for 15 minutes on a shaker and incubated 3 hours at room temperature, fluorescent polarization was measured by Ultra plate reader (Tecan). All SMAC-mimics and the fluorescent peptide were stocked in DMSO.

5.4 Binding Affinities for BIR3 Domain of XIAP of Homo- and Heterodimeric Smac Mimetics with [4.3.0] and [5.3.0] Bicyclic Lactam Systems The $IC_{50}$s of some examples are reported in the Table below, as an average value from three independent measurements, together with their standard deviation.

| Compound No. | $IC_{50}$ (av) [nM] | RSD % |
|---|---|---|
| 28a | 25.4 | 11.3 |
| 29a | 58.3 | 8.3 |
| 30a | 29.9 | 12.8 |
| 30b | 26.7 | 16.0 |
| 30c | 24.5 | 11.7 |
| 30d | 26.0 | 13.8 |
| 34a | 31.1 | 30.5 |
| 35a | 29.7 | 29.0 |
| 36a | 31.2 | 29.1 |
| SM164[a] | 42.0 | 16.0 |

[a] from J. Am. Chem. Soc. 2007, 129, 15279

The values of the tested compounds clearly show high potency (nanomolar) on the relevant in vitro assay, with an indication of structure-activity relationships among congeners.

5.5 Cloning, Expression and Purification of Human MAP Linker-BIR2-BIR3

A pET28 vector (Novagen) with the cDNA coding for human XIAP from residue 124 to 356 (linker-BIR2-BIR3), coding for BIR2 and BIR3 domains and the linker region preceding BIR2, was used to transform *Escherichia coli* strain BL21. Protein expression was induced by adding isopropyl-β-D-thiogalactopyranoside (IPTG) to a final concentration of 1 mM and 100 µM zinc acetate (ZnAc) for 3 hours at 37° C. Bacteria grown in LB medium plus kanamycin were harvested, resuspended in a buffer containing 50 mM Tris HCl pH 7.5, 200 mM NaCl, 50 µM ZnAc and protease inhibitors, treated with 100 µg/ml lysozyme for 30 minutes in ice and then lysed by sonication. After elimination of debris by centrifugation, recombinant protein was purified using Ni-NTA (His-trap Ffcrude, Ge-Healthcare) followed by gel filtration (Superdex 200, Ge-Healthcare). The linker-BIR2-BIR3-His-tag was eluted with 250 mM imidazole and thereafter stored in 20 mM Tris pH 7.5, 200 mM NaCl, 50 µM ZnAc, and 10 mM Dithiothreitol.

5.6 Saturation Binding Experiment—Human MAP Linker-BIR2-BIR3

Fluorescent polarization experiments were performed in black, flat-bottom 96-well microplates (PBI) and fluorescent polarization was measured by Ultra plate reader (Tecan). Fluorescent-labelled dimeric Smac peptide SMAC-1F (Nikolovska-Coleska et al., Analyt. Biochem. 374:87, 2008) to a final concentration of 1 nM and increasing concentration of linker-BIR2-BIR3-His-tag from 0 to 2 µM were added to an assay buffer. The final volume in each well was 120 µl, with the assay buffer consisting of 100 mM potassium phosphate, pH 7.5; 100 µg/ml bovine γ-globulin; 0.02% sodium azide. After a 15 minutes shaking, the plate was incubated for 3 hours at room temperature. Fluorescence polarization was measured at an excitation and emission wavelengths of 485 nm and 530 nm respectively. The equilibrium binding graphs were constructed by plotting millipolarization units (mP) as function of the XIAP linker-BIR2-BIR3 concentration. Data were analyzed using Prism 4.0 software (Graphpad Software).

5.7 Competitive Binding Experiments—Human MAP Linker-BIR2-BIR3

SMAC-mimic compounds were evaluated for their ability to displace SMAC-1F probe from recombinant protein. 1 nM of SMAC-1F, 3 nM of XIAP linker-BIR2-BIR3-His-tag and serial dilutions of the SMAC-mimic compounds (concentrations ranging from 2 µM to 0.2 nM) were added to each well to a final volume of 120 µl in the assay buffer described above. After being mixed for 15 minutes on a shaker and incubated 3 hours at room temperature, fluorescent polarization was measured by Ultra plate reader (Tecan). All SMAC-mimics and the fluorescent peptide were stocked in DMSO.

5.8 Binding Affinities for the Linker-BIR2-BIR3 Domains of MAP of Homo- and Heterodimeric Smac Mimetics with [4.3.0] and [5.3.0] Bicyclic Lactam Systems The IC50s of some examples are reported in the Table below, as an average value from three independent measurements, together with their standard deviation.

| Compound No. | IC50 (av) [nM] | RSD % |
|---|---|---|
| 28a | 0.8 | 25.0 |
| 29a | 4.4 | 22.0 |
| 30a | 0.3 | 22.0 |
| 30b | 0.8 | 17.8 |
| 30c | 0.1 | 17.5 |
| 30d | 0.2 | 18.3 |
| 34a | 0.11 | 24.1 |
| 35a | 0.13 | 25.7 |
| 36a | 0.08 | 26.0 |
| SM164[a] | 0.76 | 24.7 |

[a] from J. Am. Chem. Soc. 2007, 129, 15279

The values of the tested compounds clearly show extremely high potency (nanomolar) on the relevant in vitro assay, with an indication of structure-activity relationships among congeners.

5.9 Cloning, Expression and Purification of Human cIAP1 BIR3 and cIAP2 BIR3 Domains The sequence coding for the 245-357 residues (XIAP-BIR3 structural homology numbering) constituting the cIAP1- and cIAP2-BIR3 domains were cloned in pET21(b) vector (Novagen) with a C-terminal 6×His-tag. The plasmids were used to transform *Escherichia coli* strain BL21 (DE3). The recombinant proteins were purified using Ni-NTA (His-trap FFcrude, Ge-Healthcare), followed by gel filtration (Superdex 200, Ge-Healthcare). The recombinant proteins were eluted in 20 mM Tris pH 8.0, 250 mM NaCl and 10 mM DTT. Aliquoted proteins were conserved at −80° C.

5.10 Binding Affinities for the BIR3 Domain of cIAP1 and cIAP2 of Homo- and Heterodimeric Smac Mimetics with [4.3.0] and [5.3.0] Bicyclic Lactam Systems The fluorescently-labelled Smac peptide (AbuRPF-K(5-Fam)-NH2, final concentration of 2 nM), and increasing concentrations of cIAP1- and cIAP2-BIR3 from 0 to 20 µM, were added to an assay buffer consisting of 100 mM potassium phosphate, pH 7.5, 100 µg/ml bovine γ-globulin, 0.02% sodium azide. After shaking (15 min) the plate was incubated for 3 hours at room temperature. Fluorescence polarization was measured on an Ultra plate reader (Tecan), at excitation and emission wavelengths of 485 nm and 530 nm, respectively. The equilibrium binding curves were drawn by plotting experimental data (millipolarization units, mP) as a function of recombinant concentration and the Kd values were evaluated as 4.8±0.6 nM for cIAP1-BIR3, and 23.6±1.6 nM for cIAP2-BIR3. All experiments were performed in black, flat-bottom 96-well microplates (Greiner bio-one). 4-substituted azabicyclo[5.3.0]alkane Smac-mimetics were evaluated for their ability to displace the fluorescent probe from recombinant protein. Fluorescent probe (2 nM), cIAP1-BIR3 (10 nM) or cIAP2 (25 nM) and serial dilutions of 4-substituted azabicyclo[5.3.0]alkane Smac-mimetics (concentration ranging from 1 μM to 0.1 nM) were added to each well, to a final volume of 120 μl in the assay buffer described above. After 15 minutes mixing on a shaker, and 3 hours incubation at room temperature, fluorescent polarization was measured on the Ultra plate reader (Tecan).

The IC50s of some examples are reported in the Table below, as an average value from three independent measurements, together with their standard deviation.

| Compound No. | cIAP1 | | cIAP2 | |
|---|---|---|---|---|
| | IC50 (av) [nM] | RSD % | IC50 (av) [nM] | RSD % |
| 28a | 5.4 | 12.2 | 2.5 | 17.6 |
| 29a | 17.6 | 12.2 | 12.1 | 18.4 |
| 30a | 1.9 | 12.0 | 1.8 | 21.2 |
| 30b | 2.6 | 11.0 | 2.9 | 16.8 |
| 30c | 1.1 | 18.1 | 1.1 | 5.3 |
| 30d | 1.5 | 17.0 | 2.2 | 6.0 |
| 34a | 3.2 | 10.3 | 0.3 | 24.5 |
| 35a | 5.0 | 16.8 | 0.4 | 24.2 |
| 36a | 1.5 | 4.9 | 0.2 | 23.7 |
| SM164[a] | 0.46 | 23.0 | 0.51 | 30.0 |

[a]from J. Am. Chem. Soc. 2007, 129, 15279

The values of the tested compounds clearly show extremely high potency (nanomolar) on the relevant in vitro assay, with an indication of structure-activity relationships among congeners.

Example 6

Cellular Cytotoxicity Assays 6.1 Cytotoxicity—Cells and Treatments

Human cell lines MDA-MB-231 (breast epithelial adenocarcinoma), HL-60 (promieloblast cells) and PC-3 (prostate adenocarcinoma cells) were purchased from Istituto Zooprofilattico di Brescia (www.bs.izs.it). Reagents for cell culture were purchased from Sigma, unless otherwise indicated. Cells were grown on Plastic Petri dishes (Falcon) in RPMI 1640 medium supplemented with 2 mM L-glutamine, Penicillin (100 U/mL)/Streptomicin (100 μg/mL), 10% Fetal Bovine Serum. A sub-cultivation ratio of 1:4 was used. Cells were maintained at 37° C. in an atmosphere of 95% air and 5% $CO_2$.

6.2 Cytotoxicity—Standalone—Experimental Protocols

Cells were seeded in 96-well flat bottom cell culture plates at a density of 5000 cells/well in 100 μL of culture medium. HL-60 cells were immediately stimulated with the indicated compounds for 96 hours in the incubator. MDA-MB-231 and PC-3 cells were allowed to adhere for 24 hours. prior to be exposed to the compounds for 96 hours in the incubator. Cells were exposed to the following concentrations of the compounds: 50 nM, 100 nM, 200 nM, 500 nM, 1 μM, 5 μM, 10 μM, 50 μM and 100 μM. Each point was done in triplicate. The cellular growth inhibitory effect of our compounds was evaluated using the MTT assay (Sigma). After 96 hours of treatment, 10 μL of MTT reagent solution (5 mg of MTT powder/mL diluted in Phosphate Buffer Salt saline solution) were added in each well and allowed to react for 3 hours in the incubator. After 3 hours cells were solubilized in Lysis Buffer (10% SDS/0.1% HCl in water, 100 μL for each well) for 24 hours at 37° C. Finally, the absorbance was measured at 570 nm using a multiplate reader. Absorbance values were collected and $IC_{50}$ values were determined using GraphPad Prism5 software. The experiments were repeated twice.

6.3 Cytotoxicity of Homo- and Heterodimeric Smac Mimetics—Standalone—Results

After 96 hours of treatment, 10 μl of MTT reagent solution (5 mg of MIT powder/ml diluted in Phosphate Buffer Salt saline solution) were added in each well and allowed to react for 3 hours in the incubator. After 3 hours cells were solubilized in Lysis Buffer (10% SDS/0.1% HCl in water, 100 μl for each well) for 24 hours at 37° C. Finally, the absorbance was measured at 570 nm using a multiplate reader. Absorbance values were collected and $IC_{50}/IC_{80}$ values were determined using GraphPad Prism5 software. The experiments were repeated twice, and some results are reported below as an activity range—A, $IC_{50}$<1 μM; B, 1 μM<$IC_{50}$<10 μM; C, 10 μM<$IC_{50}$<50 μM; D, $IC_{50}$>50 μM.

| Compound | MDA-MB-231 $IC_{50}$ (μM ± standard Deviation) | HL-60 $IC_{50}$ (μM ± standard Deviation) | PC-3 $IC_{50}$ (μM ± standard Deviation) |
|---|---|---|---|
| 28a | A | A | D |
| 29a | A | — | — |
| 30a | A | — | — |
| 30b | C | — | — |
| 30c | C | — | — |
| 30d | C | C | D |
| 34a | C | — | — |
| 35a | B | — | — |
| 36a | B | — | — |
| SM164[a] | A | A | C |

[a]from J. Am. Chem. Soc. 2007, 129, 15279

The values of the tested compounds clearly show cytotoxic activity, with an indication of structure-activity relationships among congeners.

Example 7

Animal Studies 7.1 Animals and Experimental Model.

All Experiments of Antitumor Activity were carried out using female athymic Swiss nude mice, 8-10 weeks-old (Charles River, Calco, Italy). Mice were maintained in laminar flow rooms keeping temperature and humidity constant. Mice had free access to food and water. Experiments were approved by the Ethics Committee for Animal Experimentation of the Istituto Nazionale Tumori of Milan according to institutional guidelines. The IGROV-1 human ovarian tumor xenograft derived from an ovarian carcinoma cell line obtained from an untreated patient (Benard et al., Cancer Res., 45:4970, 1985) was used in the study because it can be inoculated at different sites.

7.2 Drugs.

Compound 28a was dissolved in saline at a concentration of 0.5 mg/ml, whereas standard compound SM-164 (S. Wang, et. al., J. Am. Chem. Soc. 2007, 129, 15279) was dissolved in a mixture of ethanol and cremophor employing a magnetic stirrer and suspended in saline at a final concentration of 5+5+90%. The drugs were freshly dissolved at the beginning of the weekly administration following analysis of stability by HPLC-MS, which under the present conditions was maintained up to 5 days. The drugs were delivered i.p. in a volume of 10 ml/Kg of body weight.

7.3 Ovarian Tumor i.p. Xenografts.

The IGROV-1 tumor was adapted to grow in the peritoneal cavity (i.p.) and maintained by serial i.p. passages of ascitic cells into healthy mice. In this tumor model, hemorrhagic ascites with diffuse peritoneal carcinomatosis develops and the animal eventually die. For evaluation of antitumor activity, $2.5 \times 10^6$ ascitic cells in 0.2 ml of saline were injected i.p. into mice. Locoregional administration was employed. In particular, treatments started 1 day after cell inoculum. 28a was delivered i.p. at a dose of 5 mg/Kg and administered for 4-5 days a week for two weeks (qdx4-5/wx2w), starting the day after cell injection. For antitumor activity studies, experimental groups were inspected daily and weighed three times weekly. Prior to impending death, mice were sacrificed by cervical dislocation and day of sacrifice was considered as day of death and the median survival time (MST) was calculated for each group. Antitumor activity was assessed as T/C %, i.e., the ratio of MST in treated mice over that of control mice x 100. For statistical analysis, percent survivorship over time was estimated by the Kaplan-Meier product method and compared using the log-rank test.

7.4 Ovarian Tumor Subcutaneous Xenografts.

For subcutaneous (s.c.) growth, exponentially growing tumor cells ($5 \times 10^6$ cells/mouse) were s.c. injected into the right flank of athymic nude mice. The tumor line was achieved by serial s.c. passages of fragments (about 2×2×6 mm) from regrowing tumors into healthy mice. Groups of five mice bearing bilateral s.c. tumors were employed. Tumor fragments were implanted on day 0 and tumor growth was followed by biweekly measurements of tumor diameters with a Vernier caliper. Tumor volume (TV) was calculated according to the formula: TV (mm$^3$)=$d^2$xD/2 where d and D are the shortest and the longest diameter, respectively. 28a was delivered i.p. and administered for 5 days a week for three weeks (qdx5/wx3w). Treatment started three days after tumor implant, when tumors were just palpable. The efficacy of the drug treatment was assessed as tumor volume inhibition percentage (TVI %) in treated versus control mice, calculated as: TVI %=100−(mean TV treated/mean TV control×100). The toxicity of the drug treatment was determined as body weight loss and lethal toxicity. Deaths occurring in treated mice before the death of the first control mouse were ascribed to toxic effects. Student t test (two tailed) exact test was used for statistical comparison of tumor volumes in mice.

7.5 Activity of SMAC Mimetics Against i.p Ovarian Tumors.

Mice xenografted i.p. with IGROV-1 human ovarian carcinoma cells were injected i.p. with 28a or standard compound SM-164 both delivered qd4-5/wx2 at a dose of 5 mg/kg. Treatment started the day after tumor cell inoculation. Control mice were treated i.p. with saline when evaluating the antitumor activity of 28a or with vehicle when the effect of the standard was examined. Results are summarized in Table 1 and mice survival is shown in FIG. 1. The i.p. delivery of 28a led to a significant increased survival time compared with controls (P<0.05) with a T/C value of 180%. Under the same experimental conditions, the T/C value obtained using the standard was 164% (P<0.05). Thus, although 28a appeared superior to the standard in this experimental setting, both compounds were endowed with antitumor activity on the i.p. IGROV-1 tumor.

TABLE 1

Efficacy of i.p. SMAC mimetic agents, 5 mg/kg, qdx4-5/wx2-3w, on the ovarian carcinoma IGROV-1 xenografted i.p. in athymic nude mice.

| Agent | MST[1] | Range[2] | T/C %[3] | P[4] |
|---|---|---|---|---|
| saline | 20 | 14-26 | | |
| 28a | 36 | 28-56 | 180 | 0.0001 |
| vehicle | 22.5 | 20-30 | | |
| SM164 | 37 | 24-49 | 164 | 0.0007 |

[1]Median survival time (day).
[2]Range of the days of death.
[3]Ratio of MST in treated over control mice x 100.
[4]By two-sided log-rank test on survival curves over control mice.

7.6 Activity of SMAC Mimetics Against s.c. Ovarian Tumors.

When mice were xenografted s.c. with IGROV-1, a significant inhibition of tumor growth was observed with 28a administration (i.p., 5 mg/Kg, qdx5/wx3), the TVI being of 66% (Table 2, P<0.05 vs controls). In contrast, the standard used at the same dose and with the same schedule as 28a did not display any antitumor effect.

Moreover, 28a was well tolerated. These results support that 28a is endowed with a promising antitumor effect.

TABLE 2

Efficacy of i.p. SMAC mimetic agents, 5 mg/kg,, qdx4-5/wx3w, on the ovarian carcinoma IGROV-1 xenografted s.c. in athymic nude mice

| Agent | TVI %[1] | BWL %[2] | Tox[3] | P[4] |
|---|---|---|---|---|
| 28a | 66 | 2 | 0/4 | 0.034 |
| SM164 | 0 | 5 | 0/4 | n.s. |

[1]Tumor volume inhibition % in treated over control mice assessed 7 days after last treatment.
[2]Body weight loss % induced by treatment; the highest change is reported.
[3]Dead/treated mice.
[4]By Student's t test on tumor volumes over control mice.

The invention claimed is:
1. A method of treating cancer in a mammalian subject, wherein the cancer is breast cancer, ovarian cancer, acute myeloid leukemia (AML), or prostate cancer characterized by overexpression of an inhibitor of apoptosis protein (IAP) family member, said method comprising administering to the mammalian subject a compound of formula (I)

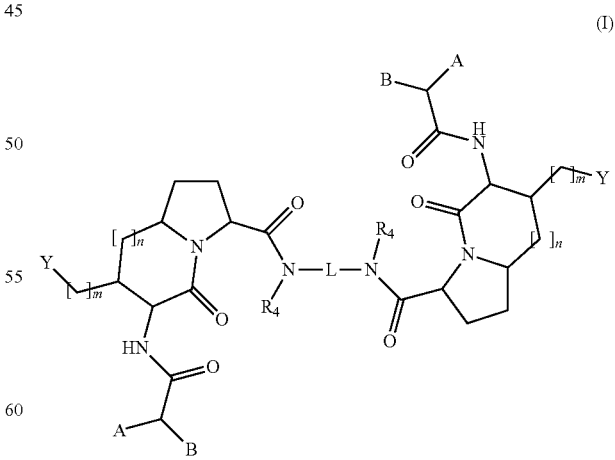

or pharmaceutically acceptable salt thereof, wherein
n is 1 or 2
m is an integer from 0 to 3
A is $NR_1R_2$
$R_1$ and $R_2$ are, each independently, hydrogen;
C<sub>1-8</sub> alkyl, C<sub>2-8</sub> alkenyl, C<sub>2-8</sub> alkynyl;
optionally substituted aryl or alkylaryl;
R$_4$ are each independently
  hydrogen;
  optionally substituted $C_{1-18}$ alkyl, $C_{2-18}$ alkenyl, $C_{2-18}$ alkynyl;
  optionally substituted aryl or alkylaryl;
B is
  $C_{1-4}$ alkyl; $C_{2-4}$ alkenyl; $C_{2-4}$ alkynyl;
  aryl or alkylaryl;
  all optionally substituted by one or more halogen;
Y is selected among $OR_5$, $NHR_5$, $NR_5R_6$, $NH-S(O)_2-R_5$, $N^+(R_5)_3$, $SR_5$, $N_3$, $C(O)OR_5$, $CN$, $C(S)OR_5$, $C(S)NHR_5$, $C(NH)NHR_5$, $NH(CNH)NHR_5$, $NH(CS)NHR_5$, $NH(CO)NHR_5$ or

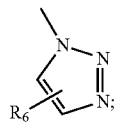

$R_5$ is
  hydrogen;
  optionally substituted $C_{1-8}$ alkyl; $C_{2-8}$ alkenyl; $C_{2-8}$ alkynyl;
  optionally substituted aryl or alkylaryl;
$R_6$ is
  optionally substituted $C_{1-8}$ alkyl; $C_{2-8}$ alkenyl; or $C_{2-8}$ alkynyl;
  optionally substituted aryl or alkylaryl;
L is a linker, wherein the linker is L1
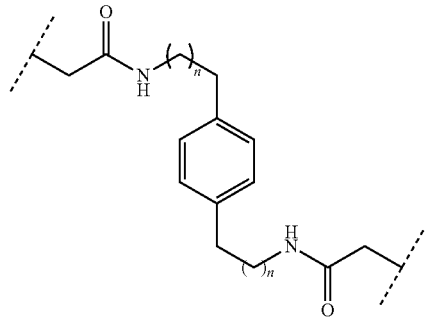
wherein each n is independently 1-6,

L2 wherein each n is independently 1-6,

L3
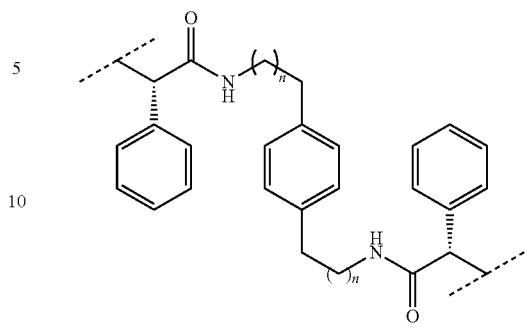
wherein each n is independently 1-6,

L4
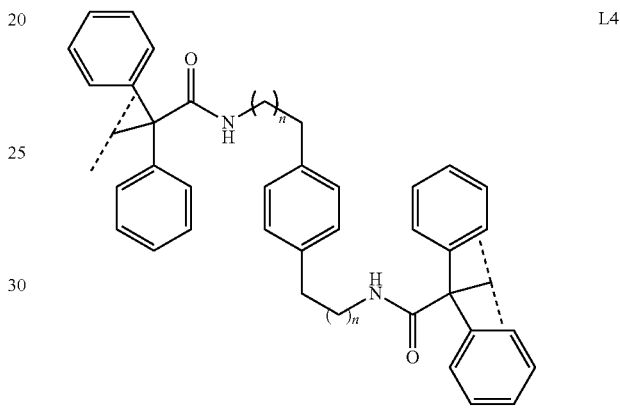
wherein each n is independently 1-6,

L5
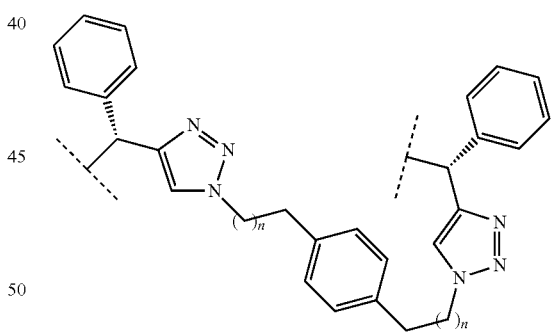
wherein each n is independently 1-6,

L6
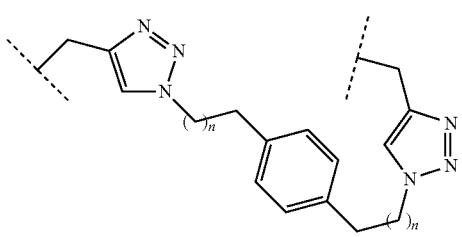
wherein each n is independently 1-6,

293
-continued
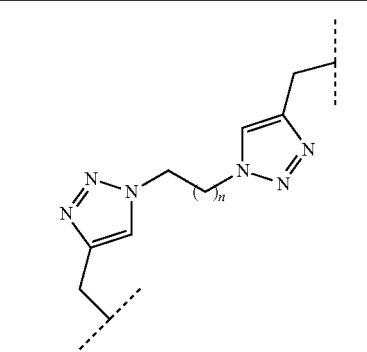
L7
wherein each n is independently 1-10
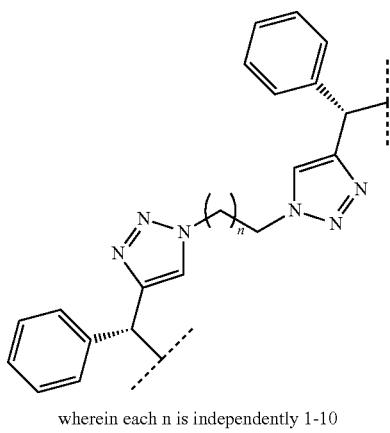
L8
wherein each n is independently 1-10
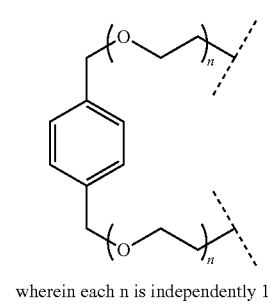
L9
wherein each n is independently 1-3,
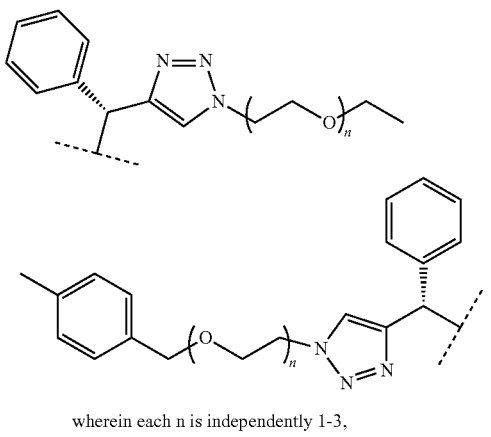
L10
wherein each n is independently 1-3,
294
-continued
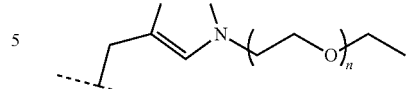
L11
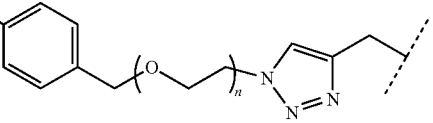
wherein each n is independently 1-3,
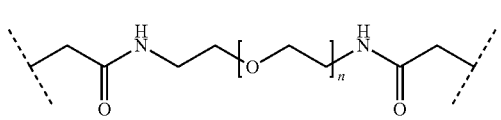
L12
wherein each n is independently 1-4,
L13
wherein each n is independently 1-4,
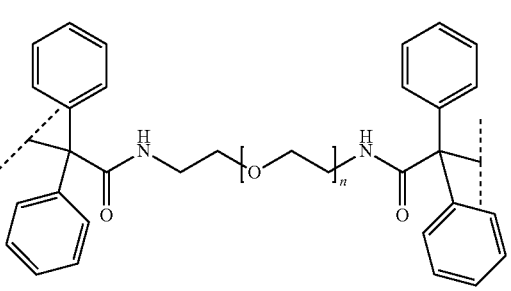
L14
wherein each n is independently 1-4,
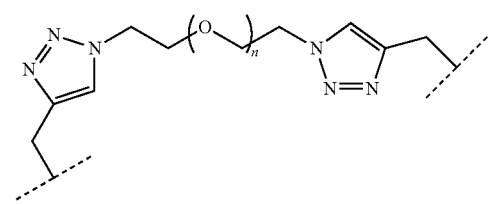
L15
wherein each n is independently 1-4,
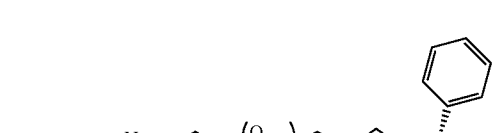
L16
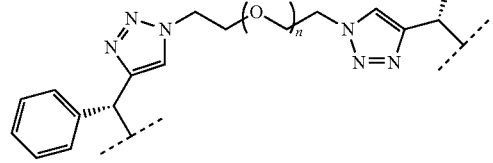
wherein each n is independently 1-4,

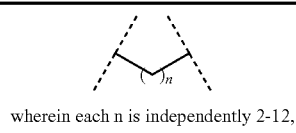

L17 wherein each n is independently 2-12,

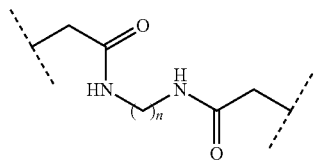

L18 wherein each n is independently 2-12,

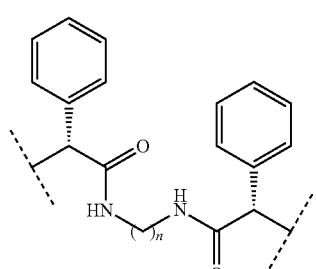

L19 wherein each n is independently 2-12,

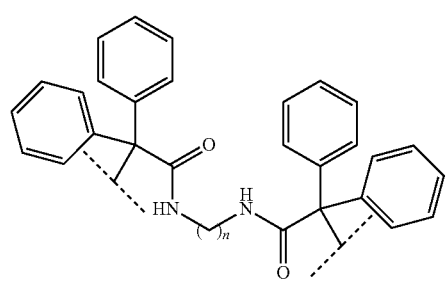

L20 wherein each n is independently 2-12,

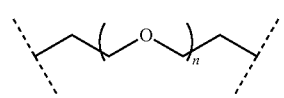

L21 wherein each n is independently 1-5,

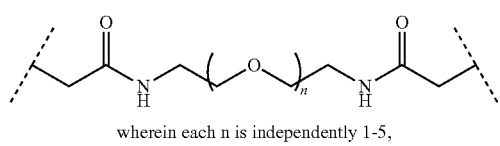

L22 wherein each n is independently 1-5,

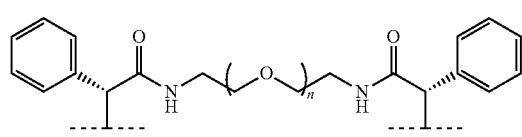

L23 wherein each n is independently 1-5,

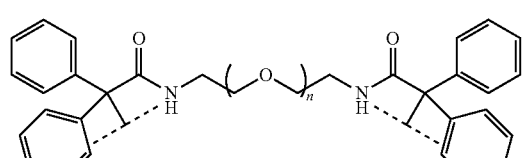

L24 wherein each n is independently 1-5,

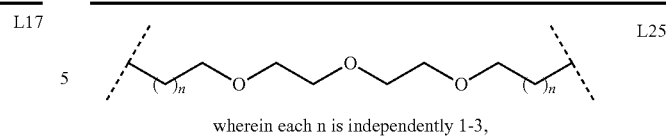

L25 wherein each n is independently 1-3,

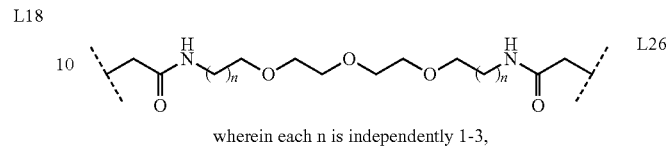

L26 wherein each n is independently 1-3,

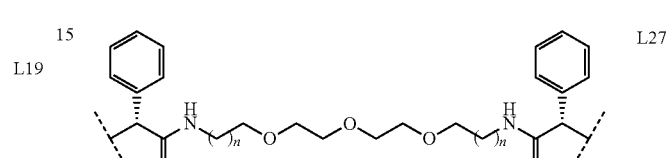

L27 wherein each n is independently 1-3,

L28

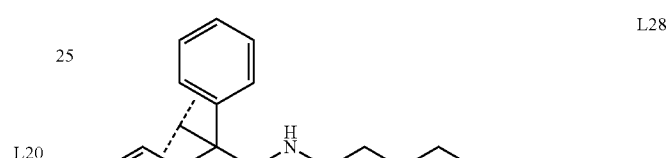

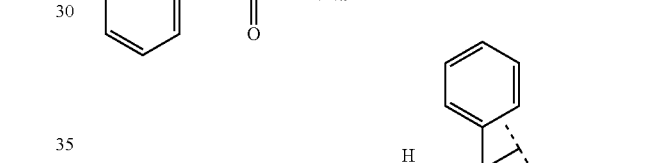

wherein each n is independently 1-3,

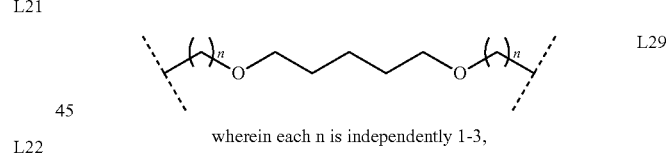

L29 wherein each n is independently 1-3,

L30 wherein each n is independently 1-3,

L31

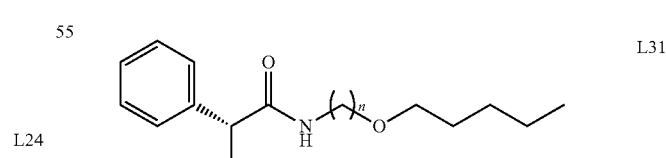

wherein each n is independently 1-3,

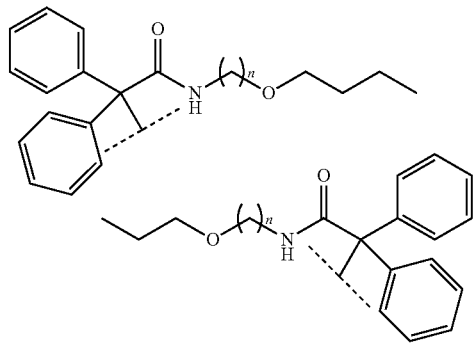
wherein each n is independently 1-3,
L32
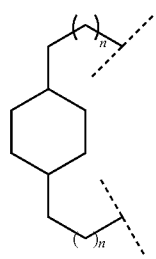
wherein each n is independently 1-6,
L33
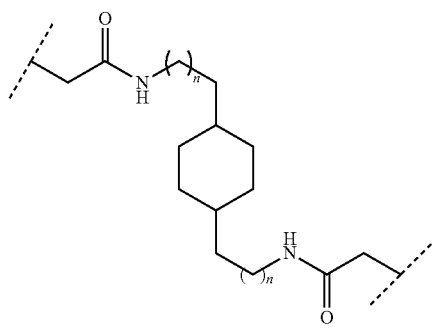
wherein each n is independently 1-6,
L34
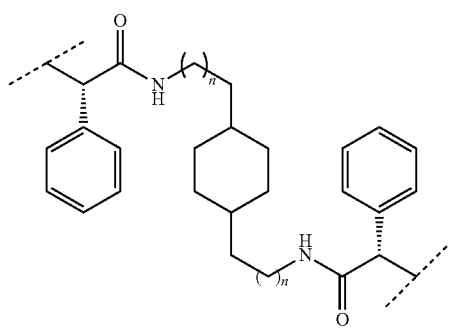
wherein each n is independently 1-6,
L35
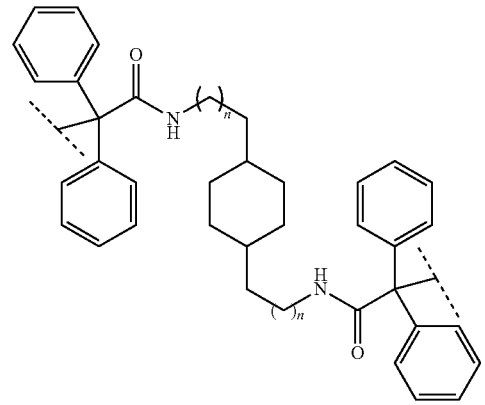
wherein each n is independently 1-6,
L36
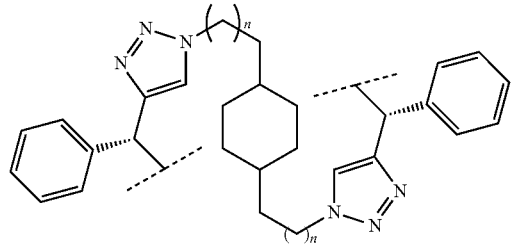
wherein each n is independently 1-6,
L37
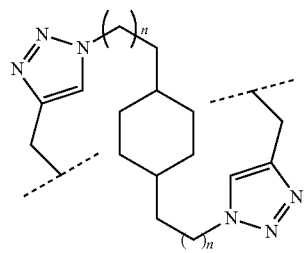
wherein each n is independently 1-6,
L38
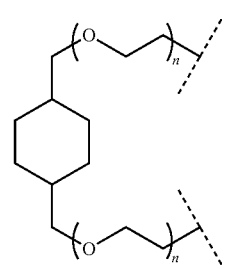
wherein each n is independently 1-3,
L39
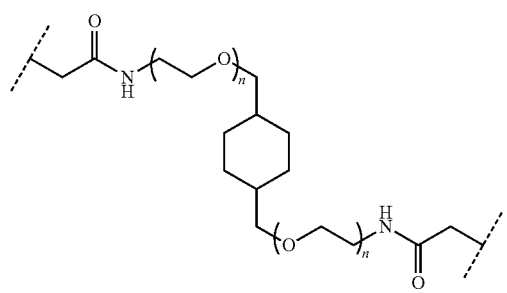
wherein each n is independently 1-3,
L40

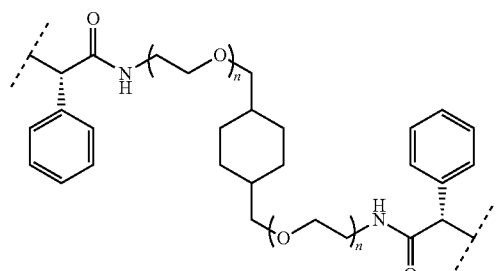
wherein each n is independently 1-3,
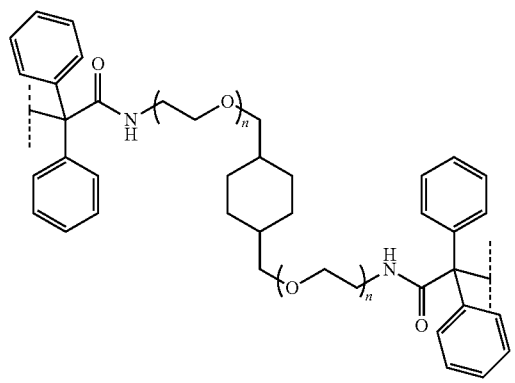
wherein each n is independently 1-3,
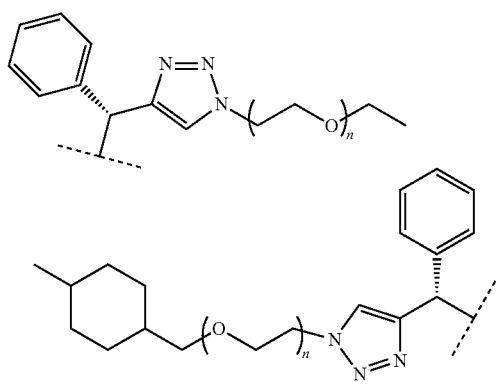
wherein each n is independently 1-3,
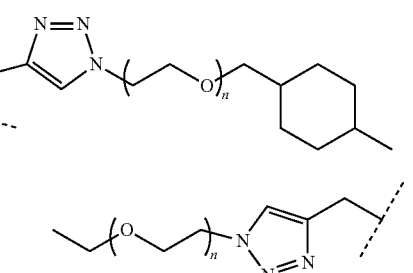
wherein each n is independently 1-3,
L41
L42
L43
L44
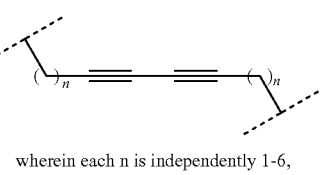
wherein each n is independently 1-6,
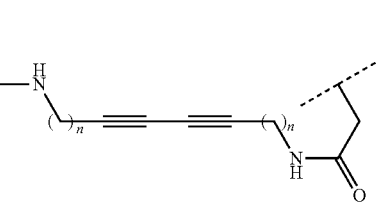
wherein each n is independently 1-6,
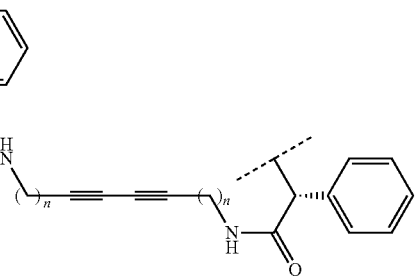
wherein each n is independently 1-6,
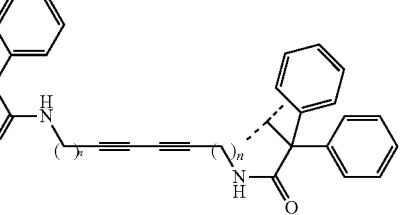
wherein each n is independently 1-6,
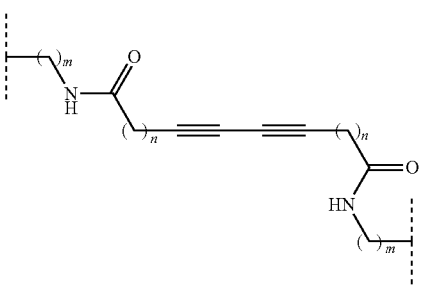
n, m = 1-6,
L45
L46
L47
L48
L49

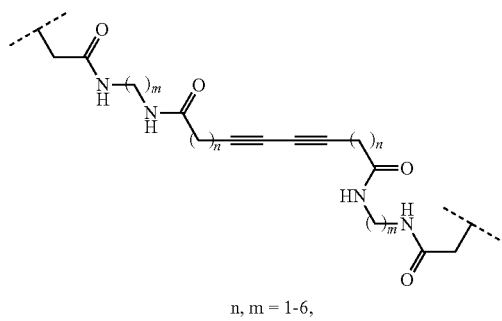

L50 n, m = 1-6,

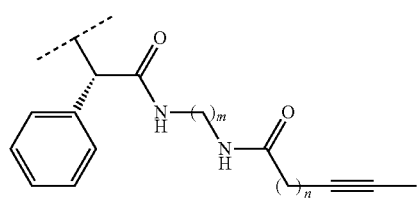

L51

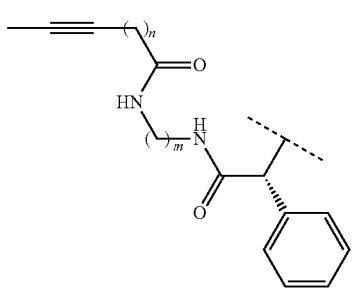

n, m = 1-6,

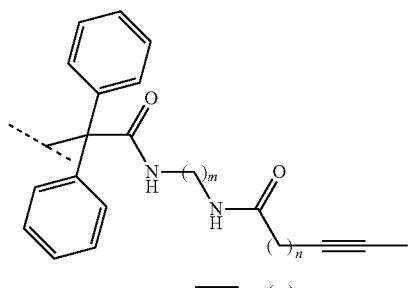

L52

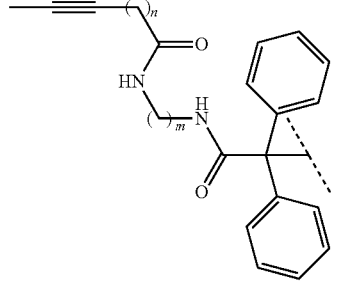

n, m = 1-6,

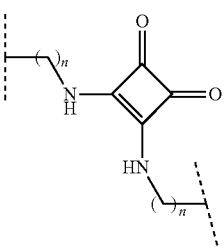

L53 wherein each n is independently 1-6,

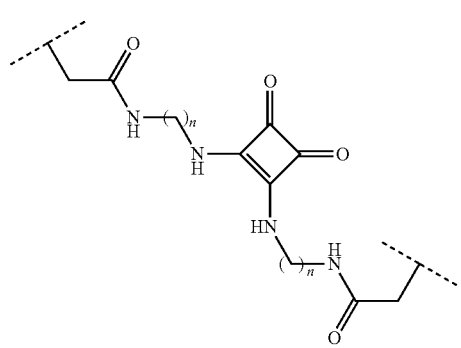

L54 wherein each n is independently 1-6,

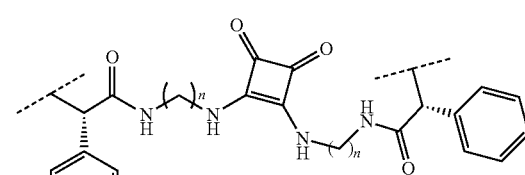

L55 wherein each n is independently 1-6, or

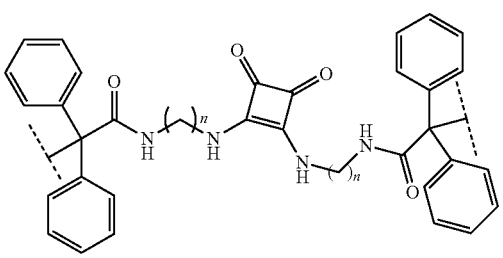

L56 wherein each n is independently 1-6 wherein unless otherwise indicated, an "optionally substituted" moiety is one that is optionally substituted by alkyl, cycloalkyl, aryl, alkylaryl, $OR_4'$, $SR_4'$, $NR_4'R_5'$, $COOR_4'$, an oxo group or a thioxo group, wherein $R_4'$ is hydrogen, $C_{1-18}$ alkyl, $C_{2-18}$ alkenyl, $C_{2-18}$ alkynyl, aryl or alkylaryl, and $R_5'$ is hydrogen, $C_{1-8}$ alkyl, $C_{2-8}$ alkenyl, $C_{2-8}$ alkynyl, aryl or alkylaryl.

2. A method of treating cancer in a mammalian subject, wherein the cancer is breast cancer, ovarian cancer, acute myeloid leukemia (AML), or prostate cancer characterized by overexpression of an inhibitor of apoptosis protein (IAP) family member, said method comprising administering to the mammalian subject a compound of formula (II)

(II)

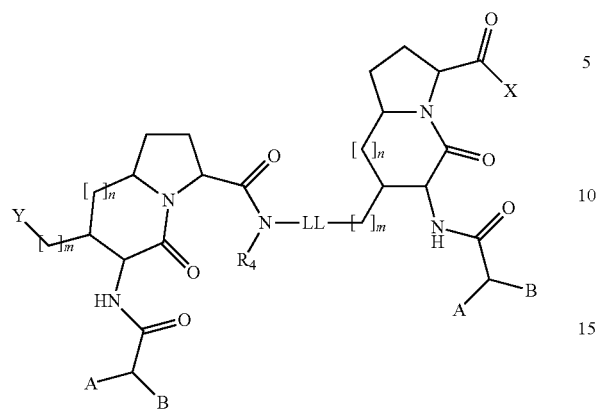

or a pharmaceutically acceptable salt thereof, wherein
n is 1 or 2
m is an integer from 0 to 3
A is $NR_1R_2$
$R_1$ and $R_2$ are, each independently,
  hydrogen;
  $C_{1-8}$ alkyl, $C_{2-8}$ alkenyl, $C_{2-8}$ alkynyl;
  optionally substituted aryl or alkylaryl;
  or
$R_4$ is
  hydrogen;
  optionally substituted $C_{1-18}$ alkyl, $C_{2-18}$ alkenyl, $C_{2-18}$ alkynyl;
  optionally substituted aryl or alkylaryl;
B are each independently
  $C_{1-4}$ alkyl; $C_{2-4}$ alkenyl; $C_{2-4}$ alkynyl;
  aryl or alkylaryl;
  all optionally substituted by one or more halogen;
Y is selected among $OR_5$, $NHR_5$, $NR_5R_6$, $NH—S(O)_2—R_5$, $N^+(R_5)_3$, $SR_5$, $N_3$, $C(O)OR_5$, $CN$, $C(S)OR_5$, $C(S)NHR_5$, $C(NH)NHR_5$, $NH(CNH)NHR_5$, $NH(CS)NHR_5$, $NH(CO)NHR_5$ or

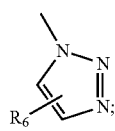

$R^5$ is
  hydrogen;
  optionally substituted $C_{1-8}$ alkyl; $C_{2-8}$ alkenyl; $C_{2-8}$ alkynyl;
  optionally substituted aryl;
$R_6$ is
  optionally substituted $C_{1-8}$ alkyl; $C_{2-8}$ alkenyl; or $C_{2-8}$ alkynyl;
  optionally substituted aryl;
X is optionally substituted $C_{1-18}$ alkyl, $C_{2-18}$ alkenyl, $C_{2-18}$ alkynyl or aryl, and one or more hydrogens in $CH$, $CH_2$ or $CH_3$ groups is optionally replaced by a branched or unbranched alkyl or cycloalkyl, an optionally substituted aryl or alkylaryl, or $OR_7$, $SR_7$, or $NR_7R_8$; and LL is a linker, wherein the linker is

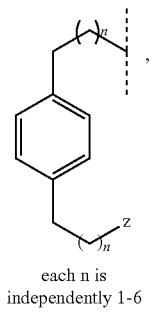

each n is
independently 1-6

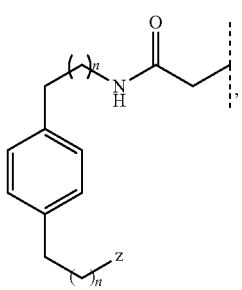

each n is independently 1-6

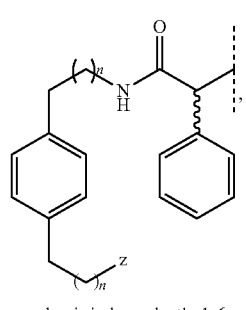

each n is independently 1-6

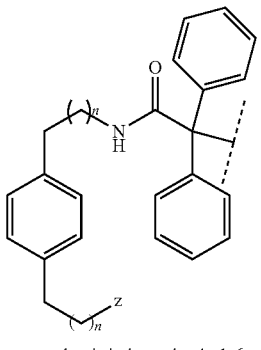

each n is independently 1-6

L61
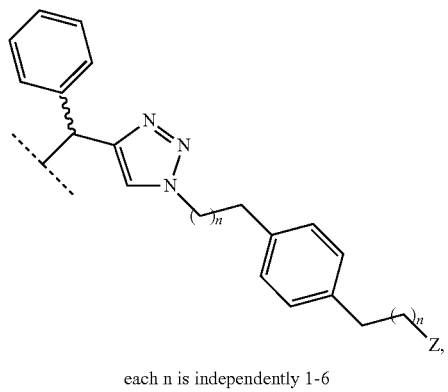
each n is independently 1-6
L62
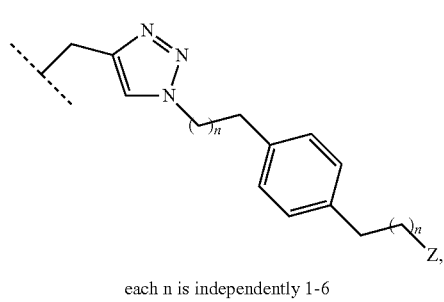
each n is independently 1-6
L63
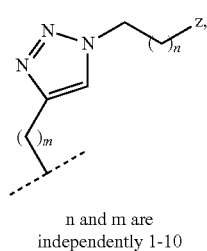
n and m are independently 1-10
L64
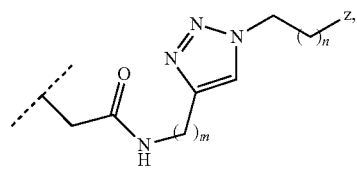
n and m are independently 1-10
L65
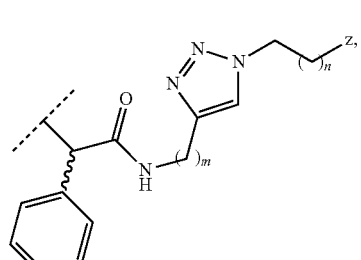
n and m are independently 1-10
L66
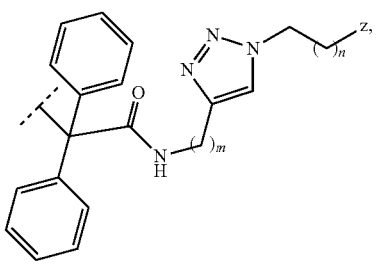
n and m are independently 1-10
L67
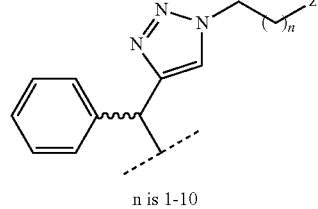
n is 1-10
L68
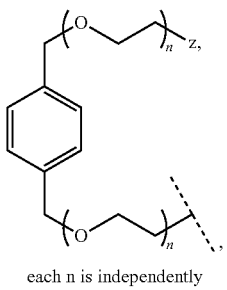
each n is independently 1-3
L69
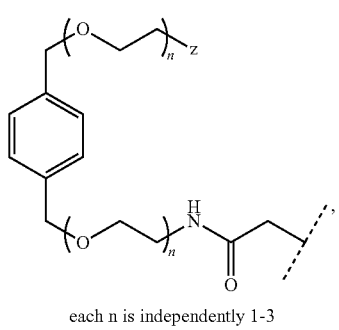
each n is independently 1-3
L70
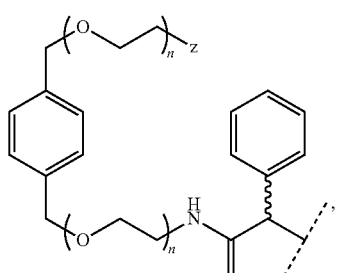
each n is independently n is 1-3

L71
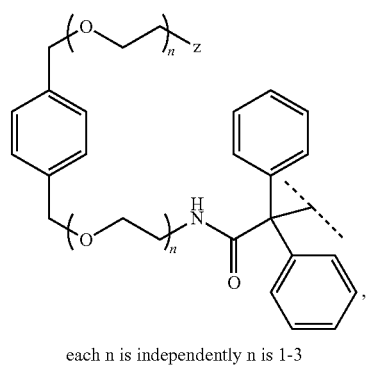
each n is independently n is 1-3
L72
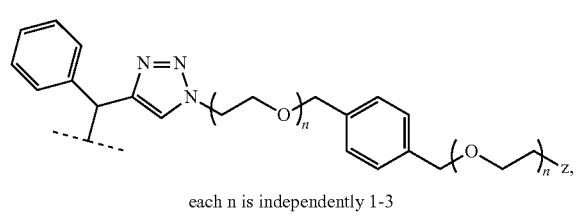
each n is independently 1-3
L73
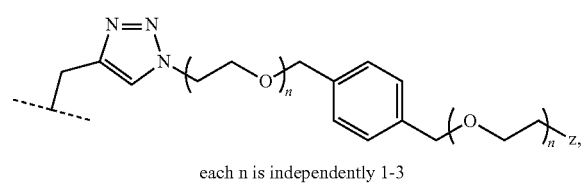
each n is independently 1-3
L74
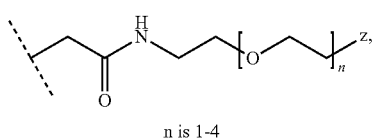
n is 1-4
L75
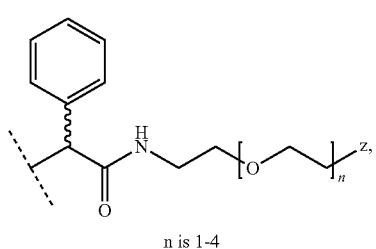
n is 1-4
L76
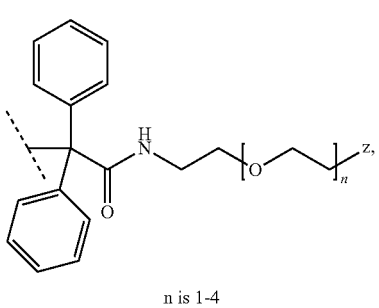
n is 1-4
L77
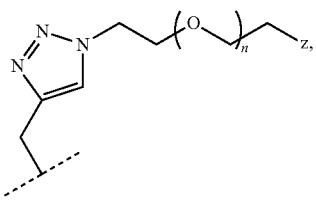
n is 1-4
L78
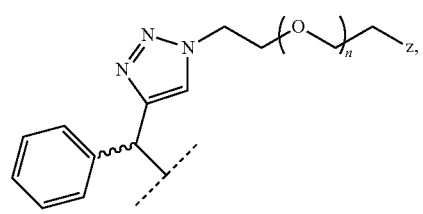
n is 1-4
L79
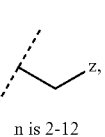
n is 2-12
L80
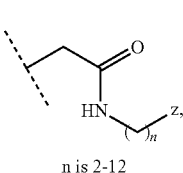
n is 2-12
L81
n is 2-12
L82
n is 2-12
L83
n is 1-5

L84
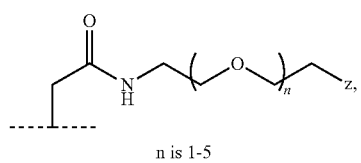
n is 1-5
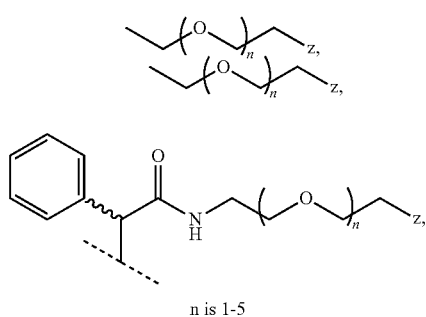
n is 1-5
L85
n is 1-5
L86
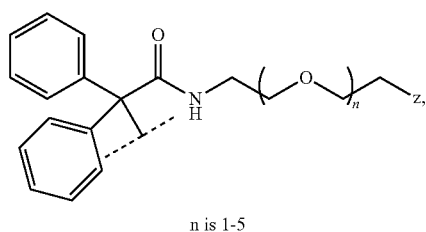
n is 1-5
L87
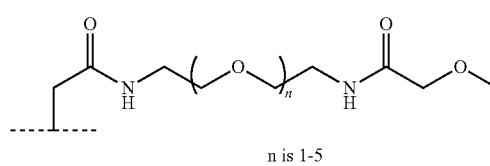
n is 1-5
L88
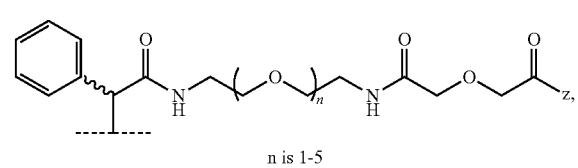
n is 1-5
L89
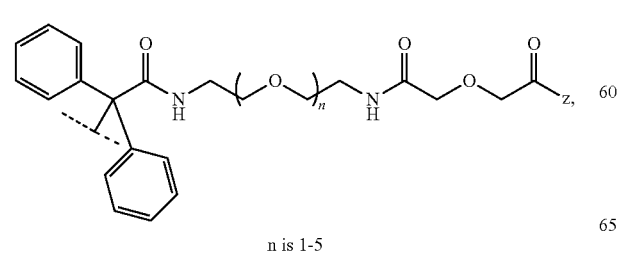
n is 1-5
L90
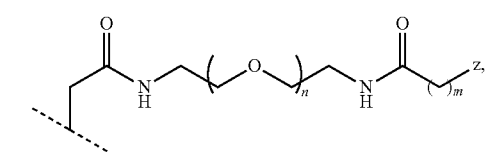
n is 1-5 and m is 1-12
L91
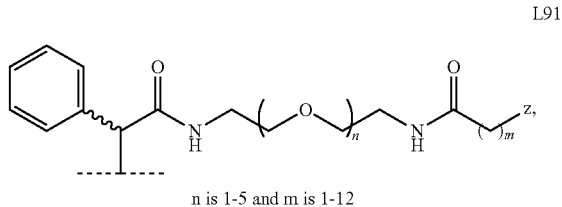
n is 1-5 and m is 1-12
L92
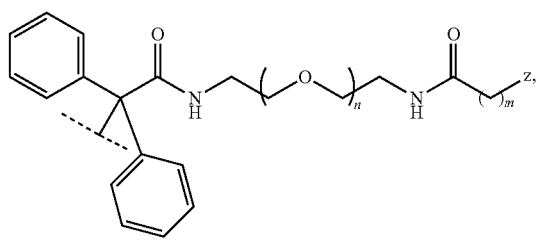
n is 1-5 and m is 1-12
L93
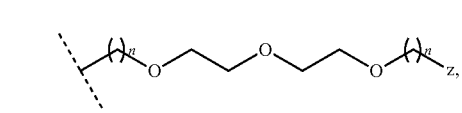
each n is independently 1-5
L94
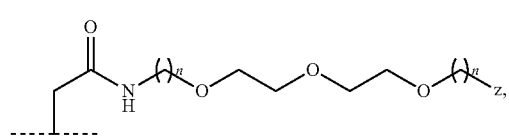
each n is independently 1-5
L95
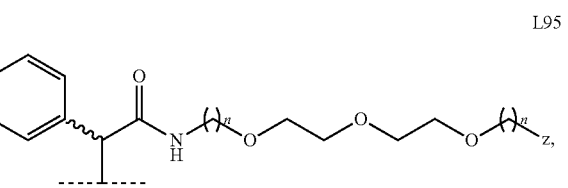
each n is independently 1-5
L96
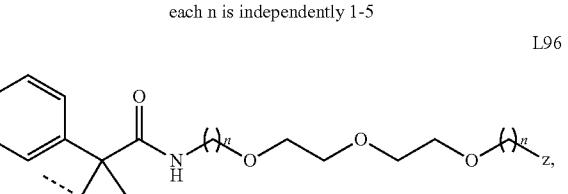
each n is independently 1-5
L97
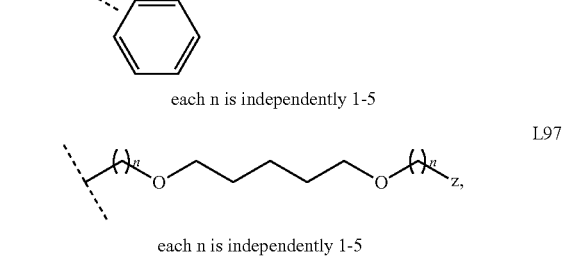
each n is independently 1-5

L98 each n is independently 1-5

L99 each n is independently 1-5

L100 each n is independently 1-5

L101 each n is independently 1-6

L102 each n is independently 1-6

L103 each n is independently 1-6

L104 each n is independently 1-6

L105 each n is independently 1-6

L106 each n is independently 1-6

L107 each n is independently 1-3

L108 each n is independently 1-3

L109
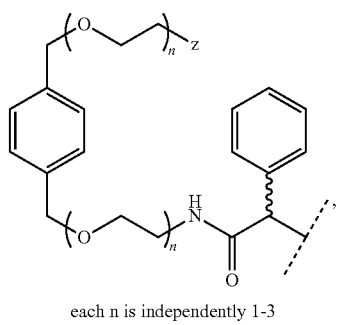
each n is independently 1-3
L110
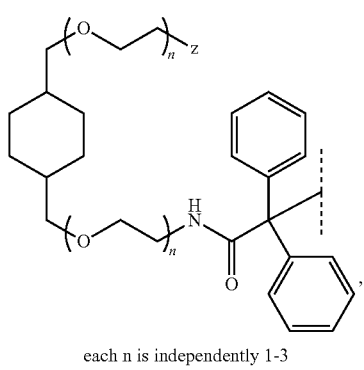
each n is independently 1-3
L111
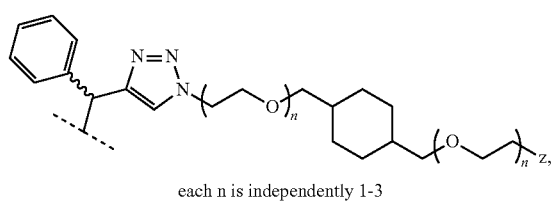
each n is independently 1-3
L112
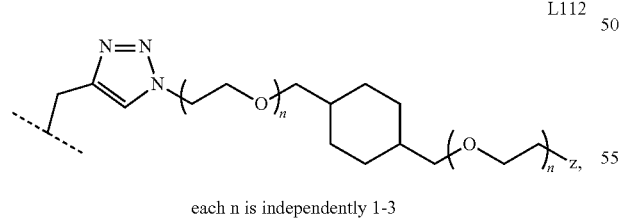
each n is independently 1-3
L113
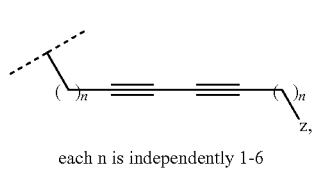
each n is independently 1-6
L114
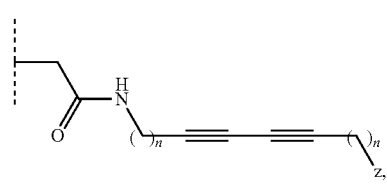
each n is independently 1-6
L115
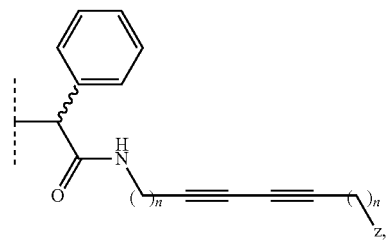
each n is independently 1-6
L116
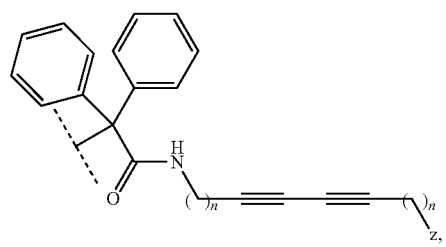
each n is independently 1-6
L117
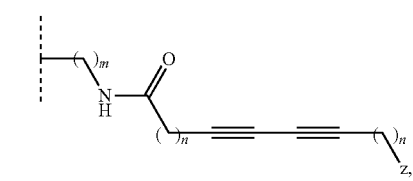
m and each n are independently 1-6
L118
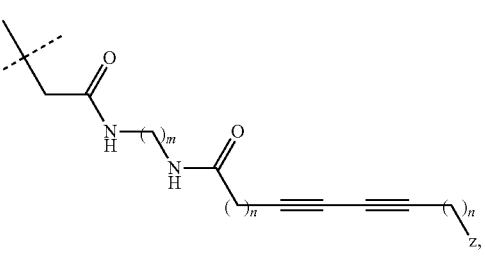
m and each n are independently 1-6

-continued

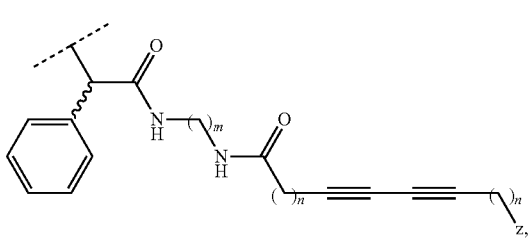

L119 m and each n are independently 1-6

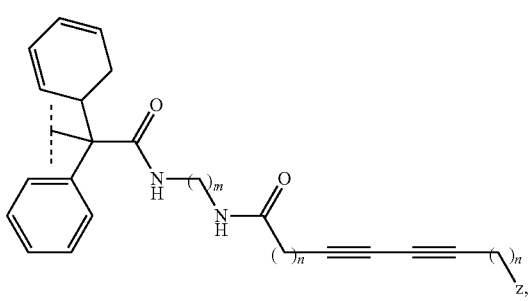

L120 m and each n are independently 1-6

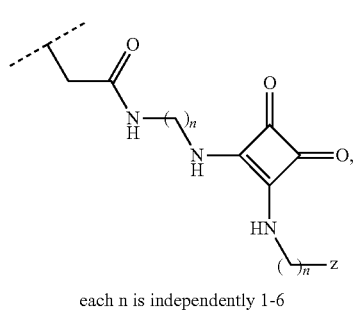

L121 each n is independently 1-6

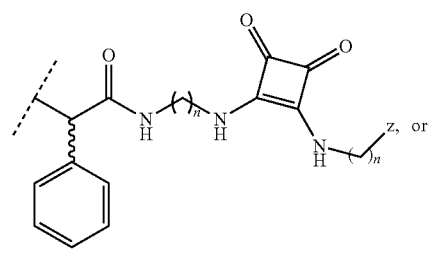

L122 each n is independently 1-6

L123

-continued

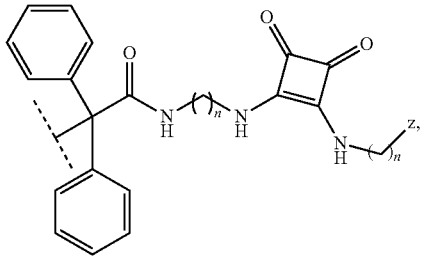

L124 each n is independently 1-6 wherein Z is $CR_7R_8$, O, $NR_7$, $NR_7C(O)$, S, $C(O)O$, $C(S)O$, $C(S)NR_7$, $C(NR_8)NR_7$, $NR_7C(NR_8)NR_9$, $NR_7C(O)NR_8$, $NR_7C(S)NR_8$

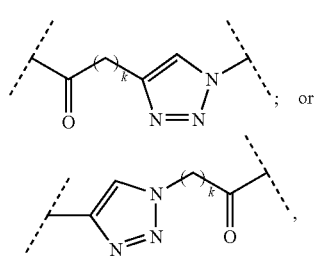

wherein k=1-10 each independently; and $R_7$, $R_8$, $R_9$ are independently hydrogen or optionally substituted $C_{1-4}$ alkyl, $C_{2-5}$ alkenyl, or $C_{2-5}$ alkynyl, in which one or more carbons can be replaced by an O, S, or N, or optionally substituted aryl or alkylaryl;

wherein unless otherwise indicated, an "optionally substituted" moiety is one that is optionally substituted by alkyl, cycloalkyl, aryl, alkylaryl, $OR_4'$, $SR_4'$, $NR_4'R_5'$, $COOR_4'$, an oxo group or a thioxo group, wherein $R_4'$ is hydrogen, $C_{1-18}$ alkyl, $C_{2-18}$ alkenyl, $C_{2-18}$ alkynyl, aryl or alkylaryl, and $R_5'$ is hydrogen, $C_{1-8}$ alkyl, $C_{2-8}$ alkenyl, $C_{2-8}$ alkynyl, or aryl.

3. The method according to claim 1, wherein the cancer is ovarian cancer.

4. The method according to claim 1, wherein the cancer is metastatic.

5. The method according to claim 1, wherein the cancer is resistant to common anticancer agents.

6. The method according to claim 1, wherein the compound is comprised in a pharmaceutical composition further comprising a pharmaceutically acceptable carrier.

7. The method according to claim 6, wherein the pharmaceutical composition further comprises at least one additional therapeutic agent selected from chemotherapeutics and apoptosis modulators.

8. The method according to claim 1, wherein L is linker L5 wherein each n is independently selected from an integer from 1 to 6.

9. The method according to claim 1, wherein $R_4$ is hydrogen, m=1, n=2,

Y is OH,

A is $NR_1R_2$ wherein $R_1$ is hydrogen and $R_2$ is $C_{1-8}$ alkyl, and

B is $C_{1-4}$ alkyl.

10. The method according to claim 1, wherein
L is linker L5 with n=2,
$R_4$ is hydrogen,
m=1, n=2,
Y is OH,
A is $NR_1R_2$ wherein $R_1$ is hydrogen and $R_2$ is $C_1$ alkyl, and
B is $C_2$ alkyl.

11. The method according to claim 1, wherein
L is linker L5 with n=2,
$R_4$ is hydrogen,
m=1, n=2,
Y is $NR_5R_6$ wherein $R_5$ is hydrogen and $R_6$ is $CH_2Phe$,
A is $NR_1R_2$ wherein $R_1$ is hydrogen and $R_2$ is $C_1$ alkyl, and
B is $C_2$ alkyl.

12. The method according to claim 1, wherein
L is linker L19,
$R_4$ is hydrogen,
m=1, n=2,
Y is OH,
A is $NR_1R_2$ wherein $R_1$ is hydrogen and $R_2$ is $C_1$ alkyl ($CH_3$), and
B is $C_2$ alkyl.

13. The method according to claim 1, wherein
L is linker L55,
$R_4$ is hydrogen,
m=1, n=2,
Y is OH,
A is $NR_1R_2$ wherein $R_1$ is hydrogen and $R_2$ is $C_1$ alkyl ($CH_3$), and
B is $C_2$ alkyl.

14. The method according to claim 1, wherein
L is linker L51,
$R_4$ is hydrogen,
m=1, n=2,
Y is OH,
A is $NR_1R_2$ wherein $R_1$ is hydrogen and $R_2$ is $C_1$ alkyl ($CH_3$), and
B is $C_2$ alkyl.

15. The method according to claim 1, wherein
L is linker L27 with n=2,
$R_4$ is hydrogen,
m=1, n=2,
Y is OH,
A is $NR_1R_2$ wherein $R_1$ is hydrogen and $R_2$ is $C_1$ alkyl ($CH_3$), and
B is $C_2$ alkyl.

16. The method according to claim 2, wherein
LL is L88 wherein n=3,
A is $NR_1R_2$ wherein $R_1$ is hydrogen and $R_2$ is $C_1$ alkyl ($CH_3$),
B is $C_2$ alkyl,
$R_4$ is hydrogen,
Y is OH,
m=1, n=2,
X is $NR_7R_8$ wherein $R_7$ is hydrogen and $R_8$ is substituted $C_1$ alkyl with two aryl groups, and
Z is $NR_7$ wherein $R_7$ is hydrogen.

17. The method according to claim 1, wherein the compound has the formula

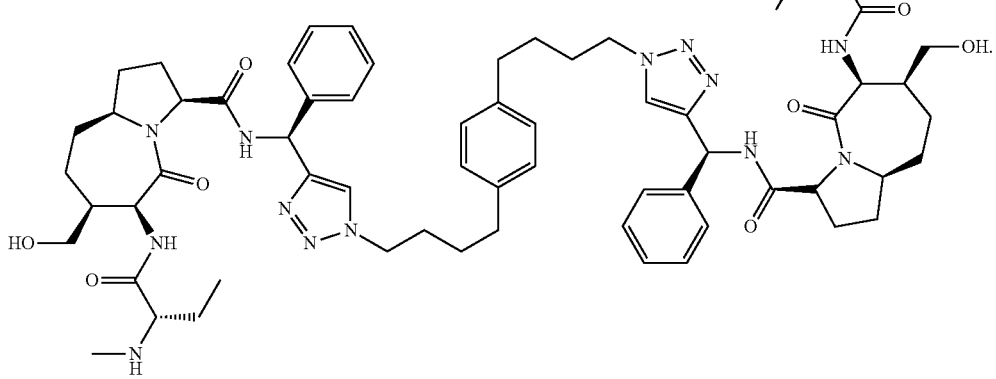

18. The method according to claim 2, wherein the cancer is ovarian cancer.

19. The method according to claim 2, wherein the cancer is metastatic.

20. The method according to claim 2, wherein the cancer is resistant to common anticancer agents.

21. The method according to claim 2, wherein the compound is comprised in a pharmaceutical composition further comprising a pharmaceutically acceptable carrier.

22. The method according to claim 21, wherein the pharmaceutical composition further comprises at least one additional therapeutic agent selected from chemotherapeutics and apoptosis modulators.

23. The method according to claim 1, wherein the IAP family member is selected from X-linked IAP (XIAP), cellular IAP 1 (cIAP-1) and cellular IAP 2 (cIAP-2).

24. The method according to claim 2, wherein the IAP family member is selected from X-linked IAP (XIAP), cellular IAP 1 (cIAP-1) and cellular IAP 2 (cIAP-2).

* * * * *